US00RE46792E

(19) United States
(12) Reissued Patent
Okada et al.

(10) Patent Number: US RE46,792 E
(45) Date of Reissued Patent: Apr. 17, 2018

(54) OXAZOLE COMPOUND AND PHARMACEUTICAL COMPOSITION

(71) Applicant: Otsuka Pharmaceutical Co., Ltd., Tokyo (JP)

(72) Inventors: Minoru Okada, Ako (JP); Masaya Kato, Ako (JP); Norifumi Sato, Ako (JP); Tetsuyuki Uno, Ako (JP); Hideki Kitagaki, Ako (JP); Junpei Haruta, Ako (JP); Hidetaka Hiyama, Ako (JP); Tomonori Shibata, Ako (JP)

(73) Assignee: Otsuka Pharmaceutical Co., Ltd., Tokyo (JP)

(21) Appl. No.: 15/623,249

(22) Filed: Jun. 14, 2017

Related U.S. Patent Documents

Reissue of:
(64) Patent No.: 8,637,559
Issued: Jan. 28, 2014
Appl. No.: 12/090,951
PCT Filed: Nov. 14, 2006
PCT No.: PCT/JP2006/323066
§ 371 (c)(1),
(2) Date: Mar. 26, 2009
PCT Pub. No.: WO2007/058338
PCT Pub. Date: May 24, 2007

(30) Foreign Application Priority Data

Nov. 15, 2005 (JP) ..... 2005-330590

(51) Int. Cl.

| | |
|---|---|
| ***A61K 31/5377*** | (2006.01) |
| ***A61K 31/497*** | (2006.01) |
| ***A61K 31/496*** | (2006.01) |
| ***A61K 31/4709*** | (2006.01) |
| ***A61K 31/4439*** | (2006.01) |
| ***A61K 31/422*** | (2006.01) |
| ***A61K 31/421*** | (2006.01) |
| ***C07D 413/12*** | (2006.01) |
| ***C07D 413/06*** | (2006.01) |
| ***C07D 263/32*** | (2006.01) |
| ***C07D 263/34*** | (2006.01) |

(52) U.S. Cl.
CPC ..... *C07D 413/12* (2013.01); *C07D 263/32* (2013.01); *C07D 263/34* (2013.01); *C07D 413/06* (2013.01)

(58) Field of Classification Search
CPC .. C07D 263/32; C07D 413/12; C07D 413/06; C07D 263/34
See application file for complete search history.

(56) References Cited

U.S. PATENT DOCUMENTS

| | | | | |
|---|---|---|---|---|
| 4,735,961 | A | 4/1988 | Baldwin et al. | |
| 5,814,651 | A | 9/1998 | Duplantier et al. | |
| 6,020,339 | A | 2/2000 | Perrier et al. | |
| 6,479,494 | B1 | 11/2002 | Rochus et al. | |
| 7,655,680 | B2 * | 2/2010 | Takemura | C07D 277/24 514/365 |
| 2004/0106793 | A1 | 6/2004 | Adams et al. | |
| 2004/0209933 | A1 | 10/2004 | Bossenmaier et al. | |
| 2008/0039511 | A1 | 2/2008 | Takemura et al. | |
| 2008/0090882 | A1 * | 4/2008 | Dorsch et al. | 514/365 |
| 2009/0176799 | A1 | 7/2009 | Ruiping et al. | |

FOREIGN PATENT DOCUMENTS

| | | | |
|---|---|---|---|
| DE | 10 2004 051277 | A1 | 4/2006 |
| EP | 332332 | A * | 9/1989 |
| IN | 99/KOLNP/2007 | | 6/2007 |
| JP | 11-322730 | | 11/1999 |
| JP | 2001-503022 | A | 3/2001 |
| JP | 2001-519344 | A | 10/2001 |
| JP | 2004-203871 | A | 7/2004 |
| JP | 2005-508961 | A | 4/2005 |
| WO | WO 96/00218 | A | 1/1996 |

(Continued)

OTHER PUBLICATIONS

Baumer et al., "Effects of the Phosphodiesterase 4 Inhibitors SB 207499 and and AWD 12-281 on the Inflammatory Reaction in a Model of Allergic Dermatitis," European Journal of Pharmacology 2002, 446, 195-200.
Bielekova et al., J. Immunol. 2000. 164, 1117-1124.
Blednov et al., Frontiers in Neuroscience 2014, 8, Articie 129, 1-11.
First Examination Report for corresponding IN Application No. 4398/DELNP/2008 dated Nov. 20, 2013.
Golub et al., "Molecular Classification of Cancer: Class Discovery and Class Prediction by Gene Expression Monitoring," Science, vol. 286, Oct. 15, 1999, pp. 531-537.
Houslay et al., "Phosphodiesterase-4 as a Therapeutic Target," Drug Discovery Today 2005, 10, 1503-1519.
International Search Report for PCT/JP2006/323066 dated Apr. 24, 2007.

(Continued)

*Primary Examiner* — Jerry D Johnson
(74) *Attorney, Agent, or Firm* — Finnegan, Henderson, Farabow, Garrett & Dunner, LLP

(57) ABSTRACT

The present invention provides a oxazole compound represented by Formula (1), or a salt thereof:

(1)

wherein $R^1$ is an aryl group which may have one or more substituents; $R^2$ is an aryl group or a nitrogen atom-containing heterocyclic group each of which may have one or more substituents; and W is a divalent group represented by —$Y^1$-$A^1$- or or —$Y^2$—C(=O)— wherein $Y^1$ is a group such as —C(=O)—, $A^1$ is a group such as a lower alkylene group, and $Y^2$ is a group such as a piperazinediyl group. The oxazole compound has a specific inhibitory action against phosphodiesterase 4.

16 Claims, No Drawings

(56) References Cited

FOREIGN PATENT DOCUMENTS

| | | | |
|---|---|---|---|
| WO | WO 98/06830 | A | 3/1998 |
| WO | WO 98/08830 | A | 3/1998 |
| WO | WO 98/15274 | | 4/1998 |
| WO | WO 03/072102 | A1 | 9/2003 |
| WO | WO 2006/019833 | A1 | 2/2006 |
| WO | WO 2006/045350 | A1 | 5/2006 |
| WO | WO 2006103045 | A1 * | 10/2006 |

OTHER PUBLICATIONS

Kanes et al., "Rolipram: A Specific Phosphodiesterase 4-Inhibitor With Potential Antipsychotic Activity," Neuroscience 2007, 144, 239-246.

Luo et al., "Principles of Cancer Therapy: Oncogene and Non-oncogene Addiction," Cell 2009, 136, 823-837.

Nih, How Can Asthma be Prevented? Obtained from http://www.nhibi.nih.gov/health/health-topics/topics/asthama/prevention on Jul. 26, 2015.

Nih, How Can COPD be Prevented? Obtained from http://www.nhibi.nih.gov/health/health-topics/topics/copd/prevention on Jul. 26, 2015.

Popa et al., Journal of Lipid Research, 2007, 48, 751-762.

Sengupta et al., Trends in Pharmacological Sciences 2011, 32, 337-344.

Tabei et al., "Ring-transformation of 1,2,4-Oxadiazines. Raney Nickel Hydrogenation of Z-3-Aryl-5,6-dihydro-5-(substituted)methylene-4H-1,2,4-oxadiazine Derivatives [8]," J. Heterocyclic Chem. 1985, 22, 569-574.

Young et al., "4-Bromomethyl-2-chlorooxazole-a versatile oxazole cross-coupling for the synthesis of 2,4-disubstituted oxazoles," Tetrahedron Letters 2004, 45, 3797-3801.

Malamas et al. J. Med. Chem. 1996, 39, 237-245.*

MedlinePlus Medical Dictionary entry for dermatosis, last accessed Mar. 23, 2010.*

Michael S. Malamas et al., "Azole Phenoxy Hydroxyureas as Selective and Orally Active Inhibitors of 5-Lipoxygenase," Journal of Medicinal Chemistry, American Chemical Society, Washington, U.S. vol. 39, No. 1, 1996, pp. 237-245, XP-002093481.

* cited by examiner

OXAZOLE COMPOUND AND PHARMACEUTICAL COMPOSITION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*This patent application is a reissue application of U.S. Pat. No. 8,637,559, issued Jan. 28, 2014, on application Ser. No. 12/090,951, § 371(c) date of Mar. 26, 2009, which is the National Stage of PCT/JP2006/323066, filed Nov. 14, 2006.*

TECHNICAL FIELD

The present invention relates to new oxazole compounds and pharmaceutical compositions.

BACKGROUND ART

Various oxazole compounds have been developed and are disclosed in documents such as WO 03/072102, WO 98/15274, etc. However, the oxazole compounds of the present invention are not disclosed in any literature.

Some compounds having a specific inhibitory action against phosphodiesterase 4 (PDE4) have been reported. However, known PDE4 inhibitors have problems of side effects such as vomit induction, nausea, etc. and/or a defect of insufficient PDE4 inhibitory action. Therefore, known PDE4 inhibitors are not clinically used as therapeutic agents.

DISCLOSURE OF THE INVENTION

An object of the present invention is to provide a compound that has a PDE4 inhibitory action and is free from the above-mentioned problems of the prior art.

The present inventors conducted extensive research to solve the above problems, and succeeded in synthesizing an oxazole compound with a novel structure, the compound having high specificity and a strong PDE4 inhibitory action. Further, the present inventors found that the oxazole compound is capable of exhibiting preventive and/or therapeutic effects on PDE-mediated diseases, and in particular atopic dermatitis, based on its PDE4 inhibitory action. Furthermore, the inventors found that the compound has low penetration into blood when administered transdermally, and thus has low systemic side effects.

The present inventors further found that the oxazole compound is capable of exhibiting a tumor necrosis factor-α (TNF-α) production inhibitory action.

In chronic inflammatory diseases such as autoimmune diseases and allergic diseases, cytokines produced by immunocompetent cells are known to be important inflammatory mediators, and among such cytokines, TNF-α is presumed to play a particularly important role. Therefore, the oxazole compound of the present invention is extremely effective for the treatment of TNF-α-mediated diseases.

The present invention has been accomplished by further research based on the above findings.

The present invention provides a oxazole compound, a pharmaceutical composition comprising said compound, a use of said compound, a method for treating or preventing a disorder, and a process for producing said compound, as described in Item 1 to 14 below.

Item 1. An oxazole compound represented by Formula (1)

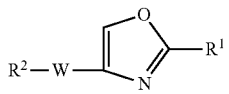

(1)

wherein $R^1$ is an aryl group which may have one or more substituents selected from the following (1-1) to (1-11):

(1-1) hydroxy groups, (1-2) unsubstituted or halogen-substituted lower alkoxy groups, (1-3) lower alkenyloxy groups, (1-4) lower alkynyloxy groups, (1-5) cyclo $C_{3-8}$ alkyl lower alkoxy groups, (1-6) cyclo $C_{3-8}$ alkyloxy groups, (1-7) cyclo $C_{3-8}$ alkenyloxy groups, (1-8) dihydroindenyloxy groups, (1-9) hydroxy lower alkoxy groups, (1-10) oxiranyl lower alkoxy groups, and (1-11) protected hydroxy groups;

$R^2$ is an aryl group or a nitrogen atom-containing heterocyclic group each of which may have one or more substituents selected from the following (2-1) to (2-10):

(2-1) hydroxy groups, (2-2) unsubstituted or halogen-substituted lower alkoxy groups, (2-3) unsubstituted or halogen-substituted lower alkyl groups, (2-4) lower alkenyloxy groups, (2-5) halogen atoms, (2-6) lower alkanoyl groups, (2-7) lower alkylthio groups, (2-8) lower alkylsulfonyl groups, (2-9) oxo groups, and (2-10) lower alkoxy lower alkoxy groups; and W is a divalent group represented by Formula (i) or (ii):

Formula (i) —$Y^1$-$A^1$-

Formula (ii) —$Y^2$—C(═O)— wherein $A^1$ is a lower alkenylene group, or a lower alkylene group which may have one or more substituents selected from the group consisting of hydroxy groups and lower alkoxycarbonyl groups, $Y^1$ is a direct bond, —C(═O)—, —C(═O)—N($R^3$)—, —N($R^4$)—C(═O)—, —S(O)$_m$—NH—, or —S(O)$_n$— wherein $R^3$ and $R^4$ are each independently a hydrogen atom or a lower alkyl group, and m and n are each independently an integer from 0 to 2, and $Y^2$ is a piperazinediyl group, or a divalent group represented by Formula (iii) or (iv):

Formula (iii) —C(═O)-$A^2$-N($R^5$)—

Formula (iv) -$A^3$-N($R^6$)— wherein $A^2$ and $A^3$ are each independently a lower alkylene group, and $R^5$ and $R^6$ are each independently a hydrogen atom or a lower alkyl group;

or a salt thereof.

Item 2. The compound according to item 1, wherein $R^1$ is a phenyl group which has 1 to 3 substituents selected from the following (1-2), (1-3), (1-4) and (1-5):

(1-2) unsubstituted or halogen-substituted lower alkoxy groups, (1-3) lower alkenyloxy groups, (1-4) lower alkynyloxy groups, and (1-5) cyclo $C_{3-8}$ alkyl lower alkoxy groups;

$R^2$ is a phenyl group or a pyridyl group each of which may have 1 to 3 substituents selected from the group consisting of the following (2-2), (2-3), (2-4) and (2-5):

(2-2) unsubstituted or halogen-substituted lower alkoxy groups, (2-3) unsubstituted or halogen-substituted lower alkyl groups, (2-4) lower alkenyloxy groups, and (2-5) halogen atoms;

W is a divalent group represented by Formula (i):

$$—Y^1\text{-}A^1\text{-} \qquad \text{Formula (i)}$$

wherein $A^1$ is a lower alkylene group, and $Y^1$ is —C(═O)— or —C(═O)—N($R^3$)— wherein $R^3$ is a hydrogen atom.

Item 3. The compound according to item 2, wherein $R^1$ is a phenyl group having two substituents selected from the following (1-2), (1-3), (1-4) and (1-5):

(1-2) unsubstituted or halogen-substituted lower alkoxy groups, (1-3) lower alkenyloxy groups, (1-4) lower alkynyloxy groups, and (1-5) cyclo $C_{3-8}$ alkyl lower alkoxy groups;

$R^2$ is a phenyl group or a pyridyl group each of which may have 1 to 2 substituents selected from the following (2-2), (2-3), (2-4) and (2-5):

(2-2) unsubstituted or halogen-substituted lower alkoxy groups, (2-3) unsubstituted or halogen-substituted lower alkyl groups, (2-4) lower alkenyloxy groups, and (2-5) halogen atoms; and W is a divalent group represented by Formula (i):

$$—Y^1\text{-}A^1\text{-} \qquad \text{Formula (i)}$$

wherein $A^1$ is a lower alkylene group, and $Y^1$ is —C(═O)— or —C(═O)—N($R^3$)— wherein $R^3$ is a hydrogen atom.

Item 4. The compound according to item 3, wherein $R^1$ is a phenyl group substituted on the phenyl ring with two lower alkoxy groups, a phenyl group substituted on the phenyl ring with one lower alkoxy group and one Cyclo $C_{3-8}$ alkyl lower alkoxy group, a phenyl group substituted on the phenyl ring with one lower alkoxy group and one halogen-substituted lower alkoxy group, a phenyl group substituted on the phenyl group with one lower alkoxy group and one lower alkenyloxy group, a phenyl group substituted on the phenyl ring with one halogen-substituted lower alkoxy group and one cyclo $C_{3-8}$ alkyl lower alkoxy group, a phenyl group substituted on the phenyl ring with one halogen-substituted lower alkoxy group and one lower alkenyloxy group, or a phenyl group substituted on the phenyl ring with two halogen-substituted lower alkoxy groups;

$R^2$ is a lower alkoxyphenyl group, a lower alkenyloxyphenyl group, a halogen-substituted lower alkoxyphenyl group, a lower alkylpyridyl group, or a phenyl group substituted on the phenyl ring with one lower alkoxy group and one halogen atom; and W is a divalent group represented by Formula (i):

$$—Y^1\text{-}A^1\text{-} \qquad \text{Formula (i)}$$

wherein $A^1$ is a $C_{1-4}$ alkylene group, and $Y^1$ is —C(═O)— or —C(═O)—N($R^3$)— wherein $R^3$ is a hydrogen atom.

Item 5. The compound according to item 4, wherein $R^1$ is a phenyl group substituted on the phenyl ring with two lower alkoxy groups, a phenyl group substituted on the phenyl ring with one lower alkoxy group and one cyclo $C_{3-8}$ alkyl lower alkoxy group, a phenyl group substituted on the phenyl ring with one lower alkoxy group and one halogen-substituted lower alkoxy group, a phenyl group substituted on the phenyl group with one lower alkoxy group and one lower alkenyloxy group, a phenyl group substituted on the phenyl ring with one halogen-substituted lower alkoxy group and one cyclo $C_{3-8}$ alkyl lower alkoxy group, a phenyl group substituted on the phenyl ring with one halogen-substituted lower alkoxy group and one lower alkenyloxy group, or a phenyl group substituted on the phenyl ring with two halogen-substituted lower alkoxy groups;

$R^2$ is a lower alkoxyphenyl group, a lower alkenyloxy phenyl group, a halogen-substituted lower alkoxyphenyl group, a lower alkylpyridyl group, or a phenyl group substituted on the phenyl ring with one lower alkoxy group and one halogen atom; and W is a divalent group represented by Formula (i)

$$—Y^1\text{-}A^1\text{-} \qquad \text{Formula (i)}$$

wherein $A^1$ is a $C_{1-4}$ alkylene group, and $Y^1$ is —C(═O)—.

Item 6. The compound according to item 4, wherein $R^1$ is a phenyl group substituted on the phenyl ring with one lower alkoxy group and one halogen-substituted lower alkoxy group, a phenyl group substituted on the phenyl ring with one halogen-substituted lower alkoxy group and one cyclo $C_{3-8}$ alkyl lower alkoxy group, or a phenyl group substituted on the phenyl ring with one halogen-substituted lower alkoxy group and one lower alkenyloxy group;

$R^2$ is a lower alkoxyphenyl group or a lower alkylpyridyl group; and

W is a divalent group represented by Formula (i):

$$—Y^1\text{-}A^1\text{-} \qquad \text{Formula (i)}$$

wherein $A^1$ is a $C_{1-4}$ alkylene group, and $Y^1$ is —C(═O)—N($R^3$)— wherein $R^3$ is a hydrogen atom.

Item 7. A pharmaceutical composition comprising the compound or salt according to any one of items 1 to 6 as an active ingredient and a pharmaceutically acceptable carrier.

Item 8. A pharmaceutical composition for treating or preventing phosphodiesterase 4-mediated and/or tumor necrosis factor-α-mediated diseases, the composition comprising the compound or salt according to any one of items 1 to 6.

Item 9. A pharmaceutical composition for treating or preventing atopic dermatitis, the composition comprising the compound or salt according to any one of items 1 to 6.

Item 10. A process for producing a pharmaceutical composition, the process comprising mixing the compound or salt according to any one of items 1 to 6 with a pharmaceutically acceptable carrier.

Item 11. Use of the compound or salt according to any one of items 1 to 6 as a drug.

Item 12. Use of the compound or salt according to any one of items 1 to 6 as a phosphodiesterase 4 inhibitor and/or tumor necrosis factor-α production inhibitor.

Item 13. A method for treating or preventing phosphodiesterase 4-mediated and/or tumor necrosis factor-α-mediated diseases, the method comprising administering the compound or salt according to any one of items 1 to 6 to human or animal.

Item 14. A process for producing an oxazole compound represented by Formula (1):

(1)

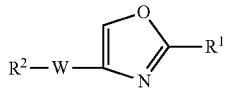

wherein $R^1$, $R^2$ and W are the same as defined in item 1, or a salt thereof, the process comprising a reaction of a compound represented by Formula (2):

(2)

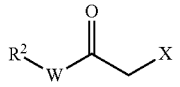

wherein $R^2$ and W are the same as defined above, and X is a halogen atom, or a salt thereof, with a compound represented by Formula (3):

(3)

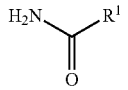

wherein $R^1$ is the same as defined above, or a salt thereof.

In Formula (1), $R^1$ is preferably a phenyl group. The phenyl group represented by $R^1$ preferably has 1 to 3, and more preferably 2, substituents selected from the group consisting of (1-2) unsubstituted or halogen-substituted lower alkoxy groups, (1-3) lower alkenyloxy groups, (1-4) lower alkynyloxy groups, and (1-5) cyclo $C_{3-8}$ alkyl lower alkoxy groups.

In Formula (1), $R^2$ is preferably a phenyl group or a pyridyl group. The phenyl group or pyridyl group represented by $R^2$ preferably has 1 to 3, and more preferably 1, substituents selected from the group consisting of (2-2) unsubstituted or halogen-substituted lower alkoxy groups, (2-3) unsubstituted or halogen-substituted lower alkyl groups, (2-4) lower alkenyloxy groups, and (2-5) halogen atoms.

In Formula (1), W is preferably a divalent group represented by Formula (i) $—Y^1\text{-}A^1\text{-}$. A is preferably a lower alkylene group; $Y^1$ is preferably —C(═O)— or —C(═O)—N($R^3$)—; and $R^3$ is preferably a hydrogen atom.

Among the oxazole compounds of the present invention, those represented by Formula (1A) and salts thereof are preferable, and those represented by Formula (1B) and salts thereof are more preferable.

Formula (1A):

(1A)

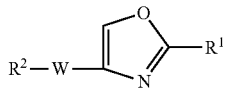

wherein $R^1$ is a phenyl group having two substituents selected from the following (1-2), (1-3), (1-4) and (1-5):

(1-2) unsubstituted or halogen-substituted lower alkoxy groups, (1-3) lower alkenyloxy groups, (1-4) lower alkynyloxy groups, and (1-5) cyclo $C_{3-8}$ alkyl lower alkoxy groups;

$R^2$ is a phenyl group or a pyridyl group each of which may have one or more substituents selected from the following (2-2), (2-3), (2-4) and (2-5):

(2-2) unsubstituted or halogen-substituted lower alkoxy groups, (2-3) unsubstituted or halogen-substituted lower alkyl groups, (2-4) lower alkenyloxy groups, and (2-5) halogen atoms; and W is a divalent group represented by Formula (i):

$$—Y^1\text{-}A^1\text{-} \qquad \text{Formula (i)}$$

wherein $A^1$ is a lower alkylene group, and $Y^1$ is —C(═O)— or —C(═O)—N($R^3$)— wherein $R^3$ is a hydrogen atom.

Formula (1B):

(1B)

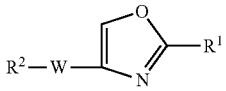

wherein $R^1$ is a phenyl group substituted on the phenyl ring with two lower alkoxy groups, a phenyl group substituted on the phenyl ring with one lower alkoxy group and one cyclo $C_{3-8}$ alkyl lower alkoxy group, a phenyl group substituted on the phenyl ring with one lower alkoxy group and one halogen-substituted lower alkoxy group, a phenyl group substituted on the phenyl group with one lower alkoxy group and one lower alkenyloxy group, a phenyl group substituted on the phenyl ring with one halogen-substituted lower alkoxy group and one cyclo $C_{3-8}$ alkyl lower alkoxy group, a phenyl group substituted on the phenyl ring with one halogen-substituted lower alkoxy group and one lower alkenyloxy group, or a phenyl group substituted on the phenyl ring with two halogen-substituted lower alkoxy groups;

$R^2$ is a lower alkoxyphenyl group, a lower alkenyloxyphenyl group, a halogen-substituted lower alkoxyphenyl group, a lower alkylpyridyl group, or a phenyl group substituted on the phenyl ring with one lower alkoxy group and one halogen atom; and W is a divalent group represented by Formula (i):

$$—Y^1\text{-}A^1\text{-} \qquad \text{Formula (i)}$$

wherein $A^1$ is a $C_{1-4}$ alkylene group, and $Y^1$ is —C(═O)— or —C(═O)—N($R^3$)— wherein $R^3$ is a hydrogen atom.

The present invention is described below in further detail.

Compound Represented by Formula (1)

In Formula (1), $R^1$ is an aryl group. The aryl group may have 1 to 3, and preferably 2, substituents selected from the group consisting of (1-1) hydroxy groups, (1-2) unsubstituted or halogen-substituted lower alkoxy groups, (1-3) lower alkenyloxy groups, (1-4) lower alkynyloxy groups, (1-5) cyclo $C_{3-8}$ alkyl lower alkoxy groups, (1-6) cyclo $C_{3-8}$ alkyloxy groups, (1-7) cyclo $C_{3-8}$ alkenyloxy groups, (1-8) dihydroindenyloxy groups, (1-9) hydroxy lower alkoxy groups, (1-10) oxiranyl lower alkoxy groups, and (1-11) protected hydroxy groups.

In Formula (1), $R^2$ is an aryl group or a nitrogen atom-containing heterocyclic group. The aryl group and heterocyclic group may have 1 to 3, and preferably 1, substituent selected from the group consisting of (2-1) hydroxy groups, (2-2) unsubstituted or halogen-substituted lower alkoxy groups, (2-3) unsubstituted or halogen-substituted lower alkyl groups, (2-4) lower alkenyloxy groups, (2-5) halogen atoms, (2-6) lower alkanoyl groups, (2-7) lower alkylthio groups, (2-8) lower alkylsulfonyl groups, (2-9) oxo groups, and (2-10) lower alkoxy lower alkoxy groups.

In Formula (1), W is a divalent group represented by Formula (i) or (ii):

$$—Y^1\text{-}A^1\text{-} \qquad \text{Formula (i)}$$

$$—Y^2—C(=O)— \qquad \text{Formula (ii)}$$

wherein $A^1$ is a lower alkenylene group, or a lower alkylene group which may have 1 to 3, and preferably 1, substituent selected from the group consisting of hydroxy groups and lower alkoxycarbonyl groups;

$Y^1$ is a direct bond, —C(=O)—, —C(=O)—N($R^3$)—, —N($R^4$)—C(=O)—, —S(O)$_m$—NH—, or —S(O)$_n$— wherein $R^3$ and $R^4$ are each independently a hydrogen atom or a lower alkyl group, and m and n are each independently an integer from 0 to 2; and $Y^2$ is a piperazinediyl group, or a divalent group represented by Formula (iii) or (iv):

$$—C(=O)\text{-}A^2\text{-}N(R^5)— \qquad \text{Formula (iii)}$$

$$\text{-}A^3\text{-}N(R^6)— \qquad \text{Formula (iv)}$$

wherein $A^2$ and $A^3$ are each independently a lower alkylene group, and $R^5$ and $R^6$ are each independently a hydrogen atom or a lower alkyl group.

Examples of aryl groups include phenyl, naphthyl, etc.

Examples of halogen atoms include fluorine, chlorine, bromine, iodine, etc.

Lower alkyl groups are straight- or branched-chain alkyl groups having 1 to 6 carbon atoms, and examples thereof include methyl, ethyl, n-propyl, isopropyl, n-butyl, isobutyl, tert-butyl, sec-butyl, 1-ethylpropyl, n-pentyl, neopentyl, n-hexyl, isohexyl, 3-methylpentyl, etc.

Unsubstituted or halogen-substituted lower alkyl groups are straight- or branched-chain alkyl groups having 1 to 6 carbon atoms as defined above, or such alkyl groups substituted with 1 to 7 halogen atoms. Examples thereof include methyl, ethyl, n-propyl, isopropyl, n-butyl, isobutyl, tert-butyl, sec-butyl, 1-ethylpropyl, n-pentyl, neopentyl, n-hexyl, isohexyl, 3-methyl pentyl, fluoromethyl, difluoromethyl, trifluoromethyl, chloromethyl, dichloromethyl, trichloromethyl, bromomethyl, dibromomethyl, dichlorofluoromethyl, 2-fluoroethyl, 2,2-difluoroethyl, 2,2,2-trifluoroethyl, pentafluoroethyl, 2-chloroethyl, 3,3,3-trifluoropropyl, heptafluoropropyl, heptafluoroisopropyl, 3-chloropropyl, 2-chloropropyl, 3-bromopropyl, 4,4,4-trifluorobutyl, 4,4,4,3,3-pentafluorobutyl, 4-chlorobutyl, 4-bromobutyl, 2-chlorobutyl, 5,5,5-trifluoropentyl, 5-chloropentyl, 6,6,6-trifluorohexyl, 6-chlorohexyl, etc.

Lower alkenyloxy groups are groups composed of an oxygen atom and a $C_{2-6}$ straight- or branched-chain alkenyl group having 1 to 3 double bonds. Lower alkenyloxy groups have cis and trans forms. More specific examples thereof include vinyloxy, 1-propenyloxy, 2-propenyloxy, 1-methyl-1-propenyloxy, 2-methyl-1-propenyloxy, 2-methyl-2-propenyloxy, 2-propenyloxy, 2-butenyloxy, 1-butenyloxy, 3-butenyloxy, 2-pentenyloxy, 1-pentenyloxy, 3-pentenyloxy, 4-pentenyloxy, 1,3-butadienyloxy, 1,3-pentadienyloxy, 2-penten-4-yloxy, 3-methyl-2-butenyloxy, 2-hexenyloxy, 1-hexenyloxy, 5-hexenyloxy, 3-hexenyloxy, 4-hexenyloxy, 3,3-dimethyl-1-propenyloxy, 2-ethyl-1-propenyloxy, 1,3,5-hexatrienyloxy, 1,3-hexadienyloxy, 1,4-hexadienyloxy, etc.

Examples of lower alkynyloxy groups include groups composed of an oxygen atom and a $C_{2-6}$ straight- or branched-chain alkynyl group having 1 to 3 triple bonds. More specific examples thereof include ethynyloxy, 2-propynyloxy, 2-butynyloxy, 3-butynyloxy, 1-methyl-2-propynyloxy, 2-pentynyloxy, 2-hexynyloxy, etc.

Examples of cyclo $C_{3-8}$ alkyl groups include cyclopropyl, cyclobutyl, cyclopentyl, cyclohexyl, cycloheptyl, cyclooctyl, etc.

Preferable examples of lower alkoxy groups include $C_{1-6}$ straight- or branched-chain alkoxy groups. Specifically, such groups include methoxy, ethoxy, n-propoxy, isopropoxy, n-butoxy, isobutoxy, tert-butoxy, sec-butoxy, 1-ethylpropoxy, n-pentoxy, neopentoxy, n-hexyloxy, isohexyloxy, 3-methylpentoxy, etc.

Examples of cyclo $C_{3-8}$ alkyl lower alkoxy groups include the above-mentioned lower alkoxy groups which have 1 to 3, and preferably 1, cyclo $C_{3-8}$ alkyl group as listed above. More specific examples thereof include cyclopropylmethoxy, cyclobutylmethoxy, cyclohexylmethoxy, 2-cyclopropylethoxy, 1-cyclobutylethoxy, cyclopentylmethoxy, 3-cyclopentylpropoxy, 4-cyclohexylbutoxy, 5-cycloheptylpentoxy, 6-cyclooctylhexyloxy, 1,1-dimethyl-2-cyclohexylethoxy, 2-methyl-3-cyclopropylpropoxy, etc.

Examples of cyclo $C_{3-8}$ alkyloxy groups include cyclopropyloxy, cyclobutyloxy, cyclopentyloxy, cyclohexyloxy, cycloheptyloxy, cyclooctyloxy, etc.

Examples of cyclo $C_{3-8}$ alkenyloxy groups include cyclopropenyloxy, cyclobutenyloxy, cyclopentenyloxy, cyclohexenyloxy, cycloheptenyloxy, cyclooctenyloxy, etc.

Examples of dihydroindenyloxy groups include 2,3-dihydroinden-1-yloxy, 2,3-dihydroinden-2-yloxy, etc.

Examples of hydroxy lower alkoxy groups include lower alkoxy groups (preferably $C_{1-6}$ straight- or branched-chain alkoxy groups) having 1 to 5, and preferably 1 to 3, hydroxy groups. More specific examples thereof include hydroxymethyloxy, 2-hydroxyethyloxy, 1-hydroxyethyloxy, 3-hydroxypropyloxy, 2,3-dihydroxypropyloxy, 4-hydroxybutyloxy, 3,4-dihydroxybutyloxy, 1,1-dimethyl-2-hydroxyethyloxy, 5-hydroxypentyloxy, 6-hydroxyhexyloxy, 3,3-dimethyl-3-hydroxypropyloxy, 2-methyl-3-hydroxypropyloxy, 2,3,4-trihydroxybutyloxy, perhydroxyhexyloxy, etc.

Examples of oxiranyl lower alkoxy groups include $C_{1-6}$ straight- or branched-chain alkoxy groups having 1 or 2 oxyranyl groups such as, for example, oxiranylmethoxy, 2-oxiranylethoxy, 1-oxiranylethoxy, 3-oxiranylpropoxy, 4-oxiranylbutoxy, 5-oxiranylpentyloxy, 6-oxiranylhexyloxy, 1,1-dimethyl-2-oxiranylethoxy, 2-methyl-3-oxiranylpropoxy, etc.

Examples of protecting groups of protected hydroxy groups include lower alkanoyl and other acyl groups; phenyl (lower)alkyl groups which may have one or more suitable substituents (e.g., benzyl, phenethyl, 3-phenylpropyl, 4-methoxybenzyl, trityl, etc.); trisubstituted silyl groups [e.g., tri(lower)alkylsilyl groups (e.g., trimethylsilyl, t-butyldimethylsilyl, etc.) and the like]; tetrahydropyranyl; etc.

Examples of nitrogen atom-containing heterocyclic groups include pyrrolidinyl, imidazolidinyl, piperidyl, hexahydropyrimidinyl, piperazinyl, octahydroisoindolyl, azepanyl, azocanyl, pyrrolyl, dihydropyrrolyl, imidazolyl, dihydroimidazolyl, triazolyl, dihydrotriazolyl, pyrazolyl, pyridyl and N-oxides thereof, dihydropyridyl, pyrimidinyl, dihydropyrimidinyl, pyrazinyl, dihydropyrazinyl, pyridazinyl, tetrazolyl, indolyl, isoindolyl, indolinyl, isoindolinyl, hexahydroisoindolinyl, benzoimidazolyl, quinolyl, isoquinolyl, indazolyl, quinazolinyl, dihydroquinazolinyl, benzotriazolyl, carbazolyl, oxazolyl, isooxazolyl, oxadiazolyl, oxazolidinyl, isooxazolidinyl, morpholinylbenzoxazolyl, dihydrobenzoxazolyl, benzoxazinyl, dihydrobenzoxazinyl, benzoxazolyl, benzooxadiazolyl, thiazolyl, dihydrothiazolyl, isothiazolyl, thiadiazolyl, dihydrothiazinyl, thiazolyzinyl, benzothiazolyl, benzothiadiazolyl, etc.

Unsubstituted or halogen-substituted lower alkoxy groups are straight- or branched-chain alkoxy groups having 1 to 6 carbon atoms, or such alkoxy groups substituted with 1 to 7 halogen atoms. Examples thereof include methoxy, ethoxy, n-propoxy, isopropoxy, n-butoxy, isobutoxy, tert-butoxy, sec-butoxy, 1-ethylpropoxy, n-pentoxy, neopentoxy, n-hexyloxy, isohexyloxy, 3-methylpentoxy, fluoromethoxy, difluoromethoxy, trifluoromethoxy, chloromethoxy, dichloromethoxy, trichloromethoxy, bromomethoxy, dibromomethoxy, dichlorofluoromethoxy, 2-fluoroethoxy, 2,2-difluoroethoxy, 2,2,2-trifluoroethoxy, pentafluoroethoxy, 2-chloroethoxy, 3,3,3-trifluoropropoxy, heptafluoropropoxy, heptafluoroisopropoxy, 3-chloropropoxy, 2-chloropropoxy, 3-bromopropoxy, 4,4,4-trifluorobutoxy, 4,4,4,3,3-pentafluorobutoxy, 4-chlorobutoxy, 4-bromobutoxy, 2-chlorobutoxy, 5,5,5-trifluoropentoxy, 5-chloropentoxy, 6,6,6-trifluorohexyloxy, 6-chlorohexyloxy, etc.

Examples of lower alkanoyl groups include formyl, acetyl, propionyl, butyryl, isobutyryl, pentanoyl, tert-butylcarbonyl, hexanoyl, and other $C_{1-6}$ straight- or branched-chain alkanoyl groups.

Examples of lower alkylthio groups include methylthio, ethylthio, n-propylthio, isopropylthio, n-butylthio, tert-butylthio, n-pentylthio, n-hexylthio, and other $C_{1-6}$ straight- or branched-chain alkylthio groups.

Preferable examples of lower alkylsulfonyl groups include $C_{1-6}$ straight- or branched-chain alkylsulfonyl groups. More specific examples thereof include methylsulfonyl, ethylsulfonyl, n-propylsulfonyl, isopropylsulfonyl, n-butylsulfonyl, isobutylsulfonyl, tert-butylsulfonyl, sec-butylsulfonyl, n-pentylsulfonyl, isopentylsulfonyl, neopentylsulfonyl, n-hexylsulfonyl, isohexylsulfonyl, 3-methylpentylsulfonyl, etc.

Lower alkenylene groups include, for example, vinylidene, propylene, butenylene, and other $C_{2-6}$ straight- or branched-chain alkenylene groups having 1 to 3 double bonds.

Preferable examples of lower alkoxycarbonyl groups include groups composed of a $C_{1-6}$ straight- or branched-chain alkoxy group and a carbonyl group. Specific examples thereof include methoxycarbonyl, ethoxycarbonyl, n-propoxycarbonyl, isopropoxycarbonyl, n-butoxycarbonyl, isobutoxycarbonyl, tert-butoxycarbonyl, sec-butoxycarbonyl, n-pentoxycarbonyl, neopentoxycarbonyl, n-hexyloxycarbonyl, isohexyloxycarbonyl, 3-methylpentoxycarbonyl, etc.

Lower alkylene groups include, for example, ethylene, trimethylene, 2-methyltrimethylene, 2,2-dimethyltrimethylene, 1-methyltrimethylene, methylmethylene, ethylmethylene, tetramethylene, pentamethylene, hexamethylene, and other $C_{1-6}$ straight- or branched-chain alkylene groups.

Examples of lower alkoxy lower alkoxy groups include alkoxyalkoxy groups in which the two alkoxy moieties are each independently a $C_{1-6}$ straight- or branched-chain alkoxy group. Specific examples thereof include methoxymethoxy, 2-methoxyethoxy, 3-methoxypropoxy, 4-methoxybutoxy, 5-methoxypentoxy, 6-methoxyhexyloxy, ethoxymethoxy, 2-ethoxyethoxy, n-propoxymethoxy, isopropoxymethoxy, n-butoxymethoxy, etc.

Examples of $C_{1-4}$ alkylene groups include ethylene, trimethylene, 2-methyltrimethylene, 2,2-dimethyltrimethylene, 1-methyltrimethylene, methylmethylene, ethylmethylene, tetramethylene, and other $C_{1-4}$ straight- or branched-chain alkylene groups.

Production Process for Compound Represented by Formula (1)

The oxazole compound represented by Formula (1) can be produced by various processes, one example of which is shown in Reaction Scheme 1.

Reaction Scheme 1

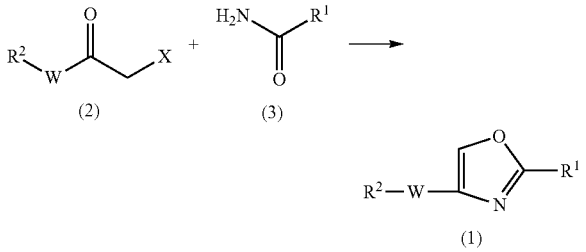

wherein $R^1$, $R^2$ and W are as defined in Formula (1), and X is a halogen atom.

Compound (1) is produced by reacting Compound (2) with Compound (3).

The reaction of Compound (2) with Compound (3) is usually performed in a suitable solvent. A wide variety of known solvents can be used as long as they do not inhibit the reaction. Examples of such solvents include dimethylformamide, dimethylsulfoxide, acetonitrile, and other aprotic polar solvents; acetone, methyl ethyl ketone, and other ketone solvents; benzene, toluene, xylene, tetralin, liquid paraffin, and other hydrocarbon solvents; methanol, ethanol, isopropanol, n-butanol, tert-butanol, and other alcohol solvents; tetrahydrofuran, dioxane, dipropyl ether, diethyl ether, dimethoxyethane, diglyme, and other ether solvents; ethyl acetate, methyl acetate, and other ester solvents; mixtures thereof; etc. Such solvents may contain water.

The proportion of Compound (3) to Compound (2) is usually 0.5 to 5 mol, and preferably 0.5 to 3 mol, per mol of Compound (2).

The reaction of Compound (2) with Compound (3) is usually performed by continuing stirring at −20 to 200° C., and preferably at 0 to 150° C., for 30 minutes to 60 hours, and preferably 1 to 30 hours.

Compound (3) used as a starting material is an easily available known compound. Compound (2) encompasses novel compounds, and a production process for such a compound is described hereinafter (Reaction Scheme 9).

Among the oxazole compounds represented by Formula (1), those in which W is a divalent group represented by —$Y^1$-$A^1$- wherein $Y^1$ is —C(═O)—N($R^3$)— (hereinafter referred to as "Compound (1a)") can be produced by, for example, the process shown in Reaction Scheme 2.

Reaction Scheme 2

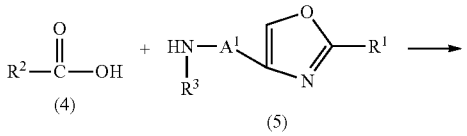

-continued

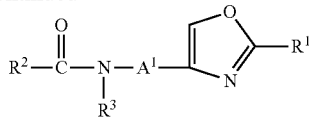

(1a)

wherein $R^1$, $R^2$, $R^3$ and $A^1$ are as defined in Formula (1).

Compound (1a) is produced by reacting Compound (4) or a reactive derivative thereof at the carboxy group, with Compound (5) or a reactive derivative thereof at the amino or imino group.

Preferable examples of reactive derivatives of Compound (4) include acid halides, acid anhydrides, activated amides, activated esters, etc. Preferable examples of reactive derivatives include acid chlorides; acid azides; dialkylphosphoric acids, phenylphosphoric acid, diphenylphosphoric acid, dibenzylphosphoric acid, phosphoric acid halides, and other substituted phosphoric acids, dialkylphosphorous acid, sulfurous acid, thiosulfuric acid, sulfuric acid, methanesulfonic acid, and other sulfonic acids, acetic acid, propionic acid, butyric acid, isobutyric acid, pivalic acid, pentanoic acid, isopentanoic acid, 2-ethylbutyric acid, trichloroacetic acid, and other aliphatic carboxylic acids, and mixed acid anhydrides with acids such as benzoic acid or other aromatic acids; symmetrical acid anhydrides; activated amides with imidazole, 4-substituted imidazole, dimethylpyrazole, triazole or tetrazole; cyanomethyl ester, methoxymethyl ester, dimethyliminomethyl ester, vinyl ester, propargyl ester, p-nitrophenyl ester, 2,4-dinitrophenyl ester, trichlorophenyl ester, pentachlorophenyl ester, mesylphenyl ester, and other activated esters, esters with N,N-dimethylhydroxylamine, 1-hydroxy-2-(1H)-pyridone, N-hydroxysuccinimide, N-hydroxyphthalimide, 1-hydroxy-1H-benzotriazol, and other N-hydroxy compounds; etc. Such reactive derivatives can be selected as desired, according to the type of Compound (4) used.

When using Compound (4) in the form of a free acid or a salt thereof in the above reaction, it is preferable to perform the reaction in the presence of condensing agent(s). A wide variety of condensing agents known in this field can be used, including, for example, N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide and hydrochlorides thereof; N,N'-carbonylbis(2-methylimidazole); pentamethyleneketene-N-cyclohexylimine; diphenylketene-N-cyclohexylimine; ethoxyacetylene, 1-alkoxy-1-chloroethylene; trialkyl phosphite; ethyl polyphosphate; isopropyl polyphosphate; phosphorus oxychloride (phosphoryl chloride); phosphorus trichloride; phosphoryl diphenyl azide; thionyl chloride; oxalyl chloride; ethyl chloroformate, isopropyl chloroformate, and other lower alkyl haloformates; triphenylphosphine; 2-ethyl-7-hydroxybenzisooxazolium salt; 2-ethyl-5-(m-sulfophenyl)isooxazolium hydroxide inner salts; hexafluorophosphoric acid benzotriazol-1-yloxy-tris(dimethylamino)phosphonium; 1-(p-chlorobenzene-sulfonyloxy)-6-chloro-1H-benzotriazol;

so-called Vilsmeier reagents prepared by reacting N,N-dimethylformamide with thionyl chloride, phosgene, trichloromethyl chloroformate, phosphorus oxychloride, etc.; and the like. It is more preferable to perform the reaction in the presence of such condensing agent(s) and active esterifying agent(s) such as N-hydroxysuccinimide, N-hydroxyphthalimide, 1-hydroxy-1H-benzotriazol, or the like.

Preferable examples of reactive derivatives of Compound (5) include Schiff base imino- or enamine-type tautomers produced by reacting Compound (5) with carbonyl compounds such as aldehydes, ketones, etc.; silyl derivatives produced by reacting Compound (5) with silyl compounds such as bis(trimethylsilyl)acetamide, mono(trimethylsilyl) acetamide, bis(trimethylsilyl)urea, etc.; derivatives produced by reacting Compound (5) with phosphorus trichloride, phosgene, etc.; and the like.

The reaction is usually carried out in a known solvent that does not adversely affect the reaction. Such solvents include, for example, water; methanol, ethanol, isopropanol, n-butanol, trifluoroethanol, ethylene glycol, and other alcohol solvents; acetone, methyl ethyl ketone, and other ketone solvents; tetrahydrofuran, dioxane, diethyl ether, diisopropyl ether, diglyme, and other ether solvents; methyl acetate, ethyl acetate, and other ester solvents; acetonitrile, N,N-dimethylformamide, dimethyl sulfoxide, and other aprotic polar solvents; n-pentane, n-hexane, n-heptane, cyclohexane, and other hydrocarbon solvents; methylene chloride, ethylene chloride, and other halogenated hydrocarbon solvents; other organic solvents; and mixed solvents thereof.

The reaction may be performed in the presence of base(s). A wide variety of known inorganic and organic bases are usable. Inorganic bases include, for example, alkali metals (e.g., sodium, potassium, etc.), alkali metal hydrogencarbonates (e.g., lithium hydrogencarbonate, sodium hydrogencarbonate, potassium hydrogencarbonate etc.), alkali metal hydroxides (e.g., lithium hydroxide, sodium hydroxide, potassium hydroxide, cesium hydroxide, etc.), alkali metal carbonates (e.g., lithium carbonate, sodium carbonate, potassium carbonate, cesium carbonate, etc.), alkali metal lower alkoxides (e.g., sodium methoxide, sodium ethoxide, etc.), and alkali metal hydrides (e.g., sodium hydride, potassium hydride, etc.). Organic bases include, for example, trialkylamines [e.g., trimethylamine, triethylamine, N-ethyldiisopropylamine, etc.], pyridine, quinoline, piperidine, imidazole, picoline, dimethylaminopyridine, dimethylaniline, N-methylmorpholine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), etc. When such bases are liquid, they can also be used as solvents.

Such bases can be used singly or in combination.

The amount of base(s) is usually 0.1 to 10 moles, and preferably 0.1 to 3 moles, per mole of Compound (4).

The proportion of Compound (4) to Compound (5) in Reaction Scheme 1 is usually at least 1, and preferably about 1 to about 5 mol of the former per mol of the latter.

The reaction temperature is not limited, and the reaction can usually be performed with cooling, at room temperature, or with heating. It is suitable to perform the reaction in a temperature range from room temperature to 100° C., for 30 minutes to 30 hours, and preferably for 30 minutes to 5 hours.

In the above reaction, Compound (4) for use as a starting material is an easily available known compound. Compound (5) encompasses novel compounds. A production process for Compound (5) is described hereinafter (Reaction Scheme 10).

Among the oxazole compounds represented by Formula (1), those in which W is a divalent group represented by —$Y^1$-$A^1$- wherein $Y^1$ is —C(=O)— and $A^1$ is a lower alkylene group having one lower alkoxycarbonyl group (hereinafter referred to as "Compound (1b)") can be produced, for example, by the process shown in Reaction Scheme 3.

Reaction Scheme 3

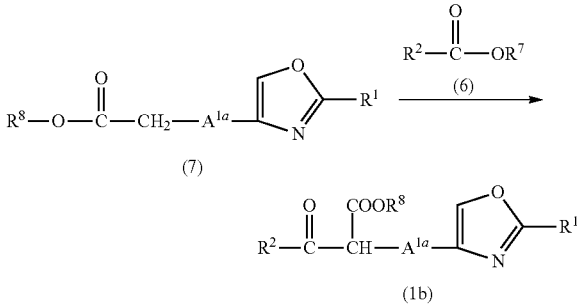

wherein $R^1$ and $R^2$ are as defined in Formula (1), $R^7$ and $R^8$ are each independently a lower alkyl group, and $A^{1a}$ is a $C_{1-5}$ alkylene group.

The —$COOR^8$ group in Formula (1b) is the same as the lower alkoxycarbonyl group defined as a substituent of $A^1$ in Formula (1). The lower alkyl group represented by $R^7$ may be the same as the lower alkyl group as defined above.

Examples of the $C_{1-5}$ alkylene group represented by $A^{1a}$ include ethylene, trimethylene, 2-methyltrimethylene, 2,2-dimethyltrimethylene, 1-methyltrimethylene, methylmethylene, ethylmethylene, tetramethylene, pentamethylene, and other $C_{1-5}$ straight- or branched-chain alkylene groups.

Compound (1b) is produced by reacting Compound (6) with Compound (7).

The reaction is usually performed in a known solvent that does not adversely affect the reaction. Such solvents include, for example, water; methanol, ethanol, isopropanol, n-butanol, trifluoroethanol, ethylene glycol, and other alcohol solvents; acetone, methyl ethyl ketone, and other ketone solvents; tetrahydrofuran, dioxane, diethyl ether, dimethoxyethane, diglyme, and other ether solvents; methyl acetate, ethyl acetate, and other ester solvents; acetonitrile, N,N-dimethylformamide, dimethyl sulfoxide, N-methylpyrrolidone, and other aprotic polar solvents; methylene chloride, ethylene chloride, and other halogenated hydrocarbon solvents; other organic solvents; and mixed solvents thereof.

The reaction can usually be performed in the presence of suitable base(s). A wide variety of known inorganic and organic bases are usable. Inorganic bases include, for example, alkali metals (e.g., lithium, sodium, potassium, etc.), alkali metal hydrogencarbonates (e.g., lithium hydrogencarbonate, sodium hydrogencarbonate, potassium hydrogencarbonate, etc.), alkali metal hydroxides (e.g., lithium hydroxide, sodium hydroxide, potassium hydroxide, cesium hydroxide, etc.), alkali metal carbonates (e.g., lithium carbonate, sodium carbonate, potassium carbonate, cesium carbonate, etc.), alkali metal lower alkoxides (e.g., sodium methoxide, sodium ethoxide, potassium tert-butoxide, sodium tert-butoxide, sodium tert-pentoxide, etc.), alkali metal hydrides (e.g., sodium hydride, potassium hydride, etc.), and the like. Organic bases include, for example, trialkylamines (e.g., trimethylamine, triethylamine, N-ethyldiisopropylamine, etc.), pyridine, quinoline, piperidine, imidazole, picoline, dimethylaminopyridine, dimethylaniline, N-methylmorpholine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), etc. When such bases are liquid, they can also be used as solvents. Such bases can be used singly or in combination.

The amount of base(s) is usually 0.5 to 10 mol, and preferably 0.5 to 6 mol, per mol of Compound (6).

The proportion of Compound (6) to Compound (7) is usually at least 1 mol, and preferably about 1 to about 5 mol of the former, per mol of the latter.

The reaction temperature is not limited, and the reaction can usually be performed with cooling, at room temperature, or with heating. It is suitable to perform the reaction in a temperature range from room temperature to 150° C., for 30 minutes to 60 hours, and preferably 1 to 30 minutes.

Compound (6) used as a starting material in the above reaction is an easily available known compound. Compound (7) encompasses novel compounds. A production process for Compound (7) is described hereinafter (Reaction Scheme 11).

Among the oxazole compounds represented by Formula (1), those in which W is a divalent group represented by —$Y^1$-$A^1$- wherein $A^1$ is a lower alkylene group (hereinafter referred to as "Compound (1d)") are produced from the corresponding compounds in which $A^l$ is a lower alkylene group having lower alkoxycarbonyl group(s) (hereinafter referred to as "Compound (1c)"), by the process shown in Reaction Scheme 4.

Reaction Scheme 4

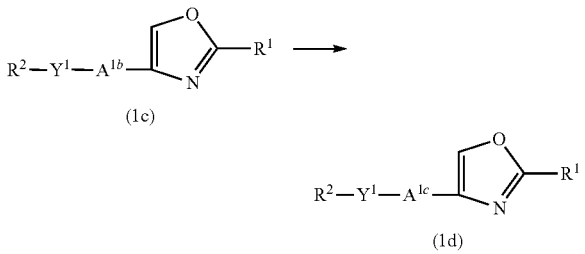

wherein $R^1$, $R^2$ and $Y^1$ are as defined in Formula (1), $A^{1b}$ is a lower alkylene group having lower alkoxycarbonyl group(s), and $A^{1c}$ is a lower alkylene group.

Compound (1d) is produced by subjecting Compound (1c) to hydrolysis-decarboxylation.

The reaction is usually performed in a known solvent that does not adversely affect the reaction. Such solvents include, for example, water; methanol, ethanol, isopropanol, n-butanol, trifluoroethanol, ethylene glycol, and other alcohol solvents; acetone, methyl ethyl ketone, and other ketone solvents; tetrahydrofuran, dioxane, diethyl ether, dimethoxyethane, diglyme, and other ether solvents; methyl acetate, ethyl acetate, and other ester solvents; acetonitrile, N,N-dimethylformamide, dimethyl sulfoxide, N-methylpyrrolidone, and other aprotic polar solvents; methylene chloride, ethylene chloride, and other halogenated hydrocarbon solvents; other organic solvents; and mixed solvents thereof.

The hydrolysis-decarboxylation of Compound (1c) is usually performed under acidic conditions. For example, an acid is added to a suspension or solution of Compound (1c) in a suitable solvent, and the resulting mixture is stirred at 0 to 120° C. to carry out the hydrolysis-decarboxylation.

Examples of usable acids include trifluoroacetic acid, acetic acid, and other organic acids, hydrochloric acid, bromic acid, hydrobromic acid, sulfuric acid, and other inorganic acids, etc. Among such organic acids, organic acids can also be used as reaction solvents.

The amount of acid(s) is usually 0.5 to 30 mol, and preferably 0.5 to 10 mol, per mol of Compound (1c).

The reaction temperature is usually 0 to 120° C., and preferably room temperature to 110° C. The reaction time is usually 30 minutes to 24 hours, preferably 30 minutes to 12 hours, and more preferably 1 to 8 hours.

Among the oxazole compounds represented by Formula (1), those in which $R^1$ is a phenyl group substituted on the phenyl ring with hydroxy group(s) (hereinafter referred to as "Compound (1f)") are produced from the corresponding compounds in which $R^1$ is a phenyl group substituted on the phenyl ring with protected hydroxy group(s) (hereinafter referred to as "Compound (1e)"), by the process shown in Reaction Scheme 5.

Reaction Scheme 5

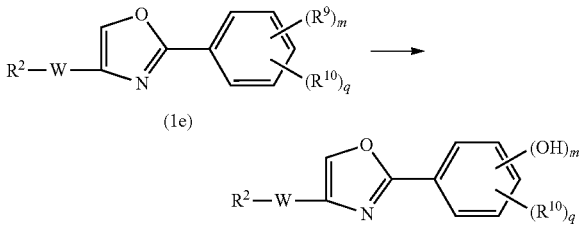

wherein $R^2$ and W are as defined in Formula (1); $R^9$ is a protected hydroxy group; $R^{10}$ is the same group as the substituent (1-2), (1-3), (1-4), (1-5), (1-6), (1-7), (1-8), (1-9) or (1-10) of the aryl group represented by $R^1$ in Formula (1); m is 1 to 5; q is 0 to 4; m $R^9$s may be the same or different; and q $R^{10}$s may be the same or different; with the proviso that $m+q \leq 5$.

Compound (1f) can be produced by subjecting Compound (1e) to an elimination reaction of the hydroxy protecting group(s).

The elimination reaction can be carried out by hydrolysis, hydrogenolysis, or other conventional methods.

The reaction is usually performed in a known solvent that does not adversely affect the reaction. Such solvents include, for example, water; methanol, ethanol, isopropanol, n-butanol, trifluoroethanol, ethylene glycol, and other alcohol solvents; acetone, methyl ethyl ketone, and other ketone solvents; tetrahydrofuran, dioxane, diethyl ether, dimethoxyethane, diglyme, and other ether solvents; methyl acetate, ethyl acetate, and other ester solvents; acetonitrile, N,N-dimethylformamide, dimethyl sulfoxide, N-methylpyrrolidone, and other aprotic polar solvents; methylene chloride, ethylene chloride, and other halogenated hydrocarbon solvents; and other organic solvents.

(i) Hydrolysis:

Hydrolysis is preferably carried out in the presence of base(s) or acid(s) (including Lewis acids).

A wide variety of known inorganic and organic bases are usable. Preferable examples of inorganic bases include alkali metals (e.g., sodium, potassium, etc.), alkaline earth metals (e.g., magnesium, calcium, etc.), hydroxides, carbonates and hydrogencarbonates thereof, etc. Preferable examples of organic bases include trialkylamines (e.g., trimethylamine, triethylamine, etc.), picoline, 1,5-diazabicyclo[4,3,0]non-5-ene, etc.

A wide variety of known organic and inorganic acids are usable. Preferable organic acids include, for example, formic acid, acetic acid, propionic acid, and other fatty acids; trichloroacetic acid, trifluoroacetic acid, and other trihaloacetic acids; and the like. Preferable inorganic acids include, for example, hydrochloric acid, hydrobromic acid, sulfuric acid, hydrogen chloride, hydrogen bromide, etc. Examples of Lewis acids include boron trifluoride ether complexes, boron tribromide, aluminium chloride, ferric chloride, etc.

When using a trihaloacetic acid or Lewis acid, it is preferable to carry out hydrolysis in the presence of a cation scavenger (e.g., anisole, phenol, etc.).

The amount of base(s) or acid(s) is not limited as long as it is an amount necessary for hydrolysis.

The reaction temperature is usually 0 to 120° C., preferably room temperature to 100° C., and more preferably room temperature to 80° C. The reaction time is usually 30 minutes to 24 hours, preferably 30 minutes to 12 hours, and more preferably 1 to 8 hours.

(ii) Hydrogenolysis:

Hydrogenolysis can be carried out by a wide variety of known methods including, for example, chemical reduction, catalytic reduction, etc.

Examples of suitable reducing agents for chemical reduction include hydrides (e.g., hydrogen iodide, hydrogen sulfide, lithium aluminium hydride, sodium borohydride, sodium cyanoborohydride, etc.); and combinations of metals (e.g., tin, zinc, iron, etc.) or metallic compounds (e.g., chromium chloride, chromium acetate, etc.), with organic or inorganic acids (e.g., formic acid, acetic acid, propionic acid, trifluoroacetic acid, p-toluenesulfonic acid, hydrochloric acid, hydrobromic acid, etc.).

Examples of suitable catalysts for catalytic reduction include platinum catalysts (e.g., platinum plates, spongy platinum, platinum black, colloidal platinum, platinum oxide, platinum wires, etc.), palladium catalysts (e.g., spongy palladium, palladium black, palladium oxide, palladium carbon, palladium/barium sulfate, palladium/barium carbonate, etc.), nickel catalysts (e.g., reduced nickel, nickel oxide, Raney nickel, etc.), cobalt catalysts (e.g., reduced cobalt, Raney cobalt, etc.), iron catalysts (e.g., reduced iron and the like), etc.

When such acids used for chemical reduction are liquid, they can also be used as solvents.

The amounts of reducing agent for chemical reduction and catalyst for catalytic reduction are not limited and may be conventional amounts.

The reaction temperature is usually 0 to 120° C., preferably room temperature to 100° C., and more preferably room temperature to 80° C. The reaction time is usually 30 minutes to 24 hours, preferably 30 minutes to 10 hours, and more preferably 30 minutes to 4 hours.

Among the oxazole compounds represented by Formula (1), those in which $R^1$ is a phenyl group substituted on the phenyl ring with $R^{11}O$— group(s) (hereinafter referred to as "Compound (1 g)") are produced from Compound (1f), by the process shown in Reaction Scheme 6.

Reaction Scheme 6

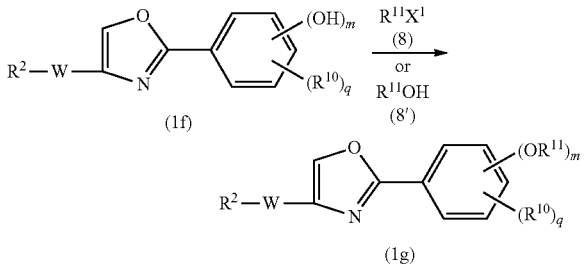

wherein $R^2$ and W are as defined in Formula (1); $R^{10}$, m and q are as defined above; $X^1$ is a halogen atom or a group that undergoes the same substitution reaction as that of a halogen atom; $R^{11}O$ is the same group as the substituent (1-2), (1-3), (1-4), (1-5), (1-6), (1-7), (1-8), (1-9) or (1-10) of the aryl group represented by $R^1$ in Formula (1); and m $R^{11}$Os may be the same or different.

In Compound (8), the halogen atom represented by $X^1$ is a fluorine atom, chlorine atom, bromine atom, or iodine atom.

Examples of the group that undergoes the same substitution reaction as that of a halogen atom, the group being represented by $X^1$, include lower alkanesulfonyloxy groups, arylsulfonyloxy groups, aralkylsulfonyloxy groups, etc.

Specific examples of lower alkanesulfonyloxy groups include methanesulfonyloxy, ethanesulfonyloxy, isopropanesulfonyloxy, n-propanesulfonyloxy, n-butanesulfonyloxy, tert-butanesulfonyloxy, n-pentanesulfonyloxy, n-hexanesulfonyloxy, and other $C_{1-6}$ straight- or branched-chain alkanesulfonyloxy groups, and the like.

Arylsulfonyloxy groups include, for example, phenylsulfonyloxy, naphthylsulfonyloxy, etc. The phenyl ring of such arylsulfonyloxy groups may have, for example, 1 to 3 substituents selected from the group consisting of $C_{1-6}$ straight- or branched-chain alkyl groups, $C_{1-6}$ straight- or branched-chain alkoxy groups, nitro groups, and halogen atoms. Specific examples of such arylsulfonyloxy groups include phenylsulfonyloxy, 4-methylphenylsulfonyloxy, 2-methylphenylsulfonyloxy, 4-nitrophenylsulfonyloxy, 4-methoxyphenylsulfonyloxy, 2-nitrophenylsulfonyloxy, 3-chlorophenylsulfonyloxy, etc. Specific examples of naphthylsulfonyloxy groups include α-naphthylsulfonyloxy, β-naphthylsulfonyloxy, etc.

Aralkylsulfonyloxy groups include, for example, phenyl-substituted $C_{1-6}$ straight- or branched-chain alkylsulfonyloxy groups which may have, on the phenyl ring, 1 to 3 substituents selected from the group consisting of $C_{1-6}$ straight- or branched-chain alkyl groups, $C_{1-6}$ straight- or branched-chain alkoxy groups, nitro groups, and halogen atoms; naphthyl-substituted $C_{1-6}$ straight- or branched-chain alkylsulfonyloxy groups; etc. Specific examples of phenyl-substituted alkylsulfonyloxy groups as mentioned above include benzylsulfonyloxy, 2-phenylethylsulfonyloxy, 4-phenylbutylsulfonyloxy, 2-methylbenzylsulfonyloxy, 4-methoxybenzylsulfonyloxy, 4-nitrobenzylsulfonyloxy, 3-chlorobenzylsulfonyloxy, etc. Specific examples of naphthyl-substituted alkylsulfonyloxy groups as mentioned above include α-naphthylmethylsulfonyloxy, β-naphthylmethylsulfonyloxy, etc.

Compound (1 g) is produced by reacting Compound (1f) with Compound (8), or by reacting Compound (1f) with Compound (8').

The reaction of Compound (1f) with Compound (8) is described below.

The reaction of Compound (1f) with Compound (8) is usually performed in a known solvent that does adversely affect the reaction. Such solvents include, for example, water; methanol, ethanol, isopropanol, n-butanol, trifluoroethanol, ethylene glycol, and other alcohol solvents; acetone, methyl ethyl ketone, and other ketone solvents; tetrahydrofuran, dioxane, diethyl ether, diglyme, and other ether solvents; methyl acetate, ethyl acetate, and other ester solvents; acetonitrile, N,N-dimethylformamide, dimethyl sulfoxide, and other aprotic polar solvents; methylene chloride, ethylene chloride, and other halogenated hydrocarbon solvents; other organic solvents; mixed solvents thereof; etc.

The reaction of Compound (1f) with Compound (8) is usually carried out in the presence of base(s). Usable bases include known inorganic and organic bases. Inorganic bases include, for example, alkali metals (e.g., sodium, potassium, etc.), alkali metal hydrogencarbonates (e.g., lithium hydrogencarbonate, sodium hydrogencarbonate, potassium hydrogencarbonate, etc.), alkali metal hydroxides (e.g., lithium hydroxide, sodium hydroxide, potassium hydroxide, cesium hydroxide, etc.), alkali metal carbonates (e.g., lithium carbonate, sodium carbonate, potassium carbonate, cesium carbonate, etc.), alkali metal lower alkoxides (e.g., sodium methoxide, sodium ethoxide, etc.), alkali metal hydrides (e.g., sodium hydride, potassium hydride, etc.), and the like. Organic bases include, for example, trialkylamines (e.g., trimethylamine, triethylamine, N-ethyldiisopropylamine, etc.), pyridine, quinoline, piperidine, imidazole, picoline, dimethylaminopyridine, dimethylaniline, N-methylmorpholine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), etc. When such bases are liquid, they can also be used as solvents. Such bases can be used singly or in combination.

The amount of base(s) is usually 0.5 to 10 mol, and preferably 0.5 to 6 mol, per mol of Compound (1f).

When performing the above reaction, alkali metals such as potassium iodide, sodium iodide, etc. can be added as reaction accelerators to the reaction system, as required.

The proportion of Compound (1f) to Compound (8) is usually at least 1 mol, and preferably about 1 to about 5 mol of the latter, per mol of the former.

The reaction temperature is not limited, and the reaction can usually be performed with cooling, at room temperature, or with heating. It is suitable to perform the reaction at about room temperature for 1 to 30 hours.

Next, the reaction of Compound (1f) with Compound (8') is described.

The reaction of Compound (1f) with Compound (8') is usually performed in a known solvent that does not adversely affect the reaction. Such solvents include, for example, water; methanol, ethanol, isopropanol, n-butanol, trifluoroethanol, ethylene glycol, and other alcohol solvents; acetone, methyl ethyl ketone, and other ketone solvents; tetrahydrofuran, dioxane, diethyl ether, diglyme, and other ether solvents; methyl acetate, ethyl acetate, and other ester solvents; acetonitrile, N,N-dimethylformamide, dimethyl sulfoxide, and other aprotic polar solvents; benzene, toluene, xylene, and other aromatic hydrocarbon solvents; methylene chloride, ethylene chloride, and other halogenated hydrocarbon solvents; other organic solvents; mixed solvents thereof; etc.

The reaction is usually performed in the presence of dialkyl azodicarboxylate(s) such as diisopropyl azodicarboxylate, diethyl azodicarboxylate, etc., and phosphine ligand(s) such as triphenyl phosphine, tri(n-butyl)phosphine, etc. The amount of dialkyl azodicarboxylate(s) is usually 0.5 to 10 mol, and preferably 0.5 to 6 mol, per mole of Compound (1f). The amount of phosphine ligand(s) is usually 0.5 to 10 mol, and preferably 0.5 to 6 mol, per mole of Compound (1f).

The reaction of Compound (1f) with Compound (8') can be carried out in the presence of suitable base(s). A wide variety of known inorganic and organic bases are usable. Inorganic bases include, for example, alkali metals (e.g., sodium, potassium, etc.), alkali metal hydrogencarbonates (e.g., lithium hydrogencarbonate, sodium hydrogencarbonate, potassium hydrogencarbonate, etc.), alkali metal hydroxides (e.g., lithium hydroxide, sodium hydroxide, potassium hydroxide, cesium hydroxide, etc.), alkali metal carbonates (e.g., lithium carbonate, sodium carbonate, potassium carbonate, cesium carbonate, etc.), alkali metal lower alkoxides (e.g., sodium methoxide, sodium ethoxide, etc.), alkali metal hydrides (e.g., sodium hydride, potassium hydride, etc.), and the like. Organic bases include, for example, trialkylamines (e.g., trimethylamine, triethylamine, N-ethyldiisopropylamine, etc.), pyridine, quinoline, piperidine, imidazole, picoline, dimethylaminopyridine, dimethylaniline, N-methylmorpholine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), etc. When such bases are liquid, they can also be used as solvents. Such bases can be used singly or in combination.

The amount of base(s) is usually 0.5 to 10 mol, and preferably 0.5 to 6 mol, per mol of Compound (1f).

The proportion of Compound (1f) to Compound (8') is usually at least 1 mol, and preferably about 1 to about 5 mol of the latter, per mol of the former.

The reaction temperature is not limited, and the reaction can usually be performed with cooling, at room temperature, or with heating. It is suitable to perform the reaction at about room temperature for 1 to 30 hours.

Compounds (8) and (8') used as starting materials in the above reaction are easily available known compounds.

Among the oxazole compounds represented by Formula (1), those in which W is a divalent group represented by —$Y^1$-$A^1$- wherein $Y^1$ is —C(=O) and $A^1$ is a lower alkenylene group (hereinafter referred to as "Compound (1h)") can be produced by, for example, the process shown in Reaction Scheme 7.

Reaction Scheme 7

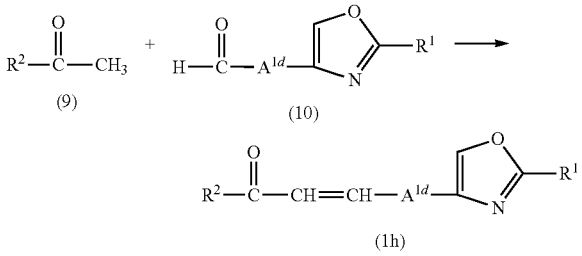

wherein $R^1$ and $R^2$ are as defined in Formula (1), and $A^{1d}$ is a $C_{2-4}$ alkenylene group, a $C_{1-4}$ alkylene group, or a direct bond.

Each of the $C_{2-4}$ alkenyl group and $C_{1-4}$ alkylene group may be straight- or branched-chain. —CH=CH-$A^{1d}$ corresponds to the lower alkenylene group represented by $A^1$ in Formula (1).

Compound (1h) is produced by reacting Compound (9) with Compound (10).

The reaction is usually performed in a known solvent that does not adversely affect the reaction. Such solvents include, for example, water; methanol, ethanol, isopropanol, n-butanol, trifluoroethanol, ethylene glycol, and other alcohol solvents; acetone, methyl ethyl ketone, and other ketone solvents; tetrahydrofuran, dioxane, diethyl ether, dimethoxyethane, diglyme, and other ether solvents; methyl acetate, ethyl acetate, and other ester solvents; acetonitrile, N,N-dimethylformamide, dimethyl sulfoxide, N-methylpyrrolidone, and other aprotic polar solvents; methylene chloride, ethylene chloride, and other halogenated hydrocarbon solvents; other organic solvents; mixed solvents thereof; etc.

The reaction can be performed in the presence of base(s). A wide variety of known inorganic and organic bases are usable. Inorganic bases include, for example, alkali metals (e.g., lithium, sodium, potassium, etc.), alkali metal hydrogencarbonates (e.g., lithium hydrogencarbonate, sodium hydrogencarbonate, potassium hydrogencarbonate, etc.), alkali metal hydroxides (e.g., lithium hydroxide, sodium hydroxide, potassium hydroxide, cesium hydroxide, etc.), alkali metal carbonates (e.g., lithium carbonate, sodium carbonate, potassium carbonate, cesium carbonate, etc.), alkali metal lower alkoxides (e.g., sodium methoxide, sodium ethoxide, potassium tert-butoxide, sodium tert-butoxide, etc.), alkali metal hydrides (e.g., sodium hydride, potassium hydride, etc.), and the like. Organic bases include, for example, trialkylamines (e.g., trimethylamine, triethylamine, N-ethyldiisopropylamine, etc.), pyridine, quinoline, piperidine, imidazole, picoline, dimethylaminopyridine, dimethylaniline, N-methylmorpholine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), etc. When such bases are liquid, they can also be used as solvents. Such bases can be used singly or in combination.

The amount of base(s) is usually 0.5 to 10 mol, and preferably 0.5 to 6 mol, per mol of Compound (9).

The proportion of Compound (9) to Compound (10) is usually at least 1 mol, and preferably about 1 to about 5 mol of the latter, per mol of the former.

The reaction temperature is not limited, and the reaction can usually be performed with cooling, at room temperature, or with heating. It is suitable to perform the reaction in a temperature range from room temperature to 150° C., for 30 minutes to 60 hours, and preferably for 1 to 30 hours.

Compound (9) used as a starting material in the above reaction is an easily available known compound. Compound (10) used as a starting material in the above reaction can be produced by the process shown in Reaction Scheme 12.

Among the oxazole compounds represented by Formula (1), those in which W is a divalent group represented by —$Y^1$-$A^1$- wherein $A^1$ is a lower alkylene group (hereinafter referred to as "Compound (1j)") can be produced from compounds in which $A^1$ is a lower alkenylene group (hereinafter referred to as "Compound (1i)"), by the process shown in Reaction Scheme 8.

Reaction Scheme 8

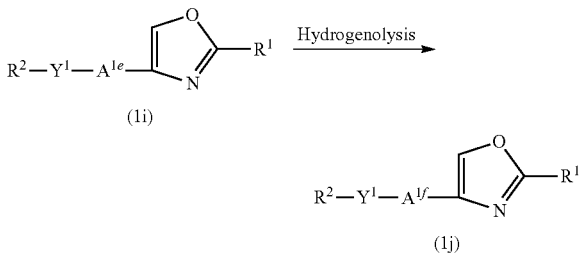

wherein $R^1$ and $R^2$ are as defined in Formula (1), $Y^1$ is as defined above, $A^{1e}$ is a lower alkenylene group, and $A^{1f}$ is a lower alkylene group.

Compound (1j) is produced by subjecting Compound (1i) to hydrogenolysis.

The reaction is performed under the same reaction conditions as of the reaction shown in Reaction Scheme 5 for the hydrogenolysis of Compound (1e) to obtain Compound (1f). Therefore, the same reagent(s) and reaction conditions (e.g., solvent, reaction temperature, etc.) as those used in the hydrogenolysis shown in Reaction Scheme 5 can be used in the above reaction.

Reaction Scheme 9

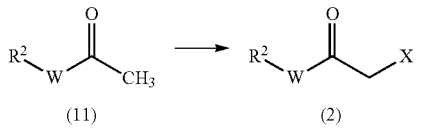

wherein $R^2$ and W are as defined in Formula (1), and X is as defined above.

The halogenation reaction of Compound (11) is performed in a suitable solvent in the presence of a halogenating agent. Usable halogenating agents include, for example, $Br_2$, $Cl_2$, and other halogen molecules; iodine chloride, sulfuryl chloride, cupric bromide, and other copper compounds; N-bromosuccinimide, N-chlorosuccinimide, and other N-halosuccinimides, etc. Usable solvents include, for example, dichloromethane, dichloroethane, chloroform, carbon tetrachloride, and other halogenated hydrocarbons; acetic acid, propionic acid, and other fatty acids; carbon disulfide; etc. The amount of halogenating agent is usually 1 to 10 mol, and preferably 1 to 5 mol, per mol of Compound (11). The reaction is usually complete at 0° C. to the boiling point temperature of the solvent, and preferably about 0 to about 100° C., in about 5 minutes to about 20 hours.

Among Compounds (5) for use as starting materials, those in which $R^3$ is a hydrogen atom (hereinafter referred to as "Compound (5a)") are produced by the process shown in Reaction Scheme 10.

Reaction Scheme 10

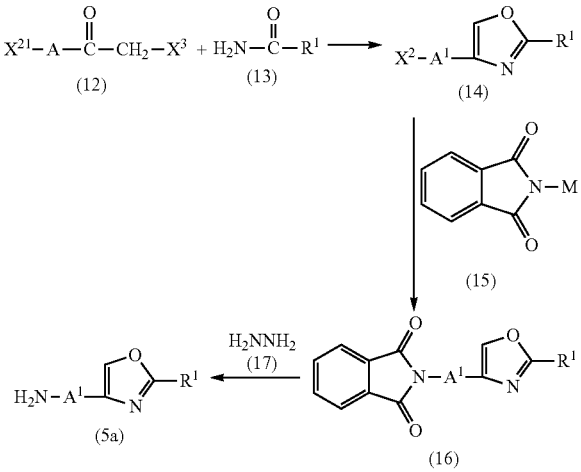

wherein $R^1$ and $A^1$ are as defined in Formula (1), $X^2$ and $X^3$ are each independently a halogen atom or a group that undergoes the same substitution reaction as that of a halogen atom as mentioned above, and M is an alkali metal.

Examples of the alkali metal represented by M include sodium, potassium, etc.

Compound (14) is produced by reacting Compound (12) with Compound (13).

The reaction of Compound (12) with Compound (13) is usually performed in a known solvent that does not adversely affect the reaction. Such solvents include, for example, water; methanol, ethanol, isopropanol, n-butanol, trifluoroethanol, ethylene glycol, and other alcohol solvents; acetone, methyl ethyl ketone, and other ketone solvents; tetrahydrofuran, dioxane, diethyl ether, dimethoxyethane, diglyme, and other ether solvents; methyl acetate, ethyl acetate, and other ester solvents; acetonitrile, N,N-dimethylformamide, dimethyl sulfoxide, N-methylpyrrolidone, and other aprotic polar solvents; methylene chloride, ethylene chloride, and other halogenated hydrocarbon solvents; and other organic solvents; etc.

The proportion of Compound (12) to Compound (13) is usually at least 1 mol, and preferably about 1 to about 5 mol of the latter, per mol of the former. The reaction of Compound (12) with Compound (13) is performed by continuing stirring usually in a temperature range from room temperature to 200° C., and preferably from room temperature to 150° C., usually for 30 minutes to 60 hours, and preferably 1 to 30 hours.

Compound (16) is produced by reacting Compound (15) with Compound (14).

The reaction of Compound (15) with Compound (14) is usually performed in a known solvent that does not adversely affect the reaction. Such solvents include, for example, water; methanol, ethanol, isopropanol, n-butanol, trifluoroethanol, ethylene glycol, and other alcohol solvents; acetone, methyl ethyl ketone, and other ketone solvents; tetrahydrofuran, dioxane, diethyl ether, diglyme, and other ether solvents; methyl acetate, ethyl acetate, and other ester solvents; acetonitrile, N,N-dimethylformamide, dimethyl sulfoxide, and other aprotic polar solvents; methylene chloride, ethylene chloride, and other halogenated hydrocarbon solvents; other organic solvents; mixtures thereof; etc.

When performing the reaction of Compound (15) with Compound (14), alkali metal iodides such as potassium iodide, sodium iodide, etc. can be added as reaction accelerators to the reaction system, as required.

The proportion of Compound (15) to Compound (14) is usually at least 1 mol, and preferably about 1 to about 5 mol of the latter, per mol of the former.

The temperature of the reaction of Compound (15) with Compound (14) is not limited, and the reaction can usually be performed with cooling, at room temperature, or with heating. It is suitable to perform the reaction in a temperature range from room temperature to 100° C., for 1 to 60 hours, and preferably for 1 to 30 hours.

In the reaction of Compound (15) with Compound (14), phthalimide can be used in place of Compound (15) and the reaction may be performed in the presence of base(s). A wide variety of known inorganic and organic bases are usable. Examples of inorganic bases include alkali metals (e.g., lithium, sodium, potassium, etc.), alkali metal hydrogencarbonates (e.g., lithium hydrogencarbonate, sodium hydrogencarbonate, potassium hydrogencarbonate, etc.), alkali metal hydroxides (e.g., lithium hydroxide, sodium hydroxide, potassium hydroxide, cesium hydroxide, etc.), alkali metal carbonates (e.g., lithium carbonate, sodium carbonate, potassium carbonate, cesium carbonate, etc.), alkali metal lower alkoxides (e.g., sodium methoxide, sodium ethoxide, potassium tert-butoxide, sodium tert-butoxide, etc.), alkali metal hydrides (e.g., sodium hydride, potassium hydride, etc.), and the like. Organic bases include, for example, trialkylamines (e.g., trimethylamine, triethylamine, N-ethyldiisopropylamine, etc.), pyridine, quinoline, piperidine, imidazole, picoline, dimethylaminopyridine, dimethylaniline, N-methylmorpholine, 1,5-diazabicyclo

[4.3.0]non-5-ene (DBN), 1,4-diazabicyclo[2.2.2]octane (DABCO), 1,8-diazabicyclo[5.4.0]undec-7-ene (DBU), etc.

The amount of base(s) is usually 0.5 to 10 mol, and preferably 0.5 to 6 mol, per mol of Compound (14).

Compound (5a) is produced by reacting Compound (16) with Compound (17).

The reaction of Compound (16) with Compound (17) is usually performed in a known solvent that does not adversely affect the reaction. Such solvents include, for example, water; methanol, ethanol, isopropanol, n-butanol, trifluoroethanol, ethylene glycol, and other alcohol solvents; acetone, methyl ethyl ketone, and other ketone solvents; tetrahydrofuran, dioxane, diethyl ether, diglyme, and other ether solvents; methyl acetate, ethyl acetate, and other ester solvents; acetonitrile, N,N-dimethylformamide, dimethyl sulfoxide, and other aprotic polar solvents; methylene chloride, ethylene chloride, and other halogenated hydrocarbon solvents; other organic solvents; mixtures thereof; etc.

The proportion of Compound (16) to Compound (17) is usually at least 1 mol, and preferably about 1 to about 5 mol of the latter, per mol of the former.

The temperature of the reaction of Compound (16) with Compound (17) is not limited, and the reaction can usually be performed with cooling, at room temperature, or with heating. It is suitable to perform the reaction at about room temperature for 1 to 30 hours.

Reaction Scheme 11

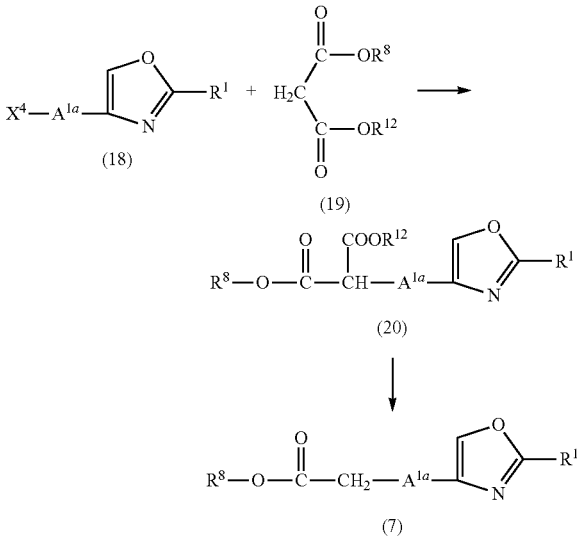

wherein $R^1$ is as defined in Formula (1); $R^8$ and $A^{1a}$ are as defined above; $X^4$ is a halogen atom or a group that undergoes the same substitution reaction as that of a halogen atom as mentioned above; and $R^{12}$ is a lower alkyl group.

Compound (20) is produced by reacting Compound (18) with Compound (19).

The reaction of Compound (18) with Compound (19) is usually performed in a known solvent that does not adversely affect the reaction. Such solvents include, for example, water; methanol, ethanol, isopropanol, n-butanol, trifluoroethanol, ethylene glycol, and other alcohol solvents; acetone, methyl ethyl ketone, and other ketone solvents; tetrahydrofuran, dioxane, diethyl ether, dimethoxyethane, diglyme, and other ether solvents; methyl acetate, ethyl acetate, and other ester solvents; acetonitrile, N,N-dimethylformamide, dimethyl sulfoxide, N-methylpyrrolidone, and other aprotic polar solvents; methylene chloride, ethylene chloride, and other halogenated hydrocarbon solvents; other organic solvents; mixtures thereof; etc.

The reaction of Compound (18) with Compound (19) can usually be performed in the presence of suitable base (s). A wide variety of known inorganic and organic bases are usable. Inorganic bases include, for example, alkali metals (e.g., lithium, sodium, potassium, etc.), alkali metal hydrogencarbonates (e.g., lithium hydrogencarbonate, sodium hydrogencarbonate, potassium hydrogencarbonate, etc.), alkali metal hydroxides (e.g., lithium hydroxide, sodium hydroxide, potassium hydroxide, cesium hydroxide, etc.), alkali metal carbonates (e.g., lithium carbonate, sodium carbonate, potassium carbonate, cesium carbonate, etc.), alkali metal lower alkoxides (e.g., sodium methoxide, sodium ethoxide, potassium tert-butoxide, sodium tert-butoxide, etc.), alkali metal hydrides (e.g., sodium hydride, potassium hydride, etc.), and the like. Organic bases include, for example, trialkylamines (e.g., trimethylamine, triethylamine, N-ethyldiisopropylamine, etc.), pyridine, quinoline, piperidine, imidazole, picoline, dimethylaminopyridine, dimethylaniline, N-methylmorpholine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), etc. When such bases are liquid, they can also be used as solvents.

Such bases can be used singly or in combination.

The amount of base(s) is usually 0.5 to 10 mol, and preferably 0.5 to 6 mol, per mol of Compound (18).

The proportion of Compound (18) to Compound (19) in Reaction Scheme 11 is usually at least 1 mol, and preferably about 1 to about 5 mol of the latter, per mol of the former.

The reaction temperature is not limited, and the reaction can usually be performed with cooling, at room temperature, or with heating. It is suitable to perform the reaction in a temperature range from room temperature to 100° C., for 30 minutes to 60 hours, and preferably 1 to 30 hours.

Compound (7) is produced by subjecting Compound (20) to hydrolysis-decarboxylation. The hydrolysis-decarboxylation of Compound (20) can be carried out by the process shown in Reference Example 48 given hereinafter, a process similar thereto, the process shown in Reaction Scheme 4 above, or a process similar thereto.

Reaction Scheme 12

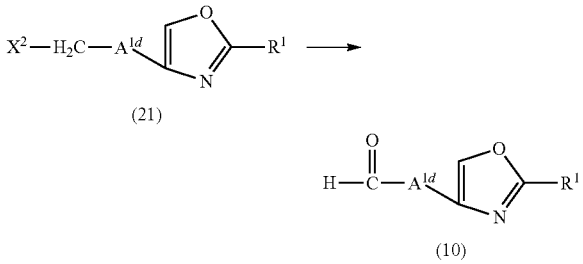

wherein $R^1$ is as defined in Formula (1), and $X^2$ and Aid are as defined above.

Compound (10) is produced by subjecting Compound (21) to an oxidation reaction. The reaction can be carried out by the process shown in Reference Example 64 given hereinafter, or a process similar thereto, and is performed in the presence of a known solvent that does not adversely affect the reaction. Such solvents include, for example, water; methanol, ethanol, isopropanol, n-butanol, trifluoroethanol, ethylene glycol, and other alcohol solvents; acetone, methyl ethyl ketone, and other ketone solvents; tetrahydrofuran, dioxane, diethyl ether, diglyme, and other ether solvents; methyl acetate, ethyl acetate, and other ester solvents; acetonitrile, N,N-dimethylformamide, dimethyl sulfoxide, and other aprotic polar solvents; methylene chloride, ethylene chloride, and other halogenated hydrocarbon solvents; other organic solvents; mixtures thereof; etc.

The reaction is usually performed using oxidizing agent(s) such as dimethyl sulfoxide, hexamethylenetetramine, triethylamine-N-oxide, etc.

If necessary, the reaction can be performed in the presence of suitable base(s). A wide variety of known inorganic and organic bases are usable. Inorganic bases include, for example, alkali metals (e.g., sodium, potassium, etc.), alkali metal hydrogencarbonates (e.g., lithium hydrogencarbonate, sodium hydrogencarbonate, potassium hydrogencarbonate, etc.), alkali metal hydroxides (e.g., lithium hydroxide, sodium hydroxide, potassium hydroxide, cesium hydroxide, etc.), alkali metal carbonates (e.g., lithium carbonate, sodium carbonate, potassium carbonate, cesium carbonate, etc.), alkali metal lower alkoxides (e.g., sodium methoxide, sodium ethoxide, etc.), alkali metal hydrides (e.g., sodium hydride, potassium hydride, etc.), and the like. Organic bases include, for example, trialkylamines (e.g., trimethylamine, triethylamine, N-ethyldiisopropylamine, etc.), pyridine, quinoline, piperidine, imidazole, picoline, dimethylaminopyridine, dimethylaniline, N-methylmorpholine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), etc. When such bases are liquid, they can also be used as solvents. Such bases can be used singly or in combination.

The amount of oxidizing agent is usually 0.5 to 10 mol, and preferably 0.5 to 6 mol, per mol of Compound (21).

The amount of base(s) is usually 0.5 to 10 mol, and preferably 0.5 to 6 mol, per mol of Compound (21).

When performing the above reaction, alkali metals such as potassium iodide, sodium iodide, etc. can be added as reaction accelerators to the reaction system, as required.

The reaction temperature is not limited, and the reaction can usually be performed with cooling, at room temperature, or with heating. It is suitable to perform the reaction in a temperature range from room temperature to 120° C. for 30 minutes to 30 hours.

The starting material compounds used in the above reaction schemes may be suitable salts, and the objective compounds obtained by the above reactions may be in the form of suitable salts.

Each of the objective compounds obtained according to the above reaction schemes can be isolated and purified from the reaction mixture by, for example, cooling the reaction mixture, separating the crude reaction product from the reaction mixture by an isolation procedure such as filtration, concentration, extraction and/or other isolation procedures, and then purifying the crude reaction product by column chromatography, recrystallization and/or other conventional purification procedures.

Suitable salts of Compound (1) are pharmaceutically acceptable salts including, for example, metal salts such as alkali metal salts (e.g., sodium salt, potassium salt, etc.), alkaline earth metal salts (e.g., calcium salt, magnesium salt, etc.), etc., ammonium salts, alkali metal carbonates (e.g., lithium carbonate, potassium carbonate, sodium carbonate, cesium carbonate, etc.), alkali metal hydrogencarbonates (e.g., lithium hydrogencarbonate, sodium hydrogencarbonate, potassium hydrogencarbonate, etc.), alkali metal hydroxides (e.g., lithium hydroxide, sodium hydroxide, potassium hydroxide, cesium hydroxide, etc.), and other salts of inorganic bases; tri(lower)alkylamines (e.g., trimethylamine, triethylamine, N-ethyldiisopropylamine, etc.), pyridine, quinoline, piperidine, imidazole, picoline, dimethylaminopyridine, dimethylaniline, N-(lower)alkylmorpholines (e.g., N-methylmorpholine and the like), DBN, DBU, DABCO, and other salts of organic bases; hydrochlorides, hydrobrmides, hydroiodides, sulfates, nitrates, phosphates, and other salts of inorganic acids; formates, acetates, propionates, oxalates, malonates, succinates, fumarates, maleates, lactates, malates, citrates, tartrates, citrates, carbonates, picrates, methanesulfonates, ethanesulfonates, p-toluenesulfonates, glutamates, and other salts of inorganic acids; etc.

The starting material compounds and objective compounds represented by the formulae in the above reaction schemes encompass solvates (e.g. hydrates, ethanolates, etc.). Preferable solvates include hydrates.

The compounds represented by Formula (1) of the present invention of course encompass isomers such as geometrical isomers, stereoisomer, optical isomers, etc.

Drug Efficacy and Use

Compounds represented by formula (1), optically active isomers thereof, and salts thereof (hereinafter referred to as "compounds of the present invention") have a specific inhibitory action against PDE4, and are hence useful as active ingredients for a PDE4 inhibitor.

Further, due to their PDE4-specific inhibitory action, the compounds of the invention can be useful as active ingredients of pharmaceutical compositions used as prophylactic and therapeutic agents for various diseases. More specifically, diseases efficiently preventable and treatable by the PED4-specific inhibitory action include various origin-generated acute and chronic (in particular, inflammatory and allergen induced) respiratory tract diseases (e.g. bronchial asthma, chronic obstructive pulmonary disease, etc.); dermatoses (in particular, hyperplastic, inflammatory, and allergic diseases) (e.g. psoriasis (vulgaris), toxic and allergic contact eczema, atopic dermatitis, alopecia areata, and other hyperplastic, inflammatory and allergic dermatoses); nervous function abnormality diseases such as learning, memory, and/or cognition disorders associated with Altzheimer's and Perkinson's diseases; diseases associated with mental function abnormality (e.g. manic-depressive psychosis, schizophrenia, anxiety disorder, etc.); systemic and local arthritic disorders (e.g. knee osteoarthritis, articular rheumatism, etc.); gastrointestinal diffuse inflammation (e.g. Crohn's disease and ulcerative colitis); allergic and/or chronic immune-mediated inflammatory diseases in the upper respiratory tract (cavum pharynges, nose) and its vicinity (sinuses, eyes) (e.g. allergic rhinitis/sinusitis, chronic rhinitis/sinusitis, allergic conjunctivitis), and the like. Among these, the compounds are particularly effective in preventing and treating atopic dermatitis, making this diseases a suitable target disease for prevention and treatment.

When used as a PDE4 inhibitor or as prophylactic or therapeutic agent for the above-mentioned various diseases, the compounds of the invention can be used as oral agents, injectable solutions, external preparations, and the like.

For oral agents, for example, the compounds may be prepared in any forms such as powders, tablets, granules, capsules, syrups, films, troches, liquids, etc. Such oral agents can contain pharmaceutically acceptable base materials and carriers, and further optionally contain as necessary binders, disintegrators, lubricants, humectants, buffers, preservatives, fragrances, and the like.

For injectable solutions, the compounds may be prepared in the form of solutions dissolved in physiological saline, grape sugar solutions and the like, or aqueous suspensions.

For external preparations, the compounds may be prepared in any forms, for example, such as liquid medicines, oily medicines, lotions, liniments, emulsions, suspensions, creams, ointments, etc. Such external preparations can optionally contain various carriers, base materials, and additives as typically used in external preparations, and examples include water, oils, surfactants, solubilized components, emulsifiers, colorants (dyes and pigments), fragrances, preservatives, disinfectants, thickeners, antioxidants, chelators, pH adjusting agents, deodorants, etc.

When used as a PDE4 inhibitor, or as prophylactic or therapeutic agent for the aforementioned various diseases, effective dose and number of doses a day of the compound vary depending on the purpose of use, kind of compound used, the age, weight, symptoms, etc. of a subject, and cannot be uniformly prescribed. For example, the inhibitor or agent can be administered in a dose of 0.1 to 1000 mg of the compound(s) of the present invention per day per adult, and may be administered in one to several portions a day.

Further, in light of other viewpoints, the present invention provides a method for treating or preventing the aforementioned various diseases comprising the step of administrating an effective dose of the compound(s) of the invention to a mammal, such as a human.

Furthermore, since the compounds of the present invention have inhibitory action against TNF-α production, they are useful as active ingredients for TNF-α production suppressants. Diseases that benefit from such TNF-α production inhibitory action include those efficiently preventable and treatable by the aforementioned PDE4-specific inhibitory action. Preparation forms, administration routes and doses of TNF-α production suppressant containing compounds of the invention are the same as those of the aforementioned PDE4 inhibitor and prophylactic and therapeutic agents.

EFFECT OF THE INVENTION

The compounds of the present invention have an inhibitory action specific against PDE4, and are hence useful as active ingredients for a PDE 4 inhibitors.

Due to their specific PDE4 inhibitory activity, the compounds of the invention are further useful as prophylactic and therapeutic agents for various diseases including atopic dermatitis.

BEST MODE FOR CARRYING OUT THE INVENTION

The present invention is described in more detail below with reference to Examples; however, the present invention is not limited thereto.

Reference Example 1

A 25 g quantity of isovanillic acid was suspended in 250 ml of methanol, and 1.5 g of p-toluenesulfonic acid monohydrate was added. The mixture was heated and refluxed overnight. After completion of the reaction, methanol was distilled off under reduced pressure. The residue was neutralized with saturated aqueous sodium bicarbonate and then extracted with ethyl acetate. After washing with saturated brine twice, the organic layer was separated and concentrated under reduced pressure. The residue was purified by silica gel column chromatography (n-hexane:ethyl acetate=1:1) to give 24.5 g of white crystalline methyl 3-hydroxy-4-methoxybenzoate.

$^1$H-NMR ($CDCl_3$) δ: 7.63-7.58 (2H, m), 6.67 (1H, d, J=8.1 Hz), 5.63 (1H, s), 3.98 (3H, s), 3.90 (3H, s)

Reference Example 2

A 20 g quantity of methyl 3-hydroxy-4-methoxybenzoate obtained in Reference Example 1 was dissolved in 200 ml of methanol, and 24.6 ml of 1,8-diazabicyclo[5,4,0]undec-7-ene and 21 g of benzyl bromide were added. The mixture was heated and refluxed overnight. After the reaction mixture was concentrated, water was added to the residue and extraction with ethyl acetate was performed. The extract was washed with saturated brine twice, and the organic layer was separated and dried over magnesium sulfate. After insolubles were removed by filtration, the filtrate was concentrated under reduced pressure to give 25.5 g of white crystalline methyl 3-benzyloxy-4-methoxybenzoate.

$^1$H-NMR ($CDCl_3$) δ: 7.68 (1H, dd, J=8.4, 1.8 Hz), 7.61 (1H, d, J=1.8 Hz), 7.48-7.28 (5H, m), 6.91 (1H, d, J=8.4 Hz), 5.17 (2H, s), 3.93 (3H, s), 3.87 (3H, s)

Reference Example 3

A 25 g quantity of the methyl 3-benzyloxy-4-methoxybenzoate obtained in Reference Example 2 was dissolved in 100 ml of acetonitrile, and a solution of 11 g of sodium hydroxide in 100 ml of water was added. The mixture was stirred with heating at 40° C. for 5 hours. The reaction mixture was cooled with ice, and concentrated hydrochloric acid was added to give a pH of about 3. The precipitated crystals were collected by filtration and dried under reduced pressure to give 22.1 g of white crystalline 3-benzyloxy-4-methoxybenzoic acid.

$^1$H-NMR ($CDCl_3$) δ: 7.77 (1H, dd, J=8.4, 1.8 Hz), 7.65 (1H, d, J=1.8 Hz), 7.48-7.29 (5H, m), 6.94 (1H, d, J=8.4 Hz), 5.19 (2H, s), 3.95 (3H, s)

Reference Example 4

A 20 g quantity of the 3-benzyloxy-4-methoxybenzoic acid obtained in Reference Example 3 was suspended in 200 ml of dichloromethane, and one drop of dimethylformamide was added. A 8.1 ml quantity of oxalyl chloride was added dropwise with ice-cooling and stirring. After 2 hours, the reaction mixture was concentrated under reduced pressure. The residue was dissolved in 50 ml of tetrahydrofuran and the resulting solution was added dropwise to 28% aqueous ammonia with ice-cooling and stirring. The obtained mixture was stirred for 1 hour and the precipitated crystals were collected by filtration and dried under reduced pressure to give 19.9 g of white powdery 3-benzyloxy-4-methoxybenzamide.

$^1$H-NMR ($CDCl_3$) δ: 7.85-7.28 (7H, m), 6.90 (1H, d, J=8.1 Hz), 5.67 (2H, br s), 5.18 (2H, s), 3.93 (3H, s)

Reference Example 5

A 15 g quantity of 3-benzyloxy-4-methoxybenzamide obtained in Reference Example 4 was suspended in 450 ml of isopropanol, and 13.9 g of 1,3-dichloro-2-propanone was added. The mixture was heated and refluxed overnight. After the reaction mixture was concentrated to half its original volume under reduced pressure, 200 ml of n-hexane was added to the concentrate and the mixture was stirred. The precipitated crystals were collected by filtration and dried under reduced pressure to give 12.2 g of white powdery 2-(3-benzyloxy-4-methoxyphenyl)-4-chloromethyl oxazole.

$^1$H-NMR ($CDCl_3$) δ: 7.73-7.71 (3H, m), 7.50-7.29 (5H, m), 6.95 (1H, d, J=5.7 Hz), 5.20 (2H, s), 4.56 (2H, s), 3.93 (3H, s)

Reference Example 6

A 11 g quantity of 2-(3-benzyloxy-4-methoxyphenyl)-4-chloromethyl oxazole obtained in Reference Example 5 was suspended in 220 ml of ethanol, and 7.5 g of sodium iodide and 9.3 g of potassium phthalimide were added. The mixture was heated and refluxed overnight. The reaction mixture was cooled with ice, and the precipitated crystals were collected by filtration. The obtained crude crystals were suspended and washed with 100 ml of water. The resulting crystals were dried under reduced pressure to give 9.4 g of white powdery 2-[2-(3-benzyloxy-4-methoxyphenyl)oxazol-4-ylmethyl]isoindolin-1,3-dione.

$^1$H-NMR ($CDCl_3$) δ: 7.91-7.85 (2H, m) 7.76-7.69 (2H, m), 7.61-7.58 (3H, m) 7.46 (2H, d, J=6.6 Hz), 7.39-7.26 (3H, m), 6.91 (1H, d, J=9 Hz), 5.18 (2H, s), 4.85 (2H, s), 3.90 (3H, s)

Reference Example 7

A 9 g quantity of the 2-[2-(3-benzyloxy-4-methoxyphenyl)oxazol-4-ylmethyl]isoindolin-1,3-dione obtained in Reference Example 6 was suspended in 200 ml of ethanol, and 3.1 ml of hydrazine monohydrate was added. The mixture was heated and refluxed for 3 hours. After cooing the reaction mixture, 200 ml of dichloromethane was added and the mixture was stirred. Insolubles were removed by filtration, and the filtrate was concentrated under reduced pressure. The residue was purified by silica gel column chromatography (NH silica, product of Fuji Sylisia Chemical Ltd., dichloromethane:methanol=20:1) to give 4.5 g of pale yellow powdery [2-(3-benzyloxy-4-methoxyphenyl) oxazol-4-yl]methylamine.

$^1$H-NMR ($CDCl_3$) δ: 7.63-7.59 (2H, m) 7.53-7.46 (3H, m), 7.41-7.27 (3H, m) 6.94 (1H, d, J=9 Hz), 5.20 (2H, s), 3.89 (3H, s), 3.87 (2H, s), 2.14 (2H, br s)

Reference Example 8

A 15 g quantity of methyl 3-hydroxy-4-methoxybenzoate obtained in Reference Example 1 was dissolved in 150 ml of dimethylformamide, and 34 g of potassium carbonate and 22.2 g of (bromomethyl)cyclopropane were added. The mixture was heated at 90° C. overnight. Ice water was added to the reaction mixture, and the precipitated crystals were collected by filtration and washed with an excess of water. The obtained crystals were dried under reduced pressure at room temperature to give 18.3 g of white crystalline methyl 3-cyclopropylmethoxy-4-methoxybenzoate.

$^1$H-NMR ($CDCl_3$) δ: 7.67 (1H, dd, J=8.4, 1.8 Hz), 7.52 (1H, d, J=2.1 Hz), 6.89 (1H, d, J=8.4 Hz), 3.94-3.86 (8H, m), 1.43-1.29 (1H, m), 0.70-0.58 (2H, m), 0.45-0.30 (2H, m)

Reference Example 9

Using 18 g of methyl 3-cyclopropylmethoxy-4-methoxybenzoate obtained in Reference Example 8 and following the procedure of Reference Example 3, 16.6 g of white crystalline 3-cyclopropylmethoxy-4-methoxybenzoic acid was obtained.

$^1$H-NMR ($CDCl_3$) δ: 7.76 (1H, dd, J=8.4, 1.8 Hz), 7.58 (1H, d, J=2.1 Hz), 6.92 (1H, d, J=8.4 Hz), 3.98-3.92 (8H, m), 1.43-1.29 (1H, m), 0.70-0.58 (2H, m), 0.46-0.35 (2H, m)

Reference Example 10

Using 16.5 g of 3-cyclopropylmethoxy-4-methoxybenzoic acid obtained in Reference Example 9 and following the procedure of Reference Example 4, 16.2 g of pale yellow powdery 3-cyclopropylmethoxy-4-methoxybenzamide was obtained.

$^1$H-NMR ($CDCl_3$) δ: 7.43 (1H, d, J=2.1 Hz), 7.31 (1H, dd, J=8.4, 2.1 Hz), 6.88 (1H, d, J=8.1 Hz), 5.75 (2H, br s), 3.97-3.89 (5H, m), 1.40-1.28 (1H, m), 0.69-0.62 (2H, m), 0.39-0.33 (2H, m)

Reference Example 11

Using 13 g of 3-cyclopropylmethoxy-4-methoxybenzamide obtained in Reference Example 10 and following the procedure of Reference Example 5, 10.5 g of pale yellow powdery 4-chloromethyl-2-(3-cyclopropylmethoxy-4-methoxyphenyl)oxazole was obtained.

$^1$H-NMR ($CDCl_3$) δ: 7.65 (1H, d, J=0.9 Hz), 7.20 (1H, dd, J=8.7, 2.1 Hz), 7.53 (1H, d, J=2.1 Hz), 6.93 (1H, d, J=8.4 Hz), 4.57 (2H, s), 3.97-3.90 (5H, m), 1.43-1.32 (1H, m), 0.71-0.63 (2H, m), 0.41-0.35 (2H, m)

Reference Example 12

Using 8 g of 4-chloromethyl-2-(3-cyclopropylmethoxy-4-methoxyphenyl)oxazole obtained in Reference Example 11 and following the procedure of Reference Example 6, 10 g of white crystalline 2-[2-(3-cyclopropylmethoxy-4-methoxyphenyl)oxazol-4-ylmethyl]isoindolin-1,3-dione was obtained.

$^1$H-NMR ($CDCl_3$) δ: 7.90-7.84 (2H, m), 7.76-7.69 (2H, m), 7.62 (1H, s), 7.57 (1H, dd, J=8.4, 2.1 Hz), 7.48 (1H, d, J=2.1 Hz), 6.89 (1H, d, J=8.4 Hz), 4.85 (2H, s), 3.95-3.90 (5H, m), 1.41-1.31 (1H, m), 0.69-0.62 (2H, m), 0.41-0.35 (2H, m)

Reference Example 13

Using 9.5 g of 2-[2-(3-cyclopropylmethoxy-4-methoxyphenyl)oxazol-4-ylmethyl]isoindolin-1,3-dione obtained in Reference Example 12 and following the procedure of Reference Example 7, 5.1 g of white powdery [2-(3-cyclopropylmethoxy-4-methoxyphenyl)oxazol-4-yl]methylamine was obtained.

$^1$H-NMR ($CDCl_3$) δ: 7.61-7.55 (1H, m), 7.53-7.50 (2H, m), 6.92 (1H, d, J=8.4 Hz), 3.96-3.87 (5H, m), 3.83 (2H, s), 1.41-1.33 (1H, m), 0.70-0.63 (2H, m), 0.41-0.35 (2H, m)

Reference Example 14

A 5 g quantity of methyl 3-hydroxy-4-methoxybenzoate obtained in Reference Example 1 was dissolved in 100 ml of dimethylformamide, and 11.3 g of potassium carbonate and 5.64 g of isobutyl bromide were added. The mixture was heated at 80° C. for 6 hours. Ice water was added to the reaction mixture, and the precipitated crystals were collected by filtration and washed with an excess of water. The resulting crystals were dried under reduced pressure at room temperature to give 5.85 g of white powdery methyl 3-isobutoxy-4-methoxybenzoate.

$^1$H-NMR ($CDCl_3$) δ: 7.65 (1H, dd, J=8.4, 2.1 Hz), 7.53 (1H, d, J=1.8 Hz), 6.88 (1H, d, J=8.1 Hz), 3.96 (3H, s), 3.91 (3H, s), 3.82 (2H, d, J=6.9 Hz), 2.20-2.11 (1H, m), 1.05 (6H, d, J=6.6 Hz)

Reference Example 15

Using 5.85 g of methyl 3-isobutoxy-4-methoxybenzoate obtained in Reference Example 14 and following the procedure of Reference Example 3, 5.6 g of white powdery 3-isobutoxy-4-methoxybenzoic acid was obtained.

$^1$H-NMR ($CDCl_3$) δ: 7.75 (1H, dd, J=8.4, 1.8 Hz), 7.58 (1H, d, J=2.1 Hz), 6.91 (1H, d, J=8.7 Hz), 3.94 (3H, s), 3.83 (2H, d, J=6.6 Hz), 2.26-2.12 (1H, m), 1.05 (6H, d, J=6.6 Hz)

Reference Example 16

Using 5.5 g of 3-isobutoxy-4-methoxybenzoic acid obtained in Reference Example 15 and following the procedure of Reference Example 4, 5.1 g of pale yellow powdery 3-isobutoxy-4-methoxybenzamide was obtained.

$^1$H-NMR ($CDCl_3$) δ: 7.43 (1H, d, J=2.1 Hz), 7.31 (1H, dd, J=8.4, 2.1 Hz), 6.87 (1H, d, J=8.7 Hz), 5.78 (2H, br s), 3.91 (3H, s), 3.83 (2H, d, J=6.6 Hz), 2.25-2.11 (1H, m), 1.04 (6H, d, J=6.6 Hz)

Reference Example 17

Using 5 g of 3-isobutoxy-4-methoxybenzamide obtained in Reference Example 16 and following the procedure of Reference Example 5, 3.4 g of pale yellow powdery 4-chloromethyl-2-(3-isobutoxy-4-methoxyphenyl)oxazole was obtained.

$^1$H-NMR ($CDCl_3$) δ: 7.65 (1H, s), 7.60 (1H, dd, J=8.4, 2.1 Hz), 7.53 (1H, d, J=2.1 Hz), 6.92 (1H, d, J=8.4 Hz), 4.57 (2H, s), 3.91 (3H, s), 3.85 (2H, d, J=6.9 Hz), 2.27-2.13 (1H, m), 1.05 (6H, d, J=6.6 Hz)

Reference Example 18

Using 3.3 g of 4-chloromethyl-2-(3-isobutoxy-4-methoxyphenyl)oxazole obtained in Reference Example 17 and following the procedure of Reference Example 6, 4.4 g of white powdery 2-[2-(3-isobutoxy-4-methoxyphenyl)oxazol-4-ylmethyl]isoindolin-1,3-dione was obtained.

$^1$H-NMR ($CDCl_3$) δ: 7.91-7.84 (2H, m), 7.76-7.71 (2H, m), 7.62 (1H, s), 7.55 (1H, dd, J=8.4, 2.1 Hz), 7.49 (1H, d, J=2.1 Hz), 6.88 (1H, d, J=8.4 Hz), 4.85 (2H, s), 3.89 (3H, s), 3.83 (2H, d, J=6.6 Hz), 2.23-2.13 (1H, m), 1.05 (6H, d, J=6.6 Hz)

Reference Example 19

Using 4.4 g of 2-[2-(3-isobutoxy-4-methoxyphenyl)oxazol-4-ylmethyl]isoindolin-1,3-dione obtained in Reference Example 18 and following the procedure of Reference Example 7, 2 g of white solid [2-(3-isobutoxy-4-methoxyphenyl)oxazol-4-yl]methylamine was obtained.

$^1$H-NMR ($CDCl_3$) δ: 7.60-7.51 (3H, m), 6.92 (1H, d, J=8.4 Hz), 3.91 (3H, s), 3.87-3.84 (4H, m), 2.27-2.13 (1H, m), 1.71 (2H, br s), 1.06 (6H, d, J=6.6 Hz)

Reference Example 20

Using 10 g of methyl 3-hydroxy-4-methoxybenzoate obtained in Reference Example 1 and following the procedure of Reference Example 14, 12.5 g of white powdery methyl 4-methoxy-3-(2,2,2-trifluoroethoxy)benzoate was obtained.

$^1$H-NMR ($CDCl_3$) δ: 7.79 (1H, dd, J=8.7, 1.8 Hz), 7.63 (1H, s), 6.94 (1H, d, J=8.7 Hz), 4.42 (2H, q, J=8.1 Hz), 3.94 (3H, s), 3.91 (3H, s)

Reference Example 21

Using 12 g of methyl 4-methoxy-3-(2,2,2-trifluoro ethoxy)benzoate obtained in Reference Example 20 and following the procedure of Reference Example 3, 11.5 g of white powdery 4-methoxy-3-(2,2,2-trifluoroethoxy)benzoic acid was obtained.

$^1$H-NMR ($CDCl_3$) δ: 7.86 (1H, dd, J=8.4, 1.8 Hz), 7.67 (1H, d, J=1.8 Hz), 6.97 (1H, d, J=8.4 Hz), 4.43 (2H, q, J=8.4 Hz), 3.96 (3H, s)

Reference Example 22

Using 11.5 g of 4-methoxy-3-(2,2,2-trifluoroethoxy)benzoic acid obtained in Reference Example 21 and following the procedure of Reference Example 4, 10.8 g of white powdery 4-methoxy-3-(2,2,2-trifluoroethoxy)benzamide was obtained.

$^1$H-NMR ($CDCl_3$) δ: 7.50 (1H, br s), 7.49 (1H, dd, J=8.4, 2.4 Hz), 6.94 (1H, d, J=8.4 Hz), 4.43 (2H, q, J=8.4 Hz), 3.93 (3H, s)

Reference Example 23

Using 10.5 g of 4-methoxy-3-(2,2,2-trifluoroethoxy)benzamide obtained in Reference Example 22 and following the procedure of Reference Example 5, 7.1 g of pale yellow powdery 4-chloromethyl-2-[4-methoxy-3-(2,2,2-trifluoroethoxy)phenyl]oxazole was obtained.

$^1$H-NMR ($CDCl_3$) δ: 7.75 (1H, dd, J=8.4, 2.1 Hz), 7.66 (1H, br s), 7.64 (1H, d, J=2.1 Hz), 6.98 (1H, d, J=8.4 Hz), 4.56 (2H, s), 4.45 (2H, q, J=8.4 Hz), 3.94 (3H, s)

Reference Example 24

Using 3 g of 4-chloromethyl-2-[4-methoxy-3-(2,2,2-trifluoroethoxy)phenyl]oxazole obtained in Reference Example 23 and following the procedure of Reference Example 6, 3.6 g of white powdery 2-{2-[4-methoxy-3-(2,2,2-trifluoroethoxy)phenyl]oxazol-4-ylmethyl}isoindolin-1,3-dione was obtained.

$^1$H-NMR ($CDCl_3$) δ: 7.91-7.85 (2H, m), 7.76-7.64 (3H, m), 7.60 (1H, s), 7.59 (1H, d, J=2.1 Hz), 6.94 (1H, d, J=8.7 Hz), 4.85 (2H, s), 4.43 (2H, q, J=8.4 Hz), 3.91 (3H, s)

Reference Example 25

Using 3.6 g of 2-{2-[4-methoxy-3-(2,2,2-trifluoro ethoxy)phenyl]oxazol-4-ylmethyl}isoindolin-1,3-dione obtained in Reference Example 24 and following the procedure of Reference Example 7, 1.93 g of white powdery {2-[4-methoxy-3-(2,2,2-trifluoroethoxy)phenyl]oxazol-4-yl}methylamine was obtained.

$^1$H-NMR ($CDCl_3$) δ: 7.73 (1H, dd, J=8.4, 2.1 Hz), 7.63 (1H, d, J=2.1 Hz), 7.52 (1H, s), 6.98 (1H, d, J=8.4 Hz), 4.46 (2H, q, J=8.4 Hz), 3.93 (3H, s), 3.83 (2H, s), 1.55 (2H, br s)

Reference Example 26

Using 9.5 g of ethyl vanillate and following the procedure of Reference Example 14, 11 g of white powdery ethyl 3-methoxy-4-(2,2,2-trifluoroethoxy)benzoate was obtained.

$^1$H-NMR ($CDCl_3$) δ: 7.65 (1H, dd, J=8.4, 2.1 Hz), 7.60 (1H, d, J=2.1 Hz), 6.96 (1H, d, J=8.4 Hz), 4.49-4.33 (4H, m), 3.93 (3H, s), 1.39 (3H, t, J=6.9 Hz)

Reference Example 27

A 12 g quantity of ethyl 3-methoxy-4-(2,2,2-trifluoroethoxy)benzoate obtained in Reference Example 26 was suspended in 120 ml of 47% hydrobromic acid, and the suspension was heated and refluxed overnight. The reaction mixture was poured into ice water, and the precipitated crystals were collected by filtration, washed with an excess of water, and then dried under reduced pressure to give 8.4 g of pale red powdery 3-hydroxy-4-(2,2,2-trifluoroethoxy) benzoic acid.

$^1$H-NMR ($CDCl_3$) δ: 7.71-7.66 (2H, m), 6.91 (1H, d, J=5.1 Hz), 5.55 (1H, br s), 4.50 (2H, q, J=7.8 Hz)

Reference Example 28

An 8.4 g quantity of 3-hydroxy-4-(2,2,2-trifluoro ethoxy) benzoic acid obtained in Reference Example 27 was suspended in 150 ml of ethanol, and 0.5 ml of concentrated sulfuric acid was added. The mixture was heated and refluxed overnight. After completion of the reaction, ethanol was distilled off under reduced pressure. The residue was neutralized with saturated aqueous sodium bicarbonate and then extracted with ethyl acetate. After washing with saturated brine twice, the organic layer was separated and concentrated under reduced pressure. The residue was purified by silica gel column chromatography (n-hexane:ethyl acetate=1:1) to give 7.2 g of white crystalline ethyl 3-hydroxy-4-(2,2,2-trifluoroethoxy)benzoate.

$^1$H-NMR ($CDCl_3$) δ: 7.66-7.60 (2H, m), 6.87 (1H, d, J=8.1 Hz), 5.54 (1H, s), 4.48 (2H, q, J=7.8 Hz), 4.35 (2H, q, J=7.2 Hz), 1.38 (3H, t, J=7.2 Hz)

Reference Example 29

Using 7 g of ethyl 3-hydroxy-4-(2,2,2-trifluoro ethoxy) benzoate obtained in Reference Example 28 and following the procedure of Reference Example 14, 8.5 g of white powdery ethyl 3-cyclopropylmethoxy-4-(2,2,2-trifluoroethoxy)benzoate was obtained.

$^1$H-NMR ($CDCl_3$) δ: 7.63 (1H, dd, J=8.7, 2.1 Hz), 7.58 (1H, d, J=2.1 Hz), 7.00 (1H, d, J=8.7 Hz), 4.48 (2H, q, J=8.1 Hz), 4.35 (2H, q, J=6.9 Hz), 3.92 (2H, d, J=7.2 Hz), 1.41-1.25 (4H, m), 0.69-0.60 (2H, m), 0.40-0.32 (2H, m)

Reference Example 30

Using 8.5 g of ethyl 3-cyclopropylmethoxy-4-(2,2,2-trifluoroethoxy)benzoate obtained in Reference Example 29 and following the procedure of Reference Example 3, 7.5 g of white powdery 3-cyclopropylmethoxy-4-(2,2,2-trifluoroethoxy)benzoic acid was obtained.

$^1$H-NMR ($CDCl_3$) δ: 7.71 (1H, dd, J=8.4, 1.8 Hz), 7.63 (1H, d, J=2.1 Hz), 7.02 (1H, d, J=8.1 Hz), 4.51 (2H, q, J=8.1 Hz), 3.93 (2H, d, J=7.2 Hz), 1.37-1.25 (1H, m), 0.69-0.60 (2H, m), 0.41-0.35 (2H, m)

Reference Example 31

Using 7 g of 3-cyclopropylmethoxy-4-(2,2,2-trifluoroethoxy)benzoic acid obtained in Reference Example 30 and following the procedure of Reference Example 4, 7.35 g of white solid 3-cyclopropylmethoxy-4-(2,2,2-trifluoroethoxy) benzamide was obtained.

$^1$H-NMR ($CDCl_3$) δ: 7.48 (1H, d, J=2.1 Hz), 7.28-7.25 (1H, m), 7.01 (1H, d, J=8.4 Hz), 4.48 (2H, q, J=8.4 Hz), 3.93 (2H, d, J=6.9 Hz), 1.37-1.25 (1H, m), 0.69-0.60 (2H, m), 0.41-0.35 (2H, m)

Reference Example 32

Using 5 g of 3-cyclopropylmethoxy-4-(2,2,2-trifluoroethoxy)benzamide obtained in Reference Example 31 and following the procedure of Reference Example 5, 3.1 g of white powdery 4-chloromethyl-2-[3-cyclopropylmethoxy-4-(2,2,2-trifluoroethoxy)phenyl]oxazole was obtained.

$^1$H-NMR ($CDCl_3$) δ: 7.67 (1H, s), 7.59-7.56 (2H, m), 7.05 (1H, d, J=9.0 Hz), 4.56 (2H, s), 4.48 (2H, q, J=8.4 Hz), 1.35-1.26 (1H, m), 0.70-0.63 (2H, m), 0.41-0.35 (2H, m)

Reference Example 33

Using 0.85 g of 4-chloromethyl-2-[3-cyclopropylmethoxy-4-(2,2,2-trifluoroethoxy)phenyl]oxazole obtained in Reference Example 32 and following the procedure of Reference Example 6, 0.6 g of white powdery 2-{2-[3-cyclopropylmethoxy-4-(2,2,2-trifluoroethoxy)phenyl]oxazol-4-ylmethyl}isoindolin-1,3-dione was obtained.

$^1$H-NMR ($CDCl_3$) δ: 7.91-7.84 (2H, m), 7.76-7.69 (2H, m), 7.64 (1H, s), 7.60-7.51 (2H, m), 7.01 (1H, d, J=8.7 Hz), 4.85 (2H, s), 4.46 (2H, q, J=8.4 Hz), 3.93 (2H, d, J=6.9 Hz), 1.35-1.24 (1H, m), 0.68-0.61 (2H, m), 0.40-0.34 (2H, m)

Reference Example 34

Using 0.55 g of 2-{2-[3-cyclopropylmethoxy-4-(2,2,2-trifluoroethoxy)phenyl]oxazol-4-ylmethyl}isoindolin-1,3-dione obtained in Reference Example 33 and following the procedure of Reference Example 7, 0.32 g of white powdery {2-[3-cyclopropyl methoxy-4-(2,2,2-trifluoroethoxy)phenyl]oxazol-4-yl}methylamine was obtained.

$^1$H-NMR ($CDCl_3$) δ: 7.61-7.52 (3H, m), 7.05 (1H, d, J=8.7 Hz), 4.48 (2H, q, J=8.4 Hz), 3.95 (2H, d, J=7.2 Hz), 3.84 (2H, s), 1.56 (2H, br s), 1.35-1.24 (1H, m), 0.70-0.61 (2H, m), 0.41-0.35 (2H, m)

Reference Example 35

Using 20 g of 3,4-diethoxybenzamide and following the procedure of Reference Example 5, 24.5 g of white powdery 4-chloromethyl-2-(3,4-diethoxyphenyl)oxazole was obtained.

$^1$H-NMR ($CDCl_3$) δ: 7.65 (1H, s), 7.58 (1H, dd, J=8.4, 1.8 Hz), 7.54 (1H, d, J=1.8 Hz), 6.92 (1H, d, J=8.4 Hz), 4.56 (2H, s), 4.18 (2H, q, J=6.9 Hz), 4.15 (2H, q, J=6.9 Hz), 1.48 (6H, t, J=6.9 Hz)

Reference Example 36

Using 8 g of 4-chloromethyl-2-(3,4-diethoxyphenyl)oxazole obtained in Reference Example 35 and following the procedure of Reference Example 6, 10 g of white powdery 2-[2-(3,4-diethoxyphenyl)oxazol-4-ylmethyl]isoindolin-1,3-dione was obtained.

$^1$H-NMR ($CDCl_3$) δ: 7.88 (2H, m), 7.72 (2H, m), 7.62 (1H, s), 7.54 (1H, d, J=8.4, 2.1 Hz), 7.50 (1H, d, J=2.1 Hz), 6.88 (1H, d, J=8.4 Hz), 4.85 (2H, s), 4.16 (2H, q, J=6.9 Hz), 4.11 (2H, q, J=6.9 Hz), 1.47 (6H, t, J=6.9 Hz)

Reference Example 37

Using 10 g of 2-[2-(3,4-diethoxyphenyl)oxazol-4-ylmethyl]isoindolin-1,3-dione obtained in Reference Example 36 and following the procedure of Reference Example 7, 5.7 g of white powdery [2-(3,4-diethoxyphenyl)oxazol-4-yl] methylamine was obtained.

$^1$H-NMR ($CDCl_3$) δ: 7.56 (1H, d, J=8.4, 1.8 Hz), 7.54 (1H, d, J=1.8 Hz), 7.51 (1H, s), 6.91 (1H, d, J=8.4 Hz), 4.18 (2H, q, J=6.9 Hz), 4.14 (2H, q, J=6.9 Hz), 1.80 (1H, br s), 3.84 (2H, s), 1.48 (3H, t, J=6.9 Hz), 1.48 (3H, t, J=6.9 Hz)

Reference Example 38

Using 2.0 g of 3,4-dimethoxybenzamide and following the procedure of Reference Example 5, 2.4 g of white powdery 4-chloromethyl-2-(3,4-dimethoxyphenyl)oxazole was obtained.

$^1$H-NMR ($CDCl_3$) δ: 7.66 (1H, s), 7.62 (1H, dd, J=8.4, 1.8 Hz), 7.55 (1H, d, J=1.8 Hz), 6.93 (1H, d, J=8.4 Hz), 4.52 (2H, s), 3.95 (3H, s), 3.91 (3H, s)

Reference Example 39

Using 2.4 g of 4-chloromethyl-2-(3,4-dimethoxyphenyl) oxazole obtained in Reference Example 38 and following the procedure of Reference Example 6, 2.3 g of white powdery 2-[2-(3,4-dimethoxyphenyl)oxazol-4-ylmethyl] isoindolin-1,3-dione was obtained.

Reference Example 40

Using 2.3 g of the 2-[2-(3,4-dimethoxyphenyl)oxazol-4-ylmethyl]isoindolin-1,3-dione obtained in Reference Example 39 and following the procedure of Reference Example 7, 1.3 g of white powdery [2-(3,4-dimethoxyphenyl)oxazol-4-yl]methylamine was obtained. $^1$H-NMR ($CDCl_3$) δ: 7.60 (1H, d, J=8.1, 2.1 Hz), 7.54 (1H, d, J=2.1 Hz), 6.92 (1H, d, J=8.1 Hz), 3.96 (3H, s), 3.93 (3H, s), 3.85 (2H, s), 1.81 (2H, br s)

Reference Example 41

A 9 g quantity of 4-difluoromethoxy-3-hydroxy benzaldehyde was dissolved in 180 ml of acetonitrile, and 13.1 g of potassium carbonate and 8.6 ml of benzyl bromide were added. The mixture was stirred at room temperature for 4 hours. After insolubles were removed by filtration, the filtrate was concentrated and the residue was purified by silica gel column chromatography (n-hexane:ethyl acetate=1:1) to give 11.9 g of colorless oily 3-benzyloxy-4-difluoromethoxybenzaldehyde.

$^1$H-NMR ($CDCl_3$) δ: 10.21 (1H, s), 7.56 (1H, t, J=74.1 Hz), 7.53-7.28 (7H, m), 6.68 (1H, d, J=8.4 Hz), 5.20 (2H, s)

Reference Example 42

A 6 g quantity of 3-benzyloxy-4-difluoromethoxybenzaldehyde obtained in Reference Example 41 was dissolved in 500 ml of acetone, and 17 g of potassium permanganate was added. The mixture was heated and refluxed overnight. After distilling off acetone from the reaction mixture, 100 ml of 5N sodium hydroxide was added to the residue, and insolubles were removed by filtration. Concentrated hydrochloric acid was added to the filtrate to give a pH of about 3, and the precipitated crystals were collected by filtration. The obtained crystals were dried under reduced pressure to give 2.1 g of brownish powdery 3-benzyloxy-4-difluoromethoxybenzoic acid.

$^1$H-NMR ($CDCl_3$) δ: 7.78-7.72 (2H, m), 7.73-7.32 (5H, m), 7.33-7.24 (1H, m), 6.67 (1H, t, J=74.1 Hz), 5.20 (2H, s)

Reference Example 43

A 2 g quantity of 3-benzyloxy-4-difluoromethoxybenzoic acid obtained in Reference Example 42 was suspended in 40 ml of dichloromethane, and one drop of dimethylformamide was added. A 0.7 ml quantity of oxalyl chloride was added dropwise with ice-cooling and stirring. After 2 hours, the reaction mixture was concentrated under reduced pressure. The residue was dissolved in 5 ml of acetone and the resulting solution was added dropwise to 28% aqueous ammonia with ice-cooling and stirring. The obtained mixture was stirred for 1 hour and the precipitated crystals were collected by filtration and dried under reduced pressure to give 1.9 g of white powdery 3-benzyloxy-4-difluoromethoxybenzamide.

$^1$H-NMR ($CDCl_3$) δ: 7.62 (1H, d, J=1.8 Hz), 7.45-7.20 (7H, m), 6.63 (1H, t, J=74.4 Hz), 5.19 (2H, s), 4.73 (2H, br s)

Reference Example 44

A 1.8 g quantity of 3-benzyloxy-4-difluoromethoxybenzamide obtained in Reference Example 43 was suspended in 50 ml of isopropanol, and 1.17 g of 1,3-dichloro-2-propanone was added. The mixture was heated and refluxed overnight. The reaction mixture was concentrated, and the resulting residue was purified by silica gel column chromatography (dichloromethane). The obtained crude crystals were recrystallized from isopropanol to give 0.7 g of white powdery 2-(3-benzyloxy-4-difluoromethoxyphenyl)-4-chloromethyloxazole.

$^1$H-NMR ($CDCl_3$) δ: 7.44 (1H, d, J=1.8 Hz), 7.70 (1H, s), 7.48-7.32 (5H, m), 7.28-7.24 (1H, m), 6.63 (1H, t, J=74.7 Hz), 5.21 (2H, s), 4.57 (2H, s)

Reference Example 45

A 0.37 g quantity of 2-(3-benzyloxy-4-difluoromethoxyphenyl)-4-chloromethyloxazole obtained in Reference Example 44 was dissolved in 20 ml of ethanol, and 0.23 g of sodium iodide and 0.27 g of potassium phthalimide were added. The mixture was heated and refluxed for 4 hours. After the reaction mixture was concentrated, water was added to the residue and extraction with ethyl acetate was performed. The organic layer was washed with water twice and concentrated by removing the solvent and the residue was purified by silica gel column chromatography (dichloromethane:methanol=20:1) to give 0.3 g of white powdery 2-[2-(3-benzyloxy-4-difluoromethoxyphenyl)oxazol-4-ylmethyl]isoindolin-1,3-dione.

$^1$H-NMR ($CDCl_3$) δ: 7.90-7.84 (2H, m), 7.76-7.71 (4H, m), 7.59 (1H, dd, J=8.4, 2.1 Hz), 7.47-7.30 (5H, m), 7.22 (1H, d, J=2.4 Hz), 6.60 (1H, t, J=74.7 Hz), 5.20 (2H, s), 4.87 (2H, s)

Reference Example 46

A 0.3 g quantity of 2-[2-(3-benzyloxy-4-difluoromethoxyphenyl)oxazol-4-ylmethyl]isoindolin-1,3-dione obtained in Reference Example 45 was suspended in 10 ml of ethanol, and 0.1 ml of hydrazine monohydrate was added. The mixture was heated and refluxed for 2 hours. After cooling the reaction mixture, the precipitated insolubles were removed by filtration. The filtrate was concentrated under reduced pressure to give 0.13 g of colorless oily [2-(3-benzyloxy-4-difluoromethoxyphenyl)oxazol-4-yl] methylamine.

$^1$H-NMR ($CDCl_3$) δ: 7.74 (1H, d, J=1.8 Hz), 7.61 (1H, dd, J=7.8, 1.8 Hz), 7.47 (1H, d, J=1.8 Hz), 7.45-7.31 (5H, m), 7.26-7.20 (1H, m), 6.62 (1H, t, J=74.7 Hz), 5.21 (2H, s), 3.85 (2H, br s).

Reference Example 47

A 5.25 g quantity of sodium hydride was suspended in 150 ml of tetrahydrofuran, and a solution of 14.4 g of dimethyl malonate in 75 ml of tetrahydrofuran was added dropwise with ice-cooling over 15 minutes. After stirring for 30 minutes, a solution of 25 g of the 2-(3-benzyloxy-4-methoxyphenyl)-4-chloromethyloxazole obtained in Reference Example 5 in 150 ml of dimethylformamide was added dropwise over 15 minutes. After the dropwise addition, the mixture was stirred at 50 to 60° C. for 4 hours, and an aqueous saturated ammonium chloride solution was added with ice-cooling. After stirring the mixture for 30 minutes, water was added and extraction with ethyl acetate was performed. The extract was dried over anhydrous magnesium sulfate, and the solvent was distilled off. The residue was recrystallized from a mixture of ethyl acetate and diisopropyl ether to give 26.5 g of white powdery dimethyl 2-[2-(3-benzyloxy-4-methoxyphenyl)oxazol-4-ylmethyl] malonate.

$^1$H-NMR (DMSO-$d_6$) δ: 7.89 (1H, s), 7.59-7.31 (7H, m), 7.15 (1H, d, J=7.8 Hz), 5.16 (2H, s), 3.90-3.84 (4H, m), 3.71 (6H, s), 3.04 (2H, d, J=7.8 Hz)

Reference Example 48

A 26.52 g quantity of the dimethyl 2-[2-(3-benzyloxy-4-methoxyphenyl)oxazol-4-ylmethyl]malonate obtained in Reference Example 47 was suspended in 53 ml of dimethyl sulfoxide, and 2.62 g of lithium chloride and 1.12 ml of purified water were added. The mixture was stirred at 130° C. for 4 hours. After the reaction mixture was allowed to cool, water was added and extraction with ethyl acetate was performed. The extract was dried over anhydrous magnesium sulfate, and the solvent was distilled off. The residue was purified by silica gel column chromatography (n-hexane:ethyl acetate=3:1) to give 16 g of white powdery methyl 3-[2-(3-benzyloxy-4-methoxyphenyl)oxazol-4-yl] propionate.

$^1$H-NMR ($CDCl_3$) δ: 7.62-7.59 (2H, m), 7.47 (2H, d, J=6.9 Hz), 7.40-7.31 (4H, m), 6.93 (1H, d, J=8.4 Hz), 5.20 (2H, s), 3.92 (3H, s), 3.69 (3H, s), 2.91 (2H, t, J=7.2 Hz), 2.72 (2H, t, J=7.2 Hz)

Reference Example 49

A 0.48 g quantity of sodium hydride was suspended in 15 ml of tetrahydrofuran, and a solution of 1.31 g of dimethyl malonate in 7.5 ml of tetrahydrofuran was added dropwise over 15 minutes. After the mixture was stirred for 30 minutes, a solution of 3.0 g of 4-chloromethyl-2-[3-cyclopropylmethoxy-4-(2,2,2-trifluoroethoxy)phenyl]oxazole obtained in Reference Example 32 dissolved in 15 ml of dimethylformamide was added over 15 minutes. After the dropwise addition, the mixture was heated at 50 to 60° C. with stirring for 4 hours. An aqueous saturated ammonium chloride solution was added to the reaction mixture with ice-cooling and stirred was continued for 30 minutes. Water was added and extraction with ethyl acetate was performed. The extract was dried over anhydrous magnesium sulfate, and the solvent was distilled off. A 8.0 ml quantity of dimethylsulfoxide, 0.35 g of lithium chloride, and 0.15 ml of purified water were added to the residue, and the mixture was heated with stirring at 130° C. for 4 hours. After the reaction mixture was allowed to cool, water was added and extraction with ethyl acetate was performed. The extract was dried over anhydrous magnesium sulfate and the solvent was distilled off. The residue was purified by silica gel column chromatography (n-hexane:ethyl acetate=4:1) to give 1.63 g of colorless oily methyl 3-{2-[3-cyclopropylmethoxy-4-(2,2,2-trifluoroethoxy)phenyl]oxazol-4-yl}propionate.

$^1$H-NMR ($CDCl_3$) δ: 7.56-7.53 (2H, m), 7.43 (1H, s), 7.04 (1H, d, J=8.4 Hz), 4.47 (2H, q, J=8.4 Hz), 3.94 (2H, d, J=6.6 Hz), 3.69 (3H, s), 2.91 (2H, t, J=7.2 Hz), 2.72 (2H, t, J=7.2 Hz), 0.88 (1H, t, J=6.6 Hz), 0.69-0.65 (2H, m), 0.40-0.35 (2H, m)

Reference Example 50

A 0.5 g quantity of 2-cyclopropylethanol and 3.1 ml of triethylamine were dissolved in 10 ml of ethyl acetate, and 0.75 ml of methanesulfonyl chloride was added with ice-cooling and stirring. After stirring for 30 minutes, water was added to the reaction mixture and extraction was performed. The organic layer was washed with water twice and concentrated by removing the solvent under reduced pressure to give 1 g of pale yellow oily 2-cyclopropylethyl methanesulfonate.

$^1$H-NMR ($CDCl_3$) δ: 4.29 (2H, t, J=6.6 Hz), 3.03 (3H, s), 1.66 (2H, q, J=6.6 Hz), 0.84-0.70 (1H, m), 0.54-0.47 (2H, m), 0.20-0.10 (2H, m)

Reference Example 51

Using 2 g of 2-cyclopentylethanol and following the procedure of Reference Example 50, 3.4 g of pale yellow oily 2-cyclopentylethyl methanesulfonate was obtained.

$^1$H-NMR ($CDCl_3$) δ: 4.24 (2H, t, J=6.6 Hz), 3.03 (3H, s), 1.95-1.73 (5H, m), 1.70-1.48 (4H, m), 1.29-1.06 (2H, m)

Reference Example 52

Using 0.5 g of cyclopentylmethanol and following the procedure of Reference Example 50, 0.7 g of pale yellow oily cyclopentylmethyl methanesulfonate was obtained.

$^1$H-NMR ($CDCl_3$) δ: 4.11 (2H, d, J=6.9 Hz), 3.04 (3H, s), 2.38-2.23 (1H, m), 1.86-1.76 (2H, m), 1.74-1.53 (4H, m), 1.36-1.24 (2H, m)

Reference Example 53

A 25 g quantity of 1-(2-hydroxyphenyl)ethanone and 76 g of potassium carbonate were suspended in 500 ml of acetonitrile, and 31 ml of allyl bromide was added. The mixture was stirred at room temperature for 48 hours. The reaction mixture was filtered to remove insolubles, and the filtrate was concentrated under reduced pressure. The obtained residue was purified by silica gel column chromatography (n-hexane:ethyl acetate=4:1) to give 34 g of pale yellow oily 1-(2-allyloxyphenyl)ethanone.

$^1$H-NMR ($CDCl_3$) δ: 7.73 (1H, dd, J=7.8, 1.8 Hz), 7.46-7.40 (1H, m), 7.02-6.93 (2H, m), 6.15-6.02 (1H, m), 5.47-5.30 (2H, m), 4.66-4.61 (2H, m), 2.64 (3H, s)

Reference Example 54

A 40 g quantity of 3,4-diethoxybenzamide and 80 g of methyl 5-bromo-4-oxopentanoate (containing about 35% of methyl 3-bromo-4-oxopentanoate) were added to 400 ml of dimethylformamide, and the mixture was stirred at 130° C. for 16 hours. The reaction mixture was concentrated under reduced pressure and diluted with ethyl acetate. Ethyl acetate (500 ml) and saturated sodium bicarbonate solution (500 ml) were gradually added with stirring, and stirring was continued. The organic layer was dried over anhydrous magnesium sulfate and then concentrated under reduced pressure. The residue was purified by silica gel column chromatography (ethyl acetate:n-hexane=1:8 to 1:4) to give 18 g of white powdery methyl 3-[2-(3,4-diethoxyphenyl) oxazol-4-yl]propionate.

$^1$H-NMR ($CDCl_3$) δ: 7.65-7.55 (2H, m), 7.51 (1H, s), 6.93 (1H, d, J=8.1 Hz), 4.19 (2H, q, J=6.9 Hz), 4.15 (2H, q, J=6.9 Hz), 3.80 (3H, s), 3.00-2.90 (2H, m), 2.70-2.60 (2H, m), 1.50 (3H, t, J=6.9 Hz), 1.49 (3H, t, J=6.9 Hz)

Reference Example 55

A 37.9 g quantity of 3,4-dibenzyloxybenzamide and 28.8 g of 1,3-dichloro-2-propanone were suspended in 500 ml of propanol, and the suspension was heated and refluxed for 3 days. After cooling, the reaction mixture was concentrated to half its original volume under reduced pressure and 300 ml of diisopropyl ether was added. The precipitated crystals were collected by filtration and recrystallized from acetone-methanol-diisopropyl ether. The obtained crystals were dried under reduced pressure to give 20.1 g of colorless powdery 2-(3,4-bis(benzyloxy)phenyl)-4-chloromethyloxazole.

$^1$H-NMR ($CDCl_3$) δ: 7.66 (1H, d, J=2.1 Hz), 7.64 (1H, s), 7.59 (1H, dd, J=8.4, 2.1 Hz), 7.50-7.28 (10H, m), 6.99 (1H, d, J=8.4 Hz), 5.22 (2H, s), 5.21 (2H, s), 4.55 (2H, s)

Reference Example 56

Using 10 g of 2-(3,4-bis(benzyloxy)phenyl)-4-chloromethyloxazole obtained in Reference Example 55 and following the procedure of Reference Example 47, 12.3 g of colorless oily dimethyl 2-[2-(3,4-bis(benzyloxy)phenyl)oxazol-4-ylmethyl]malonate was obtained.

$^1$H-NMR ($CDCl_3$) δ: 7.61 (1H, d, J=2.1 Hz), 7.58-7.27 (12H, m), 6.97 (1H, d, J=8.4 Hz), 5.23-5.20 (4H, m), 3.89 (1H, t, J=7.5 Hz), 3.75 (3H, s), 3.73 (3H, s), 3.18 (2H, d, J=7.5 Hz)

Reference Example 57

Using 12.3 g of dimethyl 2-[2-(3,4-bis(benzyloxy)phenyl) oxazol-4-ylmethyl]malonate obtained in Reference Example 56 and following the procedure of Reference Example 48, 4 g of pale red powdery methyl 3-[2-(3,4-bis (benzyloxy)phenyl)oxazol-4-yl]propionate was obtained.

$^1$H-NMR ($CDCl_3$) δ: 7.63 (1H, d, J=2.1 Hz), 7.57-7.27 (12H, m), 6.97 (1H, d, J=8.4 Hz), 5.21 (2H, d, J=7.2 Hz), 3.69 (3H, s), 2.90 (2H, t, J=7.2 Hz), 2.72 (2H, d, J=7.2 Hz)

Reference Example 58

Using 29.4 g of 3-ethoxy-4-methoxybenzamide and 57 g of 1,3-dichloro-2-propanone and following the procedure of Reference Example 55, 19.9 g of white powdery 4-chloromethyl-2-(3-ethoxy-4-methoxyphenyl)oxazole was obtained.

$^1$H-NMR ($CDCl_3$) δ: 7.65 (1H, s), 7.61 (1H, dd, J=8.1, 2.1 Hz), 7.55 (1H, d, J=2.1 Hz), 6.92 (1H, d, J=8.1 Hz), 4.56 (2H, s), 4.18 (2H, q, J=6.9 Hz), 3.93 (3H, s), 1.50 (3H, t, J=6.9 Hz)

Reference Example 59

A 25 g quantity of ethyl 3,4-dihydroxybenzoate was dissolved in 250 ml of dimethylformamide, and 5.5 g of sodium hydride was added with ice-cooling and stirring. The mixture was stirred, and a solution of 16.3 ml of benzylbromide in 10 ml of dimethylformamide was added dropwise. After the dropwise addition, the mixture was stirred at room temperature overnight. Water was added to the reaction mixture and extraction with ethyl acetate was performed. The organic layer was washed with water twice and concentrated by removing the solvent under reduced pressure. The obtained residue was purified by silica gel column chromatography (n-hexane:ethyl acetate=2:1) to give 15 g of crude crystals. The crude crystals were recrystallized from a mixture of 30 ml of n-hexane and 15 ml of ethyl acetate to give 8.6 g of colorless plate crystalline ethyl 4-benzyloxy-3-hydroxybenzonate.

$^1$H-NMR ($CDCl_3$) δ: 7.67-7.47 (2H, m), 7.41-7.30 (5H, m), 6.94 (1H, d, J=8.7 Hz), 5.67 (1H, s), 5.16 (2H, s), 4.34 (2H, q, J=7.2 Hz), 1.37 (3H, t, J=7.2 Hz)

Reference Example 60

Using ethyl 4-benzyloxy-3-hydroxybenzonate obtained in Reference Example 59 and following the procedure of Reference Example 2, ethyl 4-benzyloxy-3-ethoxybenzoate was obtained.

$^1$H-NMR ($CDCl_3$) δ: 7.61-7.55 (2H, m), 7.45-7.27 (5H, m), 6.90 (1H, d, J=8.1 Hz), 5.21 (2H, s), 4.34 (2H, q, J=6.9 Hz), 4.17 (2H, q, J=6.9 Hz), 1.48 (3H, t, J=6.9 Hz), 1.37 (3H, t, J=6.9 Hz)

Reference Example 61

Using ethyl 4-benzyloxy-3-ethoxybenzoate obtained in Reference Example 60 and following the procedure of Reference Example 3,4-benzyloxy-3-ethoxybenzoic acid was obtained.

$^1$H-NMR ($CDCl_3$) δ: 7.68 (1H, dd, J=8.4, 1.2 Hz), 7.61 (1H, d, J=1.2 Hz), 7.45-7.28 (5H, m), 6.92 (1H, d, J=8.4 Hz), 5.23 (2H, s), 4.17 (2H, q, J=6.9 Hz), 1.48 (3H, t, J=6.9 Hz)

Reference Example 62

Using 4-benzyloxy-3-ethoxybenzoic acid obtained in Reference Example 61 and following the procedure of Reference Example 4, colorless needle crystalline 4-benzyloxy-3-ethoxybenzamide was obtained.

$^1$H-NMR ($CDCl_3$) δ: 7.47-7.21 (7H, m), 6.88 (1H, d, J=8.1 Hz), 5.21 (2H, s), 4.18 (2H, q, J=7.2 Hz), 1.48 (3H, t, J=7.2 Hz)

Reference Example 63

Using 4-benzyloxy-3-ethoxybenzamide obtained in Reference Example 62 and following the procedure of Reference Example 5, colorless powdery 4-chloromethyl-2-(4-benzyloxy-3-ethoxyphenyl)oxazole was obtained.

$^1$H-NMR ($CDCl_3$) δ: 7.64 (1H, s), 7.57-7.30 (7H, m), 6.94 (1H, d, J=8.4 Hz), 5.20 (2H, s), 4.56 (2H, s), 4.20 (2H, q, J=7.2 Hz), 1.49 (3H, t, J=7.2 Hz)

Reference Example 64

A 6.81 g quantity of sodium iodide and 5.09 g of sodium bicarbonate were added to a suspension of 10 g of 2-(3-benzyloxy-4-methoxyphenyl)-4-chloromethyloxazole obtained in Reference Example 5 in 60 ml of dimethylsulfoxide. The mixture was heated at 120° C. with stirring for 30 minutes. After the reaction mixture was allowed to cool, saturated brine was added and extraction with ethyl acetate was performed. The organic layer was washed with saturated brine and dried over anhydrous magnesium sulfate, and the solvent was then distilled off under reduced pressure. The obtained residue was purified by silica gel column chromatography (n-hexane:ethyl acetate=3:1) to give 2.98 g of yellow oily 2-(3-benzyloxy-4-methoxyphenyl)oxazole-4-carbaldehyde.

$^1$H-NMR ($CDCl_3$) δ: 9.98 (1H, s), 8.26 (1H, s), 7.71 (1H, dd, J=8.1, 2.1 Hz), 7.69 (1H, br s), 7.48 (2H, br d, J=8.4 Hz), 7.42-7.31 (3H, m), 6.98 (1H, d, J=8.1 Hz), 5.21 (2H, s), 3.95 (3H, s)

Reference Example 65

Using 4-chloromethyl-2-[4-methoxy-3-(2,2,2-trifluoroethoxy)phenyl]oxazole obtained in Reference Example 23 and following the procedure of Reference Example 64, colorless powdery 2-[4-methoxy-3-(2,2,2-trifluoroethoxy) phenyl]oxazole-4-carbaldehyde was obtained.

$^1$H-NMR ($CDCl_3$) δ: 9.99 (1H, s), 8.28 (1H, s), 7.82 (1H, dd, J=8.4, 2.1 Hz), 7.71 (1H, d, J=2.1 Hz), 7.01 (1H, d, J=8.4 Hz), 4.46 (2H, q, J=8.4 Hz), 3.95 (3H, s)

Reference Example 66

Using 4-chloromethyl-2-(3,4-diethoxyphenyl)oxazole obtained in Reference Example 35 and following the procedure of Reference Example 64, pale yellow powdery 2-(3,4-diethoxyphenyl)oxazole-4-carbaldehyde was obtained.

$^1$H-NMR ($CDCl_3$) δ: 9.99 (1H, s), 8.26 (1H, s), 7.65 (1H, dd, J=8.4, 2.1 Hz), 7.62 (1H, d, J=2.1 Hz), 6.94 (1H, d, J=8.4 Hz), 4.19 (2H, q, J=7.2 Hz), 4.17 (2H, q, J=7.2 Hz), 1.50 (6H, t, J=7.2 Hz)

Reference Example 67

Using 12.7 g of 3-isopropoxy-4-methoxybenzoic acid and following the procedure of Reference Example 4, white powdery 3-isopropoxy-4-methoxybenzamide was obtained.

$^1$H-NMR ($CDCl_3$) δ: 7.46 (1H, d, J=2.1 Hz), 7.34 (1H, dd, J=8.4, 2.1 Hz), 6.87 (1H, d, J=8.4 Hz), 5.93 (1H, br s), 4.62 (1H, m), 3.90 (3H, s), 1.38 (6H, d, J=6.0 Hz).

Reference Example 68

Using 11.4 g of 3-isopropoxy-4-methoxybenzamide obtained in Reference Example 67 and 25 g of 1,3-dichloro-2-propanone and following the procedure of Reference Example 5, 12.2 g of white powdery 4-chloromethyl-2-(3-isopropoxy-4-methoxyphenyl)oxazole was obtained.

$^1$H-NMR ($CDCl_3$) δ: 7.65 (1H, s), 7.61 (1H, dd, J=8.4, 2.1 Hz), 7.57 (1H, d, J=2.1 Hz), 6.93 (1H, d, J=8.4 Hz), 4.64 (1H, m), 4.53 (2H, s), 3.90 (3H, s), 1.40 (6H, d, J=6.0 Hz)

Reference Example 69

Using 4-chloromethyl-2-(3-isopropoxy-4-methoxyphenyl) oxazole obtained in Reference Example 68 and following the procedure of Reference Example 64, pale yellow powdery 2-(3-isopropoxy-4-methoxyphenyl)oxazole-4-carbaldehyde was obtained.

$^1$H-NMR ($CDCl_3$) δ: 9.99 (1H, s), 8.27 (1H, s), 7.68 (1H, dd, J=8.1, 2.1 Hz), 7.64 (1H, d, J=2.1 Hz), 6.95 (1H, d, J=8.1 Hz), 4.67 (1H, sept., J=6.3 Hz), 3.92 (3H, s), 1.41 (6H, d, J=6.3 Hz)

Reference Example 70

A 10 g quantity of 1-(2-hydroxyphenyl)ethanone was dissolved in 100 ml of dimethylformamide, and 11.2 ml of chloromethyl methyl ether and 25.4 g of potassium carbonate were added. The mixture was stirred at 50° C. for 6 hours and then at room temperature for 4 days. After insolubles were removed from the reaction mixture by filtration, ice water was added to the filtrate and extraction with ethyl acetate was performed. The organic layer was washed with water and dried over anhydrous magnesium sulfate. The organic layer was concentrated under reduced pressure, and the residue was purified by silica gel column chromatography (n-hexane:ethyl acetate=5:1) to give 6.26 g of colorless oily 1-(2-methoxymethoxyphenyl)ethanone.

$^1$H-NMR ($CDCl_3$) δ: 7.71 (1H, dd, J=7.8, 1.8 Hz), 7.43 (1H, td, J=7.8, 1.8 Hz), 7.18 (1H, d, J=7.8 Hz), 7.05 (1H, t, J=7.8 Hz), 5.28 (2H, s), 3.52 (3H, s), 2.64 (3H, s)

Reference Example 71

A 3 g quantity of methyl 3-[2-(3,4-diethoxyphenyl)oxazol-4-yl]propionate obtained in Reference Example 54 was suspended in 5 ml of methanol, and 5 ml of a 20% aqueous sodium hydroxide solution was added. The mixture was heated and refluxed for 4 hours. After cooling the reaction mixture to room temperature, extraction with dichloromethane was performed. The dichloromethane layer was washed with water and dried over anhydrous magnesium sulfate. The solvent was distilled off and the obtained crystals were dried to give 2.8 g of white powdery 3-[2-(3,4-dimethoxyphenyl)oxazol-4-yl]propionic acid.

$^1$H-NMR ($CDCl_3$) δ: 7.65-7.55 (3H, m), 7.51 (1H, d, J=2.1 Hz), 6.91 (1H, d, J=8.4 Hz), 4.17 (2H, q, J=6.9 Hz), 4.15 (2H, q, J=6.9 Hz), 3.00-2.90 (2H, m), 2.90-2.80 (2H, m), 1.48 (3H, t, J=6.9 Hz), 1.48 (3H, t, J=6.9 Hz)

Reference Example 72

Using 10 g of 4-benzyloxy-3-methoxybenzamide and following the procedure of Reference Example 54, 2 g of white powdery methyl 3-[2-(4-benzyloxy-3-methoxyphenyl)oxazol-4-yl]propionate was obtained.

$^1$H-NMR ($CDCl_3$) δ: 7.54-7.28 (8H, m) 6.93 (1H, d, J=8.1 Hz), 5.20 (2H, s), 3.97 (3H, s), 3.68 (3H, s), 2.91 (2H, t, J=7.5 Hz), 2.64 (2H, t, J=7.5 Hz)

Reference Example 73

Using 2 g of methyl 3-[2-(4-benzyloxy-3-methoxyphenyl)oxazol-4-yl]propionate obtained in Reference Example 72 and following the procedure of Reference Example 71, 1.03 g of white powdery 3-[2-(4-benzyloxy-3-methoxyphenyl)oxazol-4-yl]propionic acid was obtained.

$^1$H-NMR ($CDCl_3$) δ: 12.20 (1H, s), 7.86 (1H, s), 7.51-7.31 (7H, m) 7.17 (1H, d, J=8.4 Hz), 5.15 (2H, s), 3.85 (3H, s), 2.75 (2H, t, J=7.5 Hz), 2.59 (2H, t, J=7.5 Hz)

Reference Example 74

A 0.4 g quantity of 4-chloromethyl-2-(3,4-diethoxy phenyl)oxazole obtained in Reference Example 35 was dissolved in 15 ml of methylamine (40% methanol solution), and was heated and refluxed for 1 hour. The reaction mixture was concentrated and the obtained residue was dried under reduced pressure to give 0.23 g of yellow oily [2-(3,4-dimethoxyphenyl)oxazol-4-ylmethyl]methylamine.

$^1$H-NMR ($CDCl_3$) δ: 8.00 (1H, s), 7.58-7.50 (2H, m), 6.90 (1H, d, J=8.4 Hz), 4.21-4.10 (6H, m), 2.76 (3H, s), 1.51-1.45 (6H, m)

Reference Example 75

Using ethyl 2-chloroacetoacetate and 16 g of 3,4-diethoxybenzamide and following the procedure of Reference Example 5, 3.8 g of ethyl [2-(3,4-dimethoxyphenyl)oxazol-4-yl]acetate was obtained.

$^1$H-NMR ($CDCl_3$) δ: 7.64 (1H, s), 7.60-7.50 (2H, m), 6.91 (1H, d, J=8.1 Hz), 4.25-4.10 (6H, m), 3.58 (2H, s), 1.50-1.40 (6H, m), 1.29 (3H, t, J=6.9 Hz)

Reference Example 76

A 0.35 g quantity of lithium aluminum hydride was added to 30 ml of tetrahydrofuran with ice-cooling and stirring, and ethyl [2-(3,4-dimethoxyphenyl)oxazol-4-yl]acetate obtained in Reference Example 75 was slowly added with stirring. After stirring at room temperature for 3 hours, the mixture was stirred with ice-cooling for 3 hours, and 0.35 ml of water, 0.35 ml of a 15% aqueous sodium hydroxide solution, and 1.05 ml of water were added in that order. The reaction mixture was dried over anhydrous magnesium sulfate, and insolubles were then removed by filtration. The filtrate was concentrated under reduced pressure to give 2.5 g of colorless crystalline 2-[2-(3,4-dimethoxyphenyl)oxazol-4-yl] ethanol.

$^1$H-NMR ($CDCl_3$) δ: 7.56 (1H, d, J=8.4, 2.1 Hz), 7.52 (1H, d, J=2.1 Hz), 7.46 (1H, s), 6.91 (1H, d, J=8.4 Hz), 4.17 (2H, q, J=7.2 Hz), 4.15 (2H, q, J=7.2 Hz), 3.94 (2H, q, J=5.4 Hz), 2.94 (1H, t, J=5.4 Hz), 2.81 (2H, t, J=5.4 Hz), 1.48 (3H, t, J=7.2 Hz), 1.48 (3H, t, J=7.2 Hz)

Reference Example 77

A 2.0 g quantity of 2-[2-(3,4-dimethoxyphenyl)oxazol-4-yl]ethanol obtained in Reference Example 76 and 2.3 g of triphenylphosphine were added to 20 ml of dichloromethane, and 2.9 g of carbon tetrabromide was slowly added with ice-cooling and stirring. After the temperature of the mixture had reached room temperature, stirring was continued for 1.5 hours. The reaction mixture was concentrated, and the residue was purified by silica gel column chromatography (n-hexane:ethyl acetate=8:1) to give 1.9 g of colorless crystalline 4-(2-bromoethyl)-2-(3,4-diethoxyphenyl)oxazole.

$^1$H-NMR ($CDCl_3$) δ: 7.60-7.50 (3H, m), 6.91 (1H, d, J=8.4 Hz), 4.18 (2H, q, J=7.2 Hz), 4.14 (2H, q, J=7.2 Hz), 3.67 (2H, t, J=6.9 Hz), 3.14 (2H, t, J=6.9 Hz), 1.48 (3H, t, J=7.2 Hz), 1.48 (3H, t, J=7.2 Hz)

Reference Example 78

Using 1.5 g of 4-(2-bromoethyl)-2-(3,4-diethoxyphenyl) oxazole obtained in Reference Example 77 and following the procedures of Reference Examples 6 and 7, 0.8 g of yellow oily 2-[2-(3,4-diethoxyphenyl)oxazol-4-yl]ethylamine was obtained.

$^1$H-NMR ($CDCl_3$) δ: 7.60-7.50 (3H, m), 6.91 (1H, d, J=8.4 Hz), 4.17 (2H, q, J=7.2 Hz), 4.15 (2H, q, J=7.2 Hz), 3.90-3.80 (2H, m), 3.00-2.90 (2H, m), 1.85 (2H, brs), 1.48 (3H, t, J=7.2 Hz), 1.48 (3H, t, J=7.2 Hz)

Reference Example 79

Using 10.4 g of 3,4-diethoxybenzamide and 19.5 g of ethyl 3-bromo-2-oxopropionate and following the procedure of Reference Example 5, 12.9 g of white powdery ethyl 2-(3,4-diethoxyphenyl)oxazole-4-carboxylate was obtained.

$^1$H-NMR ($CDCl_3$) δ: 8.21 (1H, d, J=0.9 Hz), 7.64 (1H, dd, J=8.1, 0.9 Hz), 7.63 (1H, s), 6.92 (1H, d, J=8.1 Hz), 4.42 (2H, q, J=7.2 Hz), 4.17 (2H, q, J=6.9 Hz), 4.15 (2H, q, J=6.9 Hz), 1.48 (3H, t, J=6.9 Hz), 1.41 (3H, t, J=7.2 Hz)

Reference Example 80

Using 10 g of the ethyl 2-(3,4-diethoxyphenyl)oxazole-4-carboxylate obtained in Reference Example 79 and following the procedure of Reference Example 71, 8.6 g of white powdery 2-(3,4-diethoxyphenyl)oxazole-4-carboxylic acid was obtained.

$^1$H-NMR ($CDCl_3$) δ: 8.24 (1H, s), 7.60-7.50 (3H, m), 6.02 (1H, brs), 4.13 (4H, q, J=6.9 Hz), 1.46 (3H, t, J=6.9 Hz), 1.39 (3H, t, J=6.9 Hz)

Reference Example 81

Using 0.4 g of ethyl [2-(3,4-diethoxyphenyl)oxazol-4-yl] acetate obtained in Reference Example 75 and following the procedure of Reference Example 71, 0.35 g of white powdery [2-(3,4-diethoxyphenyl)oxazol-4-yl]acetic acid was obtained.

$^1$H-NMR ($CDCl_3$) δ: 7.65-7.55 (3H, m), 7.51 (1H, d, J=2.1 Hz), 6.91 (1H, d, J=8.4 Hz), 4.17 (2H, q, J=6.9 Hz), 4.15 (2H, q, J=6.9 Hz), 3.73 (2H, s), 1.49 (6H, t, J=6.9 Hz)

Reference Example 82

Using 3 g of 4-chloromethyl-2-[4-methoxy-3-(2,2,2-trifluoroethoxy)phenyl]oxazole obtained in Reference Example 23 and following the procedure of Reference Example 47, 1.91 g of colorless oily dimethyl 2-{2-[4-methoxy-3-(2,2,2-trifluoroethoxy)phenyl]oxazol-4-ylmethyl}malonate was obtained.

$^1$H-NMR ($CDCl_3$) δ: 7.70 (1H, dd, J=8.4, 2.1 Hz), 7.60 (1H, d, J=2.1 Hz), 7.42 (1H, s), 6.96 (1H, d, J=8.4 Hz), 4.44 (2H, q, J=6.9 Hz), 3.93 (3H, s), 3.89 (1H, t, J=7.5 Hz), 3.18 (2H, d, J=7.5 Hz)

Reference Example 83

Using 1.9 g of dimethyl 2-{2-[4-methoxy-3-(2,2,2-trifluoroethoxy)phenyl]oxazol-4-ylmethyl}malonate obtained in Reference Example 82 and following the procedure of Reference Example 48, 1.44 g of colorless oily methyl 3-{2-[4-methoxy-3-(2,2,2-trifluoroethoxy)phenyl]oxazol-4-yl}propionate was obtained.

$^1$H-NMR ($CDCl_3$) δ: 7.70 (1H, dd, J=8.4, 2.1 Hz), 7.60 (1H, d, J=2.1 Hz), 7.42 (1H, s), 6.96 (1H, d, J=8.4 Hz), 4.45 (2H, q, J=6.9 Hz), 3.92 (3H, s), 3.75 (3H, s), 2.91 (2H, t, J=7.5 Hz), 2.72 (2H, t, J=7.5 Hz)

Example 1

A 3.5 g quantity of the [2-(3-benzyloxy-4-methoxy phenyl)oxazol-4-yl]methylamine obtained in Reference Example 7 was suspended in 70 ml of acetone. To the obtained suspension were added 2.3 g of 1-hydroxybenzotriazole, 3.3 g of 1-ethyl-3-(3-dimethylaminopropyl)carbodiimide hydrochloride and 3.8 g of 2-ethoxybenzoic acid, and the mixture was heated and refluxed for one hour. The reaction mixture was cooled, and acetone was distilled off under reduced pressure. Water was added to the residue, and extraction was then performed with ethyl acetate. The organic layer was washed with water twice, and concentrated under reduced pressure. The obtained residue was purified by silica gel column chromatography (dichloromethane:methanol=20:1) to give 4.6 g of white powdery N-[2-(3-benzyloxy-4-methoxyphenyl)oxazol-4-ylmethyl]-2-ethoxybenzamide.

$^1$H-NMR ($CDCl_3$) δ: 8.55 (1H, br s) 8.23 (1H, dd, J=7.8, 1.8 Hz), 7.65-7.61 (3H, m), 7.49-7.29 (6H, m), 7.09 (1H, t, J=7.5 Hz), 7.04-6.92 (2H, m), 5.20 (2H, s), 4.61 (2H, d, J=5.4 Hz), 4.16 (2H, q, J=6.9 Hz), 3.93 (3H, s), 1.26 (3H, t, J=6.9 Hz)

Example 2

A 4.65 g quantity of the N-[2-(3-benzyloxy-4-methoxyphenyl)oxazol-4-ylmethyl]-2-ethoxybenzamide obtained in Example 1 was dissolved in 90 ml of ethanol, and 0.45 g of 10% palladium carbon powder was added thereto. The mixture was stirred in a hydrogen atmosphere at room temperature for one hour. The catalyst was removed by filtration, and the filtrate was then concentrated under reduced pressure to give 3.7 g of white crystalline N-[2-(3-hydroxy-4-methoxyphenyl)oxazol-4-ylmethyl]-2-ethoxybenzamide.

$^1$H-NMR ($CDCl_3$) δ: 8.58 (1H, br s) 8.23 (1H, dd, J=7.8, 1.8 Hz), 7.62-7.55 (3H, m), 7.41 (1H, td, J=7.5 Hz, 1.8 Hz), 7.06 (1H, t, J=7.2 Hz), 6.95-6.88 (2H, m), 5.74 (1H, s), 4.62 (2H, d, J=5.1 Hz), 4.17 (2H, q, J=6.9 Hz), 3.95 (3H, s), 1.47 (3H, t, J=6.9 Hz)

Example 3

A 0.2 g quantity of the N-[2-(3-hydroxy-4-methoxy phenyl)oxazol-4-ylmethyl]-2-ethoxybenzamide obtained in Example 2 and 0.3 ml of 1,8-diazabicyclo[5,4,0]undec-7-ene were dissolved in 4 ml of ethanol, and 0.14 g of (bromomethyl)cyclopropane was added thereto. The mixture was heated and refluxed overnight. The reaction mixture was allowed to cool, water was then added thereto, and extraction was performed with ethyl acetate. After washing with water twice, the organic layer was concentrated under reduced pressure. The obtained residue was purified by silica gel column chromatography (n-hexane:ethyl acetate=3:1) to give 0.18 g of white powdery N-[2-(3-cyclopropylmethoxy-4-methoxyphenyl)oxazol-4-ylmethyl]-2-ethoxybenzamide.

$^1$H-NMR ($CDCl_3$) δ: 8.55 (1H, br s) 8.24 (1H, dd, J=7.8, 2.1 Hz), 7.62-7.59 (2H, m), 7.53 (1H, d, J=2.1 Hz), 7.45-7.39 (1H, m), 7.07 (1H, td, J=8.1 Hz, 1.2 Hz), 6.95-6.91 (2H, m), 4.62 (2H, d, J=5.4 Hz), 4.18 (2H, q, J=6.9 Hz), 3.94-3.92 (5H, m), 1.49 (3H, t, J=6.9 Hz), 1.42-1.34 (1H, m), 0.71-0.64 (2H, m), 0.41-0.35 (2H, m)

Example 4

A 0.3 g quantity of the N-[2-(3-hydroxy-4-methoxy phenyl)oxazol-4-ylmethyl]-2-ethoxybenzamide obtained in Example 2 and 0.22 g of potassium carbonate were dissolved in 10 ml of dimethylformamide, and 0.34 g of 1,1,1-trifluoro-2-iodoethane was added thereto. The mixture was stirred with heating at 50° C. overnight. The reaction mixture was allowed to cool, water was then added thereto, and extraction was performed with ethyl acetate. After washing with water twice, the organic layer was concentrated under reduced pressure. The obtained residue was purified by silica gel column chromatography (n-hexane: ethyl acetate=3:1) to give 0.14 g of white powdery N-{2-[4-methoxy-3-(2,2,2-trifluoroethoxy)phenyl]oxazol-4-ylmethyl}-2-ethoxybenzamide.

$^1$H-NMR ($CDCl_3$) δ: 8.56 (1H, br s) 8.24 (1H, dd, J=7.8, 2.1 Hz), 7.73 (1H, dd, J=8.4, 2.1 Hz), 7.65-7.63 (2H, m), 7.45-7.39 (1H, m), 7.09-7.01 (1H, m), 6.99-6.90 (2H, m), 4.62 (2H, d, J=5.4 Hz), 4.55 (2H, q, J=8.4 Hz), 4.32 (2H, q, J=6.9 Hz), 3.93 (3H, s), 1.49 (3H, t, J=6.9 Hz)

Using 0.2 g of the N-[2-(3-hydroxy-4-methoxyphenyl)oxazol-4-ylmethyl]-2-ethoxybenzamide obtained in Example 2, compounds of Examples 5 to 14 were obtained in the same manner as in Example 3.

Example 5

N-[2-(3-butoxy-4-methoxyphenyl)oxazol-4-ylmethyl]-2-ethoxy benzamide

Yield 0.2 g
White Powder $^1$H-NMR ($CDCl_3$) δ: 8.56 (1H, br s) 8.24 (1H, dd, J=7.8, 2.1 Hz), 7.62-7.54 (3H, m), 7.45-7.39 (1H, m), 7.07 (1H, t, J=8.1 Hz), 6.96-6.90 (2H, m), 4.62 (2H, d, J=5.4 Hz), 4.18 (2H, q, J=6.9 Hz), 4.10 (2H, t, J=6.9 Hz), 3.92 (3H, s), 1.92-1.82 (2H, m), 1.59-1.47 (5H, m) 1.00 (3H, t, J=7.5 Hz)

Example 6

N-[2-(3-cyclopentyloxy-4-methoxyphenyl)oxazol-4-ylmethyl]-2-ethoxybenzamide

Yield 0.22 g
Colorless Oily Substance $^1$H-NMR ($CDCl_3$) δ: 8.57 (1H, br s) 8.24 (1H, dd, J=7.8, 2.1 Hz), 7.62-7.54 (3H, m), 7.45-7.39 (1H, m), 7.07 (1H, t, J=8.1 Hz), 6.96-6.90 (2H, m), 4.91-4.86 (1H, m), 4.62 (2H, d, J=5.4 Hz), 4.17 (2H, q, J=6.9 Hz), 3.90 (3H, s), 2.02-1.60 (8H, m), 1.49 (3H, t, J=6.9 Hz)

Example 7

N-{2-[3-(3-hydroxypropoxy)-4-methoxyphenyl]oxazol-4-ylmethyl}-2-ethoxybenzamide

Yield 0.12 g
White Powder $^1$H-NMR ($CDCl_3$) δ: 8.56 (1H, br s) 8.24 (1H, d, J=7.8 Hz), 7.62-7.54 (3H, m), 7.45-7.39 (1H, m), 7.09-7.06 (1H, m), 6.96-6.90 (2H, m), 4.62 (2H, d, J=5.4 Hz), 4.29-4.16 (4H, m), 3.92-3.79 (5H, m), 2.57 (1H, br s), 2.12 (2H, t, J=5.4 Hz), 1.49 (3H, t, J=6.9 Hz)

Example 8

N-[2-(4-methoxy-3-(2-propynyloxy)phenyl)oxazol-4-ylmethyl]-2-ethoxybenzamide

Yield 0.19 g
White Powder $^1$H-NMR ($CDCl_3$) δ: 8.58 (1H, br s) 8.24 (1H, dd, J=7.8, 1.8 Hz), 7.70-7.63 (3H, m), 7.45-7.39 (1H, m), 7.07 (1H, td, J=8.4, 0.9 Hz), 6.98-6.93 (2H, m), 4.84 (2H, d, J=2.4 Hz), 4.63 (2H, dd, J=5.4, 0.9 Hz), 4.19 (2H, q, J=7.2 Hz), 3.94 (3H, s), 2.54 (1H, t, J=2.4 Hz), 1.50 (3H, t, J=7.2 Hz)

Example 9

N-[2-(3-ethoxy-4-methoxyphenyl)oxazol-4-ylmethyl]-2-ethoxy benzamide

Yield 0.22 g
White Powdery
$^1$H-NMR ($CDCl_3$) δ: 8.55 (1H, br s) 8.24 (1H, dd, J=7.8, 1.8 Hz), 7.62-7.54 (3H, m), 7.44-7.39 (1H, m), 7.07 (1H, t, J=8.1 Hz), 6.96-6.91 (2H, m), 4.62 (2H, d, J=5.4 Hz), 4.23-4.14 (4H, m), 3.93 (3H, s), 1.53-1.46 (6H, m)

Example 10

N-[2-(4-methoxy-3-(2-oxiranylmethoxy)phenyl) oxazol-4-ylmethyl]-2-ethoxybenzamide Yield 27 mg
White Powder
$^1$H-NMR ($CDCl_3$) δ: 8.54 (1H, br s) 8.24 (1H, dd, J=7.8, 1.8 Hz), 7.67-7.58 (3H, m), 7.45-7.38 (1H, m), 7.07 (1H, t, J=7.8 Hz), 6.95 (2H, d, J=8.4 Hz), 4.62 (2H, d, J=5.1 Hz), 4.36-4.07 (4H, m), 3.93 (3H, s), 3.46-3.41 (1H, m), 2.92 (1H, t, J=4.5 Hz), 2.80-2.76 (1H, m), 1.48 (3H, t, J=7.2 Hz)

Example 11

N-[2-(4-methoxy-3-propoxyphenyl)oxazol-4-ylmethyl]-2-ethoxy benzamide

Yield 0.19 g
White Powder
$^1$H-NMR ($CDCl_3$) δ: 8.56 (1H, br s) 8.24 (1H, dd, J=7.8, 1.8 Hz), 7.63-7.54 (3H, m), 7.45-7.39 (1H, m), 7.07 (1H, td, J=8.4, 1.2 Hz), 6.96-6.91 (2H, m), 4.63 (2H, dd, J=5.1, 0.9 Hz), 4.18 (2H, q, J=6.9 Hz), 4.06 (2H, t, J=6.9 Hz), 3.92 (3H, s), 1.97-1.85 (2H, m), 1.49 (3H, t, J=6.9 Hz), 1.07 (3H, t, J=7.2 Hz)

Example 12

N-[2-(3-isopropoxy-4-methoxyphenyl)oxazol-4-ylmethyl]-2-ethoxy benzamide

Yield 0.17 g
White Powder
$^1$H-NMR ($CDCl_3$) δ: 8.57 (1H, br s) 8.24 (1H, dd, J=7.8, 1.8 Hz), 7.62-7.55 (3H, m), 7.45-7.38 (1H, m), 7.07 (1H, t, J=7.8 Hz), 6.96-6.91 (2H, m), 4.72-4.59 (3H, m), 4.18 (2H, q, J=6.9 Hz), 3.91 (3H, s), 1.49 (3H, t, J=6.9 Hz), 1.41 (6H, d, J=6.3 Hz)

Example 13

N-[2-(3-(3-butenyloxy)-4-methoxyphenyl)oxazol-4-ylmethyl]-2-ethoxybenzamide

Yield 0.21 g
White Powder
$^1$H-NMR ($CDCl_3$) δ: 8.56 (1H, br s) 8.23 (1H, dd, J=7.8, 1.8 Hz), 7.63-7.55 (3H, m), 7.45-7.38 (1H, m), 7.07 (1H, t, J=7.8 Hz), 6.96-6.91 (2H, m), 5.97-5.88 (1H, m), 5.23-5.10 (2H, m), 4.62 (2H, dd, J=5.1, 0.9 Hz), 4.21-4.12 (4H, m), 3.92 (3H, s), 2.68-2.60 (2H, m), 1.49 (3H, t, J=6.9 Hz)

Example 14

N-[2-(3-isobutoxy-4-methoxyphenyl)oxazol-4-ylmethyl]-2-ethoxy benzamide

Yield 84 mg
White Powder
$^1$H-NMR ($CDCl_3$) δ: 8.54 (1H, br s), 8.23 (1H, dd, J=7.8, 1.8 Hz) 7.62-7.53 (2H, m), 7.44 (1H, d, J=1.8 Hz), 7.41 (2H, td, J=7.8, 1.8 Hz), 7.06 (1H, t, J=7.8 Hz), 6.95-6.90 (2H, m), 4.62 (2H, d, J=5.4 Hz), 4.18 (2H, q, J=6.9 Hz), 3.91 (3H, s), 3.85 (2H, d, J=6.9 Hz), 2.20 (1H, qt, J=6.9, 6.6 Hz), 1.49 (3H, t, J=6.9 Hz), 1.06 (6H, d, J=6.6 Hz)

Example 15

Using 0.2 g of the N-[2-(3-hydroxy-4-methoxyphenyl) oxazol-4-ylmethyl]-2-ethoxybenzamide obtained in Example 2, N-{2-[4-methoxy-3-(3,3,3-trifluoropropoxy) phenyl]oxazol-4-ylmethyl}-2-ethoxybenzamide was obtained in the same manner as in Example 4.

Yield 60 mg
White Powder
$^1$H-NMR ($CDCl_3$) δ: 8.55 (1H, br s) 8.23 (1H, dd, J=7.8, 1.8 Hz), 7.68-7.63 (2H, m), 7.56 (1H, d, J=2.1 Hz), 7.45-7.39 (1H, m), 7.07 (1H, t, J=7.2 Hz), 6.97-6.93 (2H, m), 4.62 (2H, d, J=5.4 Hz), 4.32 (2H, t, J=6.9 Hz), 4.18 (2H, q, J=6.9 Hz), 3.92 (3H, s), 2.78-2.67 (2H, m), 1.49 (3H, t, J=6.9 Hz)

Example 16

A 1.5 g quantity of the [2-(3-benzyloxy-4-methoxy phenyl)oxazol-4-yl]methylamine obtained in Reference Example 7 was suspended in 30 ml of acetone. To the obtained suspension were added 1.0 g of 1-hydroxybenzotriazole, 1.4 g of 1-ethyl-3-(3-dimethylaminopropyl)carbodiimide hydrochloride and 0.8 g of 3-methylpicolinic acid, and the mixture was heated and refluxed for 30 minutes. The reaction mixture was cooled, and acetone was distilled off under reduced pressure. Water was added to the residue, and extraction was then performed with ethyl acetate. The organic layer was washed with water twice, and the solvent was concentrated under reduced pressure. The obtained residue was purified by silica gel column chromatography (dichloromethane:methanol=20:1) to give 1.5 g of white powdery N-[2-(3-benzyloxy-4-methoxyphenyl)oxazol-4-ylmethyl]-3-methylpicolinamide.

$^1$H-NMR ($CDCl_3$) δ: 8.57 (1H, br s), 8.39 (1H, d, J=7.5 Hz), 7.65-7.28 (10H, m), 6.94 (1H, d, J=9.0 Hz), 5.21 (2H, s), 4.58 (2H, dd, J=5.7, 0.9 Hz), 3.93 (3H, s), 2.76 (3H, s)

Example 17

A 1.5 g quantity of the N-[2-(3-benzyloxy-4-methoxy phenyl)oxazol-4-ylmethyl]-3-methylpicolinamide obtained in Example 16 was dissolved in 50 ml of ethanol, and 0.1 g of 10% palladium carbon powder was added thereto. The mixture was stirred in a hydrogen atmosphere at 50° C. for two hours. The catalyst was removed by filtration, and the filtrate was then concentrated to give 1.3 g of white crystalline N-[2-(3-hydroxy-4-methoxyphenyl)oxazol-4-ylmethyl]-3-methylpicolinamide.

$^1$H-NMR ($CDCl_3$) δ: 8.58 (1H, br s), 8.38 (1H, dd, J=4.5, 0.9 Hz), 7.63 (1H, s), 7.62-7.54 (3H, m), 7.32-7.27 (1H, m), 6.90 (1H, d, J=8.4 Hz), 5.75 (1H, br s), 4.58 (2H, dd, J=6.0, 0.9 Hz), 3.94 (3H, s), 2.75 (3H, s)

Example 18

A 0.15 g quantity of the N-[2-(3-hydroxy-4-methoxyphenyl)oxazol-4-ylmethyl]-3-methylpicolinamide obtained in Example 17 and 0.5 ml of 1,8-diazabicyclo[5,4,0]undec-7-ene were dissolved in 4 ml of ethanol, and 0.13 g of bromocyclopentane was added thereto. The mixture was heated and refluxed for 3 hours. The reaction mixture was allowed to cool, water was then added thereto, and extraction was performed with ethyl acetate. The extract was washed with water twice, and the organic layer was concentrated under reduced pressure. The obtained residue was purified by silica gel column chromatography (n-hexane: ethyl acetate=3:1) to give 0.11 g of white powdery N-[2-(3-cyclopentyloxy-4-methoxyphenyl)oxazol-4-ylmethyl]-3-methylpicolinamide.

$^1$H-NMR ($CDCl_3$) δ: 8.57 (1H, br s), 8.39 (1H, dd, J=4.8, 0.9 Hz), 7.62-7.53 (4H, m), 7.32-7.27 (1H, m), 6.91 (1H, d, J=8.4 Hz), 4.88 (1H, tt, J=3.3 Hz), 4.59 (2H, dd, J=5.7, 0.9 Hz), 3.89 (3H, s), 2.76 (3H, s), 2.07-1.79 (6H, m), 1.70-1.60 (2H, m)

Example 19

A 0.15 g quantity of the N-[2-(3-hydroxy-4-methoxy phenyl)oxazol-4-ylmethyl]-3-methylpicolinamide obtained in Example 17 and 0.18 g of potassium carbonate were dissolved in 4 ml of dimethylformamide, and 0.19 g of 1,1,1-trifluoro-2-iodoethane was added thereto. The mixture was stirred with heating at 80° C. overnight. The reaction mixture was allowed to cool, water was then added thereto, and extraction was performed with ethyl acetate. The extract was washed with water twice, and the organic layer was concentrated under reduced pressure. The obtained residue was purified by silica gel column chromatography (n-hexane:ethyl acetate=3:1) to give 0.11 g of white powdery N-{2-[4-methoxy-3-(2,2,2-trifluoroethoxy)phenyl]oxazol-4-ylmethyl}-3-methylpicolinamide.

$^1$H-NMR ($CDCl_3$) δ: 8.58 (1H, br s), 8.39 (1H, dd, J=4.5, 1.2 Hz), 7.73 (1H, dd, J=8.7, 2.1 Hz), 7.63-7.57 (3H, m), 7.32-7.27 (1H, m), 6.97 (1H, d, J=8.4 Hz), 4.59 (2H, dd, J=5.7, 0.9 Hz), 4.46 (2H, q, J=8.4 Hz), 3.93 (3H, s), 2.76 (3H, s)

Example 20

Using 0.2 g of the N-[2-(3-hydroxy-4-methoxyphenyl) oxazol-4-ylmethyl]-3-methylpicolinamide obtained in Example 17, 0.11 g of N-[2-(3-ethoxy-4-methoxyphenyl) oxazol-4-ylmethyl]-3-methylpicolinamide was obtained in the same manner as in Example 3.

Colorless Crystals $^1$H-NMR ($CDCl_3$) δ: 8.57 (1H, br s), 8.39 (1H, dd, J=4.8, 1.5 Hz), 7.65-7.50 (4H, m), 7.30 (1H, dd, J=7.8, 4.8 Hz), 6.92 (1H, d, J=8.1 Hz), 4.59 (1H, dd, J=6.0, 0.6 Hz), 4.19 (2H, q, J=6.9 Hz), 4.17 (2H, q, J=6.9 Hz), 3.92 (3H, s), 2.76 (3H, s), 1.50 (3H, t, J=6.9 Hz)

Example 21

Using 0.15 g of the N-[2-(3-hydroxy-4-methoxyphenyl) oxazol-4-ylmethyl]-3-methylpicolinamide obtained in Example 17, 45 mg of N-[2-(3-allyloxy-4-methoxyphenyl) oxazol-4-ylmethyl]-3-methylpicolinamide was obtained in the same manner as in Example 3.

Colorless Crystal $^1$H-NMR ($CDCl_3$) δ: 8.58 (1H, br s), 8.39 (1H, dd, J=4.5, 1.5 Hz), 7.65-7.50 (4H, m), 7.30 (1H, dd, J=7.8, 4.5 Hz), 6.93 (1H, d, J=8.4 Hz), 6.12 (1H, m), 5.45 (1H, m), 5.32 (1H, dd, J=9.6, 1.5 Hz), 4.70 (2H, d, J=5.4 Hz), 4.59 (1H, d, J=6.0 Hz), 3.92 (3H, s), 2.76 (3H, s).

Example 22

A 170 mg quantity of the N-[2-(3-hydroxy-4-methoxy phenyl)oxazol-4-ylmethyl]-3-methylpicolinamide obtained in Example 17 was dissolved in 10 ml of tetrahydrofuran. To the obtained solution were added 134 mg of 2-hydroxyindane, 0.5 ml of diisopropyl azodicarboxylate (40% toluene solution) and 202 mg of tri(n-butyl)phosphine, and the mixture was stirred at room temperature overnight, and at 50° C. for 2.5 hours. To the reaction mixture were added 100 mg of 2-hydroxyindane, 0.5 ml of diisopropyl azodicarboxylate (40% toluene solution) and 200 mg of tri(n-butyl) phosphine, and the mixture was stirred at 50° C. for 5 hours, and at room temperature overnight. The reaction mixture was concentrated under reduced pressure. The residue was purified by silica gel column chromatography (n-hexane: ethyl acetate:methylene chloride=1:1:1) to give 92 mg of N-{2-[3-(indan-2-yloxy)-4-methoxyphenyl]oxazol-4-ylmethyl}-3-methylpicolinamide.

Pale Yellow Oily Substance $^1$H-NMR ($CDCl_3$) δ: 8.59 (1H, br s), 8.39 (1H, d, J=3.3 Hz), 7.65-7.16 (9H, m), 6.93 (1H, d, J=8.1 Hz), 5.30 (1H, tt, J=6.6, 3.9 Hz), 4.60 (2H, d, J=5.7 Hz), 3.86 (3H, s), 3.46 (2H, dd, J=16.8, 6.6 Hz), 3.27 (2H, dd, J=16.8, 3.9 Hz), 2.76 (3H, s)

Example 23

Using 0.88 g of the [2-(3-benzyloxy-4-methoxyphenyl) oxazol-4-yl]methylamine obtained in Reference Example 7, 1.03 g of white powdery N-[2-(3-benzyloxy-4-methoxyphenyl)oxazol-4-ylmethyl]-2-trifluoromethylbenzamide was obtained in the same manner as in Example 1.

$^1$H-NMR ($CDCl_3$) δ: 7.72-7.46 (9H, m), 7.40-7.27 (3H, m), 6.95 (1H, d, J=8.4 Hz) 6.34 (1H, br s), 5.20 (2H, s), 4.59 (2H, d, J=5.4 Hz), 3.93 (3H, s)

Example 24

Using 1.0 g of the N-[2-(3-benzyloxy-4-methoxyphenyl) oxazol-4-ylmethyl]-2-trifluoromethylbenzamide obtained in Example 23, 0.66 g of white powdery N-[2-(3-hydroxy-4-methoxyphenyl) oxazol-4-ylmethyl]-2-trifluoromethylbenzamide was obtained in the same manner as in Example 2.

$^1$H-NMR ($CDCl_3$) δ: 7.71-7.50 (7H, m), 6.90 (1H, d, J=8.4 Hz), 6.39 (1H, br s), 5.76 (1H, s), 4.59 (2H, d, J=5.4 Hz), 3.94 (3H, s)

Example 25

Using 0.2 g of the N-[2-(3-hydroxy-4-methoxyphenyl) oxazol-4-ylmethyl]-2-trifluoromethylbenzamide obtained in Example 24, 0.18 g of white powdery N-[2-(3-cyclopropylmethoxy-4-methoxyphenyl)oxazol-4-ylmethyl]-2-trifluoromethylbenzamide was obtained in the same manner as in Example 3.

$^1$H-NMR ($CDCl_3$) δ: 7.72-7.50 (7H, m), 6.93 (1H, d, J=8.4 Hz), 6.34 (1H, s), 4.60 (2H, d, J=5.4 Hz), 3.93 (3H, s), 1.42-1.32 (1H, m), 0.70-0.63 (2H, m), 0.41-0.35 (2H, m)

Example 26

Using 0.2 g of the N-[2-(3-hydroxy-4-methoxyphenyl) oxazol-4-ylmethyl]-2-trifluoromethylbenzamide obtained in Example 24, 40 mg of white powdery N-{2-[3-(3-hydroxy-propoxy)-4-methoxyphenyl]oxazol-4-ylmethyl}-2-trifluoromethylbenzamide was obtained in the same manner as in Example 3.

$^1$H-NMR ($CDCl_3$) δ: 7.71-7.50 (7H, m), 6.92 (1H, d, J=8.4 Hz), 6.34 (1H, br s), 4.60 (2H, d, J=5.4 Hz), 4.28 (2H, q, J=5.7 Hz), 3.98-3.86 (5H, m), 2.47 (1H, t, J=5.7 Hz), 2.15-2.07 (3H, m)

Example 27

Using 0.5 g of the 2-(3-benzyloxy-4-methoxyphenyl) oxazol-4-yl]methylamine obtained in Reference Example 7, 0.62 g of white powdery N-[2-(3-benzyloxy-4-methoxyphenyl)oxazol-4-ylmethyl]-3-ethoxypicolinamide was obtained in the same manner as in Example 1.

$^1$H-NMR ($CDCl_3$) δ: 8.24-8.22 (2H, m), 7.64-7.60 (3H, m), 7.50-7.46 (2H, m), 7.41-7.28 (5H, m), 6.94 (1H, d, J=9.0 Hz), 5.20 (2H, s), 4.61 (2H, d, J=5.7 Hz), 4.17 (2H, q, J=6.9 Hz), 3.93 (3H, s), 1.50 (3H, t, J=6.9 Hz)

Example 28

Using 0.6 g of the N-[2-(3-benzyloxy-4-methoxyphenyl) oxazol-4-ylmethyl]-3-ethoxypicolinamide obtained in Example 27, 0.5 g of white amorphous N-[2-(3-hydroxy-4-methoxyphenyl)oxazol-4-ylmethyl]-3-ethoxypicolinamide was obtained in the same manner as in Example 2.

$^1$H-NMR ($CDCl_3$) δ: 8.25-8.22 (2H, m), 7.64 (1H, d, J=1.8 Hz), 7.60-7.54 (2H, m), 7.39-7.28 (2H, m), 6.91 (1H, d, J=8.1 Hz), 5.71 (1H, br s), 4.61 (2H, dd, J=5.4, 0.9 Hz), 4.17 (2H, q, J=6.9 Hz), 3.94 (3H, s), 1.52 (3H, t, J=6.9 Hz)

Example 29

Using 0.5 g of the N-[2-(3-hydroxy-4-methoxyphenyl) oxazol-4-ylmethyl]-3-ethoxypicolinamide obtained in Example 28, 0.18 g of white amorphous N-[2-(3-cyclopentyloxy-4-methoxyphenyl)oxazol-4-ylmethyl]-3-ethoxypicolinamide was obtained in the same manner as in Example 3.

$^1$H-NMR ($CDCl_3$) δ: 8.25-8.22 (2H, m), 7.64 (1H, s), 7.58 (1H, dd, J=8.4, 2.1 Hz), 7.53 (1H, d, J=1.8 Hz), 7.39-7.32 (2H, m), 6.91 (1H, d, J=8.4 Hz), 4.91-4.86 (1H, m), 4.62 (2H, dd, J=5.4, 0.9 Hz), 4.17 (2H, q, J=6.9 Hz), 3.89 (3H, s), 2.05-1.79 (6H, m), 1.66-1.60 (2H, m), 1.51 (3H, t, J=6.9 Hz)

Example 30

Using 0.31 g of the 2-(3-benzyloxy-4-methoxyphenyl) oxazol-4-yl]methylamine obtained in Reference Example 7, 0.16 g of white powdery N-[2-(3-benzyloxy-4-methoxyphenyl)oxazol-4-ylmethyl]-2-(2,2,2-trifluoroethoxy)benzamide was obtained in the same manner as in Example 1.

$^1$H-NMR ($CDCl_3$) δ: 8.22 (1H, dd, J=7.8, 1.8 Hz), 7.82 (1H, br s), 7.63-7.60 (3H, m), 7.49-7.27 (6H, m), 7.19 (1H, t, J=7.2 Hz), 6.96-6.88 (2H, m), 5.19 (2H, s), 4.62 (2H, d, J=5.4 Hz), 4.47 (2H, q, J=7.8 Hz), 3.92 (3H, s)

Example 31

Using 0.16 g of the N-[2-(3-benzyloxy-4-methoxyphenyl) oxazol-4-ylmethyl]-2-(2,2,2-trifluoroethoxy)benzamide obtained in Example 30, 0.11 g of white powdery N-[2-(3-hydroxy-4-methoxy phenyl)oxazol-4-ylmethyl]-2-(2,2,2-trifluoroethoxy)benzamide was obtained in the same manner as in Example 2.

$^1$H-NMR ($CDCl_3$) δ: 8.21 (1H, dd, J=7.8, 1.8 Hz), 7.84 (1H, br s), 7.62-7.54 (3H, m), 7.49-7.43 (1H, m), 7.19 (1H, td, J=7.8, 0.9 Hz), 5.71 (1H, s), 4.62 (2H, dd, J=5.4, 0.9 Hz), 4.48 (2H, q, J=7.8 Hz), 3.94 (3H, s)

Example 32

Using 0.11 g of the N-[2-(3-hydroxy-4-methoxyphenyl) oxazol-4-ylmethyl]-2-(2,2,2-trifluoroethoxy)benzamide obtained in Example 31, 78 mg of white amorphous N-[2-(3-cyclopropylmethoxy-4-methoxyphenyl)oxazol-4-ylmethyl]-2-(2,2,2-trifluoroethoxy)benzamide was obtained in the same manner as in Example 3.

$^1$H-NMR ($CDCl_3$) δ: 8.22 (1H, dd, J=7.8, 2.1 Hz), 7.83 (1H, br s), 7.61-7.57 (3H, m), 7.53 (1H, d, J=2.1 Hz), 7.50-7.43 (1H, m), 7.19 (1H, td, J=7.8, 0.9 Hz), 6.94-6.88 (2H, m), 4.63 (2H, dd, J=5.4, 0.9 Hz), 4.48 (2H, q, J=7.8 Hz), 1.42-1.32 (1H, m), 0.70-0.63 (2H, m), 0.41-0.35 (2H, m)

Example 33

Using 0.5 g of the 2-(3-benzyloxy-4-methoxyphenyl) oxazol-4-yl]methylamine obtained in Reference Example 7, 0.68 g of pale yellow powdery N-[2-(3-benzyloxy-4-methoxyphenyl)oxazol-4-ylmethyl]-2-methoxybenzamide was obtained in the same manner as in Example 1.

$^1$H-NMR ($CDCl_3$) δ: 8.39 (1H, br s), 8.23 (1H, dd, J=4.8, 1.8 Hz), 7.65-7.60 (3H, m), 7.50-7.28 (6H, m), 7.08 (1H, t, J=7.2 Hz), 6.98-6.93 (2H, m), 5.21 (2H, s), 4.61 (2H, dd, J=5.4, 0.9 Hz), 3.95 (3H, s), 3.93 (3H, s)

Example 34

Using 0.67 g of the N-[2-(3-benzyloxy-4-methoxyphenyl) oxazol-4-ylmethyl]-2-methoxybenzamide obtained in Example 33, 0.52 g of white amorphous N-[2-(3-hydroxy-4-methoxyphenyl)oxazol-4-ylmethyl]-2-methoxybenzamide was obtained in the same manner as in Example 2.

$^1$H-NMR ($CDCl_3$) δ: 8.43 (1H, br s), 8.23 (1H, dd, J=7.8, 2.1 Hz), 7.63 (1H, s), 7.60-7.54 (2H, m), 7.47-7.41 (1H, m), 7.10-7.05 (1H, m), 6.97 (1H, d, J=8.4 Hz), 6.91 (1H, d, J=8.1 Hz), 5.74 (1H, br s), 4.62 (2H, dd, J=5.4, 0.9 Hz), 3.97 (3H, s), 3.95 (3H, s)

Example 35

Using 0.5 g of the N-[2-(3-hydroxy-4-methoxyphenyl) oxazol-4-ylmethyl]-2-methoxybenzamide obtained in Example 34, 0.39 g of white powdery N-[2-(3-cyclopentyloxy-4-methoxyphenyl)oxazol-4-ylmethyl]-2-methoxybenzamide was obtained in the same manner as in Example 3.

$^1$H-NMR ($CDCl_3$) δ: 8.41 (1H, br s), 8.23 (1H, dd, J=7.8, 1.8 Hz), 7.63 (1H, s), 7.59 (1H, dd, J=8.4, 1.8 Hz), 7.54 (1H, d, J=1.8 Hz), 7.48-7.42 (1H, m), 7.08 (1H, t, J=7.8 Hz), 6.98 (1H, d, J=8.1 Hz), 6.92 (1H, d, J=8.4 Hz), 4.91-4.87 (1H, m), 4.62 (2H, dd, J=5.4, 0.9 Hz), 3.97 (3H, s), 3.90 (3H, s), 2.05-1.80 (6H, m), 1.66-1.59 (2H, m)

Example 36

A 0.2 g quantity of the [2-(3-cyclopropylmethoxy-4-methoxyphenyl)oxazol-4-yl]methylamine obtained in Reference Example 13 was suspended in 4 ml of acetone. To the obtained suspension were added 0.2 g of 1-hydroxybenzotriazole, 0.29 g of 1-ethyl-3-(3-dimethylaminopropyl)carbodiimide hydrochloride and 0.14 g of 3-methylpicolinic acid, and the mixture was heated and refluxed for 30 minutes. The reaction mixture was cooled, water was then added thereto, and extraction was performed with ethyl acetate. The organic layer was washed with water twice, and the solvent was concentrated under reduced pressure. The obtained residue was purified by silica gel column chromatography (n-hexane:ethyl acetate=1:1) to give 0.16 g of white powdery N-[2-(3-cyclopropylmethoxy-4-methoxyphenyl)oxazol-4-ylmethyl]-3-methylpicolinamide.

$^1$H-NMR ($CDCl_3$) δ: 8.58 (1H, br s) 8.39 (1H, dd, J=4.5, 1.2 Hz), 7.63-7.57 (3H, m), 7.52 (1H, d, J=2.1 Hz), 7.33-7.28 (1H, m), 6.92 (1H, d, J=8.4 Hz), 4.59 (2H, dd, J=6.0, 0.9 Hz), 3.97-3.90 (5H, m), 2.76 (3H, s), 1.41-1.31 (1H, m), 0.70-0.63 (2H, m), 0.41-0.35 (2H, m)

Using 0.2 g of the [2-(3-cyclopropylmethoxy-4-methoxy phenyl)oxazol-4-yl]methylamine obtained in Reference Example 13, compounds of Examples 37 to 43 were obtained in the same manner as in Example 1.

Example 37

N-[2-(3-cyclopropylmethoxy-4-methoxyphenyl) oxazol-4-ylmethyl]-2-isopropoxybenzamide Yield 0.17 g
White Powder $^1$H-NMR ($CDCl_3$) δ: 8.62 (1H, br s) 8.23 (1H, dd, J=7.8, 1.8 Hz), 7.62-7.58 (2H, m), 7.54 (1H, d, J=2.1 Hz), 7.43-7.38 (1H, m), 7.05 (1H, td, J=8.1, 0.9 Hz), 6.97-6.91 (2H, m), 4.76-4.67 (1H, m), 4.61 (2H, dd, J=5.4, 0.9 Hz), 3.94-3.90 (5H, m), 1.41-1.38 (7H, m), 0.69-0.64 (2H, m), 0.41-0.35 (2H, m)

Example 38

N-[2-(3-cyclopropylmethoxy-4-methoxyphenyl) oxazol-4-ylmethyl]-2-methylbenzamide Yield 0.16 g
White Powder $^1$H-NMR ($CDCl_3$) δ: 7.64 (1H, s) 7.59 (1H, dd, J=8.4, 2.1 Hz), 7.50 (1H, d, J=2.1 Hz), 7.41-7.16 (3H, m), 6.93 (1H, d, J=8.4 Hz), 6.31 (1H, br s), 4.58 (2H, dd, J=5.4, 0.9 Hz), 3.95-3.92 (5H, m), 2.46 (3H, s), 1.42-1.32 (1H, m), 0.70-0.63 (2H, m), 0.41-0.35 (2H, m)

Example 39

N-[2-(3-cyclopropylmethoxy-4-methoxyphenyl) oxazol-4-ylmethyl]-2-ethylbenzamide

Yield 0.15 g
White Powder $^1$H-NMR ($CDCl_3$) δ: 7.64 (1H, s) 7.59 (1H, dd, J=8.4, 2.1 Hz), 7.50 (1H, d, J=1.8 Hz), 7.41-7.16 (3H, m), 6.93 (1H, d, J=8.1 Hz), 6.31 (1H, br s), 4.57 (2H, d, J=5.4 Hz), 3.95-3.92 (5H, m), 2.81 (2H, q, J=7.5 Hz), 1.42-1.32 (1H, m), 1.23 (3H, t, J=7.5 Hz), 0.70-0.63 (2H, m), 0.41-0.35 (2H, m)

Example 40

N-[2-(3-cyclopropylmethoxy-4-methoxyphenyl) oxazol-4-ylmethyl]-2-chlorobenzamide Yield 0.17 g
White Powder $^1$H-NMR ($CDCl_3$) δ: 7.71-7.66 (2H, m), 7.59 (1H, dd, J=8.4, 1.8 Hz), 7.50 (1H, d, J=2.1 Hz), 7.42-7.29 (3H, m), 6.93 (1H, d, J=8.4 Hz), 6.75 (1H, br s), 4.62 (2H, dd, J=5.4, 0.9 Hz), 3.95-3.92 (5H, m), 1.41-1.32 (1H, m), 0.70-0.63 (2H, m), 0.41-0.35 (2H, m)

Example 41

N-[2-(3-cyclopropylmethoxy-4-methoxyphenyl) oxazol-4-ylmethyl]-5-fluoro-2-methoxybenzamide Yield 0.19 g
White Powder $^1$H-NMR ($CDCl_3$) δ: 8.45 (1H, br s), 7.94 (1H, dd, J=9.6, 3.3 Hz), 7.63 (1H, s), 7.61 (1H, dd, J=8.1, 1.8 Hz), 7.51 (1H, d, J=1.8 Hz), 7.17-7.10 (1H, m), 6.95-6.90 (2H, m), 4.61 (2H, d, J=5.4 Hz), 3.96-3.92 (8H, m), 1.40-1.30 (1H, m), 0.70-0.64 (2H, m), 0.41-0.35 (2H, m)

Example 42

N-[2-(3-cyclopropylmethoxy-4-methoxyphenyl) oxazol-4-ylmethyl]-4-fluoro-2-methoxybenzamide Yield 0.19 g
White Powder $^1$H-NMR ($CDCl_3$) δ: 8.27-8.21 (2H, m), 7.63-7.58 (2H, m), 7.52 (1H, d, J=2.1 Hz), 6.93 (1H, d, J=8.4 Hz), 6.81-6.74 (1H, m), 6.69 (1H, dd, J=10.2, 2.1 Hz), 4.60 (2H, dd, J=5.4, 0.9 Hz), 3.97-3.90 (8H, m), 1.40-1.30 (1H, m), 0.70-0.64 (2H, m), 0.41-0.35 (2H, m)

Example 43

N-[2-(3-cyclopropylmethoxy-4-methoxyphenyl) oxazol-4-ylmethyl]-2-fluoro-6-methoxybenzamide Yield 0.17 g
White Powder $^1$H-NMR ($CDCl_3$) δ: 7.65 (1H, s), 7.59 (1H, dd, J=8.4, 2.1 Hz), 7.50 (1H, d, J=2.1 Hz), 7.34-7.27 (1H, m), 6.92 (1H, d, J=8.4 Hz), 6.76-6.70 (2H, m), 6.51 (1H, br s), 4.61 (2H, d, J=5.7 Hz), 3.94-3.91 (5H, m), 3.85 (3H, s), 1.42-1.31 (1H, m), 0.70-0.63 (2H, m), 0.41-0.35 (2H, m)

Example 44

Using 0.4 g of the [2-(3-cyclopropylmethoxy-4-methoxy phenyl)oxazol-4-yl]methylamine obtained in Reference Example 13, N-[2-(3-cyclopropylmethoxy-4-methoxyphenyl)oxazol-4-ylmethyl]-2-methylsulfanylbenzamide was obtained in the same manner as in Example 1.

Yield 0.4 g
White Powder $^1$H-NMR ($CDCl_3$) δ: 7.68 (1H, s), 7.61-7.56 (2H, m), 7.50 (1H, d, J=1.8 Hz), 7.34-7.17 (3H, m), 6.95-6.90 (2H, m), 4.61 (2H, dd, J=5.4, 0.9 Hz), 3.95-3.92 (5H, m), 2.46 (3H, s), 1.42-1.31 (1H, m), 0.70-0.63 (2H, m), 0.41-0.35 (2H, m)

Example 45

Using 0.7 g of the [2-(3-cyclopropylmethoxy-4-methoxy phenyl)oxazol-4-yl]methylamine obtained in Reference Example 13, N-[2-(3-cyclopropylmethoxy-4-methoxyphenyl)oxazol-4-ylmethyl]-3-hydroxypicolinamide was obtained in the same manner as in Example 1.

Yield 0.6 g

White Powder $^1$H-NMR ($CDCl_3$) δ: 12.02 (1H, s), 8.45 (1H, br s), 8.06 (1H, dd, J=4.2, 1.8 Hz), 7.63-7.59 (2H, m), 7.52 (1H, s), 7.37-7.29 (3H, m), 6.93 (1H, d, J=8.4 Hz), 4.60 (2H, d, J=6.0 Hz), 3.96-3.93 (5H, m), 1.56-1.33 (1H, m), 0.70-0.64 (2H, m), 0.42-0.36 (2H, m)

Using 0.1 g of the [2-(3-cyclopropylmethoxy-4-methoxy phenyl)oxazol-4-yl]methylamine obtained in Reference Example 13, compounds of Examples 46 to 56 were obtained in the same manner as in Example 1.

Example 46

N-[2-(3-cyclopropylmethoxy-4-methoxyphenyl) oxazol-4-ylmethyl]-2-methoxybenzamide Yield 0.1 g White Powder $^1$H-NMR ($CDCl_3$) δ: 8.40 (1H, br s), 8.23 (1H, dd, J=7.8, 2.1 Hz) 7.64-7.58 (2H, m), 7.52 (1H, d, J=2.1 Hz), 7.48-7.42 (1H, m), 7.08 (1H, td, J=7.8, 0.9 Hz), 6.99-6.91 (2H, m), 4.62 (2H, dd, J=5.4, 0.9 Hz), 3.97-3.91 (8H, m), 1.40-1.32 (1H, m), 0.70-0.63 (2H, m), 0.41-0.35 (2H, m)

Example 47

N-[2-(3-cyclopropylmethoxy-4-methoxyphenyl) oxazol-4-ylmethyl]-2-trifluoromethoxybenzamide Yield 43 mg White Powder $^1$H-NMR ($CDCl_3$) δ: 8.02 (1H, dd, J=7.8, 1.8 Hz), 7.64-7.27 (6H, m), 7.10 (1H, br s), 6.93 (1H, d, J=8.4 Hz), 4.62 (2H, dd, J=5.4, 0.9 Hz), 3.95-3.92 (5H, m), 1.43-1.28 (1H, m), 0.69-0.63 (2H, m), 0.41-0.36 (2H, m)

Example 48

N-[2-(3-cyclopropylmethoxy-4-methoxyphenyl) oxazol-4-ylmethyl]-2-propoxybenzamide Yield 0.1 g White Powder $^1$H-NMR ($CDCl_3$) δ: 8.50 (1H, br s), 8.24 (1H, dd, J=7.8, 1.8 Hz) 7.61-7.58 (2H, m), 7.53 (1H, d, J=1.8 Hz), 7.44-7.38 (1H, m), 7.06 (1H, t, J=7.8 Hz), 6.95-6.91 (2H, m), 4.62 (2H, d, J=5.1 Hz), 4.06 (2H, t, J=6.6 Hz), 3.95-3.68 (5H, m), 1.86 (2H, td, J=7.5, 6.6 Hz), 1.41-1.31 (1H, m), 0.96 (3H, t, J=7.5 Hz), 0.70-0.61 (2H, m), 0.41-0.35 (2H, m)

Example 49

N-[2-(3-cyclopropylmethoxy-4-methoxyphenyl) oxazol-4-ylmethyl]pyrazine-2-carboxamide Yield 90 mg White Powder $^1$H-NMR ($CDCl_3$) δ: 9.42 (1H, s), 8.75 (1H, d, J=2.4 Hz), 8.52 (1H, dd, J=2.7, 1.5 Hz), 8.25 (1H, br s), 7.64 (1H, s), 7.60 (1H, dd, J=8.4, 1.8 Hz), 7.52 (1H, d, J=1.8 Hz), 6.92 (1H, d, J=8.4 Hz), 4.63 (2H, dd, J=5.4, 0.9 Hz), 4.11-3.92 (5H, m), 1.40-1.32 (1H, m), 0.70-0.63 (2H, m), 0.41-0.35 (2H, m)

Example 50

N-[2-(3-cyclopropylmethoxy-4-methoxyphenyl) oxazol-4-ylmethyl]-3-ethoxypicolinamide Yield 85 mg White Powder $^1$H-NMR ($CDCl_3$) δ: 8.24-8.22 (2H, m) 7.64 (1H, s), 7.60 (1H, dd, J=8.4, 1.8 Hz), 7.51 (1H, d, J=2.1 Hz), 7.39-7.32 (2H, m), 6.92 (1H, d, J=8.4 Hz), 4.62 (2H, dd, J=5.4, 0.9 Hz), 4.17 (2H, q, J=6.9 Hz), 3.98-3.92 (5H, m), 1.52 (3H, t, J=6.9 Hz), 1.43-1.32 (1H, m), 0.71-0.63 (2H, m), 0.41-0.35 (2H, m)

Example 51

N-[2-(3-cyclopropylmethoxy-4-methoxyphenyl) oxazol-4-ylmethyl]-2-butoxybenzamide Yield 70 mg White Powder $^1$H-NMR ($CDCl_3$) δ: 8.48 (1H, br s) 8.23 (1H, dd, J=7.8, 1.8 Hz), 7.63-7.59 (2H, m), 7.53 (1H, d, J=2.1 Hz), 7.45-7.38 (1H, m), 7.06 (1H, td, J=8.4, 0.9 Hz), 6.96-6.91 (2H, m), 4.61 (2H, d, J=5.1 Hz), 4.09 (2H, t, J=6.6 Hz), 3.94-3.91 (5H, m), 1.84-1.75 (2H, m), 1.46-1.33 (3H, m), 0.84 (3H, t, J=7.2 Hz), 0.70-0.63 (2H, m), 0.41-0.35 (2H, m)

Example 52

N-[2-(3-cyclopropylmethoxy-4-methoxyphenyl) oxazol-4-ylmethyl]-2-isobutoxybenzamide Yield 0.12 g White Powder $^1$H-NMR ($CDCl_3$) δ: 8.46 (1H, br s) 8.24 (1H, dd, J=7.8, 1.8 Hz), 7.62-7.58 (2H, m), 7.52 (1H, d, J=1.8 Hz), 7.41 (1H, t, J=7.2 Hz), 7.06 (1H, t, J=7.2 Hz), 6.95-6.91 (2H, m), 4.62 (2H, d, J=5.1 Hz), 3.95-3.92 (5H, m), 3.86 (2H, d, J=6.3 Hz), 2.20-2.10 (1H, m), 1.40-1.31 (1H, m), 0.95 (6H, d, J=6.6 Hz), 0.70-0.63 (2H, m), 0.41-0.37 (2H, m)

Example 53

N-[2-(3-cyclopropylmethoxy-4-methoxyphenyl) oxazol-4-ylmethyl]-3-isopropoxypicolinamide Yield 0.1 g White Powder $^1$H-NMR ($CDCl_3$) δ: 8.28-8.25 (2H, m) 7.63 (1H, s), 7.60 (1H, dd, J=8.4, 2.1 Hz), 7.52 (1H, d, J=2.1 Hz), 7.38-7.31 (2H, m), 6.93 (1H, d, J=8.4 Hz), 4.70-4.61 (3H, m), 3.98-3.90 (5H, m), 1.42-1.31 (7H, m), 0.70-0.61 (2H, m), 0.41-0.35 (2H, m)

Example 54

N-[2-(3-cyclopropylmethoxy-4-methoxyphenyl) oxazol-4-ylmethyl]-2-ethylsulfanylbenzamide Yield 85 mg White Powder $^1$H-NMR ($CDCl_3$) δ: 7.70-7.66 (2H, m), 7.59 (1H, dd, J=8.4, 1.8 Hz), 7.51 (1H, d, J=2.1 Hz), 7.43-7.32 (2H, m), 7.27-7.22 (2H, m), 6.92 (1H, d, J=8.7 Hz), 4.61 (2H, dd, J=5.4, 0.6 Hz), 3.95-3.92 (5H, m), 2.90 (2H, q, J=7.5 Hz), 1.40-1.34 (1H, m), 1.26 (3H, t, J=7.2 Hz), 0.70-0.63 (2H, m), 0.41-0.35 (2H, m)

Example 55

N-[2-(3-cyclopropylmethoxy-4-methoxyphenyl) oxazol-4-ylmethyl]-1-oxidepicolinamide Yield 53 mg
Pale Yellow Powder
$^1$H-NMR ($CDCl_3$) δ: 11.64 (1H, br s), 8.44 (1H, dd, J=7.8, 2.1 Hz), 8.25 (1H, d, J=6.3 Hz), 7.63-7.35 (5H, m), 6.91 (1H, d, J=8.7 Hz), 4.65 (2H, d, J=5.7 Hz), 3.97-3.88 (5H, m), 1.43-1.32 (1H, m), 0.70-0.63 (2H, m), 0.41-0.36 (2H, m)

Example 56

N-[2-(3-cyclopropylmethoxy-4-methoxyphenyl) oxazol-4-ylmethyl]-2,6-dimethoxybenzamide Yield 46 mg
White Powder
$^1$H-NMR ($CDCl_3$) δ: 7.67 (1H, s), 7.59 (1H, dd, J=8.4, 1.8 Hz), 7.50 (1H, d, J=2.1 Hz), 7.30-7.24 (1H, m), 6.92 (1H, d, J=8.4 Hz), 6.56 (2H, d, J=8.4 Hz), 6.24 (1H, br s), 4.62 (2H, dd, J=5.7, 0.9 Hz), 3.95-3.92 (5H, m), 3.81 (6H, s), 1.41-1.32 (1H, m), 0.70-0.63 (2H, m), 0.41-0.35 (2H, m)

Using 0.13 g of [2-(3-cyclopropylmethoxy-4-methoxy phenyl)oxazol-4-yl]methylamine, compounds of Examples 57 to 59 were obtained in the same manner as in Example 1.

Example 57

N-[2-(3-cyclopropylmethoxy-4-methoxyphenyl) oxazol-4-ylmethyl]-3-methoxypicolinamide Yield 24 mg
White Powder
$^1$H-NMR ($CDCl_3$) δ: 8.23-8.19 (2H, m) 7.65 (1H, s), 7.59 (1H, dd, J=8.4, 2.1 Hz), 7.51 (1H, d, J=1.8 Hz), 7.43-7.34 (2H, m), 6.92 (1H, d, J=8.7 Hz), 4.60 (2H, d, J=5.4 Hz), 3.96-3.93 (8H, m), 1.43-1.30 (1H, m), 0.70-0.63 (2H, m), 0.41-0.35 (2H, m)

Example 58

N-[2-(3-cyclopropylmethoxy-4-methoxyphenyl) oxazol-4-ylmethyl]-3-isobutoxypicolinamide Yield 0.11 g
White Powder
$^1$H-NMR ($CDCl_3$) δ: 8.24 (1H, dd, J=3.9, 1.8 Hz), 8.17 (1H, br s), 7.63 (1H, s), 7.59 (1H, dd, J=8.4, 1.8 Hz), 7.38-7.31 (2H, m), 6.92 (1H, d, J=8.4 Hz), 4.62 (2H, dd, J=5.4, 0.9 Hz), 3.95-3.92 (5H, m), 3.84 (2H, d, J=6.3 Hz), 2.20 (1H, qt, J=6.6 Hz), 1.40-1.34 (1H, m), 1.03 (6H, d, J=6.6 Hz), 0.70-0.63 (2H, m), 0.41-0.35 (2H, m)

Example 59

N-[2-(3-cyclopropylmethoxy-4-methoxyphenyl) oxazol-4-ylmethyl]-2-methylnicotinamide Yield 71 mg
White Powder
$^1$H-NMR ($CDCl_3$) δ: 8.55 (1H, dd, J=7.8, 1.8 Hz), 7.71 (1H, dd, J=7.5, 1.8 Hz), 7.65 (1H, s), 7.59 (1H, dd, J=8.4, 2.1 Hz), 7.17-7.13 (1H, m), 6.93 (2H, d, J=8.4 Hz), 6.35 (1H, br s), 4.58 (2H, dd, J=5.4, 0.9 Hz), 3.96-3.91 (5H, m), 2.69 (3H, s), 1.41-1.31 (1H, m), 0.70-0.63 (2H, m), 0.41-0.35 (2H, m)

Example 60

0.4 g of N-[2-(3-cyclopropylmethoxy-4-methoxyphenyl) oxazol-4-ylmethyl]-2-methylsulfanylbenzamide obtained in Example 44 was dissolved in 20 ml of dichloromethane, and 0.67 g of metachloroperbenzoic acid was added thereto while the solution was cooled with ice with stirring. The mixture was then stirred for an hour. The reaction mixture was concentrated under reduced pressure, the residue was purified by silica gel column chromatography (NH silica, n-hexane:ethyl acetate=1:1), and 50 mg of white powdery N-[2-(3-cyclopropylmethoxy-4-methoxyphenyl) oxazol-4-ylmethyl]-2-methanesulfonylbenzamide was obtained.

$^1$H-NMR ($CDCl_3$) δ: 8.11 (1H, dd, J=7.8, 0.9 Hz), 7.76 (1H, s), 7.69-7.55 (4H, m), 7.50 (1H, d, J=2.1 Hz), 6.93 (1H, d, J=8.4 Hz), 6.50 (1H, br s), 4.62 (2H, d, J=5.4 Hz), 3.95-3.90 (5H, m), 3.93-3.67 (1H, m), 3.37 (3H, s), 1.40-1.32 (1H, m), 1.27-1.18 (3H, m), 0.70-0.63 (2H, m), 0.41-0.35 (2H, m)

Example 61

0.1 g of N-[2-(3-cyclopropylmethoxy-4-methoxyphenyl) oxazol-4-ylmethyl]-3-hydroxypicolinamide obtained in Example 45 and 0.16 g of cesium carbonate were dissolved in 4 ml of acetonitrile, and 0.2 g of 1-bromopropane was added thereto and stirred overnight at room temperature. Water was added to the reaction mixture and extraction was performed with ethyl acetate. The extract was washed with water once, and further washed with saturated aqueous citric acid once. The organic layer was concentrated under reduced pressure, and the obtained residue was purified by silica gel column chromatography, yielding 72 mg of white powdery N-2-(3-cyclopropylmethoxy-4-methoxyphenyl) oxazol-4-ylmethyl]-3-propoxypicolinamide.

$^1$H-NMR ($CDCl_3$) δ: 8.25-8.20 (2H, m) 7.64 (1H, s), 7.60 (1H, dd, J=8.4, 1.8 Hz), 7.52 (1H, d, J=1.8 Hz), 7.39-7.32 (2H, m), 6.92 (1H, d, J=8.4 Hz), 4.62 (2H, dd, J=5.7, 0.9 Hz), 4.05 (2H, t, J=6.6 Hz), 3.94-3.92 (5H, m), 1.90 (2H, t, J=7.5, 6.6 Hz), 1.40-1.33 (1H, m), 1.04 (3H, t, J=7.5 Hz), 0.70-0.63 (2H, m), 0.41-0.35 (2H, m)

Example 62

Using 0.18 g of [2-(3-isobutoxy-4-methoxyphenyl)oxazol-4-yl]methylamine obtained in Reference Example 19, 0.16 g of white powdery N-[2-(3-isobutoxy-4-methoxyphenyl)oxazol-4-ylmethyl]-3-methylpicolinamide was obtained in the same manner as in Example 1.

$^1$H-NMR ($CDCl_3$) δ: 8.58 (1H, br s) 8.39 (1H, dd, J=4.5, 1.8 Hz), 7.63 (1H, s), 7.62-7.59 (2H, m), 7.57 (1H, d, J=0.9 Hz), 7.32-7.27 (1H, m), 6.92 (1H, d, J=8.4 Hz), 4.59 (2H, dd, J=6.0, 0.9 Hz), 3.91 (3H, s), 3.86 (2H, d, J=6.9 Hz), 2.76 (3H, s), 2.20 (1H, qt, J=6.9, 6.6 Hz), 1.06 (6H, d, J=6.6 Hz)

Using 0.15 g of [2-(3-isobutoxy-4-methoxyphenyl)oxazol-4-yl]methylamine obtained in Reference Example 19, compounds of Examples 63 to 75 were obtained in the same manner as in Example 1.

Example 63

N-[2-(3-isobutoxy-4-methoxyphenyl)oxazol-4-ylmethyl]-2-methoxybenzamide

Yield 0.12 g
White Powder
$^1$H-NMR ($CDCl_3$) δ: 8.41 (1H, br s) 8.23 (1H, dd, J=7.8, 1.8 Hz), 7.64 (1H, s), 7.59 (1H, dd, J=8.4, 2.1 Hz), 7.53 (1H, d, J=2.1 Hz), 7.48-7.42 (1H, m), 7.11-6.90 (3H, m), 4.63 (2H, dd, J=5.4, 0.9 Hz), 3.97 (3H, s), 3.91 (3H, s), 3.86 (2H, d, J=6.9 Hz), 2.21 (1H, qt, J=6.6 Hz), 1.06 (6H, d, J=6.6 Hz)

Example 64

N-[2-(3-isobutoxy-4-methoxyphenyl)oxazol-4-ylmethyl]-2-methyl sulfanylbenzamide

Yield 0.15 g
White Powder
$^1$H-NMR ($CDCl_3$) δ: 7.69 (1H, s), 7.61-7.56 (2H, m), 7.51 (1H, d, J=1.8 Hz), 7.45-7.15 (3H, m) 6.94-6.90 (2H, m), 4.61 (2H, d, J=5.7 Hz), 3.91 (3H, s), 3.85 (2H, d, J=6.9 Hz), 2.46 (3H, s), 2.20 (1H, qt, J=6.9 Hz), 1.06 (6H, d, J=6.9 Hz)

Example 65

N-[2-(3-isobutoxy-4-methoxyphenyl)oxazol-4-ylmethyl]-3-ethoxy picolinamide

Yield 80 mg
White Powder
$^1$H-NMR ($CDCl_3$) δ: 8.25-8.22 (2H, m) 7.65 (1H, s), 7.58 (1H, dd, J=8.4, 1.8 Hz), 7.52 (1H, d, J=1.8 Hz), 7.40-7.32 (2H, m), 6.92 (1H, d, J=8.4 Hz), 4.62 (2H, dd, J=5.4, 0.9 Hz), 4.18 (2H, q, J=6.9 Hz), 3.91 (3H, s), 3.86 (2H, d, J=6.9 Hz), 2.20 (1H, qt, J=6.9 Hz), 1.52 (3H, t, J=6.9 Hz), 1.06 (6H, d, J=6.6 Hz)

Example 66

N-[2-(3-isobutoxy-4-methoxyphenyl)oxazol-4-ylmethyl]-2-methoxy-4-fluorobenzamide Yield 0.11 g
White Powder
$^1$H-NMR ($CDCl_3$) δ: 8.27-8.21 (2H, m), 7.63 (1H, s), 7.59 (1H, dc, J=8.4, 2.1 Hz), 7.52 (1H, d, J=2.1 Hz), 6.93 (1H, d, J=8.4 Hz), 6.81-6.74 (1H, m), 6.69 (1H, dd, J=10.5, 2.4 Hz), 4.61 (2H, dd, J=5.4, 0.9 Hz), 3.96 (3H, s), 3.91 (3H, s), 3.85 (2H, d, J=6.6 Hz), 2.20 (1H, qt, J=6.9, 6.6 Hz), 1.06 (6H, d, J=6.6 Hz)

Example 67

N-[2-(3-isobutoxy-4-methoxyphenyl)oxazol-4-ylmethyl]-2-isopropoxy benzamide

Yield 0.15 g
Colorless Oily Substance
$^1$H-NMR ($CDCl_3$) δ: 8.64 (1H, br s) 8.24 (1H, dd, J=7.8, 1.8 Hz), 7.62-7.57 (2H, m), 7.54 (1H, d, J=1.8 Hz), 7.44-7.37 (1H, m), 7.08-7.02 (1H, m), 6.98-6.91 (2H, m), 4.72 (1H, q, J=6.0 Hz), 4.62 (2H, dd, J=5.1, 0.9 Hz), 3.92 (3H, s), 3.85 (2H, d, J=6.6 Hz), 2.20 (1H, qt, J=6.6 Hz), 1.40 (6H, d, J=6.0 Hz), 1.06 (6H, d, J=6.6 Hz)

Example 68

N-[2-(3-isobutoxy-4-methoxyphenyl)oxazol-4-ylmethyl]-2-fluoro-6-methoxybenzamide Yield 0.13 g
White Powder
$^1$H-NMR ($CDCl_3$) δ: 7.65 (1H, d, J=0.9 Hz), 7.58 (1H, dd, J=8.4, 2.1 Hz), 7.51 (1H, d, J=2.1 Hz), 7.34-7.24 (1H, m), 6.92 (1H, d, J=8.4 Hz), 6.77-6.70 (2H, m), 6.52 (1H, br s), 4.62 (2H, dd, J=5.7, 0.9 Hz), 3.91 (3H, s), 3.90-3.82 (5H, m), 2.20 (1H, qt, J=6.9 Hz), 1.06 (6H, d, J=6.9 Hz)

Example 69

N-[2-(3-isobutoxy-4-methoxyphenyl)oxazol-4-ylmethyl]-3-methoxy picolinamide

Yield 0.14 g
White Powder
$^1$H-NMR ($CDCl_3$) δ: 8.19-8.22 (2H, m), 7.65 (1H, s), 7.58 (1H, dd, J=8.4, 1.8 Hz), 7.52 (1H, d, J=2.1 Hz), 7.43-7.34 (1H, m), 6.92 (1H, d, J=8.4 Hz), 4.61 (2H, dd, J=5.7, 0.9 Hz), 3.96 (3H, s), 3.91 (3H, s), 3.86 (2H, d, J=6.6 Hz), 2.20 (1H, qt, J=6.9, 6.6 Hz), 1.06 (6H, d, J=6.9 Hz)

Example 70

N-[2-(3-isobutoxy-4-methoxyphenyl)oxazol-4-ylmethyl]-3-isobutoxy picolinamide

Yield 68 mg
White Powder
$^1$H-NMR ($CDCl_3$) δ: 8.24 (1H, dd, J=3.9, 2.1 Hz), 8.17 (1H, br s), 7.64 (1H, s), 7.58 (1H, dd, J=8.4, 2.1 Hz), 7.52 (1H, d, J=1.8 Hz), 7.38-7.28 (2H, m), 6.92 (2H, d, J=8.4 Hz), 4.63 (2H, dd, J=5.4, 0.9 Hz), 3.91 (3H, s), 3.87-3.82 (4H, m), 2.27-2.13 (2H, m), 1.07-1.02 (2H, m)

Example 71

N-[2-(3-isobutoxy-4-methoxyphenyl)oxazol-4-ylmethyl]-2-propoxy benzamide

Yield 75 mg
White Powder
$^1$H-NMR ($CDCl_3$) δ: 8.52 (1H, br s), 8.23 (1H, dd, J=7.8, 1.8 Hz), 7.62-7.58 (2H, m), 7.53 (1H, s), 7.42 (1H, td, J=7.2, 1.8 Hz), 7.06 (1H, t, J=7.8 Hz), 6.95-6.91 (2H, m), 4.62 (2H, d, J=5.1 Hz), 4.06 (2H, t, J=6.6 Hz), 3.94 (3H, s), 3.85 (2H, d, J=6.6 Hz), 2.24-2.16 (1H, m), 1.93-1.81 (2H, m), 1.06 (6H, d, J=6.6 Hz), 0.97 (3H, t, J=7.2 Hz)

Example 72

N-[2-(3-isobutoxy-4-methoxyphenyl)oxazol-4-ylmethyl]-2-butoxy benzamide

Yield 47 mg
White Powder
$^1$H-NMR ($CDCl_3$) δ: 8.48 (1H, br s), 8.23 (1H, dd, J=7.8, 1.8 Hz), 7.62-7.58 (2H, m), 7.53 (1H, s), 7.42 (1H, td, J=7.2, 1.8 Hz), 7.06 (1H, t, J=7.8 Hz), 6.95-6.91 (2H, m), 4.61 (2H, d, J=5.1 Hz), 4.10 (2H, t, J=6.6 Hz), 3.91 (3H, s), 3.85 (2H, d, J=6.6 Hz), 2.24-2.16 (1H, m), 1.85-1.75 (2H, m), 1.43-1.36 (2H, m), 1.05 (6H, d, J=6.6 Hz), 0.84 (3H, t, J=7.2 Hz)

Example 73

N-[2-(3-isobutoxy-4-methoxyphenyl)oxazol-4-ylmethyl]-2-isobutoxy benzamide

Yield 90 mg
White Powder
$^1$H-NMR ($CDCl_3$) δ: 8.52 (1H, br s), 8.23 (1H, dd, J=7.8, 1.8 Hz), 7.62-7.58 (2H, m), 7.53 (1H, s), 7.42 (1H, td, J=7.2, 1.8 Hz), 7.06 (1H, t, J=7.8 Hz), 6.93-6.90 (2H, m), 4.62 (2H, d, J=5.1 Hz), 3.91 (3H, s), 3.87-3.83 (4H, m), 2.24-2.16 (2H, m), 1.06 (6H, d, J=6.6 Hz), 0.95 (6H, d, J=6.6 Hz)

Example 74

N-[2-(3-isobutoxy-4-methoxyphenyl)oxazol-4-ylmethyl]-3-isopropoxy picolinamide

Yield 0.11 g
White Powder
$^1$H-NMR ($CDCl_3$) δ: 8.52 (1H, br s), 8.27 (1H, br s), 7.63 (1H, s), 7.58 (1H, dd, J=7.8, 1.8 Hz), 7.53 (1H, s), 7.35-7.34 (2H, m), 6.92 (1H, d, J=8.4 Hz), 4.67-4.61 (3H, m), 3.91 (3H, s), 3.85 (2H, d, J=6.6 Hz), 2.22-2.17 (1H, m), 1.42 (6H, d, J=6.6 Hz), 1.06 (6H, d, J=6.6 Hz)

Example 75

N-[2-(3-isobutoxy-4-methoxyphenyl)oxazol-4-ylmethyl]-2-methyl nicotineamide

Yield 0.13 g
White Powder
$^1$H-NMR ($CDCl_3$) δ: 8.52 (1H, br s), 7.86 (1H, d, J=7.5 Hz), 7.76 (1H, d, J=7.5 Hz), 7.69 (1H, s), 7.59 (1H, d, J=4.2 Hz), 7.56 (1H, s), 6.92 (1H, d, J=8.7 Hz), 4.58 (2H, d, J=5.1 Hz), 3.91 (3H, s), 3.84 (2H, d, J=6.9 Hz), 2.69 (3H, s), 2.23-2.15 (1H, m), 1.05 (6H, d, J=5.1 Hz)

Example 76

Using 0.2 g of {2-[4-methoxy-3-(2,2,2-trifluoroethoxy)phenyl]oxazol-4-yl}methylamine obtained in Reference Example 25, 0.24 g of white powdery N-{2-[4-methoxy-3-(2,2,2-trifluoroethoxy)phenyl]oxazol-4-ylmethyl}-3-methoxypicolinamide was obtained in the same manner as in Example 1.

$^1$H-NMR ($CDCl_3$) δ: 8.24-8.19 (2H, m), 7.72 (1H, dd, J=8.4, 1.8 Hz), 7.65 (1H, d, J=0.9 Hz), 7.62 (1H, d, J=1.8 Hz), 7.43-7.35 (2H, m), 6.98 (1H, d, J=8.4 Hz), 4.60 (2H, dd, J=5.7, 0.9 Hz), 4.46 (2H, q, J=5.4 Hz), 3.95 (3H, s), 3.93 (3H, s)

Using 0.2 g of {2-[4-methoxy-3-(2,2,2-trifluoroethoxy)phenyl]oxazol-4-yl}methylamine obtained in Reference Example 25, compounds of Example 77 to 79 were obtained in the same manner as in Example 1.

Example 77

N-{2-[4-methoxy-3-(2,2,2-trifluoroethoxy)phenyl]oxazol-4-ylmethyl}-3-ethoxypicolinamide Yield 0.24 g
White Powder
$^1$H-NMR ($CDCl_3$) δ: 8.26-8.22 (2H, m), 7.72 (1H, dd, J=8.4, 2.1 Hz), 7.65 (1H, s), 7.63 (1H, d, J=1.8 Hz), 7.40-7.32 (2H, m), 6.98 (1H, d, J=8.1 Hz), 4.62 (2H, dd, J=5.7, 0.9 Hz), 4.46 (2H, q, J=8.4 Hz), 4.18 (2H, q, J=6.9 Hz), 1.52 (3H, t, J=6.9 Hz)

Example 78

N-{2-[4-methoxy-3-(2,2,2-trifluoroethoxy)phenyl]oxazol-4-ylmethyl}-2-methoxybenzamide Yield 0.18 g
White Powder
$^1$H-NMR ($CDCl_3$) δ: 8.42 (1H, br s), 8.23 (1H, dd, J=7.5, 1.8 Hz), 7.73 (1H, dd, J=8.4, 2.1 Hz), 7.65-7.60 (2H, m), 7.48-7.42 (1H, m), 7.08 (1H, td, J=8.4, 0.9 Hz), 6.98 (1H, d, J=8.4 Hz), 4.62 (2H, dd, J=5.4, 0.9 Hz), 4.46 (2H, q, J=8.4 Hz), 3.98 (3H, s), 3.93 (3H, s)

Example 79

N-{2-[4-methoxy-3-(2,2,2-trifluoroethoxy)phenyl]oxazol-4-ylmethyl}-2-methylbenzamide Yield 0.15 g
White Powder
$^1$H-NMR ($CDCl_3$) δ: 7.72 (1H, dd, J=8.4, 2.1 Hz), 7.66 (1H, s), 7.61 (1H, d, J=2.1 Hz), 7.41-7.14 (4H, m), 6.98 (1H, d, J=8.4 Hz), 6.31 (1H, br s), 4.58 (2H, dd, J=5.4, 0.9 Hz), 4.45 (2H, q, J=8.4 Hz), 3.93 (3H, s), 2.46 (3H, s)

Using 0.15 g of {2-[4-methoxy-3-(2,2,2-trifluoroethoxy)phenyl]oxazol-4-yl}methylamine obtained Reference Example 25, compounds of Examples 80 to 82 were obtained in the same manner as in Example 1.

Example 80

N-{2-[4-methoxy-3-(2,2,2-trifluoroethoxy)phenyl]oxazol-4-ylmethyl}-2-propoxybenzamide Yield 0.15 g
White Powder
$^1$H-NMR ($CDCl_3$) δ: 8.53 (1H, br s), 8.24 (1H, dd, J=7.8, 1.8 Hz), 7.73 (1H, dd, J=8.4, 2.1 Hz), 7.65-7.60 (2H, m), 7.45-7.38 (1H, m), 7.09-6.93 (3H, m), 4.62 (2H, d, J=5.1 Hz), 4.45 (2H, q, J=8.1 Hz), 4.07 (2H, t, J=6.6 Hz), 3.94 (3H, s), 1.88 (2H, qt, J=7.5, 6.6 Hz), 0.98 (3H, t, J=7.5 Hz)

Example 81

N-{2-[4-methoxy-3-(2,2,2-trifluoroethoxy)phenyl]oxazol-4-ylmethyl}-2-isopropoxybenzamide Yield 0.18 g
White Powder
$^1$H-NMR ($CDCl_3$) δ: 8.64 (1H, br s), 8.23 (1H, dd, J=7.8, 1.8 Hz), 7.74 (1H, dd, J=8.4, 2.1 Hz), 7.65 (1H, d, J=2.1 Hz), 7.63 (1H, s), 7.44-7.37 (1H, m), 7.08-6.94 (3H, m), 4.73 (1H, tt, J=6.0 Hz), 4.62 (2H, dd, J=5.1, 0.9 Hz), 4.46 (2H, q, J=8.4 Hz), 3.94 (3H, s), 1.41 (6H, d, J=6.0 Hz)

Example 82

N-{2-[4-methoxy-3-(2,2,2-trifluoroethoxy)phenyl]oxazol-4-ylmethyl}-4-chloro-2-methoxybenzamide Yield 0.21 g
White Powder $^1$H-NMR ($CDCl_3$) δ: 8.29 (1H, br s), 8.17 (1H, d, J=8.4 Hz), 7.73 (1H, dd, J=8.4, 1.8 Hz), 7.64 (1H, d, J=1.5 Hz), 7.07 (1H, dd, J=8.4, 1.8 Hz), 7.00-6.96 (2H, m), 4.60 (2H, dd, J=5.4, 0.9 Hz), 4.46 (2H, q, J=8.4 Hz), 3.98 (3H, s), 3.93 (3H, s)

Example 83

Using 0.1 g of {2-[3-cyclopropylmethoxy-4-(2,2,2-trifluoroethoxy)phenyl]oxazol-4-yl}methylamine obtained in Reference Example 34, 0.11 g of white powdery N-{2-[3-cyclopropylmethoxy-4-(2,2,2-trifluoroethoxy)phenyl]oxazol-4-ylmethyl}-2-ethoxybenzamide was obtained in the same manner as in Example 1.

$^1$H-NMR ($CDCl_3$) δ: 8.54 (1H, br s), 8.23 (1H, dd, J=7.8, 1.8 Hz) 7.64 (1H, s), 7.60-7.55 (2H, m), 7.45-7.38 (1H, m), 7.10-7.04 (2H, m), 6.94 (1H, d, J=8.1 Hz), 4.62 (2H, dd, J=5.4, 0.9 Hz), 4.48 (2H, q, J=8.4 Hz), 4.18 (2H, q, J=6.9 Hz), 3.95 (2H, d, J=7.2 Hz), 1.48 (3H, t, J=7.2 Hz), 1.35-1.29 (1H, m), 0.70-0.63 (2H, m), 0.41-0.35 (2H, m)

Example 84

Using 0.18 g of {2-[3-cyclopropylmethoxy-4-(2,2,2-trifluoroethoxy)phenyl]oxazol-4-yl}methylamine obtained in Reference Example 34, 0.2 g of white powdery N-{2-[3-cyclopropylmethoxy-4-(2,2,2-trifluoroethoxy)phenyl]oxazol-4-ylmethyl}-3-methylpicolinamide was obtained in the same manner as in Example 1.

$^1$H-NMR ($CDCl_3$) δ: 8.57 (1H, br s), 8.39 (1H, dd, J=4.5, 1.2 Hz) 7.64 (1H, s), 7.60-7.55 (3H, m), 7.32-7.26 (1H, m), 7.06-7.03 (1H, m), 4.59 (2H, dd, J=5.7, 0.9 Hz), 4.48 (2H, q, J=8.4 Hz), 3.95 (2H, d, J=6.9 Hz), 2.76 (3H, s), 1.38-1.28 (1H, m), 0.69-0.62 (2H, m), 0.40-0.35 (2H, m)

Example 85

Using 0.3 g of [2-(3,4-diethoxyphenyl)oxazol-4-yl]methylamine obtained in Reference Example 37, 0.11 g of white powdery N-[2-(3,4-diethoxyphenyl)oxazol-4-ylmethyl]-2-propoxy benzamide was obtained in the same manner as in Example 1.

$^1$H-NMR ($CDCl_3$) δ: 8.51 (1H, br s), 8.24 (1H, dd, J=7.8, 1.8 Hz), 7.60-7.50 (3H, m), 7.41 (1H, m), 7.06 (1H, m), 7.00-6.90 (2H, m), 4.61 (2H, d, J=5.1 Hz), 4.06 (2H, t, J=6.6 Hz), 1.87 (2H, tq, J=7.2, 6.6 Hz), 1.49 (6H, t, J=6.9 Hz), 0.96 (3H, t, J=7.2 Hz)

Using 0.3 g of [2-(3,4-diethoxyphenyl)oxazol-4-yl]methylamine obtained in Reference Example 37, compounds of Examples 86 to 91 were obtained in the same manner as in Example 1.

Example 86

N-[2-(3,4-diethoxyphenyl)oxazol-4-ylmethyl]-2-trifluoromethyl benzamide

Yield 0.11 g
White Powder $^1$H-NMR ($CDCl_3$) δ: 7.75-7.50 (7H, m), 6.91 (1H, d, J=8.4 Hz), 6.32 (1H, br s), 4.59 (2H, d, J=5.4 Hz), 4.17 (2H, q, J=6.9 Hz), 4.14 (2H, q, J=6.9 Hz), 1.48 (6H, t, J=6.9 Hz)

Example 87

N-[2-(3,4-diethoxyphenyl)oxazol-4-ylmethyl]picolinamide

Yield 0.34 g
White Powder $^1$H-NMR ($CDCl_3$) δ: 8.55 (1H, m), 8.47 (1H, br s), 8.21 (1H, d, J=7.8 Hz), 7.85 (1H, m), 7.57 (1H, dd, J=8.4, 1.8 Hz), 7.55 (1H, d, J=1.8 Hz), 7.42 (1H, m), 6.91 (1H, d, J=8.4 Hz), 6.32 (1H, br s), 4.63 (2H, d, J=6.0 Hz), 4.18 (2H, q, J=6.9 Hz), 4.15 (2H, q, J=6.9 Hz), 1.48 (3H, t, J=6.9 Hz), 1.48 (3H, t, J=6.9 Hz)

Example 88

N-[2-(3,4-diethoxyphenyl)oxazol-4-ylmethyl]-2-ethoxybenzamide

Yield 0.23 g
White Powder $^1$H-NMR ($CDCl_3$) δ: 8.55 (1H, m), 8.47 (1H, br s), 8.21 (1H, d, J=7.8 Hz), 7.85 (1H, m), 7.57 (1H, dd, J=8.4, 1.8 Hz), 7.55 (1H, d, J=1.8 Hz), 7.42 (1H, m), 6.91 (1H, d, J=8.4 Hz), 6.32 (1H, br s), 4.63 (2H, d, J=6.0 Hz), 4.18 (2H, q, J=6.9 Hz), 4.15 (2H, q, J=6.9 Hz), 1.48 (3H, t, J=6.9 Hz), 1.48 (3H, t, J=6.9 Hz)

Example 89

N-[2-(3,4-diethoxyphenyl)oxazol-4-ylmethyl]-4-ethoxybenzamide

Yield 0.32 g
White Powder $^1$H-NMR ($CDCl_3$) δ: 7.80-7.70 (2H, m), 7.63 (1H, s), 7.60-7.50 (2H, m), 6.95-6.85 (3H, m), 6.66 (1H, br s), 4.57 (2H, q, J=6.0 Hz), 4.17 (2H, q, J=6.9 Hz), 4.15 (2H, q, J=6.9 Hz), 4.06 (2H, q, J=6.9 Hz), 1.48 (3H, t, J=6.9 Hz), 1.48 (3H, t, J=6.9 Hz), 1.42 (3H, t, J=6.9 Hz).

Example 90

N-[2-(3,4-diethoxyphenyl)oxazol-4-ylmethyl]-5-methoxy-2-trifluoro methoxybenzamide Yield 0.34 g
White Powder $^1$H-NMR ($CDCl_3$) δ: 7.95 (1H, br s), 7.73 (1H, d, J=3.0 Hz), 7.70-7.50 (3H, m), 6.99 (1H, dd, J=9.0, 3.0 Hz), 6.90-6.80 (2H, m), 4.61 (2H, d, J=6.0 Hz), 4.18 (2H, q, J=6.9 Hz), 4.15 (2H, q, J=6.9 Hz), 3.82 (3H, s), 1.48 (3H, t, J=6.9 Hz), 1.46 (3H, t, J=6.9 Hz)

Example 91

N-[2-(3,4-diethoxyphenyl)oxazol-4-ylmethyl]-3-ethoxybenzamide

Yield 0.12 g
White Powder $^1$H-NMR ($CDCl_3$) δ: 7.57 (1H, dd, J=8.1, 2.1 Hz), 7.53 (1H, d, J=2.1 Hz), 7.35-7.25 (3H, m), 7.01 (1H, m), 6.92 (1H, d, J=8.1 Hz), 6.68 (1H, br s), 4.58 (2H, d, J=5.4 Hz), 4.18 (2H, q, J=6.9 Hz), 4.15 (2H, q, J=6.9 Hz), 4.07 (2H, q, J=6.9 Hz), 1.49 (3H, t, J=6.9 Hz), 1.48 (3H, t, J=6.9 Hz), 1.42 (3H, t, J=6.9 Hz)

Example 92

Using 0.3 g of [2-(3,4-dimethoxyphenyl)oxazol-4-yl]methylamine obtained in Reference Example 40, 0.27 g of white powdery N-[2-(3,4-dimethoxyphenyl)oxazol-4-ylmethyl]-2-ethoxy benzamide was obtained in the same manner as in Example 1.

$^1$H-NMR ($CDCl_3$) δ: 8.56 (1H, br s), 8.24 (1H, dd, J=8.1, 1.8 Hz), 7.65-7.60 (2H, m), 7.55 (1H, d, J=1.5 Hz), 7.42 (1H, m), 7.07 (1H, m), 6.95-6.90 (2H, m), 4.63 (2H, d, J=5.1 Hz), 4.18 (2H, q, J=6.9 Hz), 3.98 (3H, s), 3.97 (3H, s), 1.26 (3H, t, J=6.9 Hz)

Example 93

Using 0.25 g of [2-(3,4-dimethoxyphenyl)oxazol-4-yl]methylamine obtained in Reference Example 40, 0.23 g of white powdery N-[2-(3,4-dimethoxyphenyl)oxazol-4-ylmethyl]-2-ethyl benzamide was obtained in the same manner as in Example 1.

$^1$H-NMR ($CDCl_3$) δ: 7.66 (1H, s), 7.60 (1H, dd, J=8.4, 1.8 Hz), 7.52 (1H, d, J=1.8 Hz), 7.40-7.20 (4H, m), 6.93 (1H, d, J=8.4 Hz), 6.34 (1H, br s), 4.58 (2H, d, J=5.4 Hz), 3.96 (3H, s), 3.94 (3H, s), 2.82 (2H, q, J=7.5 Hz), 1.20 (3H, t, J=7.5 Hz)

Example 94

Using 0.2 g of [2-(3,4-dimethoxyphenyl)oxazol-4-yl]methylamine obtained in Reference Example 40, 0.16 g of white powdery N-[2-(3,4-dimethoxyphenyl)oxazol-4-ylmethyl]-3-methyl picolinamide was obtained in the same manner as in Example 1.

$^1$H-NMR ($CDCl_3$) δ: 8.58 (1H, br s), 8.39 (1H, m), 7.65-7.55 (4H, m), 7.30 (1H, m), 6.92 (1H, d, J=8.4 Hz), 4.59 (2H, d, J=6.0 Hz), 3.97 (3H, s), 3.93 (3H, s), 2.76 (3H, s), 1.58 (3H, s)

Example 95

Using 0.2 g of [2-(3,4-dimethoxyphenyl)oxazol-4-yl]methylamine obtained in Reference Example 40, 0.12 g of white powdery N-[2-(3,4-dimethoxyphenyl)oxazol-4-ylmethyl]-3-methoxy picolinamide was obtained in the same manner as in Example 1.

$^1$H-NMR ($CDCl_3$) δ: 8.21 (1H, br s), 8.20 (1H, dd, J=3.9, 1.8 Hz), 7.65 (1H, s), 7.61 (1H, dd, J=8.4, 1.8 Hz), 7.54 (1H, d, J=1.8 Hz), 7.45-7.30 (2H, m), 6.92 (1H, d, J=8.4 Hz), 4.61 (2H, d, J=6.0 Hz), 3.97 (3H, s), 3.96 (3H, s), 3.93 (3H, s)

Example 96

0.13 g of [2-(3-benzyloxy-4-difluoromethoxyphenyl)oxazol-4-yl]methylamine obtained in Reference Example 46 was suspended in 10 ml of acetone. Then 0.14 g of 1-hydroxybenzotriazole and 0.19 g of 1-ethyl-3-(3-dimethylaminopropyl)carbodiimide hydrochloride and 0.14 g of 3-methyl picolinate were added to the obtained suspension and the mixture was refluxed for 30 minutes. The reaction mixture was concentrated under reduced pressure, and water was added to the residue. Ethyl acetate extraction was performed. The organic layer was washed twice with water, and concentrated. The residue was purified by silica gel column chromatography (n-hexane:ethyl acetate=1:1), yielding 0.16 g of white powdery N-[2-(3-benzyloxy-4-difluoromethoxyphenyl)oxazol-4-ylmethyl]-3-methylpicolinamide.

$^1$H-NMR ($CDCl_3$) δ: 8.56 (1H, br s), 8.40 (1H, d, J=3.9 Hz), 7.74-7.58 (4H, m), 7.47-7.23 (7H, m), 6.62 (1H, t, J=74.7 Hz), 5.21 (2H, s), 4.60 (2H, d, J=5.7 Hz), 2.76 (3H, s)

Example 97

0.16 g of N-[2-(3-benzyloxy-4-difluoromethoxyphenyl)oxazol-4-ylmethyl]-3-methylpicolinamide obtained in Example 96 was dissolved in 5 ml of ethanol, 20 mg of 10% palladium carbon powder was added thereto, and the mixture was stirred at room temperature for 30 minutes under a hydrogen atmosphere. The catalyst was filtered off, and the filtrate was concentrated to obtain 0.12 g of white powdery N-[2-(4-difluoromethoxy-3-hydroxyphenyl)oxazol-4-ylmethyl]-3-methylpicolinamide.

$^1$H-NMR ($CDCl_3$) δ: 8.60-8.54 (1H, m), 8.39 (1H, d, J=3.3 Hz), 7.69-7.55 (4H, m), 7.37-7.28 (1H, m), 7.18 (1H, d, J=8.4 Hz), 6.59 (1H, t, J=73.2 Hz), 5.79 (1H, br s), 4.59 (2H, dd, J=6.0, 0.9 Hz), 2.76 (3H, s)

Example 98

0.12 g of N-[2-(4-difluoromethoxy-3-hydroxyphenyl)oxazol-4-ylmethyl]-3-methylpicolinamide obtained in Example 97 and 0.15 ml of 1,8-diazabicyclo[5,4,0]undec-7-ene were dissolved in 4 ml of ethanol. 0.15 ml of (bromomethyl)cyclopropane was added thereto and refluxed with heating for 3 hours. The solvent was distilled off, and water was added to the residue. Ethyl acetate extraction was performed. The organic layer was washed twice with water, and concentrated. The residue was purified by silica gel column choromatography (n-hexane:ethyl acetate=1:1). The obtained crude crystals were recrystallized using an ethanol-n-hexane mixture, and 60 mg of white powdery N-[2-(3-cyclopropylmethoxy-4-difluoromethoxyphenyl)oxazol-4-ylmethyl]-3-methylpicolinamide was obtained.

$^1$H-NMR ($CDCl_3$) δ: 8.59-8.54 (1H, m), 8.39 (1H, dd, J=4.5, 1.2 Hz), 7.67 (1H, s), 7.63-7.56 (3H, m), 7.37-7.28 (1H, m), 7.22 (1H, d, J=8.1 Hz), 6.69 (1H, t, J=75.0 Hz), 4.59 (2H, dd, J=5.7, 0.9 Hz), 3.98 (2H, d, J=6.9 Hz), 2.76 (3H, s), 1.35-1.20 (1H, m), 0.70-0.63 (2H, m), 0.41-0.35 (2H, m)

Example 99

Using 0.2 g of [2-(3-cyclopropylmethoxy-4-methoxyphenyl)oxazol-4-yl]methylamine obtained in Reference Example 13, 0.11 g of white powdery N-[2-(3-cyclopropylmethoxy-4-methoxyphenyl)oxazol-4-ylmethyl]isoquinoline-1-carboxamide was obtained in the same manner as in Example 1.

$^1$H-NMR ($CDCl_3$) δ: 9.60 (1H, m), 8.67 (1H, br s), 8.47 (1H, d, J=2.4 Hz), 7.90-7.80 (2H, m), 7.75-7.65 (3H, m), 7.61 (1H, dd, J=8.4, 1.8 Hz), 7.53 (1H, d, J=1.8 Hz), 6.92 (1H, d, J=8.4 Hz), 4.68 (2H, d, J=6.0 Hz), 3.94 (2H, d, J=7.5 Hz), 3.92 (3H, s), 1.39 (1H, m), 0.70-0.60 (2H, m), 0.40-0.35 (2H, m)

Example 100

4.42 g of sodium hydroxide was suspended in 160 ml of dimethoxyethane. The suspension was stirred with ice cooling while 16 g of 3-[2-(3-benzyloxy-4-methoxyphenyl)oxazol-4-yl]methyl propionate obtained in Reference Example 48 and 39.23 g of 2-ethoxyperbenzoic acid were separately added, and then heating and refluxing were conducted for 7 hours. After cooling with ice, saturated ammonium chloride solution was added to the mixture and stirred for 30 minutes. Water was then added thereto, and ethyl acetate extraction was performed, followed by drying over anhydrous magnesium sulfate, and the solvent was then distilled off. The residue was subjected to silica gel column purification (n-hexane:ethyl acetate=3:1), and 13.4 g of yellow oily substance, methyl 2-[2-(3-benzyloxy-4-methoxyphenyl)oxazol-4-ylmethyl]-3-(2-ethoxyphenyl)-3-oxopropionate was obtained.

$^1$H-NMR ($CDCl_3$) δ: 7.71 (1H, d, J=7.8 Hz), 7.57-7.54 (3H, m), 7.48-7.28 (6H, m), 6.99-6.90 (3H, m), 5.16 (2H, s), 4.98 (1H, t, J=6.9 Hz), 4.14 (2H, q, J=6.9 Hz), 3.91 (3H, s), 3.70 (3H, s), 3.27-3.19 (2H, m), 1.45 (3H, t, J=6.9 Hz)

Example 101

A 13.4 g quantity of methyl 2-[2-(3-benzyloxy-4-methoxyphenyl)oxazol-4-ylmethyl]-3-(2-ethoxyphenyl)-3-oxopropionate obtained in Example 100 was suspended in 67 ml of ethanol, 67 ml of 47% hydrobromic acid was added thereto, and the suspension was heated and refluxed overnight. After standing to cool, the crystals generated were collected by filtration, washed with water and diisopropyl ether, and dried, thereby yielding 8.1 g of white powdery 1-(2-ethoxyphenyl)-3-[2-(3-hydroxy-4-methoxyphenyl)oxazol-4-yl]propan-1-one.

$^1$H-NMR ($CDCl_3$) δ: 8.30 (1H, d, J=8.7 Hz), 7.84 (1H, d, J=1.8 Hz), 7.83-7.71 (2H, m), 7.45 (1H, t, J=8.4 Hz), 7.06 (1H, d, J=8.7 Hz), 6.99-6.93 (2H, m), 4.17 (2H, q, J=6.9 Hz), 4.00 (3H, s), 3.67 (2H, t, J=6.6 Hz), 3.35 (2H, t, J=6.6 Hz), 1.55 (3H, t, J=6.9 Hz)

Example 102

A 8.1 g quantity of 1-(2-ethoxyphenyl)-3-[2-(3-hydroxy-4-methoxyphenyl)oxazol-4-yl]propan-1-one obtained in Example 101 was suspended in 220 ml of ethanol, 10 g of 1,8-diazabicyclo[5,4,0]undec-7-ene and 5.96 g of (bromomethyl)cyclopropane were added thereto, and stirring was conducted for 5 hours while heating and refluxing. After distilling off ethanol under reduced pressure, water was added, ethyl acetate extraction was performed, followed by drying over anhydrous magnesium sulfate and distilling the solvent off. The residue was subjected to silica gel column purification (n-hexane:ethyl acetate=4:1), and the obtained crude crystals were recrystallized using ethanol, thereby yielding 4.4 g of white powdery 3-[2-(3-cycropropylmethoxy-4-methoxyphenyl)oxazol-4-yl]-1-(2-ethoxy phenyl)propan-1-one.

$^1$H-NMR ($CDCl_3$) δ: 7.70 (1H, dd, J=7.5, 1.8 Hz), 7.56 (1H, dd, J=8.4, 2.1 Hz), 7.50 (1H, s), 7.45-7.39 (2H, m), 7.00-6.89 (3H, m), 4.13 (2H, q, J=7.2 Hz), 3.93-3.91 (5H, m), 3.41 (2H, t, J=6.6 Hz), 2.99 (2H, t, J=6.6 Hz), 1.51 (3H, t, J=7.2 Hz), 1.47 (1H, m), 0.67-0.64 (2H, m), 0.40-0.36 (2H, m)

Example 103

A 0.3 g quantity of 1-(2-ethoxyphenyl)-3-[2-(3-hydroxy-4-methoxyphenyl)oxazol-4-yl]propan-1-one obtained in Example 101 was suspended in 10 ml of ethanol, 0.37 g of 1,8-diazabicyclo[5,4,0]undec-7-ene and 0.26 g of ethyl iodide were added thereto, and the suspension was stirred for 4 hours while heating and refluxing. After distilling off ethanol under reduced pressure, water was added, ethyl acetate extraction was performed, followed by drying over anhydrous magnesium sulfate and distilling the solvent off. The residue was subjected to silica gel column purification (n-hexane:ethyl acetate=3:1), thereby yielding 0.15 g of white powdery 3-[2-(3-ethoxy-4-methoxyphenyl)oxazol-4-yl]-1-(2-ethoxyphenyl)propan-1-one.

$^1$H -NMR ($CDCl_3$) δ: 7.70 (1H, dd, J=7.5, 1.8 Hz), 7.56 (1H, dd, J=8.4, 1.8 Hz), 7.52-7.40 (2H, m), 6.99-6.89 (3H, m), 4.21-4.09 (4H, m), 3.91 (3H, s), 3.42 (2H, t, J=6.9 Hz), 2.99 (2H, t, J=6.9 Hz), 1.51-1.45 (6H, m)

Example 104

A 0.3 g quantity of 1-(2-ethoxyphenyl)-3-[2-(3-hydroxy-4-methoxyphenyl)oxazol-4-yl]propan-1-one obtained in Example 101 was suspended in 10 ml of ethanol, 0.37 g of 1,8-diazabicyclo[5,4,0]undec-7-ene and 0.14 ml of allyl bromide were added thereto, and stirring was conducted for 3 hours while heating and refluxing. After distilling off ethanol under reduced pressure, water was added, ethyl acetate extraction was performed, followed by drying over anhydrous magnesium sulfate and distilling the solvent off. The residue was subjected to silica gel column purification (n-hexane:ethyl acetate=3:1), thereby yielding 0.2 g of white powdery 3-[2-(3-allyloxy-4-methoxyphenyl)oxazol-4-yl]-1-(2-ethoxyphenyl)propan-1-one.

$^1$H-NMR ($CDCl_3$) δ: 7.70 (1H, dd, J=7.8, 1.8 Hz), 7.58 (1H, dd, J=8.4, 1.8 Hz), 7.52 (1H, d, J=1.8 Hz), 7.45-7.40 (2H, m), 7.00-6.90 (3H, m), 6.18-6.05 (1H, m), 5.47-5.29 (2H, m), 4.67 (2H, d, J=5.1 Hz), 4.13 (2H, q, J=6.9 Hz), 3.92 (3H, s), 3.42 (2H, t, J=7.2 Hz), 2.99 (2H, t, J=7.2 Hz), 1.47 (3H, t, J=6.9 Hz).

Using 1-(2-ethoxyphenyl)-3-[2-(3-hydroxy-4-methoxy phenyl)oxazol-4-yl]propan-1-one obtained in Example 101, compounds of Examples 105 to 110 were obtained in the same manner as in Examples 102.

Example 105

3-[2-(3-cyclopentyloxy-4-methoxyphenyl)oxazol-4-yl]-1-(2-ethoxyphenyl)propan-1-one $^1$H-NMR ($CDCl_3$) δ: 7.70 (1H, dd, J=7.5, 1.8 Hz), 7.57-7.51 (2H, m), 7.45-7.39 (2H, m), 6.99-6.88 (3H, m), 4.88 (1H, br s), 4.12 (2H, q, J=6.9 Hz), 3.88 (3H, s), 3.42 (2H, t, J=6.9 Hz), 2.99 (2H, t, J=6.9 Hz), 2.04-1.87 (6H, m), 1.65-1.60 (2H, m), 1.47 (3H, t, J=6.9 Hz)

Example 106

3-[2-(3-isobutoxy-4-methoxyphenyl)oxazol-4-yl]-1-(2-ethoxyphenyl)propan-1-one $^1$H-NMR ($CDCl_3$) δ: 7.70 (1H, dd, J=7.5, 1.8 Hz), 7.55 (1H, dd, J=8.4, 1.8 Hz), 7.50 (1H, d, J=2.1 Hz), 7.45-7.40 (2H, m), 4.13 (2H, q, J=6.9 Hz), 3.90 (3H, s), 3.84 (2H, d, J=6.9 Hz), 3.42 (2H, t, J=7.2 Hz), 3.00 (2H, t, J=7.2 Hz), 2.23-2.14 (1H, m), 1.48 (3H, t, J=6.9 Hz), 1.05 (6H, d, J=6.9 Hz)

Example 107

1-(2-ethoxyphenyl)-3-[2-(4-methoxy-3-propoxyphenyl)oxazol-4-yl]propan-1-one $^1$H-NMR ($CDCl_3$) δ: 7.70 (1H, dd, J=7.5, 1.8 Hz), 7.56 (1H, dd, J=8.1, 1.8 Hz), 7.52 (1H, s), 7.45-7.40 (2H, m), 7.00-6.89 (3H, m), 4.13 (2H, q, J=6.9 Hz), 4.05 (2H, t, J=6.9 Hz), 3.90 (3H, s), 3.42 (2H, t, J=7.5 Hz), 3.00 (2H, t, J=7.5 Hz), 1.95-1.84 (2H, m), 1.47 (3H, t, J=6.9 Hz), 1.05 (3H, t, J=6.9 Hz)

Example 108

3-[2-(3-(3-butenyloxy)-4-methoxyphenyl)oxazol-4-yl]-1-(2-ethoxy phenyl)propan-1-one $^1$H-NMR ($CDCl_3$) δ: 7.70 (1H, dd, J=7.5, 1.8 Hz), 7.57 (1H, dd, J=8.4, 1.8 Hz), 7.52 (1H, s), 7.45-7.40 (2H, m), 6.97-6.89 (3H, m), 6.00-5.90 (1H, m), 5.22-5.10 (2H, m), 4.17-4.11 (4H, m), 3.90 (3H, s), 3.42 (2H, t, J=7.5 Hz), 3.00 (2H, t, J=7.5 Hz), 2.67-2.62 (2H, m), 1.47 (3H, t, J=6.9 Hz)

Example 109

3-[2-(3-butoxy-4-methoxyphenyl)oxazol-4-yl]-1-(2-ethoxyphenyl)propan-1-one $^1$H-NMR ($CDCl_3$) δ: 7.70 (1H, dd, J=7.5, 1.8 Hz), 7.57 (1H, dd, J=8.4, 1.8 Hz), 7.53 (1H, d, J=2.1 Hz), 7.45-7.39 (2H, m), 7.00-6.89 (3H, m), 4.16-4.07 (4H, m), 3.98 (3H, s), 3.42 (2H, t, J=7.2 Hz), 3.00 (2H, t, J=7.2 Hz), 1.90-1.86 (2H, m), 1.57-1.42 (5H, m), 0.99 (3H, t, J=7.2 Hz)

Example 110

1-(2-ethoxyphenyl)-3-[2-(4-methoxy-3-(2-propenyloxy)phenyl)oxazol-4-yl]propan-1-one $^1$H-NMR ($CDCl_3$) δ: 7.70 (1H, dd, J=7.8, 1.8 Hz), 7.66-7.63 (2H, m), 7.46-7.39 (2H, m), 7.00-6.92 (3H, m), 4.83 (2H, d, J=2.1 Hz), 4.13 (2H, q, J=6.9 Hz), 3.92 (3H, s), 3.42 (2H, t, J=7.2 Hz), 2.99 (2H, t, J=7.2 Hz), 2.52 (1H, t, J=2.1 Hz), 1.47 (3H, t, J=6.9 Hz)

Example 111

A 5.0 g quantity of 1-(2-ethoxyphenyl)-3-[2-(3-hydroxy-4-methoxyphenyl)oxazol-4-yl]propan-1-one obtained in Example 101 was dissolved in 50 ml of dimethylformamide, 3.35 g of 2-bromopropane and 5.63 g of potassium carbonate were added thereto, and stirring was conducted overnight at room temperature. Water was added to the obtained mixture, ethyl acetate extraction was performed, followed by drying over anhydrous magnesium sulfate and distilling the solvent off. The residue was subjected to silica gel column purification (n-hexane:ethyl acetate=4:1), and the obtained crude crystals were recrystallized using ethanol, thereby yielding 2.99 g of white powdery 1-(2-ethoxyphenyl)-3-[2-(3-isopropoxy-4-methoxyphenyl)oxazol-4-yl]propan-1-one.

$^1$H-NMR ($CDCl_3$) δ: 7.70 (1H, dd, J=7.5, 1.8 Hz), 7.59-7.54 (2H, m), 7.45-7.39 (2H, m), 7.00-6.89 (3H, m), 4.68-4.60 (1H, m), 4.13 (2H, q, J=6.9 Hz), 3.89 (3H, s), 3.42 (2H, t, J=7.5 Hz), 2.99 (2H, t, J=7.5 Hz), 1.47 (3H, t, J=6.9 Hz), 1.39 (6H, d, J=6.3 Hz)

Using 1-(2-ethoxyphenyl)-3-[2-(3-hydroxy-4-methoxy phenyl)oxazol-4-yl]propane-1-one obtained in Example 101, compounds of Examples 112 to 122 were obtained in the same manner as in Example 111.

Example 112

1-(2-ethoxyphenyl)-3-{2-[4-methoxy-3-(2,2,2-trifluoroethoxy)phenyl]oxazol-4-yl}propan-1-one $^1$H-NMR ($CDCl_3$) δ: 7.72-7.68 (2H, m), 7.60 (1H, d, J=1.8 Hz), 7.45-7.39 (2H, m), 7.00-6.92 (3H, m), 4.44 (2H, q, J=8.4 Hz), 4.13 (2H, q, J=6.6 Hz), 3.90 (3H, s), 3.42 (2H, t, J=6.9 Hz), 2.99 (2H, t, J=6.9 Hz), 1.48 (3H, t, J=6.6 Hz)

Example 113

3-[2-(3-cyclohexylmethoxy-4-methoxyphenyl)oxazol-4-yl]-1-(2-ethoxyphenyl)propan-1-one $^1$H-NMR ($CDCl_3$) δ: 7.70 (1H, dd, J=7.5, 1.8 Hz), 7.55 (1H, dd, J=8.4, 1.8 Hz), 7.50 (1H, d, J=1.8 Hz), 7.45-7.40 (2H, m), 7.00-6.88 (3H, m), 4.14 (2H, q, J=6.9 Hz), 3.90 (3H, s), 3.86 (2H, d, J=6.0 Hz), 3.42 (2H, t, J=7.2 Hz), 2.99 (2H, t, J=7.2 Hz), 2.00-1.86 (3H, m), 1.79-1.63 (3H, m), 1.45 (3H, t, J=6.9 Hz), 1.40-1.22 (2H, m), 1.10-1.02 (2H, m)

Example 114

3-[2-(3-cyclopentylmethoxy-4-methoxyphenyl)oxazol-4-yl]-1-(2-ethoxyphenyl)propan-1-one $^1$H-NMR ($CDCl_3$) δ: 7.70 (1H, dd, J=7.5, 1.8 Hz), 7.55 (1H, dd, J=8.4, 1.8 Hz), 7.50 (1H, d, J=1.8 Hz), 7.45-7.40 (2H, m), 7.00-6.88 (3H, m), 4.14 (2H, q, J=6.9 Hz), 3.95 (2H, d, J=7.2 Hz), 3.90 (3H, s), 3.42 (2H, t, J=7.2 Hz), 3.00 (2H, t, J=7.2 Hz), 2.48-2.44 (1H, m), 2.04-1.86 (2H, m), 1.63-1.50 (4H, m), 1.45 (3H, s), 1.39-1.35 (2H, m)

Example 115

1-(2-ethoxyphenyl)-3-[2-(4-methoxy-3-(4-pentenyloxy)phenyl) oxazol-4-yl]propan-1-one $^1$H-NMR ($CDCl_3$) δ: 7.70 (1H, dd, J=7.5, 2.1 Hz), 7.56 (1H, dd, J=8.1, 2.1 Hz), 7.51 (1H, d, J=2.1 Hz), 7.45-7.39 (2H, m), 7.00-6.89 (3H, m), 5.87-5.81 (1H, m), 5.10-4.99 (2H, m), 4.17-4.08 (4H, m), 3.91 (3H, s), 3.42 (2H, t, J=7.2 Hz), 2.99 (2H, t, J=7.2 Hz), 2.27-2.22 (2H, m), 2.04-1.95 (2H, m), 1.47 (3H, t, J=7.2 Hz)

Example 116

3-[2-(3-cyclobutylmethoxy-4-methoxyphenyl)oxazol-4-yl]-1-(2-ethoxyphenyl)propan-1-one $^1$H-NMR ($CDCl_3$) δ: 7.70 (1H, dd, J=7.5, 2.1 Hz), 7.56 (1H, dd, J=8.1, 2.1 Hz), 7.51 (1H, d, J=2.1 Hz), 7.45-7.39 (2H, m), 7.00-6.80 (3H, m), 4.13 (2H, q, J=7.2 Hz), 4.07 (2H, d, J=7.2 Hz), 3.90 (3H, s), 3.42 (2H, t, J=7.2 Hz), 3.00 (2H, t, J=7.2 Hz), 2.96-2.85 (1H, m), 2.20-2.14 (2H, m), 1.91-1.80 (2H, m), 1.45 (3H, t, J=7.2 Hz)

Example 117

1-(2-ethoxyphenyl)-3-{2-[4-methoxy-3-(3-methyl-2-butenyloxy)phenyl]oxazol-4-yl}propan-1-one $^1$H-NMR ($CDCl_3$) δ: 7.70 (1H, dd, J=7.5, 1.8 Hz), 7.57 (1H, dd, J=8.1, 1.8 Hz), 7.51 (1H, d, J=1.8 Hz), 7.00-6.89 (3H, m), 5.55 (1H, t, J=6.6 Hz), 4.64 (2H, d, J=6.6 Hz), 4.13 (2H, q, J=6.9 Hz), 3.91 (3H, s), 3.42 (2H, t, J=7.2 Hz), 3.00 (2H, t, J=7.2 Hz), 1.77 (6H, d, J=6.6 Hz), 1.45 (3H, t, J=6.9 Hz)

Example 118

3-{2-[3-(2-cyclohexenyloxy)-4-methoxyphenyl]oxazol-4-yl}-1-(2-ethoxyphenyl)propan-1-one $^1$H-NMR ($CDCl_3$) δ: 7.70 (1H, dd, J=7.5, 1.8 Hz), 7.60-7.57 (2H, m), 7.42-7.39 (2H, m), 7.00-6.89 (3H, m), 6.00-

5.92 (2H, m), 4.88 (1H, br s), 4.15 (2H, q, J=7.2 Hz), 3.89 (3H, s), 3.42 (2H, t, J=7.2 Hz), 2.99 (2H, t, J=7.2 Hz), 2.04-1.80 (4H, m), 1.72-1.53 (2H, m), 1.45 (3H, t, J=7.2 Hz)

Example 119

1-(2-ethoxyphenyl)-3-[2-(4-methoxy-3-phenethyloxyphenyl)oxazol-4-yl]propan-1-one $^1$H-NMR ($CDCl_3$) δ: 7.69 (1H, dd, J=7.8, 1.8 Hz), 7.59 (1H, dd, J=8.4, 1.8 Hz), 7.56 (1H, d, J=1.8 Hz), 7.51-6.98 (7H, m), 6.95-6.90 (3H, m), 4.27 (2H, t, J=7.2 Hz), 4.11 (2H, q, J=6.9 Hz), 3.91 (3H, s), 3.41 (2H, t, J=7.2 Hz), 3.20 (2H, t, J=7.2 Hz), 2.98 (2H, t, J=7.2 Hz), 1.54 (3H, t, J=6.9 Hz)

Example 120

1-(2-ethoxyphenyl)-3-{2-[4-methoxy-3-(3-phenylpropoxy)phenyl]oxazol-4-yl}propan-1-one $^1$H-NMR ($CDCl_3$) δ: 7.70 (1H, dd, J=7.5, 1.8 Hz), 7.58 (1H, dd, J=8.4, 1.8 Hz), 7.56 (1H, d, J=1.8 Hz), 7.49-7.39 (2H, m), 7.30-7.15 (5H, m), 6.99-6.90 (3H, m), 4.16-4.08 (4H, m), 3.92 (3H, s), 3.42 (2H, t, J=7.2 Hz), 2.98 (2H, t, J=7.2 Hz), 2.84 (2H, t, J=8.1 Hz), 2.24-2.15 (2H, m), 1.46 (3H, t, J=6.9 Hz)

Example 121

3-{2-[3-(2-cyclopropylethoxy)-4-methoxyphenyl]oxazol-4-yl}-1-(2-ethoxyphenyl)propan-1-one $^1$H-NMR ($CDCl_3$) δ: 7.70 (1H, dd, J=7.8, 1.8 Hz), 7.57-7.55 (2H, m), 7.43-7.39 (2H, m), 7.00-6.89 (3H, m), 4.19-4.10 (4H, m), 3.91 (3H, s), 3.42 (2H, t, J=6.9 Hz), 3.01 (2H, t, J=6.9 Hz), 1.81-1.74 (2H, m), 1.48 (3H, t, J=6.9 Hz), 0.88-0.83 (1H, m), 0.52-0.47 (2H, m), 0.16-0.12 (2H, m)

Example 122

3-{2-[3-(2-cyclopentylethoxy)-4-methoxyphenyl]oxazol-4-yl}-1-(2-ethoxyphenyl)propan-1-one $^1$H-NMR ($CDCl_3$) δ: 7.70 (1H, dd, J=7.8, 1.8 Hz), 7.56 (1H, dd, J=8.4, 1.8 Hz), 7.51 (1H, d, J=2.1 Hz), 7.45-7.39 (2H, m), 7.00-6.89 (3H, m), 4.17-4.07 (4H, m), 3.90 (3H, s), 3.42 (2H, t, J=6.9 Hz), 3.00 (2H, t, J=6.9 Hz), 2.00-1.81 (5H, m), 1.66-1.62 (4H, m), 1.45 (3H, t, J=6.9 Hz), 1.28-1.15 (2H, m)

Example 123

A 1.0 g quantity of methyl 3-{2-[3-cyclopropylmethoxy-4-(2,2,2-trifluoroethoxy)phenyl]oxazol-4-yl}propionate obtained in Reference Example 49 and 0.54 g of methyl 3-methoxypicolinate were added to 5 ml of dimethylformamide, and the mixture was stirred with ice cooling for 10 minutes. A 0.83 g of sodium t-pentoxide was added to the obtained mixture, which was then stirred with ice cooling for an hour, followed by further stirring at room temperature for 1 hour. The reaction mixture was stirred with ice cooling, saturated ammonium chloride solution was added thereto, and further stirred for 30 minutes. Water was added to the mixture, ethyl acetate extraction was performed, followed by drying over anhydrous magnesium sulfate and distilling the solvent off. A 5.0 ml quantity of dimethylsulfoxide, 84 mg of lithium chloride and 41 μl of purified water were added to the residue, and the mixture was stirred with heating at 110° C. overnight. After standing to cool, water was added to the obtained mixture, ethyl acetate extraction was performed, followed by drying over anhydrous magnesium sulfate and distilling the solvent off. The obtained residue was subjected to silica gel column purification (n-hexane:ethyl acetate=4:1), and the obtained crude crystals were recrystallized from a mixture of ethyl acetate and diisopropyl ether, thereby yielding 0.11 g white powdery 3-{2-[3-cyclopropyl methoxy-4-(2,2,2-trifluoroethoxy)phenyl]oxazol-4-yl}-1-(3-methoxy pyridin-2-yl)propan-1-one.

$^1$H-NMR ($CDCl_3$) δ: 8.24 (1H, d, J=4.2 Hz), 7.55-7.47 (2H, m), 7.43 (1H, s), 7.40-7.35 (2H, m), 7.03 (1H, d, J=8.4 Hz), 4.46 (2H, q, J=7.2 Hz), 3.94 (2H, d, J=6.6 Hz), 3.90 (3H, s), 3.51 (2H, d, J=7.2 Hz), 3.01 (2H, d, J=7.2 Hz), 1.31-1.26 (1H, m), 0.68-0.62 (2H, m), 0.39-0.34 (2H, m)

Example 124

A 2 g quantity of methyl 3-[2-(3-benzyloxy-4-methoxy phenyl)oxazol-4-yl]propionate obtained in Reference Example 48 and 1.1 g of methyl 3-methoxypicolinate were dissolved in 10 ml of dimethylformamide, and while stirring the solution with ice cooling 1.81 g of sodium t-pentoxide was added thereto and stirred for 30 minutes. The mixture was further stirred for 5 hours at room temperature, ice was added to the reaction mixture, followed by addition of saturated aqueous ammonium chloride solution, and the mixture was further stirred. After stirring the reaction mixture for 30 minutes, water was added thereto and ethyl acetate extraction was performed. The organic layer was washed twice with water, and concentrated under reduced pressure. The obtained residue was purified by silica gel column chromatography (n-hexane:ethyl acetate=1:1), thereby yielding 1.55 g of white amorphous methyl 2-[2-(3-benzyloxy-4-methoxy phenyl)oxazol-4-ylmethyl]-3-(3-methoxypyridin-2-yl)-3-oxopropionate.

$^1$H-NMR ($CDCl_3$) δ: 8.24 (1H, dd, J=4.5, 1.8 Hz), 7.57-7.28 (10H, m), 6.91 (1H, d, J=9.0 Hz), 5.18-5.13 (3H, m), 3.91-3.90 (6H, m), 3.64 (3H, s), 3.36-3.18 (2H, m)

Example 125

A 1.5 g quantity of methyl 2-[2-(3-benzyloxy-4-methoxyphenyl)oxazol-4-ylmethyl]-3-(3-methoxypyridin-2-yl)-3-oxopropionate obtained in Example 124 was dissolved in 22.5 ml of ethanol, 7.5 ml of 47% hydrobromic acid was added thereto, and the mixture was stirred with heating at 80° C. for 7.5 hours. While stirring with ice cooling, the reaction mixture was neutralized with a 5N sodium hydroxide solution, and ethyl acetate extraction was performed. The organic layer was washed twice with water, and concentrated under reduced pressure, and the obtained residue was purified by silica gel column chromatography (dichloromethane:methanol=20:1), thereby yielding 0.65 g of pale yellow oily substance, 3-[2-(3-hydroxy-4-methoxyphenyl)oxazol-4-yl]-3-(3-methoxypyridin-2-yl)propan-1-one.

$^1$H-NMR ($CDCl_3$) δ: 8.24 (1H, dd, J=7.2, 1.5 Hz), 7.55-7.27 (5H, m), 6.88 (1H, d, J=8.7 Hz), 5.72 (1H, s), 3.92-3.89 (6H, m), 3.51 (2H, t, J=7.5 Hz), 3.03 (2H, t, J=7.5 Hz)

Example 126

Using 0.24 g of 3-[2-(3-hydroxy-4-methoxyphenyl)oxazol-4-yl]-3-(3-methoxypyridine-2-yl)propan-1-one obtained in Example 125, 0.11 g of white powdery 3-[2-(3-cyclopropylmethoxy-4-methoxyphenyl)oxazol-4-yl]-3-(3-methoxypyridin-2-yl)propan-1-one was obtained in the same manner as in Example 102.

$^1$H-NMR ($CDCl_3$) δ: 8.24 (1H, dd, J=4.2, 1.2 Hz), 7.59-7.32 (5H, m), 6.91 (1H, d, J=8.4 Hz), 3.94-3.90 (8H, m), 3.51 (2H, t, J=7.2 Hz), 3.01 (2H, t, J=7.2 Hz), 1.40-1.30 (1H, m), 0.69-0.62 (2H, m), 0.41-0.35 (2H, m)

Using 3-[2-(3-hydroxy-4-methoxyphenyl)oxazol-4-yl]-3-(3-methoxypyridin-2-yl)propan-1-one obtained in Example 125, compounds of Examples 127 and 128 were obtained in the same manner as in Example 102.

Example 127

3-[2-(3-isobutoxy-4-methoxyphenyl)oxazol-4-yl]-3-(3-methoxy pyridin-2-yl)propan-1-one $^1$H-NMR ($CDCl_3$) δ: 8.24 (1H, dd, J=4.2, 1.5 Hz), 7.58-7.30 (5H, m), 6.91 (1H, d, J=8.4 Hz), 3.92-3.90 (6H, m), 3.84 (2H, d, J=6.9 Hz), 3.52 (2H, t, J=7.2 Hz), 3.01 (2H, t, J=7.2 Hz), 2.20 (1H, q, J=6.9 Hz), 1.06 (6H, d, J=6.9 Hz)

Example 128

3-[2-(3-cyclopentyloxy-4-methoxyphenyl)oxazol-4-yl]-1-(3-methoxy pyridin-2-yl)propan-1-one $^1$H-NMR ($CDCl_3$) δ: 8.24 (1H, dd, J=4.5, 1.5 Hz), 7.60-7.30 (5H, m), 6.90 (1H, d, J=8.7 Hz), 4.90-4.85 (1H, m), 3.90-3.88 (6H, m), 3.51 (2H, d, J=6.9 Hz), 3.01 (2H, t, J=6.9 Hz), 2.00-1.81 (6H, m), 1.64-1.60 (2H, m)

Example 129

Using 0.15 g of 3-[2-(3-hydroxy-4-methoxyphenyl)oxazol-4-yl]-3-(3-methoxypyridin-2-yl)propan-1-one obtained in Example 125, 44 mg of white powdery 1-(3-methoxypyridin-2-yl)-3-{2-[4-methoxy-3-(2,2,2-trifluoroethoxy) phenyl]oxazol-4-yl}propan-1-one was obtained in the same manner as in Example 111.

$^1$H-NMR ($CDCl_3$) δ: 8.24 (1H, dd, J=4.2, 1.2 Hz), 7.70 (1H, dd, J=8.4, 1.8 Hz), 7.60 (1H, d, J=1.8 Hz), 7.51 (1H, d, J=1.8 Hz), 7.47-7.32 (2H, m), 6.96 (1H, d, J=8.4 Hz), 4.45 (2H, q, J=8.4 Hz), 3.95-3.88 (6H, m), 3.52 (2H, t, J=7.2 Hz), 3.01 (2H, t, J=7.2 Hz)

Example 130

A 2 g quantity of methyl 3-[2-(3-benzyloxy-4-methoxy phenyl)oxazol-4-yl]propionate obtained in Reference Example 48 and 1 g of methyl 3-ethoxypicolinate were dissolved in 10 ml of dimethylformamide, and while stirring the solution with ice cooling 1.81 g of sodium t-pentoxide was added thereto and stirred for 30 minutes. The mixture was further stirred for 4 hours at room temperature, and ice was added to the reaction mixture, followed by addition of saturated aqueous ammonium chloride solution for further stirring. After stirring the reaction mixture for 30 minutes, water was added thereto and ethyl acetate extraction was performed. The organic layer was washed twice with water, and concentrated under reduced pressure. The obtained residue was purified by silica gel column chromatography (n-hexane:ethyl acetate=1:1), thereby yielding 1.5 g of colorless oily substance methyl 2-[2-(3-benzyloxy-4-methoxyphenyl)oxazol-4-ylmethyl]-3-(3-ethoxypyridin-2-yl)-3-oxopropionate.

$^1$H-NMR ($CDCl_3$) δ: 8.22 (1H, dd, J=4.2, 1.2 Hz), 7.57-7.27 (10H, m), 6.91 (1H, d, J=9.0 Hz), 5.18-5.12 (3H, m), 4.12 (2H, q, J=6.9 Hz), 3.92 (3H, s), 3.65 (3H, s), 3.30-3.23 (2H, m), 1.46 (3H, t, J=6.9 Hz)

Example 131

Using 1.5 g of methyl 2-[2-(3-benzyloxy-4-methoxyphenyl)oxazol-4-ylmethyl]-3-(3-ethoxypyridin-2-yl)-3-oxopropionate obtained in Example 130, 0.7 g of pale yellow oily substance, 1-(3-ethoxypyridin-2-yl)-3-[2-(3-hydroxy-4-methoxyphenyl)oxazol-4-yl]propan-1-one, was obtained in the same manner as in Example 125.

$^1$H-NMR ($CDCl_3$) δ: 8.23 (1H, dd, J=4.2, 1.2 Hz), 7.55-7.49 (2H, m), 7.45 (1H, s), 7.42-7.28 (2H, m), 6.88 (1H, d, J=8.7 Hz), 5.70 (1H, s), 4.11 (2H, q, J=6.9 Hz), 3.49 (2H, t, J=7.2 Hz), 3.01 (2H, t, J=6.9 Hz), 1.46 (3H, t, J=6.9 Hz)

Example 132

Using 0.2 g of 1-(3-ethoxypyridin-2-yl)-3-[2-(3-hydroxy-4-methoxyphenyl)oxazol-4-yl]propan-1-one obtained in Example 131, 0.2 g of pale yellow oily substance, 3-[2-(3-cyclopentyloxy-4-methoxyphenyl)oxazol-4-yl]-1-(3-ethoxypyridin-2-yl)propan-1-one, was obtained in the same manner as in Example 102.

$^1$H-NMR ($CDCl_3$) δ: 8.23 (1H, dd, J=4.5, 1.5 Hz), 7.57-7.45 (2H, m), 7.44 (1H, d, J=0.9 Hz), 7.38-7.28 (2H, m), 6.89 (1H, d, J=8.7 Hz), 4.89-4.87 (1H, m), 4.12 (2H, q, J=6.9 Hz), 3.94-3.91 (5H, m), 3.88 (3H, s), 3.49 (2H, t, J=7.2 Hz), 3.01 (2H, t, J=7.2 Hz), 2.01-1.81 (6H, m), 1.65-1.58 (2H, m), 1.47 (3H, t, J=6.9 Hz)

Using 1-(3-ethoxypyridin-2-yl)-3-[2-(3-hydroxy-4-methoxy phenyl)oxazol-4-yl]propan-1-one obtained in Example 131, compounds of Examples 133 and 134 were obtained in the same manner as in Example 102.

Example 133

3-[2-(3-cyclopropylmethoxy-4-methoxyphenyl)oxazol-4-yl]-1-(3-ethoxypyridin-2-yl)propan-1-one $^1$H-NMR ($CDCl_3$) δ: 8.23 (1H, dd, J=4.2, 1.5 Hz), 7.57 (1H, dd, J=8.4, 1.8 Hz), 7.50 (1H, d, J=1.8 Hz), 7.45 (1H, d, J=1.8 Hz), 7.38-7.28 (2H, m), 6.91 (1H, d, J=8.4 Hz), 4.12 (2H, q, J=6.9 Hz), 3.94-3.91 (5H, m), 3.49 (2H, t, J=7.2 Hz), 3.02 (2H, t, J=7.2 Hz), 1.46 (3H, t, J=6.9 Hz), 1.42-1.32 (1H, m), 0.69-0.62 (2H, m), 0.40-0.35 (2H, m)

Example 134

1-(3-ethoxypyridin-2-yl)-3-[2-(3-isobutoxy-4-methoxyphenyl)oxazol-4-yl]propan-1-one $^1$H-NMR ($CDCl_3$) δ: 8.23 (1H, dd, J=4.5, 1.5 Hz), 7.56 (1H, dd, J=8.4, 2.1 Hz), 7.50 (1H, d, J=2.1 Hz), 7.45 (1H, s), 7.38-7.28 (2H, m), 6.90 (1H, d, J=8.4 Hz), 4.12 (2H, q, J=6.9 Hz), 3.90 (3H, s), 3.85 (2H, d, J=6.6 Hz), 3.50 (2H, t, J=6.9 Hz), 3.02 (2H, t, J=6.9 Hz), 2.19 (2H, qt, J=6.6 Hz), 1.47 (3H, t, J=6.9 Hz), 1.05 (6H, d, J=6.6 Hz)

Example 135

A 5 g quantity of methyl 3-[2-(3-benzyloxy-4-methoxy phenyl)oxazol-4-yl]propionate obtained in Reference Example 48 and 3.2 g of methyl 3-methylpicolinate were dissolved in 150 ml of dimethoxyethane. While stirring the solution with ice cooling 1.2 g of sodium hydride was added thereto and further stirred. The reaction mixture was heated and refluxed for 4 hours. At the completion of the reaction, a saturated aqueous ammonium chloride solution was added to the mixture while stirring with ice cooling, and the mixture was further stirred. After stirring the reaction mixture for 30 minutes, water was added thereto and ethyl acetate extraction was performed. The organic layer was washed twice with water, and concentrated under reduced pressure. The obtained residue was purified by silica gel column chromatography (n-hexane:ethyl acetate=2:1), thereby yielding 5.5 g of colorless oily substance methyl 2-[2-(3-benzyloxy-4-methoxyphenyl)oxazol-4-ylmethyl]-3-(3-methylpyridin-2-yl)-3-oxopropionate.

$^1$H-NMR ($CDCl_3$) δ: 8.49 (1H, dd, J=4.8, 1.2 Hz), 7.59-7.28 (10H, m), 6.91 (1H, d, J=9.0 Hz), 5.23-5.16 (3H, m), 3.91 (3H, s), 3.65 (3H, s), 3.37-3.18 (2H, m) 2.59 (3H, s)

Example 136

A 5.5 g quantity of methyl 2-[2-(3-benzyloxy-4-methoxy phenyl)oxazol-4-ylmethyl]-3-(3-methylpyridin-2-yl)-3-oxopropionate obtained in Example 135 was dissolved in 20 ml of ethanol, 80 ml of a 5N aqueous hydrochloric acid solution was added thereto, and the mixture was stirred with heating at 80° C. for 1.5 hours. While stirring with ice cooling, the reaction mixture was neutralized with 5 N aqueous sodium hydroxide solution, and ethyl acetate extraction was performed. The organic layer was washed twice with water, concentrated under reduced pressure, and the obtained crude crystals were recrystallized with a mixture of 20 ml of ethanol and 40 ml of n-hexane, thereby yielding 1.92 g of pale yellow powdery 3-[2-(3-hydroxy-4-methoxy phenyl)oxazol-4-yl]-1-(3-methylpyridin-2-yl)propan-1-one.

$^1$H-NMR ($CDCl_3$) δ: 8.49 (1H, dd, J=4.5, 1.2 Hz), 7.60-7.51 (3H, m), 7.44 (1H, d, J=0.9 Hz), 7.41-7.29 (1H, m), 6.89 (1H, dd, J=7.8, 1.2 Hz), 5.68 (1H, s), 3.93 (3H, s), 3.58 (2H, t, J=7.5 Hz), 3.00 (2H, t, J=7.5 Hz), 2.57 (3H, s)

Example 137

A 0.3 g quantity of 3-[2-(3-hydroxy-4-methoxyphenyl)oxazol-4-yl]-1-(3-methylpyridin-2-yl)propan-1-one obtained in Example 136 and 0.4 ml of 1,8-diazabicyclo[5,4,0]undec-7-ene were dissolved in 5 ml of ethanol, 0.24 g of (bromomethyl)cyclopropane was added thereto, and the mixture was heated and refluxed for 4.5 hours. After standing to cool, water was added to the reaction mixture, and ethyl acetate extraction was performed. The extract was washed twice with water, the organic layer was then concentrated under reduced pressure, and the obtained residue was purified by silica gel column chromatography (n-hexane:ethyl acetate=2:1), thereby yielding 0.2 g of white powdery 3-[2-(3-cyclopropylmethoxy-4-methoxyphenyl)oxazol-4-yl]-1-(3-methyl pyridin-2-yl)propan-1-one.

$^1$H-NMR ($CDCl_3$) δ: 8.50 (1H, dd, J=4.5, 1.2 Hz), 7.60-7.54 (2H, m), 7.49 (1H, d, J=1.8 Hz), 7.45 (1H, s), 7.34-7.29 (1H, m), 6.91 (1H, d, J=8.7 Hz), 3.94-3.91 (5H, m), 3.60 (2H, t, J=7.5 Hz), 3.00 (2H, t, J=7.5 Hz), 2.57 (3H, s), 1.40-1.32 (1H, m), 0.69-0.62 (2H, m), 0.41-0.35 (2H, m)

Example 138

A 0.23 g quantity of 3-[2-(3-hydroxy-4-methoxy phenyl)oxazol-4-yl]-1-(3-methylpyridin-2-yl)propan-1-one obtained in Example 136 and 0.3 ml of 1,8-diazabicyclo[5,4,0]undec-7-ene were dissolved in 5 ml of ethanol, 0.21 g of ethyl iodide was added thereto, and the mixture was heated and refluxed for 4 hours. After standing to cool, water was added to the reaction mixture, and ethyl acetate extraction was performed. The extract was washed twice with water, the organic layer was then concentrated under reduced pressure, and the obtained residue was purified by silica gel column chromatography (n-hexane:ethyl acetate=2:1), thereby yielding 0.17 g of white powdery 3-[2-(3-ethoxy-4-methoxyphenyl)oxazol-4-yl]-1-(3-methylpyridin-2-yl)propan-1-one.

$^1$H-NMR ($CDCl_3$) δ: 8.24 (1H, d, J=4.2 Hz), 7.58-7.55 (2H, m), 7.51 (1H, d, J=2.1 Hz), 7.45 (1H, s), 6.90 (1H, d, J=8.4 Hz), 4.19 (2H, q, J=7.2 Hz), 3.91 (3H, s), 3.59 (2H, t, J=7.2 Hz), 3.00 (2H, t, J=7.2 Hz), 2.57 (3H, s), 1.49 (3H, t, J=7.2 Hz)

Example 139

A 0.3 g quantity of 3-[2-(3-hydroxy-4-methoxyphenyl)oxazol-4-yl]-1-(3-methylpyridin-2-yl)propan-1-one obtained in Example 136 and 0.4 ml of 1,8-diazabicyclo[5,4,0]undec-7-ene were dissolved in 5 ml of ethanol, 0.23 g of 2-bromopropane was added thereto, and the mixture was heated and refluxed for 4.5 hours. After standing to cool, water was added to the reaction mixture, and ethyl acetate extraction was performed. The extract was washed twice with water, the organic layer was then concentrated under reduced pressure, and the obtained residue was purified by silica gel column chromatography (n-hexane:ethyl acetate=2:1), thereby yielding 0.16 g of white powdery 3-[2-(3-isopropoxy-4-methoxyphenyl)oxazol-4-yl]-1-(3-methylpyridin-2-yl)propan-1-one.

$^1$H-NMR ($CDCl_3$) δ: 8.50 (1H, dd, J=4.5, 1.2 Hz), 7.59-7.53 (3H, m), 7.45 (1H, s), 7.34-7.31 (1H, m), 6.91 (1H, d, J=8.7 Hz), 4.65 (1H, sept., J=6.0 Hz), 3.89 (3H, s), 3.59 (2H, t, J=7.5 Hz), 3.00 (2H, t, J=7.5 Hz), 2.62 (3H, s), 1.39 (6H, d, J=6.0 Hz)

Example 140

A 0.3 g quantity of 3-[2-(3-hydroxy-4-methoxyphenyl)oxazol-4-yl]-1-(3-methylpyridin-2-yl)propan-1-one obtained in Example 136 and 0.3 ml of 1,8-diazabicyclo[5,4,0]undec-7-ene were dissolved in 6 ml of ethanol, 0.22 g of allyl bromide was added thereto, and the mixture was heated and refluxed for 4 hours. After standing to cool, water was added to the reaction mixture, and ethyl acetate extraction was performed. The extract was washed twice with water, the organic layer was then concentrated under reduced pressure, and the obtained residue was purified by silica gel column chromatography (n-hexane:ethyl acetate=2:1), thereby yielding 0.18 g of white powdery 3-[2-(3-allyloxy-4-methoxyphenyl)oxazol-4-yl]-1-(3-methylpyridin-2-yl)propan-1-one.

$^1$H-NMR ($CDCl_3$) δ: 8.51-8.48 (1H, m), 7.60-7.56 (2H, m), 7.52 (1H, d, J=2.1 Hz), 7.45 (1H, s), 7.34-7.29 (1H, m), 6.92 (1H, d, J=8.7 Hz), 6.16-6.05 (1H, m), 5.48-5.28 (2H, m), 4.69-4.66 (2H, m), 3.92 (3H, s), 3.60 (2H, t, J=7.2 Hz), 3.00 (2H, t, J=7.2 Hz), 2.57 (3H, s)

Example 141

A 0.15 g quantity of 3-[2-(3-hydroxy-4-methoxy phenyl)oxazol-4-yl]-1-(3-methylpyridin-2-yl)propan-1-one obtained in Example 136 and 0.15 ml of 1,8-diazabicyclo[5,4,0]undec-7-ene were dissolved in 5 ml of ethanol, 0.13 g of (bromomethyl)cyclobutane was added thereto, and the mixture was heated and refluxed overnight. After standing to cool, water was added to the reaction mixture, and ethyl acetate extraction was performed. The extract was washed twice with water, the organic layer was then concentrated under reduced pressure, and the obtained residue was purified by silica gel column chromatography (n-hexane:ethyl acetate=2:1), thereby yielding 90 mg of white powdery 3-[2-(3-cyclobutylmethoxy-4-methoxyphenyl)oxazol-4-yl]-1-(3-methylpyridin-2-yl)propan-1-one.

$^1$H-NMR ($CDCl_3$) δ: 8.50 (1H, dd, J=4.5, 1.2 Hz), 7.60-7.51 (3H, m), 7.45 (1H, d, J=2.1 Hz), 7.34-7.29 (1H, m), 6.89 (1H, d, J=8.7 Hz), 4.07 (2H, d, J=6.9 Hz), 3.89 (3H, s), 3.60 (2H, t, J=7.5 Hz), 3.01 (2H, t, J=7.5 Hz), 2.89-2.83 (1H, m), 2.57 (3H, s), 2.22-2.13 (2H, m), 2.00-1.84 (4H, m)

Using 3-[2-(3-hydroxy-4-methoxyphenyl)oxazol-4-yl]-1-(3-methylpyridin-2-yl)propan-1-one obtained in Example 136, compounds of Examples 142 to 154 were obtained in the same manner as in Example 137.

Example 142

3-[2-(3-isobutoxy-4-methoxyphenyl)oxazol-4-yl]-1-(3-methyl pyridin-2-yl)propan-1-one $^1$H-NMR ($CDCl_3$) δ: 8.50 (1H, dd, J=4.5, 1.2 Hz), 7.60-7.53 (2H, m), 7.50 (1H, d, J=1.8 Hz), 7.45 (1H, s), 7.34-7.28 (1H, m), 6.90 (1H, d, J=8.4 Hz), 3.90 (3H, s), 3.84 (2H, d, J=6.9 Hz), 3.60 (2H, t, J=7.8 Hz), 3.01 (2H, t, J=7.8 Hz), 2.57 (3H, s), 2.20 (1H, qt, J=6.9 Hz), 1.05 (6H, d, J=6.9 Hz)

Example 143

3-[2-(4-methoxy-3-propoxyphenyl)oxazol-4-yl]-1-(3-methylpyridin-2-yl)propan-1-one $^1$H-NMR ($CDCl_3$) δ: 8.50 (1H, dd, J=4.5, 1.2 Hz), 7.59-7.54 (2H, m), 7.51 (1H, d, J=1.8 Hz), 7.50 (1H, s), 7.34-7.29 (1H, m), 6.90 (1H, d, J=8.4 Hz), 4.05 (2H, t, J=6.9 Hz), 3.91 (3H, s), 3.60 (2H, t, J=7.5 Hz), 3.01 (2H, t, J=7.5 Hz), 2.57 (3H, s), 1.90 (2H, qt, J=6.9 Hz), 1.24 (3H, t, J=6.9 Hz)

Example 144

3-[2-(3-cyclopentyloxy-4-methoxyphenyl)oxazol-4-yl]-1-(3-methyl pyridine-2-yl)propane-1-one $^1$H-NMR ($CDCl_3$) δ: 8.50 (1H, dd, J=4.5, 1.2 Hz), 7.59-7.50 (3H, m), 7.44 (1H, d, J=1.2 Hz), 7.34-7.31 (1H, m), 6.89 (1H, d, J=8.4 Hz), 4.90-4.84 (1H, m), 3.88 (3H, s), 3.59 (2H, t, J=7.2 Hz), 3.00 (2H, t, J=7.2 Hz), 2.57 (3H, s), 2.03-1.80 (6H, m), 1.64-1.58 (2H, m)

Example 145

3-[2-(4-methoxy-3-(2-propenyloxy)phenyl)oxazol-4-yl]-1-(3-methylpyridin-2-yl)propan-1-one $^1$H-NMR ($CDCl_3$) δ: 8.50 (1H, d, J=4.5 Hz), 7.67-7.63 (2H, m), 7.58 (1H, d, J=8.1 Hz), 7.46 (1H, s), 7.34-7.30 (1H, m), 6.93 (1H, dd, J=6.6, 2.4 Hz), 4.82 (2H, d, J=2.4 Hz), 3.92 (3H, s), 3.60 (2H, t, J=7.2 Hz), 3.01 (2H, t, J=7.2 Hz), 2.58 (3H, s), 2.53 (1H, t, J=2.4 Hz)

Example 146

3-[2-(3-(3-butenyloxy)-4-methoxyphenyl)oxazol-4-yl]-1-(3-methylpyridin-2-yl)propan-1-one $^1$H-NMR ($CDCl_3$) δ: 8.50 (1H, dd, 1.5 Hz), 7.59-7.55 (2H, m), 7.52 (1H, d, J=2.1 Hz), 7.45 (1H, d, J=2.1 Hz), 7.34-7.29 (1H, m), 5.97-5.85 (1H, m), 5.23-5.09 (2H, m), 4.14 (2H, t, J=6.9 Hz), 3.91 (3H, s), 3.60 (2H, t, J=7.5 Hz), 3.00 (2H, t, J=7.5 Hz), 2.68-2.57 (5H, m)

Example 147

3-[2-(3-butoxy-4-methoxyphenyl)oxazol-4-yl]-1-(3-methylpyridin-2-yl)propan-1-one $^1$H-NMR ($CDCl_3$) δ: 8.50 (1H, d, J=4.8 Hz), 7.59-7.51 (3H, m), 7.45 (1H, s), 7.34-7.30 (1H, m), 6.90 (1H, d, J=8.7 Hz), 4.09 (2H, t, J=6.6 Hz), 3.90 (3H, s), 3.60 (2H, t, J=7.2 Hz), 3.01 (2H, t, J=7.2 Hz), 2.57 (3H, s), 1.86 (2H, td, J=7.2, 6.6 Hz), 1.56-1.45 (2H, m), 0.99 (3H, t, J=7.2 Hz)

Example 148

3-[2-(3-cyclohexylmethoxy-4-methoxyphenyl)oxazol-4-yl]-1-(3-methylpyridin-2-yl)propan-1-one $^1$H-NMR ($CDCl_3$) δ: 8.50 (1H, d, J=4.5 Hz), 7.61-7.53 (2H, m), 7.49 (1H, d, J=1.8 Hz), 7.45 (1H, s), 7.34-7.28 (1H, m), 6.89 (1H, d, J=8.7 Hz), 3.90-3.86 (5H, m), 3.60 (2H, t, J=7.5 Hz), 3.01 (2H, t, J=7.5 Hz), 2.57 (3H, s), 1.94-1.85 (3H, m), 1.79-1.57 (3H, m), 1.38-0.88 (5H, m)

Example 149

3-[2-(4-methoxy-3-(4-pentenyloxy)phenyl)oxazol-4-yl]-1-(3-methylpyridin-2-yl)propan-1-one $^1$H-NMR ($CDCl_3$) δ: 8.50 (1H, dd, J=4.5, 1.2 Hz), 7.59-7.54 (2H, m), 7.51 (1H, d, J=2.1 Hz), 7.45 (1H, s), 7.34-7.29 (1H, m), 6.91 (1H, d, J=8.4 Hz), 5.91-5.80 (1H, m), 5.11-4.97 (2H, m), 4.10 (2H, d, J=6.6 Hz), 3.91 (3H, s), 3.60 (2H, t, J=7.5 Hz), 3.01 (2H, t, J=7.5 Hz), 2.57 (3H, s), 2.30-2.22 (2H, m), 2.05-1.92 (2H, m)

Example 150

3-[2-(4-methoxy-3-phenethyloxyphenyl)oxazol-4-yl]-1-(3-methyl pyridin-2-yl)propan-1-one $^1$H-NMR ($CDCl_3$) δ: 8.48 (1H, dd, J=4.5, 0.9 Hz), 7.60-7.49 (3H, m), 7.43 (1H, s), 7.35-7.20 (6H, m), 6.91 (1H, d, J=8.7 Hz), 4.27 (2H, t, J=7.5 Hz), 3.91 (3H, s), 3.58 (2H, t, J=7.2 Hz), 3.19 (2H, t, J=7.5 Hz), 3.00 (2H, t, J=7.2 Hz), 2.55 (3H, s)

Example 151

3-{2-[4-methoxy-3-(3-phenylpropoxy)phenyl]oxazol-4-yl}-1-(3-methylpyridin-2-yl)propan-1-one $^1$H-NMR ($CDCl_3$) δ: 8.50 (1H, dd, J=4.5, 1.2 Hz), 7.58 (1H, d, J=2.1 Hz), 7.55 (1H, d, J=2.1 Hz), 7.49 (1H, d, J=2.1 Hz), 7.44 (1H, s), 7.34-7.15 (6H, m), 6.91 (1H, d, J=8.4 Hz), 4.11 (2H, t, J=6.6 Hz), 3.92 (3H, s), 3.60 (2H, t, J=7.5 Hz), 3.00 (2H, t, J=7.5 Hz), 2.84 (2H, t, J=7.5 Hz), 2.57 (3H, s), 2.20 (2H, tt, J=7.5, 6.6 Hz)

Example 152

Using 0.5 g of cyclopentylmethyl methanesulfonate obtained in Reference Example 52 and 0.2 g of 3-[2-(3-hydroxy-4-methoxyphenyl)oxazol-4-yl]-1-(3-methylpyridin-2-yl)propan-1-one obtained in Example 136, 90 mg of white powdery 3-[2-(3-cyclopentylmethoxy-4-methoxyphenyl)oxazol-4-yl]-1-(3-methyl pyridin-2-yl)propan-1-one was obtained in the same manner as in Example 137.

$^1$H-NMR ($CDCl_3$) δ: 8.49 (1H, d, J=3.9 Hz), 7.59-7.50 (3H, m), 7.45 (1H, s), 7.34-7.29 (1H, m), 6.90 (1H, d, J=8.4 Hz), 3.95 (2H, d, J=7.2 Hz), 3.90 (3H, s), 3.60 (2H, t, J=7.5 Hz), 3.01 (2H, t, J=7.5 Hz), 2.57 (3H, s), 2.54-2.41 (1H, m), 1.91-1.82 (2H, m), 1.68-1.56 (4H, m), 1.42-1.24 (2H, m)

Example 153

Using 0.16 g of 2-cyclopropylethyl methanesulfonate obtained in Reference Example 50 and 0.15 g of 3-[2-(3-hydroxy-4-methoxyphenyl)oxazol-4-yl]-1-(3-methylpyridin-2-yl)propan-1-one obtained in Example 136, 0.1 g of white powdery 3-{2-[3-(2-cyclopropylethoxy)-4-methoxyphenyl]oxazol-4-yl}-1-(3-methyl pyridin-2-yl)propan-1-one was obtained in the same manner as in Example 137.

$^1$H-NMR ($CDCl_3$) δ: 8.50 (1H, dd, 1.5 Hz), 7.60-7.54 (3H, m), 7.46 (1H, s), 7.35-7.27 (1H, m), 6.91 (1H, d, J=8.1 Hz), 4.18 (2H, t, J=6.9 Hz), 3.91 (3H, s), 3.61 (2H, t, J=7.5 Hz), 3.02 (2H, t, J=7.5 Hz), 2.58 (3H, s), 1.78 (2H, q, J=6.9 Hz), 0.91-0.80 (1H, m), 0.53-0.46 (2H, m), 0.16-0.11 (2H, m)

Example 154

Using 0.19 g of 2-cyclopentylethyl methanesulfonate obtained in Reference Example 51 and 0.15 g of 3-[2-(3-hydroxy-4-methoxyphenyl)oxazol-4-yl]-1-(3-methylpyridin-2-yl)propan-1-one obtained in Example 136, 0.13 g of white powdery 3-{2-[3-(2-cyclopentylethoxy)-4-methoxyphenyl]oxazol-4-yl}-1-(3-methyl pyridin-2-yl)propan-1-one was obtained in the same manner as in Example 137.

$^1$H-NMR ($CDCl_3$) δ: 8.50 (1H, dd, J=4.5, 1.2 Hz), 7.60-7.50 (3H, m), 7.45 (1H, s), 7.34-7.30 (1H, m), 6.90 (1H, d, J=8.4 Hz), 4.10 (2H, t, J=6.9 Hz), 3.92 (3H, s), 3.60 (2H, t, J=7.5 Hz), 3.01 (2H, t, J=7.5 Hz), 2.57 (3H, s), 2.01-1.79 (5H, m), 1.67-1.50 (5H, m), 1.24-1.12 (2H, m)

Example 155

A 0.23 g quantity of 3-[2-(3-hydroxy-4-methoxyphenyl)oxazol-4-yl]-1-(3-methylpyridin-2-yl)propan-1-one obtained in Example 136 and 0.28 g of potassium carbonate were dissolved in 5 ml of dimethylformamide. A 0.29 g quantity of 1,1,1-trifluoro-2-iodoethane was added thereto, and the mixture was stirred with heating at 80° C. overnight. The reaction mixture was allowed to cool, water was then added thereto, and extraction was performed with ethyl acetate. After washing with water twice, the organic layer was concentrated under reduced pressure. The obtained residue was purified by silica gel column chromatography (dichloromethane:ethyl acetate=1:1) to give 0.14 g of white powdery 3-{2-[4-methoxy-3-(2,2,2-trifluoroethoxy)phenyl]oxazol-4-yl}-1-(3-methylpyridin-2-yl)propan-1-one.

$^1$H-NMR ($CDCl_3$) δ: 8.50 (1H, dd, J=4.5, 0.9 Hz), 7.70 (1H, dd, J=8.4, 2.1 Hz), 7.60-7.56 (2H, m), 7.46 (1H, d, J=2.1 Hz), 7.35-7.30 (1H, m), 6.96 (1H, d, J=8.4 Hz), 4.45 (2H, q, J=8.4 Hz), 3.92 (3H, s), 3.60 (2H, t, J=7.5 Hz), 3.00 (2H, t, J=7.5 Hz), 2.57 (3H, s)

Example 156

Using 0.1 g of 3-[2-(3-hydroxy-4-methoxyphenyl)oxazol-4-yl]-1-(3-methylpyridin-2-yl)propan-1-one obtained in Example 136, 45 mg of pale yellow powdery 3-{2-[4-methoxy-3-(3-methyl-2-butenyloxy)phenyl]oxazol-4-yl}-1-(3-methylpyridin-2-yl)propan-1-one was obtained in the same manner as in Example 155.

$^1$H-NMR ($CDCl_3$) δ: 8.50 (1H, dd, J=4.5, 1.2 Hz), 7.59-7.52 (3H, m), 7.45 (1H, s), 7.34-7.29 (1H, m), 6.90 (1H, d, J=8.4 Hz), 5.58-5.52 (1H, m), 4.64 (2H, d, J=6.9 Hz), 3.91 (3H, s), 3.60 (2H, t, J=7.5 Hz), 3.01 (2H, t, J=7.5 Hz), 2.57 (3H, s), 1.78 (3H, d, J=0.9 Hz), 1.77 (3H, s)

Example 157

Using 0.6 g of 3-[2-(3-hydroxy-4-methoxyphenyl)oxazol-4-yl]-1-(3-methylpyridin-2-yl)propan-1-one obtained in Example 136, 0.31 g of white powdery 3-{2-[3-(2-cyclohexenyloxy)-4-methoxyphenyl]oxazol-4-yl}-1-(3-methylpyridin-2-yl)propan-1-one was obtained in the same manner as in Example 155.

$^1$H-NMR ($CDCl_3$) δ: 8.50 (1H, dd, J=4.5, 1.2 Hz), 7.60-7.56 (3H, m), 7.45 (1H, s), 7.34-7.29 (1H, m), 6.91 (1H, d, J=9.0 Hz), 5.99-5.88 (2H, m), 4.88 (1H, br s), 3.89 (3H, s), 3.60 (2H, t, J=7.2 Hz), 3.01 (2H, t, J=7.2 Hz), 2.57 (3H, s), 2.17-1.84 (5H, m), 1.71-1.61 (1H, m)

Example 158

A 0.3 g quantity of 3-{2-[3-(2-cyclohexenyloxy)-4-methoxyphenyl]oxazol-4-yl}-1-(3-methylpyridin-2-yl)propan-1-one obtained in Example 157 was dissolved in 20 ml of ethanol. A 50 mg quantity of 10% palladium-carbon powder was added thereto, and the mixture was stirred at room temperature for 2 hours. The catalyst was removed by filtration, and the filtrate was then concentrated. The obtained residue was purified by silica gel column chromatography (n-hexane:ethyl acetate=3:1) to give 0.2 g of pale yellow oily 3-[2-(3-cyclohexyloxy-4-methoxyphenyl)oxazol-4-yl]-1-(3-methylpyridin-2-yl)propan-1-one.

$^1$H-NMR ($CDCl_3$) δ: 8.50 (1H, d, J=4.5 Hz), 7.59-7.54 (3H, m), 7.45 (1H, s), 7.34-7.30 (1H, m), 6.91 (1H, d, J=8.1 Hz), 4.35-4.25 (1H, m), 3.89 (3H, s), 3.60 (2H, t, J=7.5 Hz), 3.01 (2H, t, J=7.5 Hz), 2.57 (3H, s), 2.07-2.02 (2H, m), 1.84-1.80 (2H, m), 1.60-1.51 (4H, m), 1.43-1.23 (2H, m)

Example 159

A 0.26 g quantity of 3-[2-(3-hydroxy-4-methoxyphenyl)oxazol-4-yl]-1-(3-methylpyridin-2-yl)propan-1-one obtained in Example 136 was dissolved in 10 ml of tetrahydrofuran. To the obtained solution were added 0.2 g of 2-hydroxyindane, 0.75 ml of diisopropyl azodicarboxylate (40% toluene solution) and 0.31 g of tri(n-butyl)phosphine, and the mixture was stirred at 50° C. After 3 hours, 0.2 g of 2-hydroxyindan, 0.75 ml of diisopropyl azodicarboxylate (40% toluene solution) and 0.31 g of tri(n-butyl)phosphine were further added thereto, and the mixture was stirred at 50° C. overnight. The reaction mixture was concentrated under reduced pressure. The residue was purified by silica gel column chromatography (n-hexane:ethyl acetate:dichloromethane=1:1:1), and recrystallized from acetone/diisopropyl ether to give 0.13 g of colorless powdery 3-{2-[3-(indan-2-yloxy)-4-methoxyphenyl]oxazol-4-yl}-1-(3-methylpyridin-2-yl)propan-1-one.

$^1$H-NMR ($CDCl_3$) δ: 8.51 (1H, br d, J=4.8 Hz), 7.62-7.16 (9H, m), 6.91 (1H, d, J=8.7 Hz), 5.29 (1H, tt, J=6.6, 3.9 Hz), 3.85 (3H, s), 3.63 (2H, t, J=7.2 Hz), 3.45 (2H, dd, J=16.8, 6.6 Hz), 3.26 (2H, dd, J=16.8, 3.9 Hz), 3.01 (2H, t, J=7.2 Hz), 2.58 (3H, s)

Example 160

A 2 g quantity of methyl 3-[2-(3-benzyloxy-4-methoxyphenyl)oxazol-4-yl]propionate obtained in Reference Example 48 and 1.5 g of methyl picolinate were dissolved in 40 ml of dimethoxyethane. A 0.33 g quantity of sodium hydride was added thereto with ice-cooling and stirring, and stirring was further continued. The reaction mixture was heated and refluxed for 2 hours. After the reaction, an aqueous saturated ammonium chloride solution was added thereto with ice-cooling and stirring, and the mixture was stirred. The reaction mixture was stirred for 30 minutes, water was then added thereto, and extraction was performed with ethyl acetate. The organic layer was washed twice with water and concentrated by removing the solvent under reduced pressure. The obtained residue was purified by silica gel column chromatography (n-hexane:ethyl acetate=3:1) to give 2 g of colorless oily methyl 2-[2-(3-benzyloxy-4-methoxyphenyl)oxazol-4-ylmethyl]-3-oxo-3-pyridin-2-yl-propionate.

$^1$H-NMR ($CDCl_3$) δ: 8.67 (1H, dd, J=4.2, 0.9 Hz), 8.07 (1H, dd, J=7.8, 2.1 Hz), 7.83 (1H, td, J=7.8, 1.8 Hz), 7.55-7.30 (9H, m), 6.90 (1H, d, J=9.0 Hz), 5.29 (1H, t, J=7.8 Hz), 5.16 (2H, s), 3.91 (3H, s), 3.66 (3H, s), 3.36-3.28 (2H, m)

Example 161

Using 2 g of methyl 2-[2-(3-benzyloxy-4-methoxyphenyl)oxazol-4-ylmethyl]-3-oxo-3-(pyridin-2-yl)propionate obtained in Example 160, 0.48 g of white powdery 3-[2-(3-hydroxy-4-methoxyphenyl)oxazol-4-yl]-1-(pyridin-2-yl) propan-1-one was obtained in the same manner as in Example 136.

$^1$H-NMR ($CDCl_3$) δ: 8.67 (1H, dd, J=4.2, 0.9 Hz), 8.05 (1H, dd, J=7.8, 2.1 Hz), 7.83 (1H, td, J=7.8, 1.8 Hz), 7.55-7.43 (4H, m), 6.88 (1H, dd, J=7.8, 2.1 Hz), 5.72 (1H, s), 3.93 (3H, s), 3.64 (2H, t, J=7.5 Hz), 3.03 (2H, t, J=7.5 Hz)

Example 162

A 0.15 g quantity of 3-[2-(3-hydroxy-4-methoxyphenyl) oxazol-4-yl]-1-(pyridin-2-yl)propan-1-one obtained in Example 161 and 0.2 ml of 1,8-diazabicyclo[5,4,0]undec-7-ene were dissolved in 5 ml of ethanol. A 0.14 g quantity of (bromomethyl)cyclobutane was added thereto, and the mixture was heated and refluxed overnight. The reaction mixture was allowed to cool, water was then added thereto, and extraction was performed with ethyl acetate. After washing with water twice, the organic layer was concentrated under reduced pressure. The obtained residue was purified by silica gel column chromatography (dichloromethane:ethyl acetate=5:1) to give 50 mg of white powdery 3-[2-(3-cyclobutylmethoxy-4-methoxyphenyl)oxazol-4-yl]-1-(pyridin-2-yl)propan-1-one.

$^1$H-NMR ($CDCl_3$) δ: 8.68 (1H, d, J=4.5 Hz), 8.05 (1H, d, J=7.8 Hz), 7.83 (1H, td, J=7.8, 1.8 Hz), 7.58-7.44 (4H, m), 6.90 (1H, d, J=8.4 Hz), 4.07 (2H, d, J=6.9 Hz), 3.89 (3H, s), 3.65 (2H, t, J=7.5 Hz), 3.05 (2H, t, J=7.5 Hz), 2.94-2.81 (1H, m), 2.24-2.04 (2H, m), 2.00-1.81 (4H, m)

Example 163

Using 0.3 g of 3-[2-(3-hydroxy-4-methoxyphenyl)oxazol-4-yl]-1-(pyridin-2-yl)propan-1-one obtained in Example 161, 0.28 g of white powdery 3-[2-(4-methoxy-3-(4-pentenyloxy)phenyl)oxazol-4-yl]-1-(pyridin-2-yl)propan-1-one was obtained in the same manner as in Example 102.

$^1$H-NMR ($CDCl_3$) δ: 8.69 (1H, dd, J=4.2, 1.5 Hz), 8.05 (1H, d, J=7.8 Hz), 7.85 (1H, t, J=7.8 Hz), 7.60-7.46 (4H, m), 6.91 (1H, d, J=8.4 Hz), 5.92-5.83 (1H, m), 5.11-4.99 (2H, m), 4.11 (2H, d, J=6.9 Hz), 3.91 (3H, s), 3.65 (2H, t, J=7.5 Hz), 3.05 (2H, t, J=7.5 Hz), 2.28-2.23 (2H, m), 1.98 (2H, t, J=7.5 Hz)

Example 164

A 10 g quantity of 2-(3-benzyloxy-4-methoxyphenyl)-4-chloromethyloxazole obtained in Reference Example 5 and 10.7 g of 1-(2-allyloxyphenyl)ethanone obtained in Reference Example 53 were dissolved in 200 ml of tetrahydrofuran. A 1.82 g quantity of sodium hydride was added thereto with ice-cooling and stirring, and stirring was further continued. The reaction mixture was heated and refluxed for 4 hours. After the reaction, an aqueous saturated ammonium chloride solution was added thereto with ice-cooling and stirring, and the mixture was stirred. After stirring for 30 minutes, water was added thereto, and extraction was performed with ethyl acetate. The organic layer was washed with water twice and concentrated by removing the solvent under reduced pressure. The obtained residue was purified by silica gel column chromatography (n-hexane:ethyl acetate=3:1) to give 1.4 g of white powdery 1-(2-allyloxyphenyl)-3-[2-(3-benzyloxy-4-methoxyphenyl)oxazol-4-yl] propan-1-one.

$^1$H-NMR ($CDCl_3$) δ: 7.70 (1H, dd, J=7.8, 1.8 Hz), 7.62-7.58 (2H, m), 7.49-7.30 (7H, m), 7.02-6.91 (3H, m), 6.12-6.02 (1H, m), 5.42 (1H, dd, J=17.4, 1.5 Hz), 5.30 (1H, dd, J=10.5, 1.5 Hz), 5.19 (2H, s), 4.65-4.62 (2H, m), 3.92 (3H, s), 3.42 (2H, t, J=7.2 Hz), 2.99 (2H, t, J=7.2 Hz)

Example 165

Using 1.4 g of 1-(2-allyloxyphenyl)-3-[2-(3-benzyloxy-4-methoxyphenyl)oxazol-4-yl]propan-1-one obtained in Example 164, 0.55 g of pale yellow oily 3-[2-(3-hydroxy-4-methoxyphenyl)oxazol-4-yl]-1-(2-hydroxyphenyl)propan-1-one was obtained in the same manner as in Example 101.

$^1$H-NMR ($CDCl_3$) δ: 12.5 (1H, s), 7.81 (1H, dd, J=7.8, 1.5 Hz), 7.57-7.30 (4H, m), 6.98 (1H, d, J=8.1 Hz), 6.92-6.86 (2H, m), 5.73 (1H, br s), 3.94 (3H, s), 3.44 (2H, t, J=7.5 Hz), 3.02 (2H, t, J=7.5 Hz)

Example 166

Using 0.5 g of 3-[2-(3-hydroxy-4-methoxyphenyl)oxazol-4-yl]-1-(2-hydroxyphenyl)propan-1-one obtained in Example 165, 0.61 g of white powdery 3-[2-(3-allyloxy-4-methoxyphenyl)oxazol-4-yl]-1-(2-allyloxyphenyl)propan-1-one was obtained in the same manner as in Example 111.

$^1$H-NMR ($CDCl_3$) δ: 7.70 (1H, dd, J=7.5, 2.1 Hz), 7.58 (1H, dd, J=8.1, 2.1 Hz), 7.52 (1H, d, J=2.1 Hz), 7.45-7.40 (2H, m), 7.02-6.90 (3H, m), 6.16-6.03 (2H, m), 5.47-5.27 (4H, m), 4.68-4.62 (4H, m), 3.92 (3H, s), 3.42 (2H, t, J=6.9 Hz), 2.99 (2H, t, J=6.9 Hz)

Example 167

Using 1.1 g of methyl 3-[2-(3-benzyloxy-4-methoxyphenyl)oxazol-4-yl]propionate obtained in Reference Example 48, 1 g of yellow oily methyl 2-[2-(3-benzyloxy-4-methoxyphenyl)oxazol-4-ylmethyl]-3-(2-methoxyphenyl)-3-oxopropionate was obtained in the same manner as in Example 100.

$^1$H-NMR ($CDCl_3$) δ: 7.71 (1H, dd, J=7.8, 1.8 Hz), 7.57-7.53 (3H, m), 7.48-7.30 (6H, m), 6.97 (1H, t, J=7.2 Hz), 6.91 (2H, d, J=7.8 Hz), 5.17 (2H, s), 4.99 (1H, t, J=6.9 Hz), 3.92 (3H, s), 3.90 (3H, s), 3.69 (3H, s), 3.27-3.19 (2H, m)

Example 168

Using 1 g of methyl 2-[2-(3-benzyloxy-4-methoxyphenyl)oxazol-4-ylmethyl]-3-(2-methoxyphenyl)-3-oxopropionate obtained in Example 167, 0.63 g of white powdery 3-[2-(3-hydroxy-4-methoxyphenyl)oxazol-4-yl]-1-(2-methoxyphenyl)propan-1-one was obtained in the same manner as in Example 101.

$^1$H-NMR ($CDCl_3$) δ: 7.70 (1H, dd, J=8.4, 2.1 Hz), 7.56-7.52 (2H, m), 7.44-7.41 (2H, m), 6.99-6.87 (3H, m), 3.95 (3H, s), 3.89 (3H, s), 3.38 (2H, t, J=7.2 Hz), 2.98 (2H, t, J=7.2 Hz)

Example 169

Using 0.22 g of 3-[2-(3-hydroxy-4-methoxyphenyl)oxazol-4-yl]-1-(2-methoxyphenyl)propan-1-one obtained in Example 168, 90 mg of colorless oily 3-[2-(3-isopropoxy-4-methoxyphenyl)oxazol-4-yl]-1-(2-methoxyphenyl)propan-1-one was obtained in the same manner as in Example 102.

$^1$H-NMR ($CDCl_3$) δ: 7.70 (1H, d, J=7.5 Hz), 7.57 (1H, d, J=8.1 Hz), 7.54 (1H, s), 7.47-7.40 (2H, m), 7.01-6.89 (3H, m), 4.67-4.62 (1H, m), 3.91 (6H, s), 3.38 (2H, t, J=7.2 Hz), 3.00 (2H, t, J=7.2 Hz), 1.39 (6H, d, J=6.3 Hz)

Using 3-[2-(3-hydroxy-4-methoxyphenyl)oxazol-4-yl]-1-(2-methoxyphenyl)propan-1-one obtained in Example 168, compounds of Examples 170 to 173 were obtained in the same manner as in Example 102.

Example 170

3-[2-(3-cyclopropylmethoxy-4-methoxyphenyl)oxazol-4-yl]-1-(2-methoxyphenyl)propan-1-one $^1$H-NMR ($CDCl_3$) δ: 7.69-7.40 (4H, m), 6.99-6.89 (4H, m), 3.94-3.89 (8H, m), 3.37 (2H, t, J=7.2 Hz), 3.01 (2H, t, J=7.2 Hz), 1.40-1.35 (1H, m), 0.67-0.65 (2H, m), 0.38-0.36 (2H, m)

Example 171

3-[2-(3-cyclopentyloxy-4-methoxyphenyl)oxazol-4-yl]-1-(2-methoxyphenyl)propan-1-one $^1$H-NMR ($CDCl_3$) δ: 7.70 (1H, dd, J=7.5, 1.8 Hz), 7.56 (1H, dd, J=8.4, 2.1 Hz), 7.51 (1H, s), 7.43 (1H, td, J=8.4, 1.8 Hz), 6.99-6.88 (3H, m), 4.48 (1H, br s), 3.89 (3H, s), 3.88 (3H, s), 3.38 (2H, t, J=6.6 Hz), 2.98 (2H, t, J=6.6 Hz), 2.04-1.85 (4H, m), 1.63-1.55 (4H, m)

Example 172

3-[2-(3-ethoxy-4-methoxyphenyl)oxazol-4-yl]-1-(2-methoxyphenyl)propan-1-one $^1$H-NMR ($CDCl_3$) δ: 7.70 (1H, dd, J=7.5, 1.8 Hz), 7.57 (1H, dd, J=8.1, 2.1 Hz), 7.51 (1H, d, J=1.8 Hz), 7.47-7.41 (2H, m), 7.01-6.89 (3H, m), 4.18 (2H, q, J=7.8 Hz), 3.94 (3H, s), 3.90 (3H, s), 3.38 (2H, t, J=6.6 Hz), 2.99 (2H, t, J=6.6 Hz), 1.49 (3H, t, J=7.8 Hz)

Example 173

3-[2-(3-isobutoxy-4-methoxyphenyl)oxazol-4-yl]-1-(2-methoxy phenyl)propan-1-one $^1$H-NMR ($CDCl_3$) δ: 7.70 (1H, dd, J=7.5, 1.8 Hz), 7.58-7.36 (4H, m), 7.01-6.89 (3H, m), 3.90 (6H, s), 3.84 (2H, d, J=6.6 Hz), 3.38 (2H, t, J=6.9 Hz), 2.99 (2H, t, J=6.9 Hz), 2.22-2.10 (1H, m), 1.05 (6H, d, J=6.6 Hz)

Using 3-[2-(3-hydroxy-4-methoxyphenyl)oxazol-4-yl]-1-(2-methoxyphenyl)propan-1-one obtained in Example 168, compounds of Examples 174 to 175 were obtained in the same manner as in Example 111.

Example 174

3-[2-(3-allyloxy-4-methoxyphenyl)oxazol-4-yl]-1-(2-methoxyphenyl)propan-1-one $^1$H-NMR ($CDCl_3$) δ: 7.70 (1H, dd, J=7.5, 1.8 Hz), 7.59 (1H, dd, J=8.4, 1.8 Hz), 7.52 (1H, d, J=1.8 Hz), 7.48-7.41 (2H, m), 7.02-6.90 (3H, m), 6.12-6.07 (1H, m), 5.43 (1H, dd, J=17, 1.5 Hz), 5.31 (1H, d, J=10 Hz), 4.68 (2H, d, J=5.4 Hz), 3.92 (3H, s), 3.90 (3H, s), 3.38 (2H, t, J=7.2 Hz), 2.99 (2H, t, J=7.2 Hz)

Example 175

1-(2-methoxyphenyl)-3-{2-[4-methoxy-3-(2,2,2-trifluoroethoxy)phenyl]oxazol-4-yl}propan-1-one $^1$H-NMR ($CDCl_3$) δ: 7.69 (1H, dd, J=7.5, 1.8 Hz), 7.60 (1H, d, J=1.8 Hz), 7.48-7.42 (2H, m), 7.02-6.95 (3H, m), 4.43 (2H, q, J=8.1 Hz), 3.92 (3H, s), 3.90 (3H, s), 3.38 (2H, t, J=6.9 Hz), 2.99 (2H, t, J=6.9 Hz)

Example 176

A 0.4 g quantity of sodium hydride was suspended in 20 ml of tetrahydrofuran, and 1.13 g of 1-(2-benzyloxy)ethanone and 1.46 g of 4-chloromethyl-2-(3-cyclopropylmethoxy-4-methoxyphenyl)oxazole obtained in Reference Example 11 were successively added thereto with ice-cooling. The mixture was stirred for 4 hours with heating and refluxing. An aqueous saturated ammonium chloride solution was added to the reaction mixture with ice cooling. After stirring for 15 minutes, water was added thereto, and extraction was performed with ethyl acetate. Drying was performed with anhydrous magnesium sulfate, and the solvent was removed. Purification was performed using a silica gel column (n-hexane:ethyl acetate=4:1), and the obtained compound was dissolved in 12 ml of ethanol. A 35 mg quantity of 10% palladium-carbon powder was added thereto, and stirring was performed under a hydrogen atmosphere overnight. The catalyst was removed by filtration and the obtained filtrate was concentrated. The residue was purified using a silica gel column (n-hexane:ethyl acetate=4:1) to give 0.43 g of white powdery 3-[2-(3-cyclopropylmethoxy-4-methoxyphenyl)oxazol-4-yl]-1-(2-hydroxy phenyl)propan-1-one.

$^1$H-NMR ($CDCl_3$) δ: 12.2 (1H, s), 7.83 (1H, d, J=1.5 Hz), 7.80-7.44 (4H, m), 7.00-6.87 (3H, m), 3.94-3.92 (5H, m), 3.44 (2H, t, J=7.2 Hz), 3.03 (2H, t, J=7.2 Hz), 1.37-1.26 (1H, m), 0.70-0.65 (2H, m), 0.41-0.37 (2H, m)

Example 177

A 2 g quantity of 4-chloromethyl-2-(3-cyclopropyl methoxy-4-methoxyphenyl)oxazole obtained in Reference Example 11 and 3.6 g of 1-(2-allyloxyphenyl)ethanone obtained in Reference Example 53 were dissolved in 40 ml of tetrahydrofuran. A 0.55 g quantity of sodium hydride was added thereto with ice-cooling and stirring, and the mixture was stirred. The reaction mixture was heated and refluxed for 6 hours. After the reaction completion, an aqueous saturated ammonium chloride solution was added thereto with ice-cooling, and the mixture was stirred. The reaction mixture was stirred for 30 minutes, water was then added thereto, and extraction was performed with ethyl acetate. The organic layer was washed with water twice and concentrated by removing the solvent under reduced pressure. The obtained residue was purified by silica gel column chromatography (n-hexane:ethyl acetate=3:1) to give 0.5 g of while powdery 1-(2-allyloxyphenyl)-3-[2-(3-cyclopropylmethoxy-4-methoxyphenyl) oxazol-4-yl]propan-1-one.

$^1$H-NMR ($CDCl_3$) δ: 7.70 (1H, dd, J=7.8, 1.8 Hz), 7.57 (1H, dd, J=8.4, 2.1 Hz), 7.49 (1H, d, J=2.1 Hz), 7.45-7.39 (2H, m), 7.02-6.89 (3H, m), 6.09-6.02 (1H, m), 5.45-5.26 (2H, m), 4.65-4.62 (2H, m), 3.94-3.91 (5H, m), 3.42 (2H, t, J=7.2 Hz), 2.99 (2H, t, J=7.2 Hz), 1.45-1.35 (1H, m), 0.68-0.62 (2H, m), 0.40-0.36 (2H, m)

Example 178

Using 1.4 g of 4-chloromethyl-2-(3,4-diethoxyphenyl) oxazole obtained in Reference Example 35 and 0.88 g of 1-(2-allyloxyphenyl)ethanone obtained in Reference Example 53, 0.42 g of white powdery 1-(2-allyloxyphenyl)-3-[2-(3,4-diethoxyphenyl)oxazol-4-yl]propan-1-one was obtained in the same manner as in Example 177.

$^1$H-NMR ($CDCl_3$) δ: 7.69 (1H, dd, J=7.5, 2.1 Hz), 7.56-7.51 (2H, m), 7.45-7.39 (2H, m), 7.02-6.89 (3H, m), 6.14-6.01 (1H, m), 5.42 (1H, dd, J=17, 1.5 Hz), 5.29 (1H, dd, J=10.5, 1.5 Hz), 4.65-4.62 (2H, m), 4.20-4.10 (4H, m), 3.42 (2H, t, J=7.2 Hz), 2.99 (2H, t, J=7.2 Hz), 1.50 (6H, t, J=7.2 Hz)

Example 179

Using 0.31 g of 1-(2-chlorophenyl)ethanone and 0.59 g of 4-chloromethyl-2-(3-cyclopropylmethoxy-4-methoxyphenyl)oxazole obtained in Reference Example 11, 0.11 g of colorless oily 1-(2-chlorophenyl)-3-[2-(3-cyclopropylmethoxy-4-methoxyphenyl)oxazol-4-yl]propan-1-one was obtained in the same manner as in Example 177.

$^1$H-NMR ($CDCl_3$) δ: 7.60-7.55 (2H, m), 7.49-7.43 (2H, m), 7.40 (1H, s), 7.39-7.30 (2H, m), 6.91 (1H, d, J=8.7 Hz), 3.94-3.91 (5H, m), 3.36 (2H, t, J=6.9 Hz), 3.01 (2H, t, J=6.9 Hz), 1.37-1.29 (1H, m), 0.69-0.63 (2H, m), 0.40-0.37 (2H, m)

Example 180

Using 2 g of methyl 3-[2-(3,4-diethoxyphenyl)oxazol-4-yl]propionate obtained in Reference Example 54 and 1.3 g of ethyl 3-methylpicolinate, 0.8 g of yellow oily methyl 2-[2-(3,4-diethoxyphenyl)oxazol-4-ylmethyl]-3-(3-methylpyridin-2-yl)-3-oxopropionate was obtained in the same manner as in Example 124.

$^1$H-NMR ($CDCl_3$) δ: 8.50 (1H, m), 7.60-7.40 (4H, m), 7.30 (1H, m), 6.88 (1H, d, J=8.4 Hz), 5.20 (1H, t, J=7.2 Hz), 4.20-4.05 (4H, m), 2.99 (3H, s), 3.35-3.20 (2H, m), 2.59 (3H, s), 1.47 (3H, t, J=6.9 Hz), 1.47 (3H, t, J=6.9 Hz)

Example 181

A 0.8 g quantity or methyl 2-[2-(3,4-diethoxyphenyl) oxazol-4-ylmethyl]-3-(3-methylpyridin-2-yl)-3-oxopropionate obtained in Example 180 was added to a mixture of 5 ml acetic acid and 1.5 ml of concentrated hydrochloric acid, and the resulting mixture was stirred at 110° C. for 4 hours. After cooling the obtained solution to room temperature, 30 ml of ethyl acetate and 30 ml of saturated sodium hydrogen carbonate solution were gradually added thereto with stirring, and stirring was further continued. The organic layer was dried over anhydrous magnesium sulfate, and concentrated under reduced pressure. The residue was purified by silica gel column chromatography (ethyl acetate:n-hexane=3:1), and further recrystallized from ethyl acetate/n-hexane to give 0.28 g of white powdery 3-[2-(3,4-diethoxyphenyl)oxazol-4-yl]-1-(3-methylpyridin-2-yl) propan-1-one.

$^1$H-NMR ($CDCl_3$) δ: 8.49 (1H, m), 7.60-7.50 (3H, m), 7.44 (1H, s), 7.32 (1H, m), 6.90 (1H, d, J=8.1 Hz), 4.17 (2H, q, J=6.9 Hz), 4.13 (2H, q, J=6.9 Hz), 3.51 (2H, t, J=7.2 Hz), 3.00 (2H, t, J=7.2 Hz), 2.57 (3H, s), 1.48 (3H, t, J=6.9 Hz), 1.47 (3H, t, J=6.9 Hz)

Example 182

A 2 g quantity of methyl 3-[2-(3,4-diethoxyphenyl)oxazol-4-yl]propionate obtained in Reference Example 54 and 1.5 g of ethyl 2-ethoxybenzoate were dissolved in 10 ml of dimethylformamide. A 1.81 g quantity of sodium t-pentoxide was added thereto with ice-cooling and stirring, and the mixture was stirred for 30 minutes. The reaction mixture was further stirred at room temperature for 5 hours, and ice was added thereto. An aqueous saturated ammonium chloride solution was added thereto, and the mixture was stirred. The reaction mixture was stirred for 30 minutes, water was then added thereto, and extraction was performed with ethyl acetate. The organic layer was washed with water twice and concentrated by removing the solvent under reduced pressure. The obtained residue was purified by silica gel column chromatography (n-hexane:ethyl acetate=1:1). The obtained yellow oily substance was added to a mixture of 5 ml of acetic acid and 1.5 ml of concentrated hydrochloric acid, and the resulting mixture was stirred at 110° C. for 4 hours. After cooling the mixture to room temperature, 30 ml of ethyl acetate and 30 ml of saturated sodium hydrogen carbonate solution were gradually added thereto with stirring, and stirring was further continued. The organic layer was dried over anhydrous magnesium sulfate, and concentrated under reduced pressure. The residue was purified by silica gel column chromatography (ethyl acetate:n-hexane=3:1), and the obtained crude crystals were recrystallized from ethyl acetate/n-hexane to give 0.46 g of white powdery 3-[2-(3,4-diethoxyphenyl)oxazol-4-yl]-1-(2-ethoxyphenyl)propan-1-one.

$^1$H-NMR ($CDCl_3$) δ: 7.70 (1H, dd, J=7.5, 2.1 Hz), 7.60-7.50 (2H, m), 7.45-7.35 (2H, m), 7.00-6.80 (2H, m), 4.17 (2H, q, J=7.2 Hz), 4.13 (2H, q, J=7.2 Hz), 3.42 (2H, t, J=7.2 Hz), 2.99 (2H, t, J=7.2 Hz), 1.48 (3H, t, J=7.2 Hz), 1.48 (3H, t, J=7.2 Hz), 1.48 (3H, t, J=7.2 Hz)

Using methyl 3-[2-(3,4-diethoxyphenyl)oxazol-4-yl]propionate obtained in Reference Example 54, compounds of Example 183 to 185 were obtained in the same manner as in Example 182.

Example 183

3-[2-(3,4-diethoxyphenyl)oxazol-4-yl]-1-(3-ethoxypyridin-2-yl)propan-1-one $^1$H-NMR ($CDCl_3$) δ: 8.23 (1H, dd, J=4.5, 1.2 Hz), 7.55-7.50 (2H, m), 7.40-7.25 (2H, m), 7.45 (1H, s), 6.90 (1H, d, J=8.1 Hz), 4.20-4.05 (6H, m), 3.49 (2H, t, J=7.2 Hz), 3.02 (2H, t, J=7.2 Hz), 1.47 (3H, t, J=7.2 Hz), 1.47 (3H, t, J=7.2 Hz), 1.46 (3H, t, J=7.2 Hz)

Example 184

3-[2-(3,4-diethoxyphenyl)oxazol-4-yl]-1-(3-ethoxyphenyl)propan-1-one $^1$H-NMR ($CDCl_3$) δ: 8.00-7.95 (2H, m), 7.60-7.50 (2H, m), 7.43 (1H, s), 6.95-6.85 (3H, m), 4.17 (2H, q, J=7.2 Hz), 4.17 (2H, q, J=7.2 Hz), 4.09 (2H, q, J=7.2 Hz), 3.34 (2H, t, J=7.2 Hz), 3.01 (2H, t, J=7.2 Hz), 1.48 (3H, t, J=7.2 Hz), 1.48 (3H, t, J=7.2 Hz), 1.44 (3H, t, J=7.2 Hz).

Example 185

3-[2-(3,4-diethoxyphenyl)oxazol-4-yl]-1-(4-ethoxyphenyl)propan-1-one $^1$H-NMR ($CDCl_3$) δ: 7.60-7.50 (4H, m), 7.44 (1H, s), 7.35 (1H, t, J=7.8 Hz), 7.09 (1H, dd, J=9.0, 2.4 Hz), 6.10 (1H, d, J=5.4 Hz), 4.16 (2H, q, J=7.2 Hz), 4.15 (2H, q, J=7.2 Hz), 4.08 (2H, q, J=7.2 Hz), 3.38 (2H, t, J=7.2 Hz), 3.02 (2H, t, J=7.2 Hz), 1.48 (3H, t, J=7.2 Hz), 1.48 (3H, t, J=7.2 Hz), 1.40 (3H, t, J=7.2 Hz).

Example 186

Using 2 g of dimethyl 2-[2-(3,4-bis(benzyloxy)phenyl)oxazol-4-ylmethyl]malonate obtained in Reference Example 56, 2.2 g of pale yellow oily methyl 2-[2-(3,4-bisbenzyloxyphenyl)oxazol-4-ylmethyl]-3-(3-methylpyridin-2-yl)-3-oxopropionate was obtained in the same manner as in Example 100.

$^1$H-NMR ($CDCl_3$) δ: 8.49 (1H, dd, J=4.5, 1.2 Hz), 7.59-7.28 (15H, m), 6.94 (1H, d, J=8.4 Hz), 5.23-5.17 (5H, m), 3.69 (3H, s), 3.32-3.23 (2H, m), 2.59 (3H, s)

Example 187

Using 2.2 g of methyl 2-[2-(3,4-bisbenzyloxyphenyl)oxazol-4-ylmethyl]-3-(3-methylpyridin-2-yl)-3-oxopropionate obtained in Example 186, 0.24 g of white powdery 3-[2-(3,4-dihydroxyphenyl)oxazol-4-ylmethyl]-1-(3-methylpyridin-2-yl)propan-1-one was obtained in the same manner as in Example 136.

$^1$H-NMR ($CDCl_3$) δ: 9.46 (1H, br s), 9.32 (1H, br s), 8.54 (1H, d, J=3.0 Hz), 7.80-7.76 (2H, m), 7.54-7.49 (1H, m), 7.32 (1H, d, J=2.1 Hz), 7.23 (1H, dd, J=8.4, 2.1 Hz), 6.82 (1H, d, J=8.4 Hz), 3.47 (2H, t, J=7.5 Hz), 2.83 (2H, t, J=7.5 Hz), 2.51 (3H, s)

Example 188

Using 0.12 g of 3-[2-(3,4-dihydroxyphenyl)oxazol-4-ylmethyl]-1-(3-methylpyridin-2-yl)propan-1-one obtained in Example 187, 35 mg of white powdery 3-{2-[3,4-bis-(2,2,2-trifluoroethoxy)phenyl]oxazol-4-yl}-1-(3-methylpyridin-2-yl)propan-1-one was obtained in the same manner as in Example 111.

$^1$H-NMR ($CDCl_3$) δ: 8.50 (1H, d, J=4.5 Hz), 7.68 (1H, dd, J=8.4, 1.8 Hz), 7.63 (1H, d, J=1.8 Hz), 7.58 (1H, d, J=8.4 Hz), 7.49 (1H, s), 7.35-7.28 (1H, m), 7.04 (1H, d, J=8.4 Hz), 4.50-4.39 (4H, m), 3.60 (2H, t, J=7.2 Hz), 3.01 (2H, t, J=7.2 Hz), 2.59 (3H, s)

Example 189

Using 0.76 g of 4-chloromethyl-2-(3-ethoxy-4-methoxyphenyl)oxazole obtained in Reference Example 58 and 0.5 g of 1-(2-allyloxyphenyl)ethanone obtained in Reference Example 53, 0.13 g of white powdery 1-(2-allyloxyphenyl)-3-[2-(3-ethoxy-4-methoxyphenyl)oxazol-4-yl]propan-1-one was obtained in the same manner as in Example 177.

$^1$H-NMR ($CDCl_3$) δ: 7.70 (1H, dd, J=7.5, 2.1 Hz), 7.56 (1H, dd, J=8.4, 2.1 Hz), 7.51 (1H, d, J=2.1 Hz), 7.45-7.40 (2H, m), 7.02-6.89 (3H, m), 6.12-6.01 (1H, m), 5.42 (1H, dd, J=17, 1.5 Hz), 5.28 (1H, dd, J=17, 1.5 Hz), 4.65-4.62 (2H, m), 4.18 (2H, q, J=6.9 Hz), 3.92 (3H, s), 3.42 (2H, t, J=7.2 Hz), 2.99 (2H, t, J=7.2 Hz), 1.49 (3H, t, J=6.9 Hz)

Example 190

A 2 g quantity of 4-chloromethyl-2-(4-benzyloxy-3-ethoxyphenyl)oxazole obtained in Reference Example 63 and 0.96 g of 1-(2-ethoxyphenyl)ethanone were dissolved in 20 ml of tetrahydrofuran, and 0.47 g sodium hydride was added thereto. After foaming, the reaction mixture was heated and refluxed for 3 hours. After cooling, the reaction mixture was added to ice water, and extraction was performed with ethyl acetate. The organic layer was washed with water, dried over magnesium sulfate, and concentrated under reduced pressure. The residue was purified by silica gel column chromatography (n-hexane:ethyl acetate=3:1) to give 0.4 g of colorless powdery 3-[2-(4-benzyloxy-3-ethoxyphenyl)oxazol-4-yl]-1-(2-ethoxyphenyl)propan-1-one.

$^1$H-NMR ($CDCl_3$) δ: 7.70 (1H, dd, J=7.5, 1.8 Hz), 7.55-7.30 (8H, m), 6.97 (2H, t, J=7.5 Hz), 6.93 (1H, d, J=7.5 Hz), 5.19 (2H, s), 4.18 (2H, q, J=6.9 Hz), 4.13 (2H, q, J=6.9 Hz), 3.41 (2H, t, J=6.9 Hz), 2.99 (2H, t, J=6.9 Hz), 1.48 (3H, t, J=6.9 Hz), 1.47 (3H, t, J=6.9 Hz)

Example 191

Using 3-[2-(4-benzyloxy-3-ethoxyphenyl)oxazol-4-yl]-1-(2-ethoxyphenyl)propan-1-one obtained in Example 190, colorless oily 3-[2-(3-ethoxy-4-hydroxyphenyl)oxazol-4-yl]-1-(2-ethoxy phenyl)propan-1-one was obtained in the same manner as in Example 2.

$^1$H-NMR ($CDCl_3$) δ: 7.70 (1H, dd, J=7.5, 1.8 Hz), 7.52 (1H, dd, J=8.1, 2.1 Hz), 7.49 (1H, d, J=2.1 Hz), 7.45-7.38 (2H, m), 6.97 (1H, t, J=7.5 Hz), 6.95 (1H, d, J=7.5 Hz), 6.93 (1H, d, J=8.1 Hz), 5.89 (1H, s), 4.20 (2H, q, J=7.2 Hz), 4.13 (2H, q, J=7.2 Hz), 3.41 (2H, t, J=7.2 Hz), 2.98 (2H, t, J=7.2 Hz), 1.47 (3H, t, J=7.2 Hz), 1.47 (3H, t, J=7.2 Hz)

Example 192

Using 3-[2-(3-ethoxy-4-hydroxyphenyl)oxazol-4-yl]-1-(2-ethoxyphenyl)propan-1-one obtained in Example 191, colorless needle crystalline 3-[2-(3-ethoxy-4-isopropoxy-phenyl)oxazol-4-yl]-1-(2-ethoxyphenyl)propan-1-one was obtained in the same manner as in Example 111.

$^1$H-NMR ($CDCl_3$) δ: 7.70 (1H, dd, J=7.5, 1.8 Hz), 7.54-7.51 (2H, m), 7.45-7.39 (2H, m), 6.97 (2H, br t, J=7.5 Hz), 6.93 (1H, d, J=7.5 Hz), 4.55 (1H, sept, J=6.0 Hz), 4.14 (2H, q, J=6.9 Hz), 4.13 (2H, q, J=6.9 Hz), 3.42 (2H, t, J=7.5 Hz), 2.99 (2H, t, J=7.5 Hz), 1.47 (3H, t, J=6.9 Hz), 1.45 (3H, t, J=6.9 Hz), 1.37 (6H, d, J=6.0 Hz)

Example 193

A 2.98 g quantity of 2-(3-benzyloxy-4-methoxyphenyl) oxazole-4-carbaldehyde obtained in Reference Example 64 and 1.72 g of 1-(2-propoxyphenyl)ethanone were dissolved in 50 ml of pyridine. A 2.66 g quantity of potassium carbonate was added thereto, and the mixture was heated and stirred at 120° C. for 22 hours. After cooling, the reaction mixture was added to saturated brine, and extraction was performed with ethyl acetate. The organic layer was washed with water and then dried over anhydrous magnesium sulfate, and the solvent was removed under reduced pressure. The residue was purified by silica gel column chromatography (n-hexane:ethyl acetate=3:1) to give 1.82 g of colorless oily (E)-3-[2-(3-benzyloxy-4-methoxyphenyl) oxazol-4-yl]-1-(2-propoxyphenyl)-2-propen-1-one.

$^1$H-NMR ($CDCl_3$) δ: 7.80 (1H, s), 7.79 (1H, d, J=15.3 Hz), 7.69-7.66 (3H, m), 7.51-7.32 (7H, m), 7.04-6.95 (3H, m), 5.21 (2H, s), 4.05 (2H, t, J=6.3 Hz), 3.94 (3H, s), 1.88 (2H, sext., J=6.3 Hz), 1.08 (3H, t, J=6.3 Hz)

Example 194

A 1.82 g quantity of (E)-3-[2-(3-benzyloxy-4-methoxyphenyl)oxazol-4-yl]-1-(2-propoxyphenyl)-2-propen-1-one obtained in Example 193 was dissolved in 50 ml of methanol. A 200 mg quantity of 5% palladium-carbon powder was added thereto, and the mixture was stirred under a hydrogen atmosphere at room temperature for 2 hours. The catalyst was then removed by filtration. The filtrate was diluted with 100 ml of methanol, and 500 mg of 10% palladium-carbon powder was added thereto. The mixture was stirred under a hydrogen atmosphere at room temperature for 3 hours. The catalyst was removed by filtration, and the solvent was removed under reduced pressure. Diisopropyl ether was added to the residue for crystallization to give 0.78 g of colorless powdery 3-[2-(3-hydroxy-4-methoxyphenyl)oxazol-4-yl]-1-(2-propoxyphenyl)propan-1-one.

$^1$H-NMR ($CDCl_3$) δ: 7.70 (1H, dd, J=7.5, 1.8 Hz), 7.55 (1H, d, J=2.1 Hz), 7.53 (1H, dd, J=8.1, 2.1 Hz), 7.42 (1H, ddd, J=8.1, 7.5, 1.8 Hz), 7.40 (1H, s), 6.97 (1H, td, J=7.5, 0.9 Hz), 6.93 (1H, br d, J=8.1 Hz), 6.89 (1H, d, J=8.1 Hz), 4.02 (2H, t, J=6.6 Hz), 3.94 (3H, s), 3.43 (2H, t, J=7.2 Hz), 2.99 (2H, t, J=7.2 Hz), 1.88 (2H, sext., J=6.6 Hz), 1.06 (3H, t, J=6.6 Hz)

Example 195

Using 0.15 g of 3-[2-(3-hydroxy-4-methoxyphenyl)oxazol-4-yl]-1-(2-propoxyphenyl)propan-1-one obtained in Example 194, 67 mg of colorless powdery 3-[2-(3-ethoxy-4-methoxyphenyl)oxazol-4-yl]-1-(2-propoxyphenyl)propan-1-one was obtained in the same manner as in Example 102.

$^1$H-NMR ($CDCl_3$) δ: 7.71 (1H, dd, J=7.8, 1.8 Hz), 7.59-7.40 (4H, m), 6.97 (1H, t, J=7.8 Hz), 6.94 (1H, d, J=7.8 Hz), 6.91 (1H, d, J=7.8 Hz), 4.18 (2H, q, J=6.6 Hz), 4.02 (2H, t, J=6.6 Hz), 3.92 (3H, s), 3.43 (2H, t, J=7.2 Hz), 3.00 (2H, t, J=7.2 Hz), 1.87 (2H, sext., J=6.6 Hz), 1.49 (3H, t, J=6.6 Hz), 1.06 (3H, t, J=6.6 Hz)

Example 196

Using 0.15 g of 3-[2-(3-hydroxy-4-methoxyphenyl)oxazol-4-yl]-1-(2-propoxyphenyl)propan-1-one obtained in Example 194, 67 mg of colorless oily 3-[2-(3-cyclopentyloxy-4-methoxyphenyl)oxazol-4-yl]-1-(2-propoxyphenyl) propan-1-one was obtained in the same manner as in Example 102.

$^1$H-NMR ($CDCl_3$) δ: 7.71 (1H, dd, J=7.5, 1.8 Hz), 7.55 (1H, dd, J=8.4, 1.8 Hz), 7.51 (1H, d, J=1.8 Hz), 7.42 (1H, br t, J=7.5 Hz), 7.39 (1H, s), 6.97 (1H, t, J=7.5 Hz), 6.93 (1H, d, J=7.5 Hz), 6.89 (1H, d, J=8.4 Hz), 4.90-4.84 (1H, m), 4.02 (2H, t, J=6.6 Hz), 3.88 (3H, s), 3.43 (2H, t, J=7.2 Hz), 2.99 (2H, t, J=7.2 Hz), 2.03-1.60 (10H, m), 1.05 (3H, t, J=7.2 Hz)

Example 197

Using 3-[2-(3-hydroxy-4-methoxyphenyl)oxazol-4-yl]-1-(2-propoxyphenyl)propan-1-one obtained in Example 194, colorless oily 3-[2-(3-isopropoxy-4-methoxyphenyl)oxazol-4-yl]-1-(2-propoxy phenyl)propan-1-one was obtained in the same manner as in Example 102.

$^1$H-NMR ($CDCl_3$) δ: 7.71 (1H, dd, J=7.8, 1.8 Hz), 7.57 (1H, dd, J=8.4, 2.1 Hz), 7.54 (1H, d, J=2.1 Hz), 7.42 (1H, ddd, J=8.4, 7.2, 1.8 Hz), 7.39 (1H, s), 6.97 (1H, br t, J=7.2 Hz), 6.96 (1H, br d, J=8.4 Hz), 6.91 (1H, d, J=8.4 Hz), 4.65 (1H, sept., J=6.0 Hz), 4.02 (2H, t, J=7.2 Hz), 3.90 (3H, s), 3.43 (2H, t, J=7.2 Hz), 2.99 (2H, t, J=7.2 Hz), 1.87 (2H, sext., J=7.2 Hz), 1.40 (6H, d, J=6.0 Hz), 1.06 (3H, t, J=7.2 Hz)

Example 198

Using 3-[2-(3-hydroxy-4-methoxyphenyl)oxazol-4-yl]-1-(2-propoxyphenyl)propan-1-one obtained in Example 194, colorless powdery 3-[2-(3-cyclopropylmethoxy-4-methoxyphenyl)oxazol-4-yl]-1-(2-propoxyphenyl)propan-1-one was obtained in the same manner as in Example 102.

$^1$H-NMR ($CDCl_3$) δ: 7.70 (1H, dd, J=7.5, 1.8 Hz), 7.57 (1H, dd, J=8.4, 1.8 Hz), 7.50 (1H, d, J=1.8 Hz), 7.45-7.39 (2H, m), 6.97 (1H, br t, J=7.5 Hz), 6.93 (1H, br d, J=7.5 Hz), 6.91 (1H, br d, J=8.4 Hz), 4.02 (2H, t, J=6.6 Hz), 3.92 (2H, d, J=7.2 Hz), 3.92 (3H, s), 3.43 (2H, t, J=7.2 Hz), 2.99 (2H, t, J=7.2 Hz), 1.87 (2H, sext., J=6.6 Hz), 1.41-1.32 (1H, m), 1.06 (3H, t, J=6.6 Hz), 0.69-0.63 (2H, m), 0.40-0.35 (2H, m)

Example 199

Using 3-[2-(3-hydroxy-4-methoxyphenyl)oxazol-4-yl]-1-(2-propoxyphenyl)propan-1-one obtained in Example 194, colorless needle crystalline 3-[2-(3-(3-butenyloxy)-4-methoxyphenyl)oxazol-4-yl]-1-(2-propoxyphenyl)propan-1-one was obtained in the same manner as in Example 102.

$^1$H-NMR ($CDCl_3$) δ: 7.71 (1H, dd, J=7.7, 1.5 Hz), 7.58 (1H, dd, J=8.5, 2.0 Hz), 7.52 (1H, d, J=2.0 Hz), 7.42 (1H, ddd, J=7.7, 7.5, 1.8 Hz), 7.40 (1H, s), 6.97 (1H, ddd, J=7.7, 7.5, 0.9 Hz), 6.93 (1H, br d, J=7.7 Hz), 6.91 (1H, d, J=8.5 Hz), 5.92 (1H, ddt, J=17.3, 10.3, 6.8 Hz), 5.19 (1H, ddd, J=17.3, 3.3, 1.5 Hz), 5.11 (1H, ddd, J=10.3. 3.3, 0.6 Hz), 4.14 (2H, t, J=7.2 Hz), 4.02 (2H, t, J=7.2 Hz), 3.91 (3H, s), 3.43 (2H, t, J=7.2 Hz), 2.99 (2H, t, J=7.2 Hz), 2.63 (2H, br q, J=6.9 Hz), 1.87 (2H, sext., J=7.2 Hz), 1.06 (3H, t, J=7.2 Hz)

Example 200

Using 3-[2-(3-hydroxy-4-methoxyphenyl)oxazol-4-yl]-1-(2-propoxyphenyl)propan-1-one obtained in Example 194, colorless needle crystalline 3-[2-(3-allyloxy-4-methoxyphenyl)oxazol-4-yl]-1-(2-propoxyphenyl)propan-1-one was obtained in the same manner as in Example 102.

$^1$H-NMR ($CDCl_3$) δ: 7.71 (1H, dd, J=7.7, 1.8 Hz), 7.59 (1H, dd, J=8.5, 1.8 Hz), 7.52 (1H, d, J=1.8 Hz), 7.42 (1H, ddd, J=8.3, 7.7, 1.8 Hz), 7.40 (1H, s), 6.97 (1H, td, J=7.7, 1.1 Hz), 6.93 (1H, br d, J=8.3 Hz), 6.91 (1H, d, J=8.5 Hz), 6.12 (1H, ddt, J=17.3, 10.5, 5.5 Hz), 5.44 (1H, ddd, J=17.3, 3.0, 1.5 Hz), 5.31 (1H, ddd, J=10.5. 3.0, 1.5 Hz), 4.67 (2H, dt, J=5.5, 1.5 Hz), 4.02 (2H, t, J=6.3 Hz), 3.92 (3H, s), 3.43 (2H, t, J=7.2 Hz), 2.99 (2H, t, J=7.2 Hz), 1.87 (2H, sext., J=6.3 Hz), 1.06 (3H, t, J=6.3 Hz)

Example 201

Using 0.1 g of 3-[2-(3-hydroxy-4-methoxyphenyl)oxazol-4-yl]-1-(2-propoxyphenyl)propan-1-one obtained in Example 194, 67 mg of colorless powdery 3-[2-(3-cyclobutylmethoxy-4-methoxy phenyl)oxazol-4-yl]-1-(2-propoxyphenyl)propan-1-one was obtained in the same manner as in Example 111.

$^1$H-NMR ($CDCl_3$) δ: 7.71 (1H, dd, J=7.8, 1.8 Hz), 7.56 (1H, dd, J=7.8, 1.8 Hz), 7.52 (1H, d, J=1.8 Hz), 7.45-7.40 (2H, m), 6.98 (1H, t, J=7.8 Hz), 6.94 (1H, d, J=7.8 Hz), 6.90 (1H, d, J=7.8 Hz), 4.07 (2H, d, J=6.9 Hz), 4.02 (2H, t, J=6.6 Hz), 3.90 (3H, s), 3.44 (2H, t, J=7.2 Hz), 3.00 (2H, t, J=7.2 Hz), 2.86 (1H, quint, J=7.2 Hz), 2.21-2.16 (2H, m), 1.96-1.84 (6H, m), 1.06 (3H, t, J=7.5 Hz)

Example 202

Using 2-[4-methoxy-3-(2,2,2-trifluoroethoxy)phenyl]oxazole-4-carbaldehyde obtained in Reference Example 65, pale yellow oily (E)-3-{2-[4-methoxy-3-(2,2,2-trifluoroethoxy)phenyl]oxazol-4-yl}-1-(2-propoxyphenyl)-2-propen-1-one was obtained in the same manner as in Example 193.

$^1$H-NMR ($CDCl_3$) δ: 7.83 (1H, d, J=15.0 Hz), 7.81 (1H, s), 7.76 (1H, dd, J=8.4, 2.1 Hz), 7.69 (1H, dd, J=7.8, 1.8 Hz), 7.69 (1H, d, J=2.1 Hz), 7.50 (1H, d, J=15.0 Hz), 7.45 (1H, ddd, J=8.4, 7.8, 1.8 Hz), 7.01 (1H, br t, J=8.4 Hz), 6.99 (1H, d, J=8.4 Hz), 6.98 (1H, br d, J=7.8 Hz), 4.46 (2H, q, J=8.4 Hz), 4.06 (2H, t, J=6.3 Hz), 3.94 (3H, s), 1.90 (2H, sext., J=6.3 Hz), 1.09 (3H, t, J=6.3 Hz)

Example 203

Using (E)-3-{2-[4-methoxy-3-(2,2,2-trifluoroethoxy)phenyl]oxazol-4-yl}-1-(2-propoxyphenyl)-2-propen-1-one obtained in Example 202, colorless powdery 3-{2-[4-methoxy-3-(2,2,2-trifluoroethoxy)phenyl]oxazol-4-yl}-1-(2-propoxyphenyl)propan-1-one was obtained in the same manner as in Example 194.

$^1$H-NMR (DMSO-$d_6$) δ: 7.83 (1H, s), 7.62 (1H, dd, J=7.8, 1.8 Hz), 7.57 (1H, dd, J=7.8, 1.5 Hz), 7.55 (1H, d, J=1.5 Hz), 7.51 (1H, br t, J=7.8 Hz), 7.17 (1H, d, J=7.8 Hz), 7.15 (1H, d, J=7.8 Hz), 7.01 (1H, t, J=7.8 Hz), 4.80 (2H, q, J=9.0 Hz), 4.06 (2H, t, J=6.6 Hz), 3.86 (3H, s), 3.33 (2H, t, J=7.2 Hz), 2.84 (2H, t, J=7.2 Hz), 1.79 (2H, sext., J=6.6 Hz), 0.99 (3H, t, J=6.6 Hz)

Example 204

Using 2-(3,4-diethoxyphenyl)oxazole-4-carbaldehyde obtained in Reference Example 66, pale yellow powdery (E)-3-[2-(3,4-diethoxyphenyl)oxazol-4-yl]-1-(2-propoxyphenyl)-2-propen-1-one was obtained in the same manner as in Example 193.

$^1$H-NMR ($CDCl_3$) δ: 7.81 (1H, d, J=15.0 Hz), 7.79 (1H, br d, J=7.5 Hz), 7.68 (1H, dd, J=7.8, 1.8 Hz), 7.62 (1H, d, J=1.8 Hz), 7.59 (1H, br s), 7.49 (1H, d, J=15.0 Hz), 7.44 (1H, br t, J=7.5 Hz), 7.01 (1H, br t, J=7.5 Hz), 6.97 (1H, br d, J=7.5 Hz), 6.93 (1H, d, J=7.8 Hz), 4.18 (2H, q, J=6.9 Hz), 4.16 (2H, q, J=6.9 Hz), 4.05 (2H, t, J=6.3 Hz), 1.89 (1H, br sext., J=6.9 Hz), 1.50 (3H, t, J=6.9 Hz), 1.49 (3H, t, J=6.9 Hz), 1.09 (3H, t, J=7.2 Hz)

Example 205

Using (E)-3-[2-(3,4-diethoxyphenyl)oxazol-4-yl]-1-(2-propoxyphenyl)-2-propen-1-one obtained in Example 204, colorless powdery 3-[2-(3,4-diethoxyphenyl)oxazol-4-yl]-1-(2-propoxyphenyl)propan-1-one was obtained in the same manner as in Example 194.

$^1$H-NMR ($CDCl_3$) δ: 7.60 (1H, dd, J=7.8, 1.8 Hz), 7.54 (1H, dd, J=8.4, 2.1 Hz), 7.52 (1H, d, J=2.1 Hz), 7.42 (1H, ddd, J=7.8, 7.2, 1.8 Hz), 7.39 (1H, s), 6.97 (1H, td, J=7.8, 1.2 Hz), 6.93 (1H, br d, J=7.2 Hz), 6.90 (1H, d, J=8.4 Hz), 4.17 (2H, q, J=6.9 Hz), 4.14 (2H, q, J=6.9 Hz), 4.02 (2H, t, J=6.6 Hz), 3.43 (2H, t, J=7.2 Hz), 2.99 (2H, t, J=7.2 Hz), 1.87 (2H, sept., J=6.6 Hz), 1.48 (6H, t, J=6.9 Hz), 1.05 (3H, t, J=6.6 Hz)

Example 206

Using 2-(3-benzyloxy-4-methoxyphenyl)oxazole-4-carbaldehyde obtained in Reference Example 64, pale yellow powdery (E)-3-[2-(3-benzyloxy-4-methoxyphenyl)oxazol-4-yl]-1-(2-isopropoxyphenyl)-2-propen-1-one was obtained in the same manner as in Example 193.

$^1$H-NMR ($CDCl_3$) δ: 7.79 (1H, s), 7.79 (1H, d, J=15.3 Hz), 7.69-7.65 (3H, m), 7.50-7.32 (7H, m), 7.03-6.95 (3H, m), 5.21 (2H, s), 4.66 (1H, sept, J=6.0 Hz), 3.94 (3H, s), 1.41 (6H, d, J=6.0 Hz)

Example 207

Using (E)-3-[2-(3-benzyloxy-4-methoxyphenyl)oxazol-4-yl]-1-(2-isopropoxyphenyl)-2-propen-1-one obtained in Example 206, colorless powdery 3-[2-(3-hydroxy-4-methoxyphenyl)oxazol-4-yl]-1-(2-isopropoxyphenyl)propan-1-one was obtained in the same manner as in Example 194.

$^1$H-NMR ($CDCl_3$) δ: 7.67 (1H, dd, J=7.5, 1.8 Hz), 7.55 (1H, br s), 7.54 (1H, dd, J=7.5, 1.8 Hz), 7.40 (1H, td, J=7.5, 1.8 Hz), 7.40 (1H, s), 6.95 (1H, br t, J=7.5 Hz), 6.93 (1H, br d, J=7.5 Hz), 6.89 (1H, d, J=7.5 Hz), 5.64 (1H, s), 4.68 (1H, sept., J=6.0 Hz), 3.94 (3H, s), 3.40 (2H, t, J=7.2 Hz), 2.98 (2H, t, J=7.2 Hz), 1.40 (6H, d, J=6.0 Hz)

The above compound was also obtained by the following method. A 10 g quantity of 2-(3-benzyloxy-4-methoxyphenyl-4-chloromethyloxazole obtained in Reference Example 5 and 5.4 g of 1-(2-isopropoxyphenyl)ethanone were dissolved in 100 ml of tetrahydrofuran, and 2.42 g of sodium hydride was added thereto. After foaming, the reaction mixture was heated and refluxed for 3 hours. After cooling, the reaction mixture was added to ice water, and extraction was performed with ethyl acetate. The organic layer was washed with water, dried over magnesium sulfate, and then concentrated under reduced pressure. The residue was purified by silica gel column chromatography (n-hexane:ethyl acetate=3:1) to give 4.30 g of pale yellow oily 3-[2-(3-benzyloxy-4-methoxyphenyl)oxazol-4-yl]-1-(2-isopropoxyphenyl)propan-1-one. Subsequently, 1.84 g of the obtained 3-[2-(3-benzyloxy-4-methoxyphenyl)oxazol-4-yl]-1-(2-isopropoxyphenyl)propan-1-one was dissolved in 100 ml of methanol. An 800 mg quantity of 10% palladium-carbon powder was added thereto. The mixture was stirred under a hydrogen atmosphere at room temperature for 1 hour. The catalyst was removed by filtration, and the solvent was removed. The residue was then recrystallized from acetone/diisopropyl ether to give 1.15 g of 3-[2-(3-hydroxy-4-methoxyphenyl)oxazol-4-yl]-1-(2-isopropoxyphenyl)propan-1-one.

Example 208

Using 0.15 g of 3-[2-(3-hydroxy-4-methoxyphenyl)oxazol-4-yl]-1-(2-isopropoxyphenyl)propan-1-one obtained in Example 207, 0.12 g of pale yellow oily 3-[2-(3-cyclopropylmethoxy-4-methoxyphenyl)oxazol-4-yl]-1-(2-isopropoxyphenyl)propan-1-one was obtained in the same manner as in Example 102.

$^1$H-NMR ($CDCl_3$) δ: 7.67 (1H, dd, J=7.8, 1.8 Hz), 7.57 (1H, dd, J=8.4, 2.1 Hz), 7.50 (1H, d, J=2.1 Hz), 7.41 (1H, td, J=7.8, 1.8 Hz), 7.39 (1H, s), 6.95 (1H, br t, J=7.8 Hz), 6.93 (1H, br d, J=7.8 Hz), 6.91 (1H, d, J=8.4 Hz), 4.68 (1H, sept., J=6.0 Hz), 3.92 (2H, d, J=6.9 Hz), 3.92 (3H, s), 3.41 (2H, t, J=7.2 Hz), 2.98 (2H, t, J=7.2 Hz), 1.40 (6H, d, J=6.0 Hz), 1.46-1.32 (1H, m), 0.69-0.62 (2H, m), 0.40-0.35 (2H, m)

Example 209

Using 0.15 g of 3-[2-(3-hydroxy-4-methoxyphenyl)oxazol-4-yl]-1-(2-isopropoxyphenyl)propan-1-one obtained in Example 207, 42 mg of colorless powdery 3-[2-(3-ethoxy-4-methoxyphenyl)oxazol-4-yl]-1-(2-isopropoxyphenyl)propan-1-one was obtained in the same manner as in Example 102.

$^1$H-NMR ($CDCl_3$) δ: 7.68 (1H, dd, J=7.7, 1.8 Hz), 7.57 (1H, dd, J=8.5, 2.0 Hz), 7.52 (1H, d, J=2.0 Hz), 7.41 (1H, td, J=7.7, 1.8 Hz), 7.40 (1H, s), 6.95 (1H, br t, J=7.7 Hz), 6.94 (1H, br d, J=7.7 Hz), 6.91 (1H, d, J=8.5 Hz), 4.69 (1H, sept., J=6.0 Hz), 4.18 (2H, q, J=6.9 Hz), 3.92 (3H, s), 3.41 (2H, t, J=6.9 Hz), 2.99 (2H, t, J=6.9 Hz), 1.49 (3H, t, J=6.9 Hz), 1.40 (6H, d, J=6.0 Hz)

Example 210

Using 3-[2-(3-hydroxy-4-methoxyphenyl)oxazol-4-yl]-1-(2-isopropoxyphenyl)propan-1-one obtained in Example 207, pale yellow oily 3-[2-(3-isopropoxy-4-methoxyphenyl)oxazol-4-yl]-1-(2-isopropoxyphenyl)propan-1-one was obtained in the same manner as in Example 102.

$^1$H-NMR ($CDCl_3$) δ: 7.68 (1H, dd, J=7.5, 1.8 Hz), 7.57 (1H, dd, J=7.5, 1.8 Hz), 7.54 (1H, d, J=1.8 Hz), 7.44-7.38 (2H, m), 6.95 (1H, br t, J=7.5 Hz), 6.94 (1H, d, J=7.5 Hz), 6.91 (1H, d, J=7.5 Hz), 4.67 (2H, sept., J=6.0 Hz), 3.90 (3H, s), 3.40 (2H, t, J=7.2 Hz), 2.98 (2H, t, J=7.2 Hz), 1.40 (12H, d, J=6.0 Hz)

Example 211

Using 3-[2-(3-hydroxy-4-methoxyphenyl)oxazol-4-yl]-1-(2-isopropoxyphenyl)propan-1-one obtained in Example 207, colorless oily 3-[2-(3-allyloxy-4-methoxyphenyl)oxazol-4-yl]-1-(2-isopropoxyphenyl)propan-1-one was obtained in the same manner as in Example 102.

$^1$H-NMR ($CDCl_3$) δ: 7.68 (1H, dd, J=7.7, 1.8 Hz), 7.58 (1H, dd, J=8.3, 1.8 Hz), 7.53 (1H, d, J=1.8 Hz), 7.41 (1H, ddd, J=7.9, 7.7, 1.8 Hz), 7.40 (1H, s), 6.98 (1H, td, J=7.9, 1.8 Hz), 6.94 (1H, br d, J=7.7 Hz), 6.92 (1H, d, J=8.3 Hz), 6.12 (1H, ddt, J=17.3, 10.5, 5.3 Hz), 5.44 (1H, ddd, J=17.3, 3.0, 1.7 Hz), 5.31 (1H, ddd, J=10.5. 3.0, 1.5 Hz), 4.75-4.60 (3H, m), 3.92 (3H, s), 3.41 (2H, t, J=7.2 Hz), 2.99 (2H, t, J=7.2 Hz), 1.40 (6H, d, J=6.0 Hz).

Example 212

Using 3-[2-(3-hydroxy-4-methoxyphenyl)oxazol-4-yl]-1-(2-isopropoxyphenyl)propan-1-one obtained in Example 207, colorless needle crystalline 3-[2-(3-(3-butenyloxy)-4-methoxyphenyl)oxazol-4-yl]-1-(2-isopropoxyphenyl)propan-1-one was obtained in the same manner as in Example 102.

$^1$H-NMR ($CDCl_3$) δ: 7.67 (1H, dd, J=7.9, 1.8 Hz), 7.57 (1H, dd, J=8.5, 2.0 Hz), 7.53 (1H, d, J=2.0 Hz), 7.40 (1H, ddd, J=7.9, 7.5, 1.8 Hz), 7.40 (1H, s), 6.95 (1H, br t, J=7.5 Hz), 6.93 (1H, br d, J=7.5 Hz), 6.91 (1H, d, J=8.5 Hz), 5.92 (1H, ddt, J=17.1, 10.3, 6.8 Hz), 5.19 (1H, ddd, J=17.3, 3.3, 1.5 Hz), 3.51 (1H, ddd, J=10.3. 3.3, 1.3 Hz), 4.68 (1H, sept., J=6.0 Hz), 4.14 (2H, t, J=7.2 Hz), 3.91 (3H, s), 3.41 (2H, t, J=7.2 Hz), 3.01 (2H, t, J=7.2 Hz), 2.63 (2H, br q, J=7.2 Hz), 1.40 (6H, d, J=6.0 Hz)

Example 213

Using 0.15 g of 3-[2-(3-hydroxy-4-methoxyphenyl)oxazol-4-yl]-1-(2-isopropoxyphenyl)propan-1-one obtained in Example 207, 40 mg of colorless powdery 1-(2-isopropoxyphenyl)-3-{2-[4-methoxy-3-(2,2,2-trifluoroethoxy)phenyl]oxazol-4-yl}propan-1-one was obtained in the same manner as in Example 111.

$^1$H-NMR ($CDCl_3$) δ: 7.70-7.60 (2H, m), 7.44-7.38 (2H, m), 6.98-6.91 (4H, m), 4.69 (1H, sept., J=6.0 Hz), 4.48-4.41 (2H, m), 3.93 (3H, s), 3.42 (2H, t, J=7.2 Hz), 3.00 (2H, t, J=7.2 Hz), 1.41 (6H, d, J=6.0 Hz)

Example 214

Using 3-[2-(3-hydroxy-4-methoxyphenyl)oxazol-4-yl]-1-(2-isopropoxyphenyl)propan-1-one obtained in Example 207, colorless powdery 3-[2-(3-cyclobutylmethoxy-4-methoxyphenyl)oxazol-4-yl]-1-(2-isopropoxyphenyl)propan-1-one was obtained in the same manner as in Example 111.

$^1$H-NMR ($CDCl_3$) δ: 7.68 (1H, dd, J=8.4, 1.8 Hz), 7.56 (1H, dd, J=8.4, 1.8 Hz), 7.52 (1H, d, J=1.8 Hz), 7.44-7.38 (2H, m), 6.95 (1H, br t, J=8.4 Hz), 6.94 (1H, br d, J=8.4 Hz), 6.90 (1H, d, J=8.4 Hz), 4.69 (1H, sept., J=6.0 Hz), 4.07 (2H, d, J=6.9 Hz), 3.90 (3H, s), 3.41 (2H, t, J=7.2 Hz), 2.99 (2H, t, J=7.2 Hz), 2.86 (1H, quint, J=7.2 Hz), 2.22-2.14 (2H, m), 1.99-1.84 (4H, m), 1.40 (6H, d, J=6.0 Hz)

Example 215

Using 2-(3,4-diethoxyphenyl)oxazole-4-carbaldehyde obtained in Reference Example 66, yellow oily (E)-3-[2-(3,4-diethoxyphenyl)oxazol-4-yl]-1-(2-isopropoxyphenyl)-2-propen-1-one was obtained in the same manner as in Example 193.

$^1$H-NMR ($CDCl_3$) δ: 7.81 (1H, d, J=15.3 Hz), 7.79 (1H, br s), 7.69-7.53 (3H, m), 7.46 (1H, d, J=15.3 Hz), 7.43 (1H, td, J=7.8, 1.2 Hz), 7.00 (1H, br t, J=7.8 Hz), 6.93 (1H, br d,

J=7.8 Hz), 6.91 (1H, br d, J=7.8 Hz), 4.67 (1H, sept, J=6.0 Hz), 4.22-4.11 (4H, m), 1.52-1.45 (6H, m), 1.41 (6H, d, J=6.0 Hz)

Example 216

Using (E)-3-[2-(3,4-diethoxyphenyl)oxazol-4-yl]-1-(2-isopropoxyphenyl)-2-propen-1-one obtained in Example 215, pale yellow oily 3-[2-(3,4-diethoxyphenyl)oxazol-4-yl]-1-(2-isopropoxy phenyl)propan-1-one was obtained in the same manner as in Example 194.

$^1$H-NMR ($CDCl_3$) δ: 7.67 (1H, dd, J=7.5, 1.5 Hz), 7.60-7.38 (4H, m), 6.97-6.89 (3H, m), 4.68 (1H, sept, J=6.0 Hz), 4.21-4.10 (4H, m), 3.41 (2H, t, J=7.2 Hz), 2.98 (2H, t, J=7.2 Hz), 1.48 (6H, br t, J=7.2 Hz), 1.40 (6H, d, J=6.0 Hz)

Example 217

Using 2-(3,4-diethoxyphenyl)oxazole-4-carbaldehyde obtained in Reference Example 66, colorless powdery (E)-3-[2-(3,4-diethoxyphenyl)oxazol-4-yl]-1-o-tolyl-2-propen-1-one was obtained in the same manner as in Example 193.

$^1$H-NMR ($CDCl_3$) δ: 7.81 (1H, s), 7.64-7.28 (8H, m), 6.93 (1H, d, J=8.1 Hz), 4.20 (2H, q, J=6.9 Hz), 4.16 (2H, q, J=6.9 Hz), 2.47 (3H, s), 1.50 (3H, t, J=6.9 Hz), 1.49 (3H, t, J=6.9 Hz)

Example 218

Using (E)-3-[2-(3,4-diethoxyphenyl)oxazol-4-yl]-1-o-tolyl-2-propen-1-one obtained in Example 217, colorless needle crystalline 3-[2-(3,4-diethoxyphenyl)oxazol-4-yl]-1-o-tolyl propan-1-one was obtained in the same manner as in Example 194.

$^1$H-NMR ($CDCl_3$) δ: 7.68 (1H, dd, J=7.5, 1.8 Hz), 7.55 (1H, dd, J=8.1, 1.8 Hz), 7.51 (1H, d, J=1.8 Hz), 7.43 (1H, br s), 7.36 (1H, td, J=7.5, 1.5 Hz), 7.27-7.22 (2H, m), 6.90 (1H, d, J=8.1 Hz), 4.17 (2H, q, J=6.9 Hz), 4.14 (2H, q, J=6.9 Hz), 3.32 (2H, t, J=7.2 Hz), 3.00 (2H, t, J=7.2 Hz), 2.49 (3H, s), 1.48 (6H, t, J=6.9 Hz)

Example 219

Using 2-(3-benzyloxy-4-methoxyphenyl)oxazole-4-carbaldehyde obtained in Reference Example 64, pale yellow powdery (E)-3-[2-(3-benzyloxy-4-methoxyphenyl)oxazol-4-yl]-1-o-tolyl-2-propen-1-one was obtained in the same manner as in Example 193.

$^1$H-NMR ($CDCl_3$) δ: 7.81 (1H, s), 7.69-7.26 (13H, m), 6.96 (1H, d, J=9.0 Hz), 5.23 (2H, s), 3.94 (3H, s), 2.47 (3H, s)

Example 220

Using (E)-3-[2-(3-benzyloxy-4-methoxyphenyl)oxazol-4-yl]-1-o-tolyl-2-propen-1-one obtained in Example 219, colorless powdery 3-[2-(3-hydroxy-4-methoxyphenyl)oxazol-4-yl]-1-o-tolyl propan-1-one was obtained in the same manner as in Example 194.

$^1$H-NMR ($CDCl_3$) δ: 7.67 (1H, dd, J=7.2, 1.8 Hz), 7.56 (1H, d, J=1.8 Hz), 7.53 (1H, dd, J=8.1, 1.8 Hz), 7.43 (1H, s), 7.35 (1H, td, J=7.2, 1.8 Hz), 7.26-7.22 (2H, m), 6.89 (1H, d, J=8.1 Hz), 5.69 (1H, s), 3.94 (3H, s), 3.31 (2H, t, J=7.2 Hz), 3.00 (2H, t, J=7.2 Hz), 2.49 (3H, s)

Example 221

A 0.15 g quantity of 3-[2-(3-hydroxy-4-methoxyphenyl)oxazol-4-yl]-1-o-tolylpropan-1-one obtained in Example 220 was dissolved in 10 ml of isopropyl alcohol. An 86 μl quantity of (bromomethyl)cyclopropane and 200 μl of 1,8-diazabicyclo[5,4,0]undec-7-ene were added thereto, and the mixture was heated and refluxed for 24 hours. Water was added to the reaction mixture, and extraction was then performed with ethyl acetate. The organic layer was washed with saturated brine, dried over anhydrous magnesium sulfate, and concentrated under reduced pressure. The residue was purified by silica gel column chromatography (n-hexane:ethyl acetate=3:1), and recrystallized from acetone/diisopropyl ether/n-hexane to give 71 mg of colorless needle crystalline 3-[2-(3-cyclopropylmethoxy-4-methoxyphenyl)oxazol-4-yl]-1-o-tolylpropan-1-one.

$^1$H-NMR ($CDCl_3$) δ: 7.68 (1H, dd, J=7.5, 1.5 Hz), 7.57 (1H, dd, J=8.1, 2.1 Hz), 7.49 (1H, d, J=2.1 Hz), 7.43 (1H, t, J=0.9 Hz), 7.36 (1H, td, J=7.5, 1.5 Hz), 7.25-7.22 (2H, m), 6.91 (1H, d, J=8.1 Hz), 3.93 (2H, d, J=6.9 Hz), 3.92 (3H, s), 3.32 (2H, t, J=7.2 Hz), 3.00 (2H, t, J=7.2 Hz), 2.49 (3H, s), 1.41-1.32 (1H, m), 0.69-0.63 (2H, m), 0.40-0.35 (2H, m)

Example 222

Using 2-(3-isopropoxy-4-methoxyphenyl)oxazole-4-carbaldehyde obtained in Reference Example 69, yellow powdery (E)-3-[2-(3-isopropoxy-4-methoxyphenyl)oxazol-4-yl]-1-(2-benzyloxyphenyl)-2-propen-1-one was obtained in the same manner as in Example 193.

$^1$H-NMR ($CDCl_3$) δ: 7.76 (1H, s), 7.69-6.92 (14H, m), 5.20 (2H, s), 4.63 (1H, sept., J=6.0 Hz), 1.38 (6H, d, J=6.0 Hz)

Example 223

Using (E)-3-[2-(3-isopropoxy-4-methoxyphenyl)oxazol-4-yl]-1-(2-benzyloxyphenyl)-2-propen-1-one obtained in Example 222, colorless plate crystalline 1-(2-hydroxyphenyl)-3-[2-(3-isopropoxy-4-methoxyphenyl)oxazol-4-yl]propan-1-one was obtained in the same manner as in Example 194.

$^1$H-NMR ($CDCl_3$) δ: 12.25 (1H, s), 7.82 (1H, dd, J=8.4, 1.5 Hz), 7.58 (1H, dd, J=8.4, 1.8 Hz), 7.54 (1H, d, J=1.8 Hz), 7.46 (1H, ddd, J=8.4, 7.2, 1.5 Hz), 7.45 (1H, s), 6.98 (1H, dd, J=8.4, 1.2 Hz), 6.92 (1H, d, J=8.4 Hz), 6.89 (1H, ddd, J=8.4, 7.2, 1.2 Hz), 4.65 (1H, sept., J=6.0 Hz), 3.90 (3H, s), 3.44 (2H, t, J=7.5 Hz), 3.03 (2H, t, J=7.5 Hz), 1.40 (6H, d, J=6.0 Hz)

Example 224

A 67 mg quantity of 1-(2-hydroxyphenyl)-3-[2-(3-isopropoxy-4-methoxyphenyl)oxazol-4-yl]propan-1-one obtained in Example 223 was dissolved in 5 ml of dimethylformamide. A 31 μl quantity of allyl bromide and 73 mg of potassium carbonate were added thereto, and the mixture was stirred at room temperature overnight. A 50 μl quantity of allyl bromide was further added thereto, and the mixture was stirred at 50° C. for 8 hours, and at room temperature overnight. The reaction mixture was added to water, and extraction was then performed with ethyl acetate. The organic layer was washed with saturated brine, dried over anhydrous magnesium sulfate, and the solvent was removed under reduced pressure. The residue was purified by silica gel column chromatography (n-hexane:ethyl acetate 3:1), and crystallized from n-hexane to give 33 mg of colorless powdery 1-(2-allyloxyphenyl)-3-[2-(3-isopropoxy-4-methoxyphenyl)oxazol-4-yl]propan-1-one.

$^1$H-NMR ($CDCl_3$) δ: 7.70 (1H, dd, J=7.8, 1.8 Hz), 7.57 (1H, dd, J=8.4, 2.1 Hz), 7.54 (1H, d, J=2.1 Hz), 7.44 (1H, ddd, J=7.8, 7.5, 1.8 Hz), 7.40 (1H, br s), 6.99 (1H, td, J=7.8, 1.2 Hz), 6.94 (1H, br d, J=7.5 Hz), 6.91 (1H, d, J=8.4 Hz), 6.08 (1H, ddt, J=17.1, 10.5, 5.4 Hz), 5.42 (1H, ddd, J=17.1, 3.0, 1.5 Hz), 5.29 (1H, ddd, J=10.5, 2.7, 1.5 Hz), 4.69-4.61 (3H, m), 3.89 (3H, s), 3.42 (2H, t, J=7.2 Hz), 2.99 (2H, t, J=7.2 Hz), 1.39 (6H, d, J=6.3 Hz)

Example 225

Using 0.3 g of 3-[2-(3-hydroxy-4-methoxyphenyl)oxazol-4-yl]-1-o-tolylpropan-1-one obtained in Example 220, 0.15 g of white powdery 3-[2-(3-ethoxy-4-methoxyphenyl)oxazol-4-yl]-1-o-tolylpropan-1-one was obtained in the same manner as in Example 3.

$^1$H-NMR ($CDCl_3$) δ: 7.68 (1H, m), 7.57 (1H, dd, J=8.1, 2.1 Hz), 7.51 (1H, d, J=2.1 Hz), 7.44 (1H, d, J=0.9 Hz), 7.36 (1H, m), 7.30-7.20 (3H, m), 6.91 (1H, d, J=8.4 Hz), 4.18 (2H, q, J=6.9 Hz), 3.92 (3H, s), 3.35-3.25 (2H, m), 3.05-2.95 (2H, m), 2.50 (3H, s), 1.50 (3H, t, J=6.9 Hz)

Example 226

Using 0.3 g of 3-[2-(3-hydroxy-4-methoxyphenyl)oxazol-4-yl]-1-o-tolylpropan-1-one obtained in Example 220, 0.1 g of white powdery 3-[2-(3-allyloxy-4-methoxyphenyl)oxazol-4-yl]-1-o-tolylpropan-1-one was obtained in the same manner as in Example 3.

$^1$H-NMR ($CDCl_3$) δ: 7.68 (1H, m), 7.59 (1H, dd, J=8.4, 2.1 Hz), 7.52 (1H, d, J=2.1 Hz), 7.43 (1H, s), 7.38 (1H, m), 7.35-7.25 (2H, m), 6.92 (1H, d, J=8.4 Hz), 6.13 (1H, ddd, J=17.1, 10.5, 5.4 Hz), 5.44 (1H, ddd, J=17.1, 2.7, 1.5 Hz), 5.31 (1H, ddd, J=10.5, 2.7, 1.5 Hz), 4.68 (1H, dt, J=5.4, 1.5 Hz), 3.92 (3H, s), 3.32 (2H, t, J=7.2 Hz), 3.00 (2H, t, J=7.2 Hz), 2.50 (3H, s)

Example 227

Using 0.2 g of 3-[2-(3-hydroxy-4-methoxyphenyl)oxazol-4-yl]-1-o-tolylpropan-1-one obtained in Example 220, 0.1 g of pale yellow oily 3-[2-(3-isopropoxy-4-methoxyphenyl)oxazol-4-yl]-1-o-tolylpropan-1-one was obtained in the same manner as in Example 3.

$^1$H-NMR ($CDCl_3$) δ: 7.69 (1H, m), 7.60-7.50 (2H, m), 7.50-7.30 (3H, m), 7.24 (1H, m), 6.91 (1H, dd, J=5.1, 3.0 Hz), 4.65 (1H, m), 3.90 (3H, s), 3.35-3.25 (2H, m), 3.05-2.95 (2H, m), 2.49 (3H, s), 1.40 (6H, d, J=6.0 Hz)

Example 228

A 65 mg quantity of sodium hydride was suspended in 5 ml of tetrahydrofuran. A 0.27 g quantity of 1-(2-ethoxyphenyl)ethanone and 0.3 g of 2-(3-benzyloxy-4-difluoro methoxyphenyl)-4-chloromethyloxazole obtained in Reference Example 44 was successively added thereto with ice-cooling and stirring, and the mixture was stirred for 3 hours with heating and refluxing. An aqueous saturated ammonium chloride solution was added to the reaction mixture with ice-cooling and stirring. After stirring for 15 minutes, water was added thereto, and extraction was performed with ethyl acetate. The mixture was dried over anhydrous magnesium sulfate, and the solvent was removed. The obtained residue was purified by silica gel column chromatography (n-hexane:ethyl acetate=4:1) to give 75 mg of colorless oily 3-[2-(3-benzyloxy-4-difluoromethoxyphenyl)oxazol-4-yl]-1-(2-ethoxyphenyl)propan-1-one.

$^1$H-NMR ($CDCl_3$) δ: 7.72-7.69 (2H, m), 7.59 (1H, dd, J=8.1, 1.8 Hz), 7.47-7.32 (7H, m), 7.00-6.92 (3H, m), 6.61 (1H, t, J=74.7 Hz), 5.20 (2H, s), 4.15 (2H, q, J=7.2 Hz), 3.43 (2H, t, J=7.2 Hz), 3.00 (2H, t, J=7.2 Hz), 1.48 (3H, t, J=7.2 Hz)

Example 229

A 75 mg quantity of 3-[2-(3-benzyloxy-4-difluoromethoxyphenyl)oxazol-4-yl]-1-(2-ethoxyphenyl)propan-1-one obtained in Example 228 was dissolved in 1 ml of ethanol. A 7 mg quantity of 10% palladium-carbon powder was added thereto, and the mixture was stirred under a hydrogen atmosphere at room temperature for 45 minutes. The catalyst was removed by filtration, the filtrate was concentrated, and the obtained residue was purified by silica gel column chromatography (dichloromethane:ethanol=100:1) to give 32 mg of white powdery 3-[2-(4-difluoromethoxy-3-hydroxyphenyl)oxazol-4-yl]-1-(2-ethoxyphenyl)propan-1-one.

$^1$H-NMR ($CDCl_3$) δ: 7.70 (1H, dd, J=7.5, 1.8 Hz), 7.65 (1H, d, J=1.8 Hz), 7.56-7.43 (3H, m), 7.16 (1H, d, J=6.0 Hz), 6.98-6.92 (2H, m), 6.57 (1H, t, J=74.7 Hz), 5.57 (1H, s), 4.13 (2H, q, J=7.2 Hz), 3.42 (2H, t, J=7.2 Hz), 3.00 (2H, t, J=7.2 Hz), 1.48 (3H, t, J=7.2 Hz)

Example 230

A 30 mg quantity of 3-[2-(4-difluoromethoxy-3-hydroxyphenyl)oxazol-4-yl]-1-(2-ethoxyphenyl)propan-1-one obtained in Example 229 was dissolved in 0.5 ml of dimethylformamide. An 18 mg quantity of 2-bromopropane and 30 mg of potassium carbonate were added thereto, and the mixture was stirred at room temperature overnight. Water was added to the reaction mixture, and extraction was performed with ethyl acetate. Drying was performed with anhydrous magnesium sulfate, and the solvent was removed. The obtained residue was purified by silica gel column chromatography (n-hexane:ethyl acetate=4:1) to give 23 mg of white powdery 3-[2-(4-difluoromethoxy-3-isopropoxyphenyl)oxazol-4-yl]-1-(2-ethoxyphenyl)propan-1-one.

$^1$H-NMR ($CDCl_3$) δ: 7.70 (1H, dd, J=7.8, 1.8 Hz), 7.61 (1H, d, J=1.8 Hz), 7.55 (1H, dd, J=8.4, 1.8 Hz), 7.50-7.38 (2H, m), 7.19 (1H, d, J=8.1 Hz), 7.00-6.70 (2H, m), 6.60 (1H, t, J=74.7 Hz), 4.72-4.64 (1H, m), 4.13 (2H, q, J=7.2 Hz), 3.42 (2H, t, J=7.2 Hz), 3.00 (2H, t, J=7.2 Hz), 1.48 (3H, t, J=7.2 Hz), 1.39 (6H, d, J=6.0 Hz)

Example 231

Using 2-(3-benzyloxy-4-methoxyphenyl)-4-chloromethyl oxazole obtained in Reference Example 5 and 1-(2-methoxymethoxy phenyl)ethanone obtained in Reference Example 70, yellow oily 3-[2-(3-benzyloxy-4-methoxyphenyl)oxazol-4-yl]-1-(2-methoxymethoxy phenyl)propan-1-one was obtained in the same manner as in Example 190.

$^1$H-NMR ($CDCl_3$) δ: 7.66 (1H, dd, J=7.8, 1.8 Hz), 7.59 (1H, dd, J=7.8, 1.8 Hz), 7.51 (1H, br s), 7.49-7.27 (7H, m), 7.17 (1H, br d, J=7.8 Hz), 7.04 (1H, td, J=7.5, 1.2 Hz), 6.93 (1H, br d, J=7.8 Hz), 5.25 (2H, s), 5.19 (2H, s), 3.92 (3H, s), 3.48 (3H, s), 3.39 (2H, t, J=7.2 Hz), 3.00 (2H, t, J=7.2 Hz)

Example 232

Using 3-[2-(3-benzyloxy-4-methoxyphenyl)oxazol-4-yl]-1-(2-methoxymethoxyphenyl)propan-1-one obtained in Example 231, 3-[2-(3-hydroxy-4-methoxyphenyl)oxazol-4-yl]-1-(2-methoxymethoxy phenyl)propan-1-one was obtained in the same manner as in Example 194.

$^1$H-NMR ($CDCl_3$) δ: 7.66 (1H, dd, J=7.8, 1.8 Hz), 7.55 (1H, d, J=2.1 Hz), 7.53 (1H, dd, J=8.1, 2.1 Hz), 7.41 (1H, s), 7.41 (1H, ddd, J=7.8, 7.5, 1.8 Hz), 7.17 (1H, br d, J=7.8 Hz), 7.04 (1H, td, J=7.5, 0.8 Hz), 6.89 (1H, d, J=8.1 Hz), 5.64 (1H, s), 5.26 (2H, s), 3.94 (3H, s), 3.49 (3H, s), 3.40 (2H, t, J=7.2 Hz), 2.99 (2H, t, J=7.2 Hz)

Example 233

Using 3-[2-(3-hydroxy-4-methoxyphenyl)oxazol-4-yl]-1-(2-methoxymethoxyphenyl)propan-1-one obtained in Example 232, colorless oily 3-[2-(3-isopropoxy-4-methoxyphenyl)oxazol-4-yl]-1-(2-methoxymethoxyphenyl)propan-1-one was obtained in the same manner as in Example 102.

$^1$H-NMR ($CDCl_3$) δ: 7.66 (1H, dd, J=7.5, 1.8 Hz), 7.57 (1H, dd, J=8.4, 1.8 Hz), 7.53 (1H, d, J=1.8 Hz), 7.42 (1H, ddd, J=8.4, 7.5, 1.8 Hz), 7.41 (1H, s), 7.17 (1H, dd, J=8.4, 1.2 Hz), 7.04 (1H, td, J=7.5, 1.2 Hz), 6.91 (1H, d, J=8.4 Hz), 5.26 (2H, s), 4.64 (1H, sept, J=6.0 Hz), 3.90 (3H, s), 3.49 (3H, s), 3.40 (2H, t, J=7.2 Hz), 3.00 (2H, t, J=7.2 Hz), 1.39 (6H, d, J=6.0 Hz)

Example 234

Using 0.76 g of 4-chloromethyl-2-(3-ethoxy-4-methoxyphenyl)oxazole obtained in Reference Example 58, 60 mg of white powdery 3-[2-(3-ethoxy-4-methoxyphenyl)oxazol-4-yl]-1-[2-(2,2,2-trifluoroethoxy)phenyl]propan-1-one was obtained in the same manner as in Example 228.

$^1$H-NMR ($CDCl_3$) δ: 7.76 (1H, dd, J=7.8, 2.1 Hz), 7.58-7.48 (3H, m), 7.39 (1H, s), 7.12 (1H, t, J=7.5 Hz), 6.92-6.88 (2H, m), 4.46 (2H, q, J=7.8 Hz), 4.18 (2H, q, J=7.2 Hz), 3.92 (3H, s), 3.40 (2H, t, J=7.5 Hz), 3.00 (2H, t, J=7.5 Hz), 1.49 (3H, t, J=7.2 Hz)

Example 235

Using 0.76 g of 4-chloromethyl-2-(3-ethoxy-4-methoxyphenyl)oxazole obtained in Reference Example 58 and 0.58 g of 1-(2-trifluoromethoxyphenyl)ethanone, 0.18 g of pale yellow oily 3-[2-(3-ethoxy-4-methoxyphenyl)oxazol-4-yl]-1-(2-trifluoro methoxyphenyl)propan-1-one was obtained in the same manner as in Example 228.

$^1$H-NMR ($CDCl_3$) δ: 7.71 (1H, dd, J=7.5, 1.8 Hz), 7.58-7.50 (3H, m), 7.42 (1H, s), 7.38-7.30 (2H, m), 6.91 (1H, d, J=8.4 Hz), 4.17 (2H, q, J=6.6 Hz), 3.91 (3H, s), 3.45 (2H, t, J=7.2 Hz), 3.01 (2H, t, J=7.2 Hz), 1.49 (3H, t, J=6.6 Hz)

Example 236

Using 0.5 g of 3-[2-(3,4-dimethoxyphenyl)oxazol-4-yl] propionic acid obtained in Reference Example 71, 0.32 g of white powdery 3-[2-(3,4-diethoxyphenyl)oxazol-4-yl]-1-pyrrolidin-1-yl-propan-1-one was obtained in the same manner as in Example 1.

$^1$H-NMR ($CDCl_3$) δ: 7.55 (1H, dd, J=6.75, 1.8 Hz), 7.52 (1H, d, J=1.8 Hz), 7.44 (1H, s), 6.91 (1H, d, J=8.1 Hz), 4.20-4.10 (4H, m), 3.50-3.40 (4H, m), 3.00-2.90 (2H, m), 2.70-2.60 (2H, m), 1.95-1.75 (4H, m), 1.48 (3H, t, J=7.2 Hz), 1.48 (3H, t, J=7.2 Hz)

Example 237

Using 0.3 g of 3-[2-(3,4-dimethoxyphenyl)oxazol-4-yl] propionic acid obtained in Reference Example 71, 0.28 g of white powdery 3-[2-(3,4-diethoxyphenyl)oxazol-4-yl]-1-(3-hydroxy pyrrolidin-1-yl)propan-1-one was obtained in the same manner as in Example 1.

$^1$H-NMR ($CDCl_3$) δ: 7.55 (1H, dd, J=6.75, 1.8 Hz), 7.52 (1H, d, J=1.8 Hz), 7.44 (1H, s), 6.91 (1H, d, J=8.1 Hz), 4.20-4.10 (4H, m), 3.50-3.40 (4H, m), 3.00-2.90 (2H, m), 2.70-2.60 (2H, m), 2.10-1.90 (3H, m), 1.48 (3H, t, J=6.9 Hz), 1.48 (3H, t, J=6.9 Hz)

Example 238

Using 1 g of 3-[2-(4-benzyloxy-3-methoxyphenyl)oxazol-4-yl]propionic acid obtained in Reference Example 73, 1.03 g of pale yellow powdery 3-[2-(4-benzyloxy-3-methoxyphenyl)oxazol-4-yl]-1-pyrrolidin-1-ylpropan-1-one was obtained in the same manner as in Example 1.

$^1$H-NMR ($CDCl_3$) δ: 7.61-7.27 (8H, m), 6.93 (1H, d, J=8.4 Hz), 5.20 (2H, s), 3.97 (3H, s), 3.49-3.39 (4H, m), 2.94 (2H, t, J=7.5 Hz), 2.65 (2H, t, J=7.5 Hz), 1.95-1.78 (4H, m)

Example 239

Using 1 g of 3-[2-(4-benzyloxy-3-methoxyphenyl)oxazol-4-yl]-1-pyrrolidin-1-yl-propan-1-one obtained in Example 238, 0.59 g of white powdery 3-[2-(4-hydroxy-3-methoxyphenyl)oxazol-4-yl]-1-pyrrolidin-1-ylpropan-1-one was obtained in the same manner as in Example 2.

$^1$H-NMR ($CDCl_3$) δ: 7.56-7.51 (2H, m), 7.44 (1H, s), 6.90 (1H, d, J=8.4 Hz), 5.97 (1H, s), 3.97 (3H, s), 3.49-3.39 (4H, m), 2.94 (2H, t, J=7.5 Hz), 2.66 (2H, t, J=7.5 Hz), 1.97-1.79 (4H, m)

Example 240

Using 0.15 g of 3-[2-(4-hydroxy-3-methoxyphenyl)oxazol-4-yl]-1-pyrrolidin-1-yl-propan-1-one obtained in Example 239, 0.13 g of white powdery 3-[2-(4-ethoxy-3-methoxyphenyl)oxazol-4-yl]-1-pyrrolidin-1-ylpropan-1-one was obtained in the same manner as in Example 3.

$^1$H-NMR ($CDCl_3$) δ: 7.57 (1H, dd, J=8.1, 2.1 Hz), 7.52 (1H, d, J=1.8 Hz), 7.45 (1H, s), 6.91 (1H, d, J=8.1 Hz), 4.15 (2H, q, J=6.9 Hz), 3.96 (3H, s), 3.49-3.40 (4H, m), 2.94 (2H, t, J=7.2 Hz), 2.66 (2H, t, J=7.2 Hz), 1.97-1.79 (4H, m), 1.49 (3H, t, J=6.9 Hz)

Example 241

N-[2-(3-cyclopropylmethoxy-4-methoxyphenyl)oxazol-4-ylmethyl]-2-trifluoromethylbenzamide obtained in Example 25 was dissolved in 1 ml of dimethylformamide. A 30 mg quantity of sodium hydride was added thereto with ice-cooling and stirring, and the mixture was stirred for 30 minutes. A 30 mg quantity of methyl iodide was added thereto, and the reaction mixture was stirred at room temperature for 2 hours. Water and ethyl acetate were then added thereto, and extraction was performed. The organic layer was washed with water twice and concentrated by removing the solvent under reduced pressure. The residue was purified by silica gel chromatography (n-hexane:ethyl acetate=3:1) to give 35 mg of colorless oily N-[2-(3-cyclopropylmethoxy-4-methoxyphenyl)oxazol-4-ylmethyl]-N-methyl-2-trifluoromethylbenzamide.

$^1$H-NMR ($CDCl_3$) δ: 7.72-7.34 (7H, m), 6.94 (1H, dd, J=8.4, 1.8 Hz), 4.88-4.11 (1H, m), 3.98-3.89 (5H, m), 3.17-2.88 (3H, m), 1.43-1.34 (1H, m), 0.71-0.64 (2H, m), 0.42-0.36 (2H, m)

Example 242

Using 0.14 g of [2-(3,4-diethoxyphenyl)oxazol-4-ylmethyl]methylamine obtained in Reference Example 74, 70 mg of colorless oily N-[2-(3,4-dimethoxyphenyl)oxazol-4-ylmethyl]-2-ethoxy-N-methylbenzamide was obtained in the same manner as in Example 1.

$^1$H-NMR ($CDCl_3$) δ: 7.60-7.26 (5H, m), 7.00-6.87 (3H, m), 4.23-4.02 (8H, m), 3.19-2.96 (3H, m), 1.52-1.40 (6H, m), 1.36 (3H, t, J=6.9 Hz)

Example 243

Using 0.2 g of 2-[2-(3,4-diethoxyphenyl)oxazol-4-yl]ethylamine obtained in Reference Example 78 and 0.18 g of 2-ethoxy benzoic acid, 0.14 g of white powdery N-{2-[2-(3,4-dimethoxyphenyl)oxazol-4-yl]ethyl}-2-ethoxybenzamide was obtained in the same manner as in Example 1.

$^1$H-NMR ($CDCl_3$) δ: 8.22 (1H, dd, J=7.5, 4.8 Hz), 7.60-7.50 (2H, m), 7.47 (1H, s), 7.39 (1H, m), 7.06 (1H, m), 6.95-6.85 (2H, m), 4.30-4.05 (6H, m), 4.09 (2H, q, J=6.9 Hz), 3.85 (2H, q, J=6.6 Hz), 2.91 (2H, t, J=6.6 Hz), 1.48 (6H, t, J=6.9 Hz), 1.28 (6H, t, J=6.9 Hz)

Example 244

Using 0.3 g of 2-(3,4-diethoxyphenyl)oxazole-4-carboxylic acid obtained in Reference Example 80 and 0.28 g of 1-(2-amino)ethanone, 0.32 g of white powdery N-(2-oxo-2-phenylethyl)-2-(3,4-diethoxyphenyl)oxazole-4-carboxamide was obtained in the same manner as in Example 1.

$^1$H-NMR (DMSO-$d_6$) δ: 8.67 (1H, d, J=0.9 Hz), 8.49 (1H, t, J=5.7 Hz), 8.10-8.00 (2H, m), 7.70-7.50 (5H, m), 7.16 (1H, m), 4.81 (2H, d, J=5.7 Hz), 4.13 (4H, q, J=6.9 Hz), 1.38 (6H, t, J=6.9 Hz), 1.37 (3H, t, J=6.9 Hz)

Example 245

Using 2-(3,4-diethoxyphenyl)oxazole-4-carboxylic acid obtained in Reference Example 80, 0.32 g of white powdery 1-(4-{4-[2-(3,4-diethoxyphenyl)oxazole-4-carbonyl]piperazin-1-yl}phenyl)ethanone was obtained in the same manner as in Example 1.

$^1$H-NMR ($CDCl_3$) δ: 8.20 (1H, s), 7.95-7.85 (2H, m), 7.62 (1H, dd, J=8.4, 2.1 Hz), 7.54 (1H, d, J=2.1 Hz), 7.00-6.85 (3H, m), 4.40-4.20 (2H, m), 4.19 (2H, q, J=6.9 Hz), 4.16 (2H, q, J=6.9 Hz), 4.00-3.80 (2H, m), 3.50-3.45 (4H, m), 2.53 (3H, s), 1.50 (3H, t, J=6.9 Hz), 1.50 (3H, t, J=6.9 Hz)

Example 246

Using 0.28 g of 2-(3,4-diethoxyphenyl)oxazole-4-carboxylic acid obtained in Reference Example 80 and 0.2 g of 1-(4-methoxyphenyl)piperazine, 0.36 g of white powdery 4-(2-(3,4-diethoxyphenyl)oxazol-4-yl)-1-(4-methoxyphenyl)piperazine was obtained in the same manner as in Example 1.

$^1$H-NMR ($CDCl_3$) δ: 8.16 (1H, s), 7.61 (1H, dd, J=8.7, 2.1 Hz), 7.54 (1H, s), 6.95-6.84 (5H, m), 4.40-4.30 (2H, m), 4.21-4.12 (4H, m), 4.00-3.93 (2H, m), 3.78 (3H, s), 3.14 (4H, t, J=4.8 Hz), 1.47 (6H, t, J=7.2 Hz)

Example 247

Using 0.28 g of 2-(3,4-diethoxyphenyl)oxazole-4-carboxylic acid obtained in Reference Example 80 and 1-(4-hydroxyphenyl)piperazine, white powdery 4-(2-(3,4-diethoxyphenyl)oxazol-4-yl)-1-(4-hydroxyphenyl)piperazine was obtained in the same manner as in Example 1.

$^1$H-NMR ($CDCl_3$) δ: 8.16 (1H, s), 7.61 (1H, dd, J=8.7, 2.1 Hz), 7.54 (1H, s), 6.95-6.78 (5H, m), 4.40-4.30 (2H, m), 4.21-4.12 (4H, m), 4.00-3.93 (2H, m), 3.14 (4H, t, J=4.8 Hz), 1.49 (6H, t, J=7.2 Hz)

Example 248

Using 0.28 g of 2-(3,4-diethoxyphenyl)oxazole-4-carboxylic acid obtained in Reference Example 80 and 0.14 g of 2-phenylethylamine, 0.21 g of white powdery N-phenethyl-2-(3,4-dimethoxyphenyl)oxazole-4-carboxamide was obtained in the same manner as in Example 1.

$^1$H-NMR ($CDCl_3$) δ: 8.17 (1H, s), 7.56 (1H, dd, J=8.4, 2.1 Hz), 7.50 (1H, d, J=2.1 Hz), 7.36-7.21 (5H, m), 7.12 (1H, br s), 6.93 (1H, d, J=8.4 Hz), 4.22-4.12 (4H, m), 3.74-3.66 (2H, m), 2.95 (2H, t, J=7.2 Hz), 1.57-1.46 (6H, m)

Example 249

Using 0.28 g of 2-(3,4-diethoxyphenyl)oxazole-4-carboxylic acid obtained in Reference Example 80 and 0.13 g of 1-(2-aminoethyl)pyrrolidine, 0.15 g of pale yellow powdery N-(2-(pyrrolidin-1-yl)ethyl)-2-(3,4-dimethoxyphenyl)oxazole-4-carboxamide was obtained in the same manner as in Example 1.

$^1$H-NMR ($CDCl_3$) δ: 8.17 (1H, s), 7.60 (1H, dd, J=8.4, 1.8 Hz), 7.55 (1H, d, J=1.8 Hz), 7.44 (1H, br s), 6.92 (1H, d, J=8.4 Hz), 4.23-4.12 (4H, m), 3.65-3.58 (2H, m), 2.79 (2H, t, J=6.6 Hz), 2.70-2.58 (4H, m), 1.87-1.75 (4H, m), 1.53-1.46 (6H, m)

Example 250

Using 0.15 g of [2-(3,4-diethoxyphenyl)oxazol-4-yl]acetic acid obtained in Reference Example 81 and 0.11 g of o-phenetidine, 0.12 g of white powdery 2-[2-(3,4-diethoxyphenyl)oxazol-4-yl]-N-(2-ethoxyphenyl)acetamide was obtained in the same manner as in Example 1.

$^1$H-NMR ($CDCl_3$) δ: 8.74 (1H, br s), 8.37 (1H, dd, J=7.2, 1.8 Hz), 7.70-7.65 (2H, m), 7.61 (1H, d, J=1.8 Hz), 7.00-6.90 (3H, m), 6.80 (1H, dd, J=7.8, 1.2 Hz), 4.18 (2H, q, J=6.9 Hz), 4.16 (2H, q, J=6.9 Hz), 3.97 (2H, q, J=7.2 Hz), 3.74 (2H, s), 1.49 (3H, t, J=6.9 Hz), 1.49 (3H, t, J=6.9 Hz), 1.18 (3H, t, J=7.2 Hz)

Example 251

Using 0.15 g of [2-(3,4-diethoxyphenyl)oxazol-4-yl]acetic acid obtained in Reference Example 81 and 85 mg of 2-amino-3-hydroxypyridine, 0.11 g of white powdery 2-[2-(3,4-diethoxyphenyl)oxazol-4-yl]-N-(3-hydroxypyridin-2-yl)acetamide was obtained in the same manner as in Example 1.

$^1$H-NMR ($CDCl_3$) δ: 10.37 (1H, brs), 9.88 (1H, brs), 7.84 (1H, dd, J=4.8, 1.2 Hz), 7.65-7.60 (3H, m), 7.31 (1H, dd, J=4.2, 1.2 Hz), 6.94 (1H, d, J=9.0 Hz), 4.22 (2H, q, J=6.9 Hz), 4.16 (2H, q, J=6.9 Hz), 1.51 (3H, t, J=6.9 Hz), 1.49 (3H, t, J=6.9 Hz)

Example 252

A 0.5 g quantity of 4-chloromethyl-2-(3,4-diethoxyphenyl)oxazole obtained in Reference Example 35, 0.36 g of piperazin-2-one and 0.28 g of potassium carbonate were added to 10 ml of acetonitrile, and the mixture was heated and refluxed for 7 hours. The residue was diluted with ethyl acetate, and washed with water and then with saturated brine. The organic layer was dried over anhydrous magnesium sulfate and concentrated by removing the solvent under reduced pressure. The residue was purified by silica gel column chromatography (dichloromethane:methanol=1:0 to 50:1), and the obtained crude crystals were recrystallized from ethyl acetate to give 0.25 g of colorless crystalline 4-[2-(3,4-diethoxyphenyl)oxazol-4-ylmethyl]piperazin-2-one.

$^1$H-NMR ($CDCl_3$) δ: 7.59 (1H, d, J=8.1, 2.1 Hz), 7.56 (1H, d, J=2.1 Hz), 6.91 (1H, d, J=8.1 Hz), 6.03 (1H, brs), 4.17 (2H, q, J=6.9 Hz), 4.15 (2H, q, J=6.9 Hz), 3.61 (2H, s), 3.45-3.35 (2H, m), 3.27 (2H, s), 2.80-2.75 (2H, m), 1.48 (6H, t, J=6.9 Hz)

Example 253

Using 0.5 g of 4-chloromethyl-2-(3,4-diethoxyphenyl) oxazole obtained in Reference Example 35 and 0.5 g of morpholine, 0.31 g of white powdery 4-[2-(3,4-diethoxyphenyl)oxazol-4-ylmethyl]morpholine was obtained in the same manner as in Example 252.

$^1$H-NMR ($CDCl_3$) δ: 7.70-7.50 (2H, m), 7.54 (1H, s), 6.91 (1H, d, J=8.4 Hz), 4.25-4.10 (4H, m), 3.80-3.70 (4H, m), 3.51 (2H, s), 2.60-2.50 (4H, m), 1.48 (6H, t, J=6.9 Hz)

Example 254

A 0.5 g quantity of 4-chloromethyl-2-(3,4-diethoxy phenyl)oxazole obtained in Reference Example 35, 0.28 g of 2-mercaptopyridine and 0.28 g of potassium carbonate were added to 10 ml of dimethylformamide, and the mixture was stirred at room temperature for 24 hours. The reaction mixture was diluted with ethyl acetate, and washed with water and then with saturated brine. The organic layer was dried over anhydrous magnesium sulfate and concentrated by removing the solvent under reduced pressure. The residue was purified by silica gel column chromatography (ethyl acetate:n-hexane=1:4 to 1:2), and the obtained crude crystals were recrystallized from a mixture of ethyl acetate and n-hexane to give 0.63 g of colorless crystalline 2-[2-(3,4-diethoxyphenyl)oxazol-4-ylmethylsulfanyl]pyridine.

$^1$H-NMR ($CDCl_3$) δ: 8.45 (3H, m), 7.60-7.50 (3H, m), 7.47 (1H, m), 7.18 (1H, d, J=8.1 Hz), 6.99 (1H, m), 6.89 (1H, d, J=8.1 Hz), 4.38 (2H, s), 4.17 (2H, q, J=6.9 Hz), 4.14 (2H, q, J=6.9 Hz), 1.47 (6H, t, J=6.9 Hz)

Example 255

A 0.58 g quantity of 2-[2-(3,4-diethoxyphenyl)oxazol-4-ylmethylsulfanyl]pyridine obtained in Example 254 was added to 20 ml of dichloromethane. A 0.55 g quantity of m-chloroperbenzoic acid was gradually added thereto with ice-cooling, and the mixture was then stirred. The reaction mixture was diluted with 30 ml of dichloromethane, and washed with an aqueous 10% sodium hydroxide solution and then with saturated brine. The organic layer was dried over anhydrous magnesium sulfate and concentrated by removing the solvent under reduced pressure. The residue was purified by silica gel column chromatography (ethyl acetate:n-hexane=2:1 to 3:1), and the obtained crude crystals was recrystallized from a mixture of ethyl acetate and n-hexane to give 0.49 g of colorless crystalline 2-[2-(3,4-diethoxyphenyl)oxazol-4-ylmethanesulfonyl]pyridine.

$^1$H-NMR ($CDCl_3$) δ: 8.81 (1H, m), 8.00 (1H, m), 7.91 (1H, m), 7.61 (1H, s), 7.55 (1H, m), 7.50-7.40 (2H, m), 6.87 (1H, d, J=8.4 Hz), 4.71 (2H, s), 4.13 (4H, q, J=6.9 Hz), 1.47 (6H, t, J=6.9 Hz)

Example 256

A 0.27 g quantity of [2-(3,4-diethoxyphenyl)oxazol-4-yl] methylamine obtained in Reference Example 37 and 0.3 ml of triethylamine were dissolved in 10 ml of acetonitrile. A 0.19 g quantity of o-toluenesulfonylchloride was added thereto, and the mixture was stirred at room temperature for 1 hour. Water was added to the reaction mixture, and extraction was performed with ethyl acetate. The organic layer was washed with water twice, and the solvent was removed. The obtained residue was purified using a silica gel column (n-hexane:ethyl acetate=1:1). The obtained crude crystals were recrystallized from a mixture of n-hexane and ethyl acetate to give 0.3 g of white powdery N-[2-(3,4-diethoxyphenyl)oxazol-4-ylmethyl]-2-methylbenzenesulfonamide.

$^1$H-NMR ($CDCl_3$) δ: 7.96 (1H, dd, J=7.5, 1.5 Hz), 7.48-7.16 (6H, m), 6.90 (1H, d, J=8.4 Hz), 5.11 (1H, br s), 4.21-4.11 (6H, m), 2.64 (3H, s), 1.52-1.46 (6H, m)

Example 257

A 0.5 g quantity of 3-[2-(3-cyclopropylmethoxy-4-methoxyphenyl)oxazol-4-yl]-1-(2-ethoxyphenyl)propan-1-one obtained in Example 102 and 0.18 ml of hydrazine monohydrate were added to diethylene glycol. A 0.14 g quantity of potassium hydroxide was added thereto, and the mixture was stirred at 150° C. for 1 hour. The reaction mixture was allowed to cool, water was then added thereto, and extraction was performed with ethyl acetate. Drying was performed with anhydrous magnesium sulfate, and the solvent was removed. The residue was purified by silica gel column chromatography (n-hexane:ethyl acetate=4:1) to give 0.1 g of colorless oily 2-(3-cyclopropylmethoxy-4-methoxyphenyl)-4-[3-(2-ethoxyphenyl)propyl]oxazole.

$^1$H-NMR ($CDCl_3$) δ: 7.58 (1H, dd, J=8.4, 1.8 Hz), 7.51 (1H, d, J=1.8 Hz), 7.39 (1H, s), 7.17-7.12 (2H, m), 6.93-6.81 (3H, m), 4.03 (2H, q, J=6.9 Hz), 3.94-3.92 (5H, m), 2.72 (2H, t, J=7.5 Hz), 2.62 (2H, t, J=7.5 Hz), 2.03-1.96 (2H, m), 1.43-1.25 (4H, m), 0.69-0.63 (2H, m), 0.40-0.35 (2H, m)

Example 258

A 1.6 g quantity of sodium hydride was suspended in 100 ml of tetrahydrofuran. A 2.68 g quantity of 1-(2-methylphenyl)ethanone and 6.58 g of 2-(3-benzyloxy-4-methoxyphenyl)-4-chloro methyloxazole obtained in Reference Example 5 were successively added thereto with ice-cooling and stirring, and the mixture was heated and refluxed for 4 hours. An aqueous saturated ammonium chloride solution was added thereto with ice-cooling. After stirring for 15 minutes, water was added thereto, and extraction was performed with ethyl acetate. Drying was then performed with anhydrous magnesium sulfate, and the solvent was removed. The residue was purified by silica gel column chromatography (n-hexane:ethyl acetate=4:1), and 1.6 g of the obtained crude product was dissolved in 20 ml of ethanol. A 0.16 g quantity of 10% palladium-carbon powder was added thereto, and the mixture was stirred under a hydrogen atmosphere for 18 hours. The reaction mixture was filtered, and the obtained filtrate was concentrated. The residue was purified by silica gel column chromatography (dichloromethane:ethanol=100:1) to give 0.47 g of yellow oily 2-(3-hydroxy-4-methoxyphenyl)-4-(3-o-tolyl propyl)oxazole.

$^1$H-NMR ($CDCl_3$) δ: 7.60-7.54 (2H, m), 7.38 (1H, s), 7.15-7.08 (4H, m), 6.90 (1H, d, J=8.4 Hz), 5.65 (1H, s), 3.94 (3H, s), 2.72-2.62 (4H, m), 2.37 (3H, s)

Example 259

Using 0.47 g of 2-(3-hydroxy-4-methoxyphenyl)-4-(3-o-tolylpropyl)oxazole obtained in Example 258, 0.37 g of colorless oily 2-(3-cyclopropylmethoxy-4-methoxyphenyl)-4-(3-o-tolylpropyl)oxazole was obtained in the same manner as in Example 111.

$^1$H-NMR ($CDCl_3$) δ: 7.58 (1H, dd, J=8.1, 2.1 Hz), 7.51 (1H, d, J=2.1 Hz), 7.38 (1H, s), 7.15-7.08 (4H, m), 6.92 (1H, d, J=8.1 Hz), 3.94-3.92 (5H, m), 2.72-2.62 (4H, m), 2.31 (3H, s), 2.04-1.92 (2H, m), 1.40-1.35 (1H, m), 0.69-0.63 (2H, m), 0.40-0.35 (2H, m)

Example 260

A 0.21 g quantity of 3-[2-(3-cyclopropylmethoxy-4-methoxyphenyl)oxazol-4-yl]-1-(2-ethoxyphenyl)propan-1-one obtained in Example 102 was added to 5 ml of ethanol, and the mixture was stirred with ice-cooling. A 37 mg quantity of sodium borohydride was gradually added thereto. After the temperature of the reaction mixture had reached room temperature, stirring was performed for 2 hours. An aqueous 5N hydrochloric acid solution was added to the reaction mixture, and solvent was then removed. Extraction was performed with dichloromethane, and the extract was washed with saturate brine. The extract was then dried over anhydrous magnesium sulfate, the solvent was removed, and the residue was purified by silica gel column chromatography (n-hexane:ethyl acetate=3:1) to give 0.18 g of colorless oily 3-[2-(3-cyclopropylmethoxy-4-methoxyphenyl)oxazol-4-yl]-1-(2-ethoxyphenyl)propan-1-ol.

$^1$H-NMR ($CDCl_3$) δ: 7.58 (1H, dd, J=8.4, 2.1 Hz), 7.50 (1H, d, J=1.8 Hz), 7.39-7.35 (2H, m), 7.23-7.18 (1H, m), 6.97-6.84 (3H, m), 5.00 (1H, br s), 4.07 (2H, q, J=6.6 Hz), 3.94-3.92 (5H, m), 3.44 (1H, br s), 2.80-2.60 (2H, m), 2.20-2.15 (2H, m), 1.43-1.37 (4H, m), 0.69-0.63 (2H, m), 0.40-0.37 (2H, m)

Example 261

An 80 mg quantity of 3-[2-(3-isopropoxy-4-methoxy phenyl)oxazol-4-yl]-1-(3-methylpyridin-2-yl)propan-1-one obtained in Example 139 was dissolved in 3 ml of dimethylformamide. A 0.2 g quantity of sodium hydride was added thereto with ice-cooling and stirring, and the mixture was stirred for 30 minutes. A 75 mg quantity of methyl iodide was added thereto, and the reaction mixture was stirred at room temperature for 8 hours. Water was added to the reaction mixture, and extraction was performed with ethyl acetate. The organic layer was washed with water twice, and the solvent was removed. The obtained residue was purified using a silica gel column (n-hexane:ethyl acetate=3:1) to give 35 mg of colorless oily 3-[2-(3-isopropoxy-4-methoxyphenyl)oxazol-4-yl]-2,2-dimethyl-1-(3-methylpyridin-2-yl)propan-1-one.

$^1$H-NMR ($CDCl_3$) δ: 8.41 (1H, dd, J=4.5, 1.2 Hz), 7.38-7.60 (3H, m), 7.34 (1H, s), 7.21-7.24 (1H, m), 6.90 (1H, d, J=8.7 Hz), 4.63 (1H, sept., J=6.0 Hz), 3.94 (3H, s), 3.15 (2H, s), 2.28 (3H, s), 1.38-1.49 (12H, m)

Example 262

Using 0.9 g of methyl 3-{2-[4-methoxy-3-(2,2,2-trifluoroethoxy)phenyl]oxazol-4-yl}propionate obtained in Reference Example 83, 1.05 g of yellow oily methyl 3-(3-methoxypyridin-2-yl)-2-{2-[4-methoxy-3-(2,2,2-trifluoroethoxy)phenyl]oxazol-4-ylmethyl}-3-oxopropinate was obtained in the same manner as in Example 100.

$^1$H-NMR ($CDCl_3$) δ: 8.25 (1H, dd, J=4.5, 1.5 Hz), 7.65 (1H, dd, J=8.4, 2.1 Hz), 7.55 (1H, d, J=2.1 Hz), 7.47-7.33 (3H, m), 6.94 (1H, d, J=8.4 Hz), 5.17 (1H, t, J=6.9 Hz), 4.43 (2H, q, J=8.4 Hz), 3.93 (3H, s), 3.92 (3H, s), 3.65 (3H, s), 3.32-3.23 (2H, m)

Example 263

Using 0.7 g of methyl 3-(3-methoxypyridin-2-yl)-2-{2-[4-methoxy-3-(2,2,2-trifluoroethoxy)phenyl]oxazol-4-ylmethyl}-3-oxopropionate obtained in Example 262, 0.42 g of colorless oily methyl 2-{2-[4-methoxy-3-(2,2,2-trifluoroethoxy)phenyl]oxazol-4-ylmethyl}-2-methyl-3-(3-methylpyridin-2-yl)-3-oxopropinate was obtained in the same manner as in Example 261.

$^1$H-NMR ($CDCl_3$) δ: 8.18 (1H, dd, J=6.9, 1.8 Hz), 7.64 (1H, dd, J=8.4, 2.1 Hz), 7.54 (1H, d, J=2.1 Hz), 7.42-7.34 (3H, m), 6.93 (1H, d, J=8.7 Hz), 4.43 (2H, q, J=8.4 Hz), 3.93 (3H, s), 3.91 (3H, s), 3.64 (3H, s), 3.40 (1H, d, J=15 Hz), 3.26 (1H, d, J=15 Hz)

Example 264

Using 0.42 g of methyl 2-{2-[4-methoxy-3-(2,2,2-trifluoroethoxy)phenyl]oxazol-4-ylmethyl}-2-methyl-3-(3-methyl pyridin-2-yl)-3-oxopropinate obtained in Example 263, 0.25 g of colorless oily 1-(3-methoxypyridin-2-yl)-3-{2-[4-methoxy-3-(2,2,2-trifluoroethoxy)phenyl]oxazol-4-yl}-2-methylpropan-1-one was obtained in the same manner as in Example 136.

$^1$H-NMR ($CDCl_3$) δ: 8.24 (1H, dd, J=4.5, 1.5 Hz), 7.67 (1H, dd, J=8.4, 2.1 Hz), 7.57 (1H, d, J=2.1 Hz), 7.43-7.28 (3H, m), 6.94 (1H, d, J=8.7 Hz), 4.45 (1H, q, J=8.4 Hz), 4.21 (1H, q, J=6.9 Hz), 3.91 (3H, s), 3.88 (3H, s), 3.15-3.06 (1H, m), 2.73-2.64 (1H, m), 1.23 (3H, d, J=7.2 Hz)

Example 265

Using 0.2 g of 1-(3-methoxypyridin-2-yl)-3-{2-[4-methoxy-3-(2,2,2-trifluoroethoxy)phenyl]oxazol-4-y}-2-methyl propan-1-one obtained in Example 264, 80 mg of colorless oily 1-(3-methoxypyridin-2-yl)-3-{2-[4-methoxy-3-(2,2,2-trifluoroethoxy)phenyl]oxazol-4-yl}-2,2-dimethylpropan-1-one was obtained in the same manner as in Example 261.

$^1$H-NMR ($CDCl_3$) δ: 8.17 (1H, dd, J=4.5, 1.5 Hz), 7.70 (1H, dd, J=8.4, 1.8 Hz), 7.60 (1H, d, J=1.8 Hz), 7.31-7.21 (2H, m), 6.96 (1H, d, J=8.4 Hz), 4.45 (2H, q, J=8.4 Hz), 3.92 (3H, s), 3.78 (3H, s), 3.05 (2H, s), 1.34 (6H, s)

Example 266

A 60 ml quantity of trifluoroacetic acid was stirred with ice cooling, 12.3 g of the compound obtained in Example 231 was added thereto, and stirring was conducted for one hour. At the completion of the reaction, the reaction mixture was neutralized by addition of an aqueous saturated sodium bicarbonate solution, and ethyl acetate was added to the obtained mixture. The organic layer was washed twice with water, separated, concentrated under reduced pressure, and the obtained crude crystals were recrystallized from ethanol, thereby yielding 5.9 g of white powdery 3-[2-(3-benzyloxy-4-methoxyphenyl)oxazol-4-yl]-1-(2-hydroxyphenyl)propan-1-one.

$^1$H-NMR ($CDCl_3$) δ: 12.2 (1H, s), 7.81 (1H, d, J=8.1 Hz), 7.62-7.26 (9H, m), 6.99-6.85 (3H, m), 5.19 (2H, s), 3.92 (3H, s), 3.43 (2H, t, J=7.5 Hz), 3.02 (2H, t, J=7.5 Hz)

Example 267

Using the compound obtained in Example 266 and chlorodifluoromethane, white powdery 3-[2-(3-benzyloxy-4-methoxy phenyl)oxazol-4-yl]-1-(2-difluoromethoxyphenyl) propan-1-one was obtained following the procedure of Example 19.

$^1$H-NMR ($CDCl_3$) δ: 7.71 (1H, dd, J=7.8, 1.8 Hz), 7.90-6.60 (7H, m), 6.34 (1H, t, J=73.8 Hz), 5.20 (2H, s), 3.92 (3H, s), 3.36 (2H, t, J=7.2 Hz), 2.29 (2H, t, J=7.2 Hz)

Reference Example 84

Using 2-fluoroethanol, a colorless oily 2-fluoroethyl methanesulfonate was obtained following the procedure of Reference Example 50.

$^1$H-NMR ($CDCl_3$) δ: 4.76-4.73 (1H, m), 4.60-4.58 (1H, m), 4.53-4.50 (1H, m), 4.43-4.41 (1H, m), 3.08 (3H, s)

Reference Example 85

Using 2,2-difluoroethanol, colorless oily 2,2-difluoro ethylmethanesulfonate was obtained following the procedure of Reference Example 50.

$^1$H-NMR ($CDCl_3$) δ: 6.01 (1H, tt, J=54.3, 3.9 Hz), 4.38 (2H, td, J=12.9, 3.9 Hz), 3.12 (3H, s)

Example 268

Using the compound obtained in Example 266 and the compound obtained in Reference Example 84, white powdery 3-[2-(3-benzyloxy-4-methoxyphenyl)oxazol-4-yl]-1-[2-(2-fluoroethoxy)phenyl]propan-1-one was obtained following the procedure of Example 3.

$^1$H-NMR ($CDCl_3$) δ: 7.74 (1H, dd, J=7.8, 1.8 Hz), 7.61-7.59 (2H, m), 7.49-7.31 (7H, m), 7.07 (1H, t, J=7.8 Hz), 6.92 (2H, d, J=8.7 Hz), 5.20 (2H, s), 4.90-4.87 (1H, m), 4.74-4.71 (1H, m), 4.37-4.35 (1H, m), 4.28-4.26 (1H, m), 3.92 (3H, s), 3.44 (2H, t, J=7.5 Hz), 2.99 (2H, t, J=7.5 Hz)

Example 269

Using the compound obtained in Example 266 and the compound obtained in Reference Example 85, white powdery 3-[2-(3-benzyloxy-4-methoxyphenyl)oxazol-4-yl]-1-[2-(2,2-difluoroethoxy)phenyl]propan-1-one was obtained following the procedure of Example 3.

$^1$H-NMR ($CDCl_3$) δ: 7.74 (1H, dd, J=7.8, 1.8 Hz), 7.61-7.28 (9H, m), 7.08 (1H, t, J=7.8 Hz), 6.95-6.89 (2H, m), 6.22 (1H, tt, J=54.9, 3.9 Hz), 5.19 (2H, s), 4.29 (1H, td, J=12.9, 3.9 Hz), 3.92 (3H, s), 3.38 (2H, t, J=7.5 Hz), 2.98 (2H, t, J=7.5 Hz)

Example 270

Using the compound obtained in Example 267, white powdery 1-(2-difluoromethoxyphenyl)-3-[2-(3-hydroxy-4-methoxy phenyl)oxazol-4-yl]propan-1-one was obtained following the procedure of Example 2.

$^1$H-NMR ($CDCl_3$) δ: 7.71 (1H, t, J=7.5 Hz), 7.54-7.41 (4H, m), 7.38-7.16 (2H, m), 6.89 (1H, d, J=8.1 Hz), 6.59 (1H, t, J=74.7 Hz), 5.69 (1H, s), 3.93 (3H, s), 3.36 (2H, t, J=7.2 Hz), 2.99 (2H, t, J=7.2 Hz)

Example 271

Using the compound obtained in Example 268, white powdery 1-[2-(2-fluoroethoxy)phenyl]-3-[2-(3-hydroxy-4-methoxy phenyl)oxazol-4-yl]propan-1-one was obtained following the procedure of Example 2.

$^1$H-NMR ($CDCl_3$) δ: 7.73 (1H, dd, J=7.8, 1.8 Hz), 7.55-7.42 (4H, m), 7.05 (1H, t, J=7.8 Hz), 6.91 (2H, d, J=8.7 Hz), 4.91-4.88 (1H, m), 4.75-4.72 (1H, m), 4.38-4.35 (1H, m), 4.29-4.26 (1H, m), 3.94 (3H, s), 3.43 (2H, t, J=7.5 Hz), 2.99 (2H, t, J=7.5 Hz)

Example 272

Using the compound obtained in Example 269, white powdery 1-[2-(2,2-difluoroethoxy)phenyl]-3-[2-(3-hydroxy-4-methoxyphenyl)oxazol-4-yl]propan-1-one was obtained following the procedure of Example 2.

$^1$H-NMR ($CDCl_3$) δ: 7.73 (1H, dd, J=7.8, 1.8 Hz), 7.56-7.41 (4H, m), 7.08 (1H, t, J=7.8 Hz), 6.92-6.87 (2H, m), 6.21 (1H, tt, J=54.9, 3.9 Hz), 5.67 (1H, s), 4.29 (1H, td, J=12.9, 3.9 Hz), 3.94 (3H, s), 3.38 (2H, t, J=7.2 Hz), 2.98 (2H, t, J=7.2 Hz)

Example 273

Using the compound obtained in Example 270 and 2-bromopropane, white powdery 1-(2-difluoromethoxyphenyl)-3-[2-(3-isopropoxy-4-methoxyphenyl)oxazol-4-yl]propan-1-one was obtained following the procedure of Example 3.

$^1$H-NMR ($CDCl_3$) δ: 7.70-7.25 (5H, m), 7.20-6.80 (2H, m), 6.59 (1H, t., J=73.5 Hz), 4.64 (1H, m), 3.93 (3H, s), 1.39 (3H, d, J=6.0 Hz)

Example 274

Using the compound obtained in Example 270 and ethyl iodide, white powdery 1-(2-difluoromethoxyphenyl)-3-[2-(3-ethoxy-4-methoxyphenyl)oxazol-4-yl]propan-1-one was obtained following the procedure of Example 3.

$^1$H-NMR ($CDCl_3$) δ: 7.71 (1H, dd, J=7.8, 1.8 Hz), 7.60-7.46 (3H, m), 7.42 (1H, s), 7.31-7.16 (2H, m), 6.91 (1H, d, J=8.1 Hz), 6.59 (1H, t, J=73.5 Hz), 4.18 (2H, q, J=7.2 Hz), 3.92 (3H, s), 3.37 (2H, t, J=7.2 Hz), 3.00 (2H, t, J=7.2 Hz), 1.49 (3H, t, J=7.2 Hz)

Example 275

Using the compound obtained in Example 271 and 2-bromopropane, white powdery 1-(2-fluoroethoxyphenyl)-3-[2-(3-isopropoxy-4-methoxyphenyl)oxazol-4-yl]propan-1-one was obtained following the procedure of Example 3.

$^1$H-NMR ($CDCl_3$) δ: 7.73 (1H, d, J=7.2 Hz), 7.58-7.54 (2H, m), 7.45-7.41 (2H, m), 7.04 (1H, t, J=7.2 Hz), 6.92 (2H, t, J=8.1 Hz), 4.81 (2H, dt, J=47.4, 4.2 Hz), 4.64-4.60 (1H, m), 4.32 (2H, dt, J=23.1, 4.2 Hz), 3.89 (3H, s), 3.43 (2H, t, J=7.2 Hz), 3.00 (2H, t, J=7.2 Hz), 1.39 (6H, d, J=5.7 Hz)

Example 276

Using the compound obtained in Example 271 and 4-bromo-1-butene, white powdery 3-[2-(3-but-3-enyloxy-4-methoxyphenyl)oxazol-4-yl]-1-[2-(2-fluoroethoxy)phenyl] propan-1-one was obtained following the procedure of Example 3.

$^1$H-NMR ($CDCl_3$) δ: 7.73 (1H, d, J=7.5 Hz), 7.58-7.53 (2H, m), 7.45-7.42 (2H, m), 7.03 (1H, t, J=7.8 Hz), 6.92 (2H, t, J=8.4 Hz), 6.00-5.84 (1H, m), 5.21-5.09 (2H, m) 4.81 (2H, dt, J=47.4, 4.2 Hz), 4.32 (2H, dt, J=23.1, 4.2 Hz), 4.14 (2H, t, J=7.2 Hz), 3.90 (3H, s), 3.43 (2H, t, J=7.5 Hz), 3.00 (2H, t, J=7.5 Hz), 2.64-2.61 (2H, m)

Example 277

Using the compound obtained in Example 271 and isobutyl bromide, white powdery 1-[2-(2-fluoroethoxy)phenyl]-3-[2-(3-isobutoxy-4-methoxyphenyl)oxazol-4-yl]propan-1-one was obtained following the procedure of Example 3.

$^1$H-NMR ($CDCl_3$) δ: 7.73 (1H, dd, J=7.8, 18 Hz), 7.57-7.51 (2H, m), 7.48-7.42 (2H, m), 7.40 (1H, t, J=7.5 Hz), 6.92 (2H, t, J=8.7 Hz), 4.81 (2H, dt, J=47.4, 4.2 Hz), 4.32 (2H, dt, J=23.1, 4.2 Hz), 3.90 (3H, s), 3.84 (2H, d, J=6.9 Hz), 3.43 (2H, t, J=7.5 Hz), 3.00 (2H, t, J=7.5 Hz), 2.23-2.14 (1H, m), 1.04 (6H, d, J=5.7 Hz)

Example 278

Using the compound obtained in Example 272 and 2-bromopropane, white powdery 1-[2-(2,2-difluoroethoxy)phenyl]-3-[2-(3-isopropoxy-4-methoxyphenyl)oxazol-4-yl]propan-1-one was obtained following the procedure of Example 3.

$^1$H-NMR ($CDCl_3$) δ: 7.74 (1H, dd, J=7.5, 1.8 Hz), 7.59-7.44 (3H, m), 7.41 (1H, s), 7.08 (1H, t, J=7.5 Hz), 6.91 (1H, d, J=8.4 Hz), 6.22 (1H, tt, J=54.6, 3.9 Hz) 4.65 (1H, sept., J=6.0 Hz), 4.29 (2H, td, J=12.9, 3.9 Hz), 3.90 (3H, s) 3.38 (2H, t, J=7.5 Hz) 2.99 (2H, t, J=7.5 Hz) 1.40 (6H, d, J=6.0 Hz)

Example 279

Using the compound obtained in Example 272 and 1-bromopropane, white powdery 1-[2-(2,2-difluoroethoxy)phenyl]-3-[2-(3-propoxy-4-methoxyphenyl)oxazol-4-yl]propan-1-one was obtained following the procedure of Example 3.

$^1$H-NMR ($CDCl_3$) δ: 7.74 (1H, dd, J=7.8, 1.8 Hz), 7.61-7.43 (3H, m), 7.41 (1H, s), 7.08 (1H, t, J=7.5 Hz), 6.92-6.89 (2H, m), 6.23 (1H, tt, J=54.6, 3.9 Hz), 4.29 (2H, td, J=12.9, 3.9 Hz), 4.06 (2H, t, J=6.9 Hz), 3.91 (3H, s), 3.38 (2H, t, J=1.5 Hz), 2.99 (2H, t, J=7.5 Hz), 1.90 (2H, qt, J=7.2 Hz), 1.06 (3H, t, J=7.2 Hz)

Example 280

Using the compound obtained in Example 272 and ethyl iodide, white powdery 1-[2-(2,2-difluoroethoxy)phenyl]-3-[2-(3-ethoxy-4-methoxyphenyl)oxazol-4-yl]propan-1-one was obtained following the procedure of Example 3.

$^1$H-NMR ($CDCl_3$) δ: 7.74 (1H, dd, J=7.8, 1.8 Hz), 7.61-7.44 (3H, m), 7.41 (1H, s), 7.08 (1H, t, J=7.8 Hz), 6.93-6.90 (2H, m), 6.23 (1H, tt, J=54.6, 3.9 Hz) 4.29 (2H, td, J=12.9, 3.9 Hz), 4.18 (2H, q, J=6.9 Hz), 3.92 (3H, s), 3.38 (2H, t, J=7.5 Hz), 2.99 (2H, t, J=7.5 Hz), 1.50 (3H, t, J=6.9 Hz)

Example 281

Using the compound obtained in Example 272 and ally bromide, white powdery 3-[2-(3-allyloxy-4-methoxyphenyl)oxazol-4-yl]-1-[2-(2,2-difluoroethoxy)phenyl]propan-1-one was obtained following the procedure of Example 3.

$^1$H-NMR ($CDCl_3$) δ: 7.74 (1H, dd, J=7.8, 1.8 Hz), 7.60-7.44 (3H, m), 7.41 (1H, s), 7.08 (1H, t, J=7.5 Hz), 6.94-6.89 (2H, m), 6.41-6.04 (2H, m), 5.44 (1H, dd, J=17.4, 1.5 Hz), 5.31 (1H, dd, J=10.2, 1.5 Hz), 4.29 (2H, td, J=12.9, 3.9 Hz), 3.92 (3H, s), 3.38 (2H, t, J=7.2 Hz), 2.99 (2H, t, J=7.2 Hz)

Example 282

Using the compound obtained in Example 272 and 4-bromo-1-butene, white powdery 3-[2-(3-but-3-enyloxy-4-methoxyphenyl)oxazol-4-yl]-1-[2-(2,2-difluoroethoxy)phenyl]propan-1-one was obtained following the procedure of Example 3.

$^1$H-NMR ($CDCl_3$) δ: 7.75 (1H, dd, J=7.8, 1.8 Hz), 7.60-7.44 (3H, m), 7.42 (1H, s), 7.09 (1H, t, J=7.5 Hz), 6.93-6.89 (2H, m), 6.23 (1H, tt, J=54.6, 3.9 Hz), 5.99-5.85 (1H, m), 5.23-5.10 (2H, m), 4.29 (2H, td, J=12.9, 3.9 Hz), 4.14 (2H, t, J=7.2 Hz), 3.91 (3H, s), 3.39 (2H, t, J=7.2 Hz), 2.99 (2H, t, J=7.2 Hz), 2.68-2.60 (2H, m)

Example 283

Using the compound obtained in Example 272 and (bromomethyl)cyclopropane, white powdery 3-[2-(3-cyclopropyl methoxy-4-methoxyphenyl)oxazol-4-yl]-1-[2-(2,2-difluoroethoxy)phenyl]propan-1-one was obtained following the procedure of Example 3.

$^1$H-NMR ($CDCl_3$) δ: 7.75 (1H, dd, J=7.8, 1.8 Hz), 7.58-7.44 (3H, m), 7.41 (1H, s), 7.09 (1H, t, J=7.5 Hz), 6.93-6.90 (2H, m), 6.24 (1H, tt, J=54.6, 3.9 Hz), 4.29 (2H, td, J=12.9, 3.9 Hz), 3.94-3.91 (5H, m), 3.39 (2H, t, J=7.2 Hz), 2.99 (2H, t, J=7.2 Hz), 1.43-1.33 (1H, m), 0.70-0.63 (2H, m), 0.41-0.35 (2H, m)

Example 284

Using the compound obtained in Example 272 and the compound obtained in Reference Example 85, white powdery 3-{2-[3-(2,2-difluoroethoxy)-4-methoxyphenyl]oxazol-4-yl}-1-[2-(2,2-difluoroethoxy)phenyl]propan-1-one was obtained following the procedure of Example 3.

$^1$H-NMR ($CDCl_3$) δ: 7.74 (1H, dd, J=7.8, 1.8 Hz), 7.65 (1H, dd, J=7.8, 1.8 Hz), 7.50 (1H, d, J=2.1 Hz), 7.50-7.42 (1H, m), 7.42 (1H, s), 7.08 (1H, t, J=7.5 Hz), 6.96-6.89 (2H, m), 6.42-5.95 (2H, m), 4.35-4.23 (4H, m), 3.92 (3H, s), 3.39 (2H, t, J=7.5 Hz), 3.00 (2H, t, J=7.5 Hz)

Example 285

Using the compound obtained in Example 272 and isobutyl bromide, white powdery 1-[2-(2,2-difluoroethoxy)phenyl]-3-[2-(3-isobutoxy-4-methoxyphenyl)oxazol-4-yl]-propan-1-one was obtained following the procedure of Example 3.

$^1$H-NMR ($CDCl_3$) δ: 7.74 (1H, d, J=7.5 Hz), 7.57-7.44 (3H, m), 7.41 (1H, s), 7.08 (1H, t, J=7.5 Hz), 6.92-6.89 (2H, m), 6.23 (1H, tt, J=54.6, 3.9 Hz), 4.29 (2H, td, J=12.9, 3.9 Hz), 3.90 (3H, s), 3.85 (2H, d, J=6.6 Hz), 3.38 (2H, t, J=7.5 Hz), 2.99 (2H, t, J=7.5 Hz), 2.19 (1H, qt, J=6.6 Hz), 1.05 (6H, d, J=6.6 Hz)

Example 286

Using the compound obtained in Reference Example 35 and the compound obtained in Reference Example 70, pale yellow oily 3-[2-(3,4-diethoxyphenyl)oxazol-4-yl]-1-(2methoxymethoxyphenyl)propan-1-one was obtained following the procedure of Example 190.

$^1$H-NMR ($CDCl_3$) δ: 7.66 (1H, dd, J=7.8, 1.8 Hz), 7.56-7.38 (3H, m), 7.17 (1H, d, J=8.4 Hz), 7.04 (1H, t, J=7.5 Hz), 6.92-6.88 (2H, m), 5.26 (2H, s), 4.21-4.08 (4H, m), 3.49 (3H, s), 3.40 (2H, t, J=7.2 Hz), 3.00 (2H, t, J=7.2 Hz), 1.51-1.45 (6H, m)

Example 287

Using the compound obtained in Example 286, white powdery 3-[2-(3,4-diethoxyphenyl)oxazol-4-yl]-1-(2-hydroxyphenyl)propan-1-one was obtained following the procedure of Example 266.

$^1$H-NMR ($CDCl_3$) δ: 12.25 (1H, s), 7.82 (1H, dd, J=8.1, 1.5 Hz), 7.60-7.43 (4H, m), 6.98 (1H, d, J=8.4 Hz), 6.92-6.86 (2H, m), 4.21-4.10 (4H, m), 3.44 (2H, t, J=7.2 Hz), 3.03 (2H, t, J=7.2 Hz), 1.51-1.43 (6H, m)

Example 288

Using the compound obtained in Example 287 and chlorodifluoromethane, white powdery 3-[2-(3,4-diethoxyphenyl oxazol-4-yl)-1-(2-difluoromethoxyphenyl)propan-1-one was obtained following the procedure of Example 19.

$^1$H-NMR ($CDCl_3$) δ: 7.51 (1H, d, J=8.7 Hz), 7.60-7.45 (3H, m), 7.30 (1H, s), 7.28-7.19 (2H, m), 6.90 (1H, d, J=8.7 Hz), 6.58 (1H, t, J=75 Hz), 4.15 (4H, q, J=7.2 Hz) 3.36 (2H, t, J=7.2 Hz), 3.00 (2H, t, J=7.2 Hz), 1.47 (6H, t, J=7.2 Hz)

Example 289

Using the compound obtained in Example 287 and the compound obtained in Reference Example 84, white powdery 3-[2-(3,4-diethoxyphenyl)oxazol-4-yl]-1-[2-(2-fluoroethoxy)phenyl]propan-1-one was obtained following the procedure of Example 3.

$^1$H-NMR ($CDCl_3$) δ: 7.74 (1H, dd, J=7.8, 1.8 Hz), 7.56-7.41 (4H, m), 7.04 (1H, td, J=7.5, 0.9 Hz), 6.95-6.88 (2H, m), 4.81 (2H, dt, J=47.1, 4.2 Hz), 4.32 (2H, dt, J=27.3, 4.2 Hz), 4.21-4.10 (4H, m), 3.43 (2H, t, J=7.2 Hz) 3.00 (2H, t, J=7.2 Hz) 1.50-1.45 (6H, m)

Example 290

Using the compound obtained in Example 287 and the compound obtained in Reference Example 85, white powdery 3-[2-(3,4-diethoxyphenyl)oxazol-4-yl]-1-[2-(2,2-difluoroethoxy)phenyl]propan-1-one was obtained following the procedure of Example 3.

$^1$H-NMR ($CDCl_3$) δ: 7.74 (1H, dd, J=7.5, 1.8 Hz), 7.56-7.43 (3H, m), 7.41 (1H, s), 7.08 (1H, t, J=7.5 Hz), 6.90 (1H, d, J=7.8 Hz), 6.23 (1H, tt, J=54.9, 3.9 Hz), 4.29 (2H, td, J=13.2, 3.9 Hz), 4.21-4.10 (4H, m), 3.38 (2H, t, J=7.5 Hz) 2.98 (2H, t, J=7.5 Hz), 1.50-1.45 (6H, m)

Example 291

A 0.2 g quantity of the compound obtained in Example 223 and 0.1 ml of triethylamine were dissolved in 5 ml of dichloromethane, 0.1 ml of acetyl chloride was added to the obtained solution, and the mixture was stirred for 6 hours at room temperature. At the completion of the reaction, water was added to the reaction mixture, and the obtained mixture was extracted with ethyl acetate. The organic layer was washed twice with water, and the solvent was distilled off. The residue was purified using a silica gel column (n-hexane:ethyl acetate=2:1), and the obtained crude crystals were recrystallized with ethanol, thereby yielding 15 mg of white powdery 2-{3-[2-(3-isopropoxy-4-methoxyphenyl)oxazol-4-yl]propionyl}phenyl acetate.

$^1$H-NMR ($CDCl_3$) δ: 7.83 (1H, dd, J=7.8, 1.5 Hz), 7.60-7.50 (3H, m), 7.42 (1H, s), 7.34-7.28 (1H, m), 7.12 (1H, dd, J=8.1, 0.9 Hz), 6.92 (1H, d, J=8.4 Hz), 4.69-4.61 (1H, m), 3.90 (3H, s), 3.32 (2H, t, J=7.2 Hz), 2.97 (2H, t, J=7.2 Hz), 2.35 (3H, s), 1.40 (6H, d, J=6.0 Hz)

Example 292

Using the compound obtained in Reference Example 35 and 1-(2-trifluoromethoxyphenyl)ethanone, white powdery 3-[2-(3,4-diethoxyphenyl)oxazol-4-yl]-1-(2-trifluoromethoxyphenyl)propan-1-one was obtained following the procedure of Example 190.

$^1$H-NMR ($CDCl_3$) δ: 7.70 (1H, dd, J=7.8, 1.8 Hz), 7.58-7.41 (3H, m), 7.38 (1H, s), 7.35-7.29 (2H, m), 6.90 (1H, d, J=8.4 Hz), 4.20-4.10 (4H, m), 3.34 (2H, t, J=6.9 Hz), 3.00 (2H, t, J=6.9 Hz), 1.48 (6H, t, J=6.9 Hz)

Example 293

Using the compound obtained in Reference Example 11 and 1-(2-trifluoromethoxyphenyl)ethanone, white powdery 3-[2-(3-cyclopropylmethoxy-4-methoxyphenyl)oxazol-4-yl]-1-(2-trifluoro methoxyphenyl)propan-1-one was obtained following the procedure of Example 190.

$^1$H-NMR ($CDCl_3$) δ: 7.70 (1H, d, J=8.7 Hz), 7.57-7.53 (3H, m), 7.49 (1H, s), 7.42-7.30 (2H, m), 6.90 (1H, d, J=8.7 Hz), 3.94-3.91 (5H, m), 3.34 (2H, t, J=7.2 Hz) 3.00 (2H, t, J=7.2 Hz), 1.42-1.30 (1H, m), 0.67-0.64 (2H, m), 0.40-0.36 (2H, m)

Using the compound obtained in Reference Example 35 and the corresponding acetophenone derivatives, compounds of Examples 294 to 299 were obtained following the procedure of Example 190.

Example 294

3-[2-(3,4-diethoxyphenyl)oxazol-4-yl]-1-(2,5-dimethoxyphenyl)propan-1-one

White Powder $^1$H-NMR ($CDCl_3$) δ: 7.57-7.52 (2H, m), 7.40 (1H, s), 7.01 (1H, dd, J=9.0, 3.3 Hz), 6.90 (2H, t, J=8.4 Hz), 4.20-4.10 (4H, m), 3.85 (3H, s), 3.78 (3H, s), 3.39 (2H, t, J=7.2 Hz), 2.98 (2H, t, J=7.2 Hz), 1.47 (6H, t, J=6.9 Hz)

Example 295

3-[2-(3,4-diethoxyphenyl)oxazol-4-yl]-1-(2-ethoxy-5-methylphenyl)propan-1-one

White Powder $^1$H-NMR ($CDCl_3$) δ: 7.61-7.49 (3H, m), 7.40 (1H, s), 7.25-7.20 (2H, m), 6.90 (1H, d, J=8.1 Hz), 6.83 (1H, d, J=8.4 Hz), 4.21-4.06 (6H, m), 3.41 (2H, t, J=7.5 Hz), 2.99 (2H, t, J=7.5 Hz), 2.28 (3H, s), 1.53-1.40 (9H, m)

Example 296

3-[2-(3,4-diethoxyphenyl)oxazol-4-yl]-1-(2,4-dimethylphenyl)propan-1-one

Colorless Powder $^1$H-NMR ($CDCl_3$) δ: 7.63 (1H, d, J=8.4 Hz), 7.54 (1H, dd, J=8.4, 1.8 Hz), 7.51 (1H, d, J=1.8 Hz), 7.42 (1H, s), 7.06-7.02 (2H, m), 6.90 (1H, d, J=8.4 Hz), 4.17 (2H, q, J=6.9 Hz), 4.14 (2H, q, J=6.9 Hz), 3.30 (2H, t, J=7.2 Hz), 2.99 (2H, t, J=7.2 Hz), 2.49 (3H, s), 2.34 (3H, s), 1.48 (6H, t, J=6.9 Hz)

Example 297

3-[2-(3,4-diethoxyphenyl)oxazol-4-yl]-1-(2,5-dimethylphenyl)propan-1-one

Colorless Needle Crystals $^1$H-NMR ($CDCl_3$) δ: 7.55 (1H, br s, J=8.7 Hz), 7.52 (1H, br s), 7.44 (1H, br d, J=8.7 Hz), 7.17-7.09 (2H, m), 6.90 (1H, d, J=8.7 Hz), 4.17 (2H, q, J=6.9 Hz), 4.14 (2H, q, J=6.9 Hz), 3.29 (2H, t, J=7.2 Hz), 2.99 (2H, t, J=7.2 Hz), 2.44 (3H, s), 2.33 (3H, s), 1.47 (6H, t, J=6.9 Hz)

Example 298

3-[2-(3,4-diethoxyphenyl)oxazol-4-yl]-1-(2-ethoxy-4-methylphenyl)propan-1-one

White Powder $^1$H-NMR ($CDCl_3$) δ: 7.66 (1H, d, J=7.8 Hz), 7.60-7.51 (2H, m), 7.39 (1H, s), 6.90 (1H, d, J=8.4 Hz), 6.79 (1H, d, J=8.4 Hz), 6.73 (1H, s), 4.21-4.08 (6H, m), 3.40 (2H, t, J=7.2 Hz), 2.98 (2H, t, J=7.2 Hz), 2.36 (3H, s), 1.53-1.45 (9H, m)

Example 299

3-[2-(3,4-diethoxyphenyl)oxazol-4-yl]-1-(2-ethoxy-4-fluorophenyl)propan-1-one

Colorless Needle Crystals $^1$H-NMR ($CDCl_3$) δ: 7.78 (1H, dd, J=8.7, 7.2 Hz), 7.54 (1H, dd, J=8.4, 2.1 Hz), 7.51 (1H, d, J=2.1 Hz), 7.39 (1H, br s), 6.90 (1H, d, J=8.4 Hz), 6.71-6.61 (2H, m), 4.16 (2H, q, J=6.9 Hz), 4.14 (2H, q, J=6.9 Hz), 4.11 (2H, q, J=6.9 Hz), 3.39 (2H, t, J=7.2 Hz), 2.98 (2H, t, J=7.2 Hz), 1.49 (3H, t, J=6.9 Hz), 1.47 (6H, t, J=6.9 Hz)

Example 300

The compound obtained in Reference Example 54 and methyl (2-methoxymethyl)benzoate were used and treated following the procedure of Example 100, followed by treatment according to Reference Example 48, yielding white powdery 3-[2-(3,4-diethoxy phenyl)oxazol-4-yl]-1-(2-methoxymethylphenyl)propan-1-one.

$^1$H-NMR ($CDCl_3$) δ: 7.74 (1H, dd, J=7.8, 1.2 Hz), 7.64-7.27 (6H, m), 6.91 (1H, d, J=8.4 Hz), 4.73 (2H, s), 4.21-4.10 (4H, m), 3.43 (3H, s), 3.34 (2H, t, J=7.2 Hz), 3.00 (2H, t, J=7.2 Hz), 1.51-1.43 (6H, m)

Using the compound obtained in Reference Example 54 and the corresponding methyl benzoate derivatives, compounds of Examples 301 to 303 were obtained following the procedure of the Example 300.

Example 301

3-[2-(3,4-diethoxyphenyl)oxazol-4-yl]-1-(2-ethylphenyl)propan-1-one $^1$H-NMR ($CDCl_3$) δ: 7.62-7.51 (4H, m), 7.43 (1H, s), 7.38-7.30 (2H, m), 6.90 (1H, d, J=8.7 Hz), 4.18-4.13 (4H, m), 3.31 (2H, t, J=7.2 Hz), 3.00 (2H, t, J=7.2 Hz), 2.81 (2H, q, J=7.5 Hz), 1.48 (6H, t, J=6.9 Hz), 1.20 (3H, t, J=7.5 Hz)

Example 302

3-[2-(3,4-diethoxyphenyl)oxazol-4-yl]-1-(2,3-dimethoxyphenyl)propan-1-one $^1$H-NMR ($CDCl_3$) δ: 7.56-7.51 (2H, m), 7.41 (1H, s), 7.18-7.01 (3H, m), 6.90 (1H, d, J=8.4 Hz), 4.21-4.10 (4H, m), 3.89 (6H, s), 3.38 (2H, t, J=7.2 Hz), 2.99 (2H, t, J=7.2 Hz), 1.48 (6H, t, J=6.9 Hz)

Example 303

3-[2-(3,4-diethoxyphenyl)oxazol-4-yl]-1-(2-ethoxy-3-methylphenyl)propan-1-one $^1$H-NMR ($CDCl_3$) δ: 7.55-7.51 (2H, m), 7.40 (1H, s), 7.36-7.29 (2H, m), 7.04 (1H, t, J=7.2 Hz), 6.90 (1H, d, J=8.1 Hz), 4.20-4.11 (4H, m), 3.83 (2H, q, J=7.5 Hz), 3.39 (2H, t, J=7.2 Hz), 2.98 (2H, t, J=7.2 Hz), 2.30 (3H, s), 1.48 (6H, t, J=6.9 Hz), 1.26 (3H, t, J=6.9 Hz)

Example 304

Using the compound obtained in Reference Example 58 and 1-(2-ethoxy-4-fluorophenyl)ethanone, pale yellow powdery 1-(2-ethoxy-4-fluorophenyl)-3-[2-(3-ethoxy-4-methoxyphenyl)oxazol-4-yl]propan-1-one was obtained following the procedure of Example 190.

$^1$H-NMR ($CDCl_3$) δ: 7.77 (1H, t, J=7.8 Hz), 7.56 (1H, dd, J=8.4, 1.8 Hz), 7.51 (1H, d, J=1.8 Hz), 7.40 (1H, s), 6.91 (1H, d, J=8.4 Hz), 6.71-6.61 (2H, m), 4.21-4.07 (4H, m), 3.92 (3H, s), 3.39 (2H, t, J=7.2 Hz), 2.98 (2H, t, J=7.2 Hz), 1.52-1.47 (6H, m)

Example 305

Using the compound obtained in Reference Example 58 and 1-(4-fluoro-2-isopropoxyphenyl)ethanone, colorless oily 3-[2-(3-ethoxy-4-methoxyphenyl)oxazol-4-yl]-1-(4-fluoro-2-isopropoxy phenyl)propan-1-one was obtained following the procedure of Example 190.

$^1$H-NMR ($CDCl_3$) δ: 7.77 (1H, t, J=7.8 Hz), 7.57 (1H, dd, J=8.4, 1.8 Hz), 7.51 (1H, d, J=1.8 Hz), 7.40 (1H, s), 6.91 (1H, d, J=8.4 Hz), 6.71-6.61 (2H, m), 4.63 (1H, sept, J=6.0 Hz), 4.18 (2H, q, J=6.9 Hz), 3.92 (3H, s), 3.38 (2H, t, J=7.2 Hz), 2.98 (2H, t, J=7.2 Hz), 1.50 (3H, t, J=6.9 Hz), 1.42 (6H, d, J=6.0 Hz)

Example 306

Using the compound obtained in Reference Example 68 and 1-(2-ethoxy-5-methylphenyl)ethanone, white powdery 1-(2-ethoxy-5-methylphenyl)-3-[2-(3-isopropoxy-4-methoxyphenyl)oxazol-4-yl]propan-1-one was obtained following the procedure of Example 190.

$^1$H-NMR ($CDCl_3$) δ: 7.60-7.40 (3H, m), 7.39 (1H, s), 7.24-7.19 (1H, m), 6.91 (1H, d, J=8.1 Hz), 6.83 (1H, d, J=8.4 Hz), 4.69-4.58 (1H, m), 4.10 (2H, q, J=6.9 Hz), 3.89 (3H, s), 3.41 (2H, t, J=7.2 Hz), 2.98 (2H, t, J=7.2 Hz), 2.29 (3H, s), 1.48-1.38 (9H, m)

Example 307

Using the compound obtained in Reference Example 68 and 1-(2-ethoxy-4-methylphenyl)ethanone, white powdery 1-(2-ethoxy-4-methylphenyl)-3-[2-(3-isopropoxy-4-methoxyphenyl)oxazol-4-yl]propan-1-one was obtained following the procedure of Example 190.

$^1$H-NMR ($CDCl_3$) δ: 7.66 (1H, d, J=8.1 Hz), 7.59-7.53 (2H, m), 7.39 (1H, s), 6.91 (1H, d, J=8.4 Hz), 6.79 (1H, d, J=8.1 Hz), 6.73 (1H, s), 4.58-4.71 (1H, m), 4.12 (2H, q, J=6.9 Hz), 3.90 (1H, s) 3.40 (2H, t, J=7.5 Hz), 2.98 (2H, t, J=7.5 Hz), 2.36 (3H, s), 1.48 (3H, t, J=6.9 Hz), 1.40 (6H, d, J=6.0 Hz)

Example 308

Using the compound obtained in Example 136 and chlorodifluoromethane, white powdery 3-[2-(3-difluoromethoxy-4-methoxyphenyl)oxazol-4-yl]-1-(3-methylpyridin-2-yl)propan-1-one was obtained following the procedure of Example 4.

$^1$H-NMR ($CDCl_3$) δ: 8.50 (1H, m), 7.83 (1H, dd, J=8.4, 2.1 Hz), 7.78 (1H, d, J=2.1 Hz), 7.58 (1H, d, J=7.8 Hz), 7.47 (1H, s), 7.32 (1H, m), 7.00 (1H, d, J=8.4 Hz), 6.58 (1H, t, J=74.7 Hz), 3.93 (3H, s), 3.59 (2H, t, J=7.2 Hz), 3.00 (2H, t, J=7.2 Hz), 2.57 (3H, s)

Example 309

Using the compound obtained in Example 136 and the compound obtained in Reference Example 85, white powdery 3-{2-[3-(2,2-difluoroethoxy)-4-methoxyphenyl]oxazol-4-yl}-1-(3-methyl pyridin-2-yl)propan-1-one was obtained following the procedure of Example 3.

$^1$H-NMR ($CDCl_3$) δ: 8.50 (1H, dd, J=4.5, 0.9 Hz), 7.66 (1H, dd, J=8.4, 2.1 Hz), 7.60-7.54 (2H, m), 7.46 (1H, s), 7.35-7.31 (1H, m), 6.94 (1H, d, J=8.7 Hz), 6.16 (1H, tt, J=54.9, 1.2 Hz) 4.29 (2H, td, J=12.9, 1.2 Hz), 3.92 (3H, s), 3.61 (2H, t, J=6.9 Hz), 3.01 (2H, t, J=6.9 Hz), 2.58 (3H, s)

Example 310

Using the compound obtained in Example 136 and the compound obtained in Reference Example 84, white powdery 3-{2-[3-(2-fluoroethoxy)-4-methoxyphenyl]oxazol-4-yl}-1-(3-methylpyridin-2-yl)propan-1-one was obtained following the procedure of Example 3.

$^1$H-NMR ($CDCl_3$) δ: 8.50-8.49 (1H, m), 7.63-7.54 (3H, m), 7.45 (1H, s), 7.34-7.27 (1H, m), 6.93 (1H, d, J=8.7 Hz), 4.88 (1H, t, J=4.2 Hz), 4.72 (1H, t, J=4.2 Hz) 4.39 (1H, t, J=4.2 Hz), 4.30 (1H, t, J=4.2 Hz), 3.92 (3H, s), 3.60 (2H, t, J=7.2 Hz), 3.00 (2H, t, J=7.2 Hz), 2.57 (3H, s)

Example 311

Using the compound obtained in Example 136 and 2-bromobutane, yellow oily 3-[2-(3-sec-butoxy-4-methoxyphenyl)oxazol-4-yl]-1-(3-methylpyridin-2-yl)propan-1-one was obtained following the procedure of Example 3.

$^1$H-NMR ($CDCl_3$) δ: 8.50 (1H, dd, J=4.5, 1.2 Hz), 7.59-7.55 (3H, m), 7.54 (1H, s), 7.45-7.30 (1H, m), 6.91 (1H, d, J=8.4 Hz), 4.43-4.37 (1H, m), 3.89 (3H, s), 3.60 (2H, t, J=7.5 Hz), 3.01 (2H, t, J=7.5 Hz), 2.57 (3H, s), 1.86-1.62 (2H, m), 1.34 (3H, d, J=6.6 Hz), 1.00 (3H, t, J=6.6 Hz)

Example 312

Using the compound obtained in Example 136 and 3-bromopentane, white powdery 3-{2-[3-(1-ethylpropoxy)-4-methoxy phenyl]oxazol-4-yl}-1-(3-methylpyridin-2-yl)propan-1-one was obtained following the procedure of Example 3.

$^1$H-NMR ($CDCl_3$) δ: 8.50 (1H, dd, J=4.5, 1.2 Hz), 7.61-7.53 (3H, m), 7.45 (1H, s), 7.34-7.30 (1H, m), 6.91 (1H, d, J=8.1 Hz), 4.28-4.20 (1H, m), 3.89 (3H, s), 3.60 (2H, t, J=7.5 Hz), 3.01 (2H, t, J=7.5 Hz), 2.57 (3H, s), 1.78-1.68 (4H, m), 0.98 (6H, t, J=6.6 Hz)

Example 313

Using the compound obtained in Example 101 and chlorodifluoromethane, white powdery 3-[2-(3-difluoromethoxy-4-methoxyphenyl)oxazol-4-yl]-1-(2-ethoxyphenyl)propan-1-one was obtained following the procedure of Example 4.

$^1$H-NMR ($CDCl_3$) δ: 7.85-7.80 (2H, m), 7.70 (1H, m), 7.50-7.40 (2H, m), 7.0-6.9 (3H, m), 6.58 (1H, t, J=74.4 Hz), 4.14 (2H, q, J=6.9 Hz), 3.93 (3H, s), 3.42 (2H, t, J=7.2 Hz), 2.99 (2H, t, J=7.2 Hz), 1.48 (3H, t, J=6.9 Hz)

Example 314

Using the compound obtained in Example 101 and the compound obtained in Reference Example 85, white powdery 3-{2-[3-(2,2-difluoroethoxy)-4-methoxyphenyl]oxazol-4-yl}-1-(2-ethoxy phenyl)propan-1-one was obtained following the procedure of Example 3.

$^1$H-NMR ($CDCl_3$) δ: 7.73-7.63 (2H, m), 7.55 (1H, d, J=2.1 Hz), 7.46-7.39 (2H, m), 7.01-6.91 (3H, m), 6.16 (1H, tt, J=54.9, 1.2 Hz), 4.29 (2H, td, J=12.9, 1.2 Hz), 4.14 (2H, q, J=6.9 Hz), 3.91 (3H, s), 3.43 (2H, t, J=7.2 Hz), 3.00 (2H, t, J=7.2 Hz), 1.48 (3H, t, J=7.2 Hz)

Example 315

Using the compound obtained in Example 101 and the compound obtained in Reference Example 84, white powdery 1-(2-ethoxyphenyl)-3-{2-[3-(2-fluoroethoxy)-4-methoxyphenyl]oxazol-4-yl}propan-1-one was obtained following the procedure of Example 3.

$^1$H-NMR ($CDCl_3$) δ: 7.69 (1H, dd, J=7.8, 1.8 Hz), 7.61 (1H, dd, J=8.4, 1.8 Hz), 7.55 (1H, s), 7.44-7.39 (2H, m), 7.00-6.91 (3H, m), 4.81 (2H, dt, J=47.4, 4.2 Hz), 4.32 (2H, dt, J=23.1, 4.2 Hz), 4.17-4.10 (2H, m), 3.90 (3H, s), 3.41 (2H, t, J=7.2 Hz), 2.99 (2H, t, J=7.2 Hz), 1.46 (3H, t, J=5.7 Hz)

Reference Example 86

Using the compound obtained in Reference Example 59 and the compound obtained in Reference Example 85, white powdery ethyl 4-benzyloxy-3-(2,2-difluoroethoxy)benzoate was obtained following the procedure of Example 4.

$^1$H-NMR ($CDCl_3$) δ: 7.71 (1H, dd, J=8.4, 2.1 Hz), 7.61 (1H, d, J=2.1 Hz), 7.44-7.29 (5H, m), 6.95 (1H, d, J=8.4 Hz), 6.11 (1H, tt, J=54.9, 4.2 Hz), 5.19 (2H, s), 4.38-4.21 (4H, m), 1.39 (3H, t, J=7.2 Hz)

Reference Example 87

Using the compound obtained in Reference Example 86, white powdery 4-benzyloxy-3-(2,2-difluoroethoxy)benzoic acid was obtained following the procedure of Reference Example 3.

$^1$H-NMR (DMSO $d_6$) δ: 7.61 (1H, dd, J=8.4, 1.8 Hz), 7.54 (1H, d, J=1.8 Hz), 7.50-7.30 (5H, m), 7.18 (1H, d, J=8.4 Hz), 6.38 (1H, tt, J=54.3, 3.6 Hz), 5.22 (2H, s), 4.37 (2H, td, J=14.7, 3.6 Hz)

Reference Example 88

Using the compound obtained in Reference Example 87, white powdery 4-benzyloxy-3-(2,2-difluoroethoxy)benzamide was obtained following the procedure of Reference Example 4.

$^1$H-NMR (DMSO $d_6$) δ: 7.86 (1H, br s), 7.56-7.29 (7H, m), 7.25 (1H, br s), 7.14 (1H, d, J=8.4 Hz), 6.40 (1H, tt, J=54.3, 3.6 Hz), 5.20 (2H, s), 4.34 (2H, td, J=14.7, 3.6 Hz)

Reference Example 89

Using the compound obtained in Reference Example 88, white powdery 2-[4-benzyloxy-3-(2,2-difluoroethoxy)phenyl]-4-chloromethyloxazole was obtained following the procedure of Reference Example 5.

$^1$H-NMR ($CDCl_3$) δ: 7.68-7.60 (3H, m), 7.45-7.30 (5H, m), 7.01 (1H, d, J=8.4 Hz), 6.12 (1H, tt, J=54.9, 4.2 Hz) 5.18 (2H, s), 4.56 (2H, s), 4.30 (2H, td, J=13.2, 4.2 Hz)

Reference Example 90

Using the compound obtained in Reference Example 89, white powdery dimethyl 2-{2-[4-benzyloxy-3-(2,2-difluoroethoxy)phenyl]oxazol-4-ylmethyl}malonate was obtained following the procedure of Reference Example 47.

$^1$H-NMR ($CDCl_3$) δ: 7.63-7.57 (2H, m), 7.45-7.30 (6H, m), 6.99 (1H, d, J=8.1 Hz), 6.12 (1H, tt, J=54.9, 4.2 Hz), 5.18 (2H, s), 4.29 (2H, td, J=13.2, 4.2 Hz), 3.89 (2H, t, J=7.5 Hz), 3.75 (6H, s), 3.18 (2H, t, J=7.5 Hz)

Reference Example 91

Using the compound obtained in Reference Example 90, brownish oily methyl 3-{2-[4-benzyloxy-3-(2,2-difluoro ethoxy)phenyl]oxazol-4-yl}-propionate was obtained following the procedure of Reference Example 48.

$^1$H-NMR ($CDCl_3$) δ: 7.64-7.59 (2H, m), 7.42-7.33 (6H, m), 6.99 (1H, d, J=8.1 Hz), 6.12 (1H, tt, J=54.9, 4.2 Hz), 5.18 (2H, s), 4.29 (2H, td, J=13.2, 4.2 Hz), 3.68 (3H, s), 2.91 (2H, t, J=7.5 Hz), 2.72 (2H, t, J=7.5 Hz)

Example 316

Using the compound obtained in Reference Example 91, pale yellow oily methyl 2-{2-[4-benzyloxy-3-(2,2-difluoroethoxy)-phenyl]oxazol-4-ylmethyl}-3-(3-methylpyridin-2-yl)-3-oxopropionate was obtained following the procedure of Example 100.

$^1$H-NMR ($CDCl_3$) δ: 8.50 (1H, d, J=4.5 Hz), 7.60-7.52 (3H, m), 7.46-7.30 (7H, m), 6.97 (1H, d, J=8.1 Hz), 6.11 (1H, tt, J=54.9, 4.2 Hz), 5.24-5.16 (3H, m), 4.27 (2H, td, J=13.2, 4.2 Hz), 3.66 (3H, s), 3.34-3.22 (2H, m), 2.60 (3H, s)

Example 317

Using the compound obtained in Example 316, white powdery 3-{2-[3-(2,2-difluoroethoxy)-4-hydroxyphenyl]oxazol-4-yl}-1-(3-methylpyridin-2-yl)propan-1-one was obtained following the procedure of Example 136.

$^1$H-NMR ($CDCl_3$) δ: 8.50 (1H, d, J=4.5 Hz), 7.61-7.57 (2H, m), 7.52 (1H, s), 7.45 (1H, s), 7.34-7.30 (1H, m), 7.00 (1H, d, J=8.1 Hz), 6.11 (1H, tt, J=54.9, 4.2 Hz), 6.07 (1H, s), 4.32 (2H, td, J=13.2, 4.2 Hz), 3.59 (2H, t, J=7.5 Hz), 3.00 (2H, t, J=7.5 Hz), 2.57 (3H, s)

Example 318

Using the compound obtained in Example 317 and methyl iodide, white powdery 3-{2-[3-(2,2-difluoroethoxy)-4-ethoxyphenyl]oxazol-4-yl}-1-(3-methylpyridin-2-yl)-propan-1-one was obtained following the procedure of Example 3.

$^1$H-NMR ($CDCl_3$) δ: 8.51 (1H, d, J=4.5 Hz), 7.66-7.57 (3H, m), 7.46 (1H, s), 7.34-7.30 (1H, m), 6.94 (1H, d, J=8.4 Hz), 6.14 (1H, tt, J=54.6, 3.9 Hz), 4.28 (2H, td, J=12.9, 3.9 Hz), 4.13 (2H, q, J=6.9 Hz), 3.60 (2H, t, J=7.5 Hz), 3.02 (2H, t, J=7.5 Hz), 2.57 (3H, s), 1.47 (3H, t, J=6.9 Hz)

Example 319

Using the compound obtained in Example 317 and 2-bromopropane, white powdery 3-{2-[3-(2,2-difluoroethoxy)-4-isopropoxyphenyl]oxazol-4-yl}-1-(3-methylpyridin-2-yl) propan-1-one was obtained following the procedure of Example 3.

$^1$H-NMR ($CDCl_3$) δ: 8.51 (1H, d, J=4.5 Hz), 7.65-7.57 (3H, m), 7.46 (1H, s), 7.34-7.30 (1H, m), 6.95 (1H, d, J=8.4 Hz), 6.12 (1H, tt, J=54.6, 3.9 Hz), 4.62-4.54 (1H, m), 4.26 (2H, td, J=12.9, 3.9 Hz), 3.60 (2H, t, J=7.5 Hz), 3.01 (2H, t, J=7.5 Hz), 2.57 (3H, s), 1.37 (6H, d, J=6.0 Hz)

Example 320

Using the compound obtained in Reference Example 7 and 2-difluoromethoxy benzoic acid, white powdery N-[2-(3-benzyloxy-4-methoxyphenyl)oxazol-4-ylmethyl]-2-difluoromethoxybenzamide was obtained following the procedure of Example 1.

$^1$H-NMR ($CDCl_3$) δ: 8.10 (1H, dd, J=7.8, 1.8 Hz), 7.64-7.57 (3H, m), 7.51-7.45 (4H, m), 7.40-7.26 (4H, m), 7.15 (1H, d, J=8.4 Hz), 6.95 (1H, d, J=9.0 Hz), 6.59 (1H, t, J=72.9 Hz), 5.20 (2H, s), 4.61 (2H, d, J=5.4 Hz), 3.93 (3H, s)

Example 321

Using the compound obtained in Example 320, white powdery 2-difluoromethoxy-N-[2-(3-hydroxy-4-methoxyphenyl)oxazol-4-ylmethyl]-benzamide was obtained following the procedure of Example 2.

$^1$H-NMR ($CDCl_3$) δ: 8.09 (1H, d, J=7.8 Hz), 7.64-7.45 (5H, m), 7.32 (1H, t, J=7.8 Hz), 7.15 (1H, d, J=7.8 Hz), 6.91 (1H, d, J=8.4 Hz), 6.60 (1H, t, J=72.9 Hz), 5.77 (1H, s), 4.61 (2H, d, J=5.1 Hz), 3.94 (3H, s)

Example 322

Using the compound obtained in Example 321 and allyl bromide, white powdery N-[2-(3-allyloxy-4-methoxyphenyl)-oxazol-4-ylmethyl]-2-difluoromethoxybenzamide was obtained following the procedure of Example 3.

$^1$H-NMR ($CDCl_3$) δ: 8.10 (1H, d, J=7.8 Hz), 7.64-7.30 (6H, m), 7.15 (1H, d, J=8.4 Hz), 6.94 (1H, d, J=8.1 Hz), 6.61 (1H, t, J=75 Hz), 6.17-6.08 (1H, m), 5.45 (1H, dd, J=17.1, 1.5 Hz), 5.32 (1H, dd, J=10.5, 1.5 Hz), 4.70 (2H, t, J=5.4 Hz), 4.62 (2H, t, J=5.4 Hz), 3.93 (3H, s)

Example 323

Using the compound obtained in Example 321 and 2-bromopropane, white powdery 2-difluoromethoxy-N-[2-(3-isopropoxy-4-methoxyphenyl)oxazol-4-ylmethyl]benzamide was obtained following the procedure of Example 3.

$^1$H-NMR ($CDCl_3$) δ: 8.10 (1H, d, J=7.8 Hz), 7.64-7.30 (6H, m), 7.15 (1H, d, J=8.4 Hz), 6.94 (1H, d, J=8.1 Hz), 6.61 (1H, t, J=75 Hz), 4.70-4.61 (5H, m), 3.91 (3H, s), 1.39 (6H, d, J=6.0 Hz)

Example 324

Using the compound obtained in Example 17 and 3-bromopentane, white powdery N-{2-[3-(1-ethylpropoxy)-4-methoxy phenyl]oxazol-4-ylmethyl}-3-methylpicolinamide was obtained following the procedure of Example 3.

$^1$H-NMR ($CDCl_3$) δ: 8.58 (1H, br s), 8.39 (1H, d, J=4.5 Hz), 7.63-7.55 (4H, m), 7.32-7.28 (1H, m), 6.92 (1H, d, J=8.4 Hz), 4.59 (2H, d, J=6.0 Hz), 4.28-4.20 (1H, m), 3.90 (3H, s), 2.76 (3H, s), 1.82-1.68 (4H, m), 0.99 (6H, t, J=7.5 Hz)

Example 325

Using the compound obtained in Example 2 and 3-bromopentane, white powdery 2-ethoxy-N-{2-[3-(1-ethylpropoxy)-4-methoxyphenyl]oxazol-4-ylmethyl}benzamide was obtained following the procedure of Example 3.

$^1$H-NMR ($CDCl_3$) δ: 8.57 (1H, br s), 8.24 (1H, dd, J=8.1, 1.8 Hz), 7.62-7.56 (3H, m), 7.45-7.39 (1H, m), 7.07 (1H, t, J=8.1 Hz), 6.96-6.91 (2H, m), 4.63 (2H, dd, J=5.4, 0.9 Hz), 4.26-4.14 (3H, m), 3.90 (3H, s), 1.79-1.69 (4H, m), 1.49 (3H, t, J=7.2 Hz), 1.00 (6H, t, J=7.2 Hz)

Reference Example 92

Using the compound obtained in Reference Example 44, colorless oily dimethyl 2-[2-(3-benzyloxy-4-difluoromethoxy phenyl)oxazol-4-ylmethyl]malonate was obtained following the procedure of Reference Example 47.

$^1$H-NMR ($CDCl_3$) δ: 7.70 (1H, s), 7.59 (1H, d, J=7.8 Hz), 7.48-7.22 (6H, m), 6.62 (1H, t, J=74.7 Hz), 5.21 (2H, s), 3.90 (1H, t, J=7.5 Hz), 3.73 (6H, s), 3.20 (2H, t, J=7.5 Hz)

Reference Example 93

Using the compound obtained in Reference Example 92, pale yellow oily methyl 3-[2-(3-benzyloxy-4-difluoromethoxy phenyl)oxazol-4-yl]propionate was obtained following the procedure of Reference Example 48.

$^1$H-NMR ($CDCl_3$) δ: 7.71 (1H, d, J=1.8 Hz), 7.48-7.31 (6H, m), 7.24 (1H, d, J=8.4 Hz), 6.62 (1H, t, J=74.7 Hz), 5.21 (2H, s), 3.70 (3H, s), 2.93 (2H, t, J=7.2 Hz), 2.71 (2H, t, J=7.2 Hz)

Example 326

Using the compound obtained in Reference Example 93, colorless oily methyl 2-[2-(3-benzyloxy-4-difluoromethoxy phenyl)oxazol-4-ylmethyl]-3-(3-methylpyridin-2-yl)-3-oxo propionate was obtained following the procedure of Example 100.

$^1$H-NMR ($CDCl_3$) δ: 8.50 (1H, dd, J=4.8, 1.2 Hz), 7.67-7.30 (10H, m), 7.21 (1H, d, J=8.4 Hz), 6.60 (1H, t, J=74.7 Hz), 5.18 (2H, s), 4.11 (1H, t, J=7.2 Hz), 3.65 (3H, s), 3.45-3.20 (2H, m), 2.60 (3H, s)

Example 327

The compound obtained in Example 326 was used and treated following the procedure of Example 125, followed by treatment according to the procedure of Example 2, yielding white powdery 3-[2-(4-difluoromethoxy-3-hydroxyphenyl)oxazol-4-yl]-1-(3-methylpyridin-2-yl)propan-1-one.

$^1$H-NMR ($CDCl_3$) δ: 8.50 (1H, dd, J=4.5, 1.2 Hz), 7.67-7.45 (4H, m), 7.33-7.30 (1H, m), 7.16 (1H, d, J=8.1 Hz), 6.58 (1H, t, J=75 Hz), 5.76 (1H, s), 3.60 (2H, t, J=7.5 Hz), 3.01 (2H, t, J=7.5 Hz), 2.57 (3H, s)

Example 328

A 0.15 quantity of the compound obtained in Example 327 and 0.18 ml of 1,8-diazabicyclo[5,4,0]undec-7-ene were dissolved in 3 ml of ethanol, 0.15 g of (bromomethyl) cyclopropane was then added to the obtained solution, and the obtained mixture was heated and refluxed overnight. After cooling, water was added to the obtained reaction mixture, and ethyl acetate extraction was performed. The organic layer was washed twice with water and concentrated under reduced pressure, and the obtained residue was purified by silica gel column chromatography (n-hexane:ethyl acetate=3:1). The obtained crystals were recrystallized from aqueous 80% ethanol, thereby yielding 42 mg of white powdery 3-[2-(3-cyclopropylmethoxy-4-difluoromethoxy-phenyl)oxazol-4-yl]-1-(3-methylpyridin-2-yl)propan-1-one.

$^1$H-NMR ($CDCl_3$) δ: 8.51 (1H, dd, J=4.8, 1.2 Hz), 7.60-7.53 (3H, m), 7.50 (1H, s), 7.35-7.31 (1H, m), 7.21 (1H, d, J=8.1 Hz), 6.68 (1H, t, J=75.3 Hz), 3.95 (2H, d, J=6.9 Hz), 3.60 (2H, t, J=7.5 Hz), 3.02 (2H, t, J=7.5 Hz), 2.58 (3H, s), 1.37-1.25 (1H, m), 0.69-0.63 (2H, m), 0.40-0.34 (2H, m)

Example 329

A 80 mg quantity of the compound obtained in Example 327 and 0.09 ml of 1,8-diazabicyclo[5,4,0]undec-7-ene were dissolved in 2 ml of ethanol, 80 mg of 1-bromopropane was then added to the obtained solution, and heated and refluxed overnight. After cooling, water was added to the obtained reaction mixture, and ethyl acetate extraction was performed. The organic layer was washed twice with water, concentrated under reduced pressure, and the obtained residue was purified by silica gel column chromatography (n-hexane:ethyl acetate=3:1). The obtained crystals were recrystallized from aqueous 80% ethanol, thereby yielding 25 mg of white powdery 3-[2-(4-difluoromethoxy-3-propoxyphenyl)oxazol-4-yl]-1-(3-methylpyridin-2-yl)propan-1-one.

$^1$H-NMR ($CDCl_3$) δ: 8.51 (1H, dd, J=4.8, 1.2 Hz), 7.61-7.53 (3H, m), 7.50 (1H, s), 7.35-7.31 (1H, m), 7.20 (1H, d, J=8.1 Hz), 6.61 (1H, t, J=75 Hz), 4.07 (2H, t, J=6.6 Hz), 3.60 (2H, t, J=7.5 Hz), 3.02 (2H, t, J=7.5 Hz), 2.58 (3H, s), 1.87 (2H, td, J=7.5, 6.6 Hz), 1.07 (3H, t, J=7.5 Hz)

Example 330

A 0.15 g quantity of the compound obtained in Example 327 and 0.18 ml of 1,8-diazabicyclo[5,4,0]undec-7-ene were dissolved in 3 ml of ethanol, 0.15 g of allyl bromide was then added to the obtained solution, and heating and refluxing were conducted for 2 hours. After cooling, water was added to the obtained reaction mixture, and ethyl acetate was performed. The organic layer was washed twice with water, concentrated, and the obtained residue was purified by silica gel column chromatography (n-hexane:ethyl acetate=3:1). The obtained crystals were recrystallized from aqueous 80% ethanol, thereby yielding 70 mg of white powdery 3-[2-(3-allyloxy-4-difluoromethoxyphenyl)oxazol-4-yl]-1-(3-methylpyridin-2-yl)propan-1-one.

$^1$H-NMR ($CDCl_3$) δ: 8.51 (1H, dd, J=4.5, 1.2 Hz), 7.62-7.56 (3H, m), 7.50 (1H, s), 7.50-7.31 (1H, m), 7.22 (1H, d, J=8.4 Hz), 6.62 (1H, t, J=75 Hz), 6.12-6.02 (1H, m), 5.46 (1H, dd, J=17.4, 1.5 Hz), 5.33 (1H, dd, J=10.8, 1.5 Hz), 4.68 (2H, d, J=8.1 Hz), 3.61 (2H, t, J=7.2 Hz), 3.02 (2H, t, J=7.2 Hz), 2.58 (3H, s)

Example 331

An 80 mg quantity of the compound obtained in Example 327 and 0.09 ml of 1,8-diazabicyclo[5,4,0]undec-7-ene were dissolved in 2 ml of ethanol, and 80 mg of 4-bromo-1-butene was then added to the obtained solution, and heating and refluxing were conducted overnight. After cooling, water was added to the obtained reaction mixture, and ethyl acetate extraction was performed. The organic layer was washed twice with water, concentrated under reduced pressure, and the obtained residue was purified by silica gel column chromatography (n-hexane:ethyl acetate=3:1). The obtained crystals were recrystallized from aqueous 80% ethanol, thereby yielding 22 mg of white powdery 3-[2-(3-but-3-enyloxy-4-difluoromethoxyphenyl)-oxazol-4-yl]-1-(3-methylpyridin-2-yl)propan-1-one $^1$H-NMR ($CDCl_3$) δ: 8.51 (1H, dd, J=4.8, 1.2 Hz), 7.61-7.54 (3H, m), 7.50 (1H, s), 7.35-7.31 (1H, m), 7.20 (1H, d, J=8.4 Hz), 6.62 (1H, t, J=75 Hz), 5.98-5.83 (1H, m), 5.24-5.12 (2H, m), 4.16 (2H, t, J=6.6 Hz), 3.61 (2H, t, J=7.2 Hz), 3.03 (2H, t, J=7.2 Hz), 2.64-2.58 (5H, m)

Example 332

A 0.15 g quantity of the compound obtained in Example 327 and 0.18 ml of DBU were dissolved in 3 ml of ethanol, 0.15 g of 2-bromopropane was then added to the obtained solution, and heating and refluxing were conducted overnight. After cooling, water was added to the reaction mixture, and ethyl acetate extraction was performed. The organic layer was washed twice with water, concentrated under reduced pressure, and the obtained residue was purified by silica gel column chromatography (n-hexane:ethyl acetate=3:1). The obtained crystals were recrystallized from aqueous 80% ethanol, thereby yielding 70 mg of white powdery 3-[2-(4-difluoromethoxy-3-isopropoxyphenyl)oxazol-4-yl]-1-(3-methylpyridin-2-yl)propan-1-one $^1$H-NMR ($CDCl_3$) δ: 8.51 (1H, dd, J=4.8, 0.9 Hz), 7.63-7.53 (3H, m), 7.50 (1H, s), 7.35-7.31 (1H, m), 7.20 (1H, d, J=8.1 Hz), 6.61 (1H, t, J=75 Hz), 4.73-4.65 (1H, m), 3.61 (2H, t, J=7.2 Hz), 3.02 (2H, t, J=7.2 Hz), 2.58 (3H, s), 1.39 (6H, d, J=6.0 Hz)

Example 333

Using the compound obtained in Example 327 and ethyl iodide, white powdery 3-[2-(4-difluoromethoxy-3-ethoxyphenyl)oxazol-4-yl]-1-(3-methylpyridin-2-yl)propan-1-one was obtained following the procedure of Example 330.

$^1$H-NMR ($CDCl_3$) δ: 8.50 (1H, dd, J=4.5, 1.2 Hz), 7.61-7.49 (4H, m), 7.35-7.30 (1H, m), 7.20 (1H, d, J=8.4 Hz), 6.62 (1H, t, J=75 Hz), 4.18 (2H, q, J=6.9 Hz), 3.61 (2H, t, J=7.2 Hz), 3.02 (2H, t, J=7.2 Hz), 2.58 (3H, s), 1.47 (3H, t, J=6.9 Hz)

Example 334

A 60 mg quantity of the compound obtained in Example 229 and 0.2 ml of DBU were dissolved in 4 ml of ethanol, 0.2 ml of ethyl iodide was then added to the obtained solution, and heating and refluxing were conducted for 2 hours. After cooling, water was added to the reaction mixture, and ethyl acetate extraction was performed. The organic layer was washed twice with water, concentrated under reduced pressure, and the obtained residue was purified by silica gel column chromatography (n-hexane:ethyl acetate=3:1). The obtained crystals were recrystallized from ethanol, thereby yielding 36 mg of white powdery 3-[2-(4-difluoromethoxy-3-ethoxyphenyl)oxazol-4-yl]-1-(2-ethoxyphenyl)propan-1-one.

$^1$H-NMR ($CDCl_3$) δ: 7.71 (1H, dd, J=7.5, 1.8 Hz), 7.60-7.34 (4H, m), 7.01-6.91 (2H, m), 7.20 (1H, d, J=8.1 Hz), 6.62 (1H, t, J=75 Hz), 4.22-4.07 (4H, m), 3.43 (2H, t, J=7.2 Hz), 3.00 (2H, t, J=7.2 Hz), 1.50-1.40 (6H, m)

Example 335

A 0.15 g quantity of the compound obtained in Example 229 and 0.17 ml of DBU were dissolved in 4 ml of ethanol, 0.14 g of ally bromide was then added to the obtained solution, and heating and refluxing were conducted for 2 hours. After cooling, water was added to the obtained reaction mixture, and ethyl acetate extraction was performed. The organic layer was washed twice with water, concentrated under reduced pressure, and the obtained residue was purified by silica gel column chromatography (n-hexane:ethyl acetate=3:1). The obtained crystals were recrystallized from aqueous 80% ethanol, thereby yielding 90 mg of white powdery 3-[2-(3-allyloxy-4-difluoromethoxyphenyl)oxazol-4-yl]-1-(2-ethoxyphenyl)propan-1-one.

$^1$H-NMR ($CDCl_3$) δ: 7.71 (1H, dd, J=7.5, 1.8 Hz), 7.62-7.56 (2H, m), 7.46-7.40 (2H, m), 7.22 (1H, d, J=8.1 Hz), 7.01-6.92 (2H, m), 6.62 (1H, t, J=75 Hz), 6.15-6.00 (1H, m), 5.45 (1H, dd, J=17.1, 1.5 Hz), 5.32 (1H, dd, J=10.5, 1.5 Hz), 4.67 (2H, d, J=8.1 Hz), 4.14 (2H, q, J=6.9 Hz), 3.42 (2H, t, J=7.5 Hz), 3.00 (2H, t, J=7.5 Hz), 1.48 (3H, t, J=6.9 Hz)

Example 336

A 0.12 g quantity of the compound obtained in Example 229 and 0.14 ml of DBU were dissolved in 3 ml of ethanol, 0.12 g of (bromomethyl)cyclopropane was then added to the obtained solution, and heating and refluxing were conducted overnight. After cooling, water was added to the obtained reaction mixture, and ethyl acetate extraction was performed. The organic layer was washed twice with water, concentrated under reduced pressure, and the obtained residue was purified by silica gel column chromatography (n-hexane:ethyl acetate=3:1). The obtained crystals were recrystallized from ethanol, thereby yielding 80 mg of white powdery 3-[2-(3-cyclopropylmethoxy-4-difluoromethoxy phenyl)oxazol-4-yl]-1-(2-ethoxyphenyl)propan-1-one.

$^1$H-NMR ($CDCl_3$) δ: 7.71 (1H, dd, J=7.8, 1.8 Hz), 7.59-7.54 (2H, m), 7.46-7.40 (2H, m), 7.21 (1H, d, J=8.1 Hz), 7.01-6.95 (2H, m), 6.68 (1H, t, J=75 Hz), 4.14 (2H, q, J=6.9

Hz), 3.95 (2H, d, J=6.9 Hz), 3.42 (2H, t, J=7.2 Hz), 3.00 (2H, t, J=7.2 Hz), 1.47 (3H, t, J=6.9 Hz), 1.34-1.28 (1H, m), 0.69-0.63 (2H, m), 0.40-0.34 (2H, m)

Example 337

A 0.12 g quantity of the compound obtained in Example 229 and 0.14 ml of DBU were dissolved in 3 ml of ethanol, 0.12 g of 4-bromo-1-butene was then added to the obtained solution, and heating and refluxing were conducted overnight. After cooling, water was added to the obtained reaction mixture, and ethyl acetate extract was performed. The organic layer was washed twice with water, concentrated under reduced pressure, and the obtained residue was purified by silica gel column chromatography (n-hexane: ethyl acetate=3:1). The obtained crystals were recrystallized from ethanol, thereby yielding 80 mg of white powdery 3-[2-(3-but-3-enyloxy-4-difluoromethoxyphenyl)oxazol-4-yl]-1-(2-ethoxyphenyl)propan-1-one.

$^1$H-NMR ($CDCl_3$) δ: 7.70 (1H, dd, J=7.8, 1.8 Hz), 7.61-7.54 (2H, m), 7.45-7.40 (2H, m), 7.20 (1H, d, J=8.1 Hz), 7.00-6.92 (2H, m), 6.62 (1H, t, J=75 Hz), 5.97-5.83 (1H, m), 5.23-5.12 (2H, m), 4.18-4.10 (4H, m), 3.42 (2H, t, J=7.2 Hz), 3.00 (2H, t, J=7.2 Hz), 2.63-2.56 (4H, m), 1.47 (3H, t, J=6.9 Hz)

Example 338

Using the compound obtained in Example 97 and ethyl iodide, white powdery N-[2-(4-difluoromethoxy-3-ethoxyphenyl)-oxazol-4-ylmethyl]-3-methylpicolinamide was obtained following the procedure of Example 3.

$^1$H-NMR ($CDCl_3$) δ: 8.60 (1H, br s), 8.39 (1H, d, J=3.6 Hz), 7.67-7.57 (4H, m), 7.33-7.20 (2H, m), 6.63 (1H, t, J=75 Hz), 4.60 (2H, d, J=5.7 Hz), 4.20 (2H, q, J=6.9 Hz), 2.76 (3H, s), 1.48 (3H, t, J=6.9 Hz)

Example 339

Using the compound obtained in Example 97 and allyl bromide, white solid N-[2-(3-allyloxy-4-difluoromethoxy phenyl)oxazol-4-ylmethyl]-3-methylpicolinamide was obtained following the procedure of Example 3.

$^1$H-NMR ($CDCl_3$) δ: 8.60 (1H, br s), 8.40-8.39 (1H, m), 7.67 (1H, s), 7.65-7.58 (3H, m), 7.33-7.22 (3H, m), 6.63 (1H, t, J=75 Hz), 6.13-6.03 (1H, m), 5.50-5.32 (2H, m), 4.70-4.68 (2H, m), 4.60 (2H, d, J=8.7 Hz), 2.76 (3H, s)

Example 340

Using the compound obtained in Example 97 and 1-bromopropane, white powdery N-[2-(4-difluoromethoxy-3-propoxyphenyl)oxazol-4-ylmethyl]-3-methylpicolinamide was obtained following the procedure of Example 3.

$^1$H-NMR ($CDCl_3$) δ: 8.58 (1H, br s), 8.39 (1H, d, J=7.8, Hz), 7.67-7.57 (4H, m), 7.33-7.20 (2H, m), 6.62 (1H, t, J=75 Hz), 4.60 (2H, d, J=6.0 Hz), 4.08 (2H, t, J=6.6 Hz), 2.76 (3H, s), 1.94-1.82 (2H, m), 1.07 (3H, t, J=7.5 Hz)

Example 341

Using the compound obtained in Example 97 and 2-bromopropane, white solid N-[2-(4-difluoromethoxy-3-isopropoxyphenyl)oxazol-4-ylmethyl]-3-methylpicolinamide was obtained following the procedure of Example 3.

$^1$H-NMR ($CDCl_3$) δ: 8.58 (1H, br s), 8.39-8.38 (1H, m), 7.67-7.57 (4H, m), 7.33-7.19 (2H, m), 6.62 (1H, t, J=75 Hz), 4.74-4.67 (1H, m), 4.59 (2H, d, J=6.0 Hz), 2.76 (3H, s), 1.39 (6H, d, J=6.0 Hz)

Example 342

Using the compound obtained in Example 97 and 3-bromopentane, colorless oily N-{2-[4-difluoromethoxy-3-(1-ethylpropoxy)phenyl]oxazol-4-ylmethyl}-3-methylpicolinamide was obtained following the procedure of Example 3.

$^1$H-NMR ($CDCl_3$) δ: 8.58 (1H, br s), 8.40-8.38 (1H, m), 7.67 (1H, s), 7.63-7.55 (3H, m), 7.33-7.20 (3H, m), 6.61 (1H, t, J=75 Hz), 4.59 (2H, d, J=6.0 Hz), 4.33 (1H, qt, J=6.0 Hz), 2.76 (3H, s), 1.79-1.70 (4H, m), 0.98 (6H, t, J=7.2 Hz)

Example 343

Using the compound obtained in Example 97 and 4-bromo-1-butene, colorless oily N-[2-(3-but-3-enyloxy-4-difluoromethoxy phenyl)oxazol-4-ylmethyl]-3-methylpicolinamide was obtained following the procedure of Example 3.

$^1$H-NMR ($CDCl_3$) δ: 8.58 (1H, br s), 8.40-8.38 (1H, m), 7.67 (1H, s), 7.64-7.58 (3H, m), 7.33-7.20 (2H, m), 6.63 (1H, t, J=75 Hz), 5.95-5.84 (1H, m), 5.23-5.13 (2H, m), 4.61-4.59 (2H, m), 4.18 (2H, t, J=6.6 Hz), 2.76 (3H, s), 2.64-2.58 (2H, m)

Example 344

Using the compound obtained in Example 97 and isobutyl bromide, colorless oily N-[2-(4-difluoromethoxy-3-isobutoxy phenyl)oxazol-4-ylmethyl]-3-methylpicolinamide was obtained following the procedure of Example 3.

$^1$H-NMR ($CDCl_3$) δ: 8.60 (1H, br s), 8.39 (1H, br s), 7.68 (1H, s), 7.62-7.57 (3H, m), 7.33-7.20 (2H, m), 6.61 (1H, t, J=75 Hz), 4.60 (2H, d, J=6.0 Hz), 3.88 (2H, d, J=6.3 Hz), 2.76 (3H, s), 2.19-2.04 (1H, m), 1.06 (6H, d, J=6.3 Hz)

Example 345

Using the compound obtained in Example 97 and (bromomethyl)cyclobutane, colorless oily N-[2-(3-cyclobutyl methoxy-4-difluoromethoxyphenyl)oxazol-4-ylmethyl]-3-methyl picolinamide was obtained following the procedure of Example 3.

$^1$H-NMR ($CDCl_3$) δ: 8.60 (1H, br s), 8.40 (1H, br s), 7.68 (1H, s), 7.64-7.59 (3H, m), 7.33-7.20 (2H, m), 6.61 (1H, t, J=75 Hz), 4.60 (2H, d, J=6.0 Hz), 4.08 (2H, d, J=6.6 Hz), 2.89-2.76 (4H, m), 2.25-2.12 (2H, m), 2.04-1.92 (4H, m)

Example 346

Using the compound obtained in Reference Example 46 and 2-ethoxybenzoic acid, white powdery N-[2-(3-benzyloxy-4-difluoro methoxyphenyl)oxazol-4-ylmethyl]-2-ethoxybenzamide was obtained following the procedure of Example 96.

$^1$H-NMR ($CDCl_3$) δ: 8.56 (1H, br s), 8.24 (1H, dd, J=7.8, 1.8 Hz), 7.73 (1H, d, J=1.8 Hz), 7.68-7.61 (2H, m), 7.48-7.24 (7H, m), 7.07 (1H, t, J=8.1 Hz), 6.95 (1H, d, J=8.4 Hz), 6.63 (1H, t, J=75 Hz), 5.21 (2H, s), 4.63 (2H, d, J=5.4 Hz), 4.18 (2H, q, J=6.9 Hz), 1.48 (3H, t, J=6.9 Hz)

Example 347

Using the compound obtained in Example 346, white powdery N-[2-(4-difluoromethoxy-3-hydroxyphenyl)oxazol-4-ylmethyl]-2-ethoxybenzamide was obtained following the procedure of Example 97.

$^1$H-NMR ($CDCl_3$) δ: 8.60 (1H, br s), 8.23 (1H, dd, J=7.8, 1.8 Hz), 7.71-7.60 (2H, m), 7.57 (1H, dd, J=8.4, 1.8 Hz), 7.46-7.39 (1H, m), 7.19 (1H, d, J=8.4 Hz), 7.07 (1H, t, J=8.1 Hz), 6.95 (1H, d, J=8.4 Hz), 6.61 (1H, t, J=73.2 Hz), 6.02 (1H, br s), 4.64 (2H, dd, J=5.4, 0.9 Hz), 4.19 (2H, q, J=6.9 Hz), 1.49 (3H, t, J=6.9 Hz)

Example 348

A 80 mg quantity of the compound obtained in Example 347 and 0.1 ml of DBU were dissolved in 2 ml of ethanol, 80 mg of isobutyl bromide was then added to the obtained solution, and heating and refluxing were conducted overnight. After cooling, water was added to the obtained reaction mixture, and ethyl acetate extraction was performed. The organic layer was washed twice with water, concentrated under reduced pressure, and the obtained residue was purified by silica gel column chromatography (n-hexane:ethyl acetate=3:1). The obtained crystals were recrystallized from aqueous 80% ethanol, thereby yielding 30 mg of white powdery N-[2-(4-difluoromethoxy-3-isobutoxyphenyl)oxazol-4-ylmethyl]-2-ethoxybenzamide.

$^1$H-NMR ($CDCl_3$) δ: 8.54 (1H, br s), 8.24 (1H, dd, J=7.8, 1.8 Hz), 7.67 (1H, s), 7.66-7.57 (2H, m), 7.45-7.39 (1H, m), 7.23 (1H, d, J=8.1 Hz), 7.07 (1H, t, J=8.1 Hz), 6.95 (1H, d, J=7.5 Hz), 6.62 (1H, t, J=75 Hz), 4.64 (2H, d, J=5.1 Hz), 4.19 (2H, q, J=6.9 Hz), 3.87 (2H, d, J=6.6 Hz), 2.17 (1H, qt, J=6.6 Hz), 1.49 (3H, t, J=6.9 Hz), 1.07 (6H, d, J=6.9 Hz)

Example 349

Using the compound obtained in Example 347 and ethyl iodide, white powdery N-[2-(4-difluoromethoxy-3-ethoxyphenyl)oxazol-4-ylmethyl]-2-ethoxybenzamide was obtained following the procedure of Example 348.

$^1$H-NMR ($CDCl_3$) δ: 8.56 (1H, br s), 8.24 (1H, dd, J=7.8, 1.8 Hz), 7.67-7.58 (3H, m), 7.46-7.40 (1H, m), 7.24-7.21 (1H, m), 7.08 (1H, t, J=7.8 Hz), 6.95 (1H, d, J=7.8 Hz), 6.64 (1H, t, J=75 Hz) 4.63 (1H, d, J=5.1 Hz), 4.23-4.15 (4H, m), 1.52-1.46 (6H, m)

Example 350

Using the compound obtained in Example 347 and 1-bromopropane, white powdery N-[2-(4-difluoromethoxy-3-propoxy phenyl)oxazol-4-ylmethyl]-2-ethoxybenzamide was obtained following the procedure of Example 348.

$^1$H-NMR ($CDCl_3$) δ: 8.56 (1H, br s), 8.24 (1H, dd, J=7.5, 1.8 Hz), 7.67 (1H, s), 7.64-7.57 (2H, m), 7.46-7.40 (1H, m), 7.23 (1H, d, J=7.8 Hz), 7.07 (1H, t, J=7.5 Hz), 6.95 (1H, d, J=8.4 Hz), 6.63 (1H, t, J=75 Hz), 4.64 (2H, d, J=5.4 Hz), 4.19 (2H, q, J=7.2 Hz), 4.07 (2H, t, J=6.6 Hz), 1.90 (2H, qt, J=7.2, 6.6 Hz), 1.49 (3H, t, J=6.9 Hz), 1.08 (3H, t, J=7.2 Hz)

Example 351

Using the compound obtained in Example 347 and allyl bromide, white powdery N-[2-(3-allyloxy-4-difluoromethoxy phenyl)oxazol-4-ylmethyl]-2-ethoxybenzamide was obtained following the procedure of Example 348.

$^1$H-NMR ($CDCl_3$) δ: 8.55 (1H, br s), 8.24 (1H, dd, J=7.8, 1.8 Hz), 7.68 (1H, s), 7.65-7.60 (2H, m), 7.46-7.40 (1H, m), 7.25-7.23 (1H, m), 7.08 (1H, t, J=7.8 Hz), 6.96 (1H, d, J=8.4 Hz), 6.64 (1H, t, J=74.7 Hz), 6.10-6.03 (1H, m), 5.47 (1H, dd, J=17.4, 1.5 Hz), 5.34 (1H, dd, J=10.5, 1.5 Hz), 4.69 (2H, dt, J=5.1, 1.5 Hz), 4.63 (2H, dd, J=5.4, 1.2 Hz), 4.19 (2H, q, J=6.9 Hz), 1.49 (3H, t, J=6.9 Hz)

Example 352

Using the compound obtained in Example 347 and 2-bromopropane, white powdery N-[2-(4-difluoromethoxy-3-isopropoxyphenyl)oxazol-4-ylmethyl]-2-ethoxybenzamide was obtained following the procedure of Example 348.

$^1$H-NMR ($CDCl_3$) δ: 8.57 (1H, br s), 8.24 (1H, dd, J=7.5, 1.8 Hz), 7.67 (1H, s), 7.65-7.57 (2H, m), 7.46-7.40 (1H, m), 7.26-7.21 (1H, m), 7.08 (1H, t, J=7.5 Hz), 6.95 (1H, d, J=8.4 Hz), 6.63 (1H, t, J=75 Hz), 4.74-4.62 (3H, m), 4.19 (2H, q, J=6.9 Hz), 1.49 (3H, t, J=6.9 Hz), 1.40 (6H, d, J=6.3 Hz)

Example 353

Using the compound obtained in Example 347 and (bromomethyl)cyclopropane, white powdery N-[2-(3-cyclopropyl methoxy-4-difluoromethoxyphenyl)oxazol-4-ylmethyl]-2-ethoxy benzamide was obtained following the procedure of Example 348.

$^1$H-NMR ($CDCl_3$) δ: 8.55 (1H, br s), 8.24 (1H, dd, J=8.1, 1.8 Hz), 7.67 (1H, s), 7.61-7.58 (2H, m), 7.46-7.39 (1H, m), 7.26-7.21 (1H, m), 7.07 (1H, t, J=7.5 Hz), 6.95 (1H, d, J=8.4 Hz), 6.70 (1H, t, J=75 Hz) 4.63 (2H, dd, J=5.4, 0.9 Hz), 4.19 (2H, q, J=6.9 Hz), 1.49 (3H, t, J=6.9 Hz), 1.35-1.30 (1H, m), 0.71-0.64 (2H, m), 0.41-0.35 (2H, m)

Example 354

Using the compound obtained in Example 347 and 4-bromo-1-butene, white powdery N-[2-(3-but-3-enyloxy-4-difluoromethoxy phenyl)oxazol-4-ylmethyl]-2-ethoxybenzamide was obtained following the procedure of Example 348.

$^1$H-NMR ($CDCl_3$) δ: 8.56 (1H, br s), 8.24 (1H, dd, J=7.5, 1.8 Hz), 7.67 (1H, s), 7.64-7.58 (2H, m), 7.46-7.40 (1H, m), 7.26-7.21 (1H, m), 7.08 (1H, t, J=7.5 Hz), 6.95 (1H, d, J=8.4 Hz), 6.64 (1H, t, J=75 Hz), 5.92-5.86 (1H, m), 5.24-5.13 (2H, m), 4.64 (2H, d, J=5.1 Hz), 4.22-4.14 (4H, m), 2.65-2.58 (2H, m), 1.49 (3H, t, J=6.9 Hz)

Example 355

Using the compound obtained in Example 347 and 3-bromopentane, white powdery N-{2-[4-difluoromethoxy-3-(1-ethylpropoxy)phenyl]oxazol-4-ylmethyl}-2-ethoxybenzamide was obtained following the procedure of Example 348.

$^1$H-NMR ($CDCl_3$) δ: 8.57 (1H, br s), 8.24 (1H, dd, J=7.8, 1.8 Hz), 7.67 (1H, s), 7.63-7.58 (2H, m), 7.46-7.40 (1H, m), 7.23 (1H, d, J=8.4 Hz), 7.07 (1H, t, J=8.1 Hz), 6.95 (1H, d, J=8.1 Hz), 6.63 (1H, t, J=75 Hz), 4.64 (2H, d, J=5.1 Hz), 4.33 (1H, qt, J=6.0, 5.1 Hz), 4.19 (2H, q, J=6.9 Hz), 1.79-1.70 (4H, m), 1.49 (3H, t, J=6.9 Hz), 0.99 (6H, t, J=7.5 Hz)

Reference Example 94

Using the compound obtained in Reference Example 59 and chlorodifluoromethane, white powdery ethyl 4-benzyloxy-3-difluoromethoxybenzoate was obtained following the procedure of Example 4.

$^1$H-NMR ($CDCl_3$) δ: 7.90-7.80 (2H, m), 7.45-7.30 (5H, m), 7.03 (1H, d, J=8.4 Hz), 6.59 (1H, t, J=74.4 Hz), 5.23 (2H, s), 4.35 (2H, q, J=7.2 Hz), 1.38 (3H, t, J=7.2 Hz)

Reference Example 95

Using the compound obtained in Reference Example 94, white powdery 2-(4-benzyloxy-3-difluoromethoxyphenyl)-4-chloromethyloxazole was obtained following the procedures of Reference Examples 3 to 5.

$^1$H-NMR ($CDCl_3$) δ: 7.90-7.80 (2H, m), 7.65 (1H, s), 7.45-7.30 (5H, m), 7.06 (1H, d, J=7.2 Hz), 6.60 (1H, t, J=74.7 Hz), 5.20 (2H, s), 4.56 (2H, s)

Example 356

Using the compound obtained in Reference Example 95, white powdery 3-{2-(3-difluoromethoxy-4-hydroxyphenyl) oxazol-4-yl}-1-(3-methylpyridin-2-yl)propan-1-one was obtained following the procedures of Reference Examples 92 and 93 and Examples 326 and 327.

$^1$H-NMR ($CDCl_3$) δ: 8.49 (1H, d, J=4.5 Hz), 7.76-7.72 (2H, m), 7.59 (1H, d, J=8.4 Hz), 7.57 (1H, s), 7.37-7.30 (1H, m), 7.02 (1H, d, J=8.4 Hz), 6.59 (1H, t, J=75 Hz), 3.59 (2H, t, J=7.5 Hz), 3.01 (2H, t, J=7.5 Hz), 2.57 (3H, s)

Example 357

Using the compound obtained in Example 356 and 2-bromopropane, white powdery 3-[2-(3-difluoromethoxy-4-isopropoxy phenyl)oxazol-4-yl]-1-(3-methylpyridin-2-yl)propan-1-one was obtained following the procedure of Example 3.

$^1$H-NMR ($CDCl_3$) δ: 8.50 (1H, d, J=4.5 Hz), 7.83-7.78 (2H, m), 7.58 (1H, d, J=8.4 Hz), 7.47 (1H, s), 7.34-7.30 (1H, m), 7.01 (1H, d, J=8.4 Hz), 6.58 (1H, t, J=75 Hz), 4.67-4.57 (1H, m), 3.59 (2H, t, J=7.5 Hz), 3.01 (2H, t, J=7.5 Hz), 2.57 (3H, s), 1.39 (6H, d, J=6.0 Hz)

Example 358

Using the compound obtained in Example 356 and allyl bromide, white powdery 3-[2-(4-allyloxy-3-difluoromethoxy phenyl)oxazol-4-yl]-1-(3-methylpyridin-2-yl) propan-1-one was obtained following the procedure of Example 3.

$^1$H-NMR ($CDCl_3$) δ: 8.50 (1H, dd, J=4.8, 1.2 Hz), 7.84-7.80 (2H, m), 7.60-7.56 (1H, m), 7.47 (1H, d, J=1.2 Hz), 7.34-7.30 (1H, m), 7.01 (1H, d, J=8.4 Hz), 6.60 (1H, t, J=74.7 Hz), 6.10-6.00 (1H, m), 5.44 (1H, dd, J=17.4, 1.5 Hz), 5.33 (1H, dd, J=10.5, 1.5 Hz), 4.65 (2H, dt, J=5.1, 1.5 Hz), 3.60 (2H, t, J=7.5 Hz), 3.01 (2H, t, J=7.5 Hz), 2.58 (3H, s)

Example 359

Using the compound obtained in Example 356 and 4-bromo-1-butene, white powdery 3-[2-(4-but-3-enyloxy-3-difluoromethoxy phenyl)oxazol-4-yl]-1-(3-methylpyridin-2-yl)propan-1-one was obtained following the procedure of Example 3.

$^1$H-NMR ($CDCl_3$) δ: 8.50 (1H, dd, J=4.8, 1.2 Hz), 7.84-7.78 (2H, m), 7.58 (1H, d, J=7.5 Hz), 7.46 (1H, s), 7.34-7.30 (1H, m), 7.00 (1H, d, J=8.4 Hz), 6.59 (1H, t, J=75 Hz), 5.94-5.85 (1H, m), 5.23-5.12 (2H, m), 4.12 (2H, t, J=6.6 Hz), 3.60 (2H, t, J=7.2 Hz), 3.00 (2H, t, J=7.2 Hz), 2.63-2.56 (5H, m)

Example 360

Using the compound obtained in Example 356 and (bromomethyl)cyclopropane, white powdery 3-[2-(4-cyclopropyl methoxy-3-difluoromethoxyphenyl)oxazol-4-yl]-1-(3-methylpyridin-2-yl)propan-1-one was obtained following the procedure of Example 3.

$^1$H-NMR ($CDCl_3$) δ: 8.50 (1H, dd, J=4.8, 1.2 Hz), 7.83-7.79 (2H, m), 7.57 (1H, d, J=7.5 Hz), 7.46 (1H, s), 7.34-7.30 (1H, m), 6.98 (1H, d, J=8.1 Hz), 6.65 (1H, t, J=75 Hz), 3.92 (2H, d, J=7.2 Hz), 3.59 (2H, t, J=7.2 Hz), 3.00 (2H, t, J=7.2 Hz), 2.57 (3H, s), 1.33-1.27 (1H, m), 0.69-0.63 (2H, m), 0.40-0.34 (2H, m)

Example 361

Using the compound obtained in Example 356 and 1-bromopropane, white powdery 3-[2-(3-difluoromethoxy-4-propoxy phenyl)oxazol-4-yl]-1-(3-methylpyridin-2-yl)propan-1-one was obtained following the procedure of Example 3.

$^1$H-NMR ($CDCl_3$) δ: 8.50 (1H, dd, J=4.8, 1.2 Hz), 7.84-7.78 (2H, m), 7.58 (1H, d, J=8.1 Hz), 7.47 (1H, s), 7.43-7.30 (1H, m), 7.00 (1H, d, J=8.4 Hz), 6.59 (1H, t, J=75 Hz), 4.03 (2H, t, J=6.6 Hz), 3.59 (2H, t, J=7.5 Hz), 3.01 (2H, t, J=7.5 Hz), 2.58 (3H, s), 1.87 (2H, qt, J=7.2 Hz), 1.06 (3H, t, J=7.2 Hz)

Example 362

Using the compound obtained in Example 356 and ethyl iodide, white powdery 3-[2-(3-difluoromethoxy-4-ethoxyphenyl)oxazol-4-yl]-1-(3-methylpyridin-2-yl)propan-1-one was obtained following the procedure of Example 3.

$^1$H-NMR ($CDCl_3$) δ: 8.50 (1H, d, J=4.5 Hz), 7.84-7.78 (2H, m), 7.59 (1H, d, J=8.4 Hz), 7.47 (1H, s), 7.34-7.30 (1H, m), 6.99 (1H, d, J=8.4 Hz), 6.60 (1H, t, J=75 Hz), 4.15 (2H, q, J=6.9 Hz), 3.59 (2H, t, J=7.2 Hz), 3.01 (2H, t, J=7.2 Hz), 2.57 (3H, s), 1.47 (3H, t, J=6.9 Hz)

Example 363

The compound obtained in Reference Example 95 was used and treated following the procedure of Example 228, followed by treatment according to the procedure of Example 229, yielding white powdery 3-[2-(3-difluoromethoxy-4-hydroxyphenyl)oxazol-4-yl]-1-(2-ethoxyphenyl)propan-1-one.

$^1$H-NMR ($CDCl_3$) δ: 7.80-7.75 (2H, m), 7.71 (1H, dd, J=7.8, 1.8 Hz), 7.46-7.40 (2H, m), 7.22-6.69 (3H, m), 6.59 (1H, t, J=75 Hz), 5.91 (1H, br s), 4.14 (2H, q, J=7.2 Hz), 3.42 (2H, t, J=7.5 Hz), 2.99 (2H, t, J=7.5 Hz), 1.48 (3H, t, J=7.2 Hz)

Example 364

Using the compound obtained in Example 363 and 4-bromo-1-butene, white powdery 3-[2-(4-but-3-enyloxy-3-difluoromethoxy phenyl)oxazol-4-yl]-1-(2-ethoxyphenyl) propan-1-one was obtained following the procedure of Example 3.

$^1$H-NMR ($CDCl_3$) δ: 7.84-7.79 (2H, m), 7.71 (1H, dd, J=7.8, 1.8 Hz), 7.46-7.39 (2H, m), 7.01-6.92 (3H, m), 6.59 (1H, t, J=75 Hz), 5.91-5.85 (1H, m), 5.23-5.12 (2H, m), 4.18-4.09 (4H, m), 3.42 (2H, t, J=6.9 Hz), 2.99 (2H, t, J=6.9 Hz), 2.60 (2H, m), 1.48 (3H, t, J=6.9 Hz)

Example 365

Using the compound obtained in Example 363 and allyl bromide, white powdery 3-[2-(4-allyloxy-3-difluoromethoxy phenyl)oxazol-4-yl]-1-(2-ethoxyphenyl)propan-1-one was obtained following the procedure of Example 3.

$^1$H-NMR ($CDCl_3$) δ: 7.83-7.79 (2H, m), 7.70 (1H, dd, J=7.8, 1.8 Hz), 7.46-7.39 (2H, m), 7.02-6.92 (3H, m), 6.60 (1H, t, J=74.7 Hz), 6.06-6.00 (1H, m), 5.47-5.30 (2H, m), 4.66-4.63 (2H, m), 4.14 (2H, q, J=6.9 Hz), 3.42 (2H, t, J=6.9 Hz), 2.99 (2H, t, J=6.9 Hz), 1.48 (3H, t, J=6.9 Hz)

Example 366

Using the compound obtained in Example 363 and ethyl iodide, white powdery 3-[2-(3-difluoromethoxy-4-ethoxyphenyl)oxazol-4-yl]-1-(2-ethoxyphenyl)propan-1-one was obtained following the procedure of Example 3.

$^1$H-NMR ($CDCl_3$) δ: 7.84-7.80 (2H, m), 7.71 (1H, dd, J=7.8, 1.8 Hz), 7.45-7.39 (2H, m), 7.00-6.91 (3H, m), 6.60 (1H, t, J=75 Hz) 4.18-4.10 (4H, m), 3.42 (2H, t, J=7.5 Hz), 2.99 (2H, t, J=7.5 Hz), 1.50-1.44 (6H, m)

Reference Example 96

The compound obtained in Reference Example 95 was used and treated following the procedure of Reference Example 45, followed by treatment according to the procedure of Reference Example 46, yielding pale yellow oily [2-(4-benzyloxy-3-difluoromethoxyphenyl)oxazol-4-yl] methylamine was obtained.

$^1$H-NMR ($CDCl_3$) δ: 7.89-7.82 (2H, m), 7.61 (1H, s), 7.56-7.31 (5H, m), 7.07 (1H, d, J=8.1 Hz), 6.62 (1H, t, J=75 Hz), 5.19 (2H, s), 3.83 (2H, s)

Example 367

The compound obtained in Reference Example 96 was used and treated following the procedure of Example 96, followed by treatment according to the procedure of Example 97, yielding white powdery N-[2-(3-difluoromethoxy-4-hydroxyphenyl)oxazol-4-ylmethyl]-3-methylpicolinamide.

$^1$H-NMR ($CDCl_3$) δ: 8.59 (1H, br s), 8.39 (1H, d, J=4.5 Hz), 7.79-7.76 (2H, m), 7.63-7.58 (2H, m), 7.37-7.28 (1H, m), 7.07 (1H, d, J=8.1 Hz), 6.61 (1H, t, J=75 Hz), 6.16 (1H, s), 4.58 (2H, d, J=5.4 Hz), 2.76 (3H, s)

Example 368

Using the compound obtained in Example 367 and allyl bromide, white powdery N-[2-(4-allyloxy-3-difluoromethoxy phenyl)oxazol-4-ylmethyl]-3-methylpicolinamide was obtained following the procedure of Example 98.

$^1$H-NMR ($CDCl_3$) δ: 8.60 (1H, br s), 8.39 (1H, d, J=4.5 Hz), 7.87-7.83 (2H, m), 7.65 (1H, s), 7.60-7.57 (1H, m), 7.33-7.29 (1H, m), 7.10 (1H, d, J=8.4 Hz), 6.61 (1H, t, J=75 Hz), 6.10-5.99 (1H, m), 5.55 (1H, dd, J=17.1, 1.5 Hz), 5.34 (1H, dd, J=10.5, 1.5 Hz), 4.65 (2H, d, J=5.4 Hz), 4.58 (2H, d, J=5.4 Hz), 2.76 (3H, s)

Example 369

Using the compound obtained in Example 367 and (bromomethyl)cyclobutane, white powdery N-[2-(4-cyclobutyl methoxy-3-difluoromethoxyphenyl)oxazol-4-ylmethyl]-3-methyl picolinamide was obtained following the procedure of Example 98.

$^1$H-NMR ($CDCl_3$) δ: 8.58 (1H, br s), 8.39 (1H, d, J=4.5 Hz), 7.87-7.82 (2H, m), 7.64 (1H, s), 7.59 (1H, d, J=8.4 Hz), 7.33-7.29 (2H, m), 7.01 (1H, d, J=8.4 Hz), 6.59 (1H, t, J=75 Hz), 4.59 (1H, d, J=5.4 Hz), 4.03 (2H, d, J=6.9 Hz), 2.90-2.82 (1H, m), 2.76 (3H, s), 2.22-2.13 (2H, m), 2.00-1.84 (4H, m)

Example 370

Using the compound obtained in Example 367 and isobutyl bromide, white powdery N-[2-(3-difluoromethoxy-4-isobutoxy phenyl)oxazol-4-ylmethyl]-3-methylpicolinamide was obtained following the procedure of Example 98.

$^1$H-NMR ($CDCl_3$) δ: 8.58 (1H, br s), 8.39 (1H, d, J=4.5 Hz), 7.87-7.83 (2H, m), 7.64 (1H, s), 7.60-7.57 (1H, m), 7.33-7.28 (1H, m), 7.00 (1H, d, J=8.4 Hz), 6.59 (1H, t, J=75 Hz), 4.59 (1H, d, J=5.4 Hz), 3.81 (2H, d, J=6.9 Hz), 2.76 (3H, s), 2.22-2.09 (1H, m), 1.06 (6H, d, J=6.6 Hz)

Example 371

Using the compound obtained in Example 367 and 4-bromo-1-butene, white powdery N-[2-(4-but-3-enyloxy-3-difluoromethoxy phenyl)oxazol-4-ylmethyl]-3-methylpicolinamide was obtained following the procedure of Example 98.

$^1$H-NMR ($CDCl_3$) δ: 8.59 (1H, br s), 8.39 (1H, d, J=4.5 Hz), 7.88-7.83 (2H, m), 7.65 (1H, s), 7.60-7.57 (1H, m), 7.33-7.29 (1H, m), 7.01 (1H, d, J=8.4 Hz), 6.61 (1H, t, J=75 Hz), 5.94-5.83 (1H, m), 5.24-5.12 (2H, m), 4.59 (1H, d, J=5.4 Hz), 4.13 (2H, t, J=6.6 Hz), 2.76 (3H, s), 2.63-2.57 (2H, m)

Example 372

Using the compound obtained in Example 367 and (bromomethyl)cyclopropane, white powdery N-[2-(4-cyclopropyl methoxy-3-difluoromethoxyphenyl)oxazol-4-ylmethyl]-3-methyl picolinamide was obtained following the procedure of Example 98.

$^1$H-NMR ($CDCl_3$) δ: 8.58 (1H, br s), 8.39 (1H, d, J=4.5 Hz), 7.86-7.83 (2H, m), 7.65 (1H, s), 7.59 (1H, d, J=8.4 Hz), 7.33-7.28 (1H, m), 7.00 (1H, d, J=8.4 Hz), 6.66 (1H, t, J=75 Hz), 4.59 (2H, d, J=5.4 Hz), 3.93 (2H, d, J=6.9 Hz), 2.76 (3H, s), 1.33-1.24 (1H, m), 0.70-0.64 (2H, m), 0.41-0.35 (2H, m)

Example 373

The compound obtained in Reference Example 96 was used and treated following the procedure of Example 96, followed by treatment according to the procedure of Example 97, yielding white powdery N-[2-(3-difluoromethoxy-4-hydroxyphenyl)oxazol-4-ylmethyl]-2-ethoxybenzamide.

$^1$H-NMR ($CDCl_3$) δ: 8.59 (1H, br s), 8.24 (1H, dd, J=7.8, 1.2 Hz), 7.81-7.78 (2H, m), 7.63 (1H, s), 7.46-7.40 (1H, m), 7.11-7.05 (2H, m), 6.96 (1H, d, J=8.4 Hz), 6.62 (1H, t, J=75 Hz), 5.87 (1H, br s), 4.62 (2H, d, J=5.4 Hz), 4.19 (2H, q, J=6.9 Hz), 1.50 (3H, t, J=6.9 Hz)

Example 374

Using the compound obtained in Example 373 and 2-bromopropane, white powdery N-[2-(3-difluoromethoxy-4-isopropoxy phenyl)oxazol-4-ylmethyl]-2-ethoxybenzamide was obtained following the procedure of Example 98.

$^1$H-NMR ($CDCl_3$) δ: 8.60 (1H, br s), 8.24 (1H, dd, J=7.8, 2.1 Hz), 7.85-7.82 (2H, m), 7.64 (1H, s), 7.45-7.39 (1H, m), 7.09-7.01 (2H, m), 6.95 (1H, d, J=8.1 Hz), 6.59 (1H, t, J=75

Hz), 4.71-4.61 (5H, m), 4.19 (2H, q, J=6.9 Hz), 1.51 (3H, t, J=6.9 Hz), 1.40 (6H, d, J=6.9 Hz)

Example 375

Using the compound obtained in Example 373 and (bromomethyl)cyclopropane, white powdery N-[2-(4-cyclopropyl methoxy-3-difluoromethoxyphenyl)oxazol-4-ylmethyl]-2-ethoxy benzamide was obtained following the procedure of Example 98.

$^1$H-NMR ($CDCl_3$) δ: 8.59 (1H, br s), 8.24 (1H, dd, J=7.8, 2.1 Hz), 7.85-7.82 (2H, m), 7.64 (1H, s), 7.45-7.39 (1H, m), 7.09-6.94 (3H, m), 6.66 (1H, t, J=75 Hz), 4.62 (2H, d, J=5.4 Hz), 4.19 (2H, q, J=6.9 Hz), 3.93 (2H, d, J=8.4 Hz), 1.50 (3H, t, J=6.9 Hz), 1.34-1.24 (1H, m), 0.71-0.64 (2H, m), 0.41-0.35 (2H, m)

Example 376

Using the compound obtained in Example 373 and 1-bromopropane, white powdery N-[2-(3-difluoromethoxy-4-propoxy phenyl)oxazol-4-ylmethyl]-2-ethoxybenzamide was obtained following the procedure of Example 98.

$^1$H-NMR ($CDCl_3$) δ: 8.60 (1H, br s), 8.23 (1H, dd, J=7.8, 1.8 Hz), 7.87-7.83 (2H, m), 7.64 (1H, s), 7.42 (1H, t, J=7.5 Hz), 7.09-6.85 (3H, m), 6.35 (1H, t, J=75 Hz), 4.62 (2H, d, J=6.0 Hz), 4.19 (2H, q, J=6.6 Hz), 4.04 (2H, t, J=6.0 Hz), 1.91-1.84 (2H, m), 1.50 (3H, t, J=6.9 Hz), 1.07 (3H, t, J=6.9 Hz)

Example 377

Using the compound obtained in Example 373 and allyl bromide, white powdery N-[2-(4-allyloxy-3-difluoromethoxyphenyl) oxazol-4-ylmethyl]-2-ethoxybenzamide was obtained following the procedure of Example 98.

$^1$H-NMR ($CDCl_3$) δ: 8.60 (1H, br s), 8.23 (1H, dd, J=7.8, 1.8 Hz), 7.86-7.83 (2H, m), 7.64 (1H, s), 7.42 (1H, t, J=7.5 Hz), 7.10-6.97 (3H, m), 6.61 (1H, t, J=75 Hz), 6.07-6.01 (1H, m), 5.49-5.32 (2H, m), 4.68-4.61 (4H, m), 4.19 (2H, q, J=6.9 Hz), 1.50 (3H, t, J=6.9 Hz)

Reference Example 97

Using ethyl 3,4-dihydroxybenzoate and chlorodifluoro methane, white powdery ethyl 3,4-bis-difluoromethoxybenzoate was obtained following the procedure of Example 4.

$^1$H-NMR ($CDCl_3$) δ: 8.00-7.90 (2H, m), 7.31 (1H, d, J=8.1 Hz), 6.60 (1H, t, J=72.9 Hz), 6.57 (1H, t, J=72.9 Hz), 4.39 (2H, q, J=7.2 Hz), 1.40 (3H, t, J=7.2 Hz)

Reference Example 98

Using the compound obtained in Reference Example 97, white powdery 2-(3,4-bis-difluoromethoxyphenyl)-4-chloromethyl oxazol was obtained following the procedures of Reference Examples 3 to 5.

$^1$H-NMR ($CDCl_3$) δ: 7.95-7.90 (2H, m), 7.73 (1H, s), 7.35 (1H, d, J=8.4 Hz), 6.60 (1H, t, J=72.9 Hz), 6.59 (1H, t, J=72.9 Hz), 4.57 (2H, s)

Example 378

Using the compound obtained in Reference Example 98, white powdery 3-[2-(3,4-bis-difluoromethoxyphenyl)oxazol-4-yl]-1-(2-ethoxyphenyl)propan-1-one was obtained following the procedure of Example 190.

$^1$H-NMR ($CDCl_3$) δ: 7.89-7.84 (2H, m), 7.71 (1H, dd, J=7.5, 1.8 Hz), 7.48-7.41 (2H, m), 7.32 (1H, d, J=8.4 Hz), 7.01-6.93 (2H, m), 6.58 (1H, t, J=75 Hz), 6.57 (1H, t, J=75 Hz), 4.14 (2H, q, J=6.9 Hz), 3.43 (2H, t, J=6.9 Hz), 3.00 (2H, t, J=6.9 Hz), 1.48 (3H, t, J=6.9 Hz)

Reference Example 99

The compound obtained in Reference Example 98 was used and treated following the procedure of Reference Example 45, followed by treatment according to the procedure of Reference Example 46, yielding pale yellow oily [2-(3,4-bis-difluoromethoxy phenyl)oxazol-4-yl]-methylamine.

$^1$H-NMR ($CDCl_3$) δ: 7.92-7.88 (2H, m), 7.58 (1H, s), 7.34 (1H, d, J=8.4 Hz), 6.60 (1H, t, J=75 Hz), 6.59 (1H, t, J=75 Hz), 3.85 (2H, s)

Example 379

Using the compound obtained in Reference Example 99, white powdery N-[2-(3,4-bis-difluoromethoxyphenyl)oxazol-4-ylmethyl]-3-methylpicolinamide was obtained following the procedure of Example 96.

$^1$H-NMR ($CDCl_3$) δ: 8.61 (1H, br s), 8.40 (1H, dd, J=7.5, 1.5 Hz), 7.93-7.88 (2H, m), 7.70 (1H, s), 7.60 (1H, d, J=1.5 Hz), 7.58-7.31 (2H, m), 6.60 (1H, t, J=75 Hz), 6.58 (1H, t, J=75 Hz), 4.60 (2H, dd, J=6.0, 1.2 Hz), 2.77 (3H, s)

Example 380

Using the compound obtained in Reference Example 99, white powdery N-[2-(3,4-bis-difluoromethoxyphenyl)oxazol-4-ylmethyl]-2-ethoxybenzamide was obtained following the procedure of in Example 1.

$^1$H-NMR ($CDCl_3$) δ: 8.59 (1H, br s), 8.23 (1H, dd, J=7.5, 1.8 Hz), 7.94-7.88 (2H, m), 7.70 (1H, s), 7.46-7.33 (2H, m), 7.07 (1H, t, J=7.5 Hz), 6.95 (1H, d, J=8.4 Hz), 6.60 (1H, t, J=75 Hz), 6.59 (1H, t, J=75 Hz), 4.63 (2H, d, J=6.0 Hz), 4.19 (2H, q, J=6.9 Hz), 1.50 (3H, t, J=6.9 Hz)

Example 381

Using the compound obtained in Reference Example 98, white powdery 3-[2-(3,4-bis-difluoromethoxyphenyl)oxazol-4-yl]-1-(3-methylpyridin-2-yl)propan-1-one was obtained following the procedure of Example 356.

$^1$H-NMR ($CDCl_3$) δ: 8.51 (1H, br s), 7.88-7.85 (2H, m), 7.59 (1H, d, J=8.4 Hz), 7.53 (1H, s), 7.35-7.30 (2H, m), 6.58 (1H, t, J=75 Hz), 6.57 (1H, t, J=75 Hz), 3.60 (2H, t, J=6.3 Hz), 3.02 (2H, t, J=6.3 Hz), 2.58 (3H, s)

Example 382

Using the compound obtained in Example 347 and the compound obtained in Reference Example 85, white powdery N-{2-[4-difluoro methoxy-3-(2,2-difluoroethoxy)phenyl]-oxazol-4-ylmethyl}-2-ethoxy benzamide was obtained following the procedure of Example 348.

$^1$H-NMR ($CDCl_3$) δ: 8.55 (1H, br s), 8.24 (1H, dd, J=7.8, 1.8 Hz), 7.71-7.65 (3H, m), 7.46-7.41 (1H, m), 7.29 (1H, s), 7.08 (1H, t, J=8.1 Hz), 6.96 (1H, d, J=8.1 Hz), 6.59 (1H, t, J=74.1 Hz), 6.15 (1H, tt, J=54.9, 4.2 Hz) 4.64 (2H, d, J=5.4 Hz), 4.32 (2H, td, J=12.9, 4.2 Hz), 4.20 (2H, q, J=6.9 Hz) 1.50 (3H, t, J=6.9 Hz)

Example 383

Using the compound obtained in Example 347 and 1,1,1-trifluoro-2-iodoethane, white powdery N-{2-[4-difluoromethoxy-3-(2,2,2-trifluoroethoxy)phenyl]-oxazol-4-ylmethyl}-2-ethoxy benzamide was obtained following the procedure of Example 348.

$^1$H-NMR ($CDCl_3$) δ: 8.56 (1H, br s), 8.24 (1H, dd, J=7.8, 1.8 Hz), 7.75-7.68 (3H, m), 7.46-7.40 (1H, m), 7.30 (1H, d, J=8.4 Hz), 7.08 (1H, t, J=8.1 Hz), 6.96 (1H, d, J=8.1 Hz), 6.60 (1H, t, J=74.1 Hz), 4.63 (2H, d, J=5.4 Hz), 4.49 (2H, q, J=8.1 Hz), 4.20 (2H, q, J=6.9 Hz) 1.50 (3H, t, J=6.9 Hz)

Example 384

Using the compound obtained in Example 17 and 2-bromo propane, colorless oily N-[2-(4-methoxy-3-isopropoxyphenyl)oxazol-4-ylmethyl]-3-methylpicolinamide was obtained following the procedure of Example 19.

$^1$H-NMR ($CDCl_3$) δ: 8.58 (1H, br s), 8.39 (1H, dd, J=4.8, 1.2 Hz), 7.63-7.57 (4H, m), 7.33-7.28 (1H, m), 6.93 (1H, d, J=8.4 Hz), 4.68 (1H, sept., J=6.3 Hz), 4.59 (2H, d, J=5.7 Hz), 3.89 (3H, s), 2.76 (3H, s), 1.41 (6H, d, J=6.3 Hz)

Example 385

Using the compound obtained in Example 347 and (bromomethyl)cyclobutane, white powdery N-[2-(3-Cyclobutylmethoxy-4-difluoromethoxyphenyl)oxazol-4-ylmethyl]-2-ethoxybenzamide was obtained following the procedure of Example 348.

$^1$H-NMR ($CDCl_3$) δ: 8.56 (1H, br s), 8.24 (1H, dd, J=7.8, 1.8 Hz), 7.67-7.58 (3H, m), 7.50-7.40 (1H, m), 7.23 (1H, d, J=8.4 Hz), 7.08 (1H, t, J=8.1 Hz), 6.96 (1H, d, J=8.1 Hz), 6.63 (1H, t, J=75 Hz), 4.64 (2H, d, J=5.1 Hz), 4.19 (2H, q, J=6.9 Hz), 4.08 (2H, d, J=6.6 Hz) 2.86-2.82 (1H, m), 2.19-2.12 (2H, m), 2.04-1.87 (4H, m), 1.50 (3H, t, J=6.9 Hz)

The chemical structures of the compounds obtained above in the Reference Examples and Examples are shown below in Tables 1 to 40.

TABLE 1

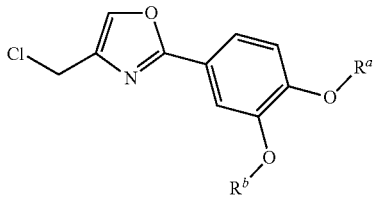

| Ref. Ex. No. | $R^a$ | $R^b$ |
|---|---|---|
| 5 | Methyl | Benzyl |
| 11 | Methyl | 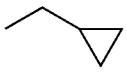 |
| 17 | Methyl | 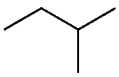 |
| 23 | Methyl | —$CH_2CF_3$ |
| 32 | —$CH_2CF_3$ | 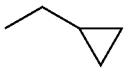 |
| 35 | Ethyl | Ethyl |
| 38 | Methyl | Methyl |
| 44 | —$CHF_2$ | Benzyl |
| 55 | Benzyl | Benzyl |
| 58 | Methyl | Ethyl |

TABLE 1-continued

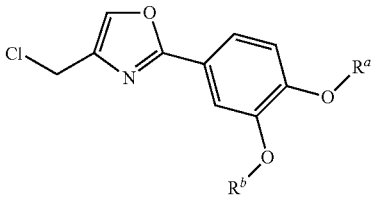

| Ref. Ex. No. | $R^a$ | $R^b$ |
|---|---|---|
| 63 | Benzyl | Ethyl |
| 68 | Methyl | iso-Propyl |

TABLE 2

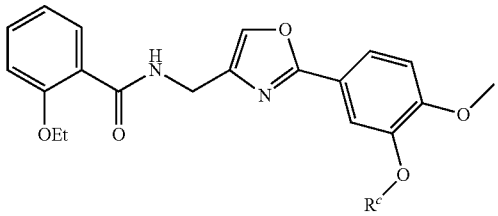

| Ex. No. | $R^c$ |
|---|---|
| 1 | Benzyl |
| 2 | H |
| 3 | 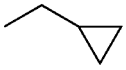 |
| 4 | —$CH_2CF_3$ |
| 5 | n-Butyl |
| 6 | Cyclopentyl |
| 7 | 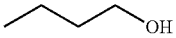 |
| 8 | 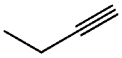 |
| 9 | Ethyl |
| 10 | 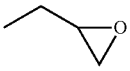 |
| 11 | n-propyl |
| 12 | iso-propyl |
| 13 | 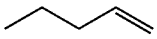 |
| 14 | iso-Butyl |
| 15 | —$CH_2CH_2CF_3$ |
| 92 | Methyl |

—OEt: Ethoxy

TABLE 3

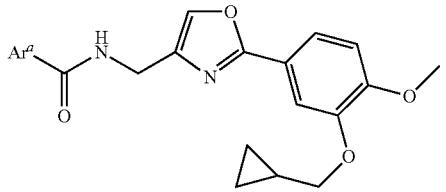

| Ex. No. | $Ar^a$ |
|---|---|
| 25 | 2-Trifluoromethylphenyl |
| 32 | 2-(2,2,2-Trifluoroethoxy)phenyl |
| 37 | 2-iso-Propoxyphenyl |
| 38 | 2-Methylphenyl |
| 39 | 2-Ethylphenyl |
| 40 | 2-Chlorophenyl |
| 41 | 5-Fluoro-2-methoxyphenyl |
| 42 | 4-Fluoro-2-methoxyphenyl |
| 43 | 6-Fluoro-2-methoxyphenyl |
| 44 | 2-Methylthiophenyl |
| 46 | 2-Methoxyphenyl |
| 47 | 2-Trifluoromethoxyphenyl |
| 48 | 2-n-Propoxyphenyl |
| 51 | 2-n-Butoxyphenyl |
| 52 | 2-iso-Butoxyphenyl |
| 54 | 2-Ethylthiophenyl |
| 56 | 2,6-Dimethoxyphenyl |
| 60 | 2-Methanesulfonylphenyl |

TABLE 4

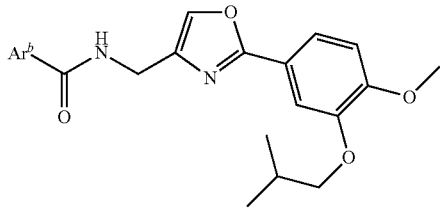

| Ex. No. | $Ar^b$ |
|---|---|
| 63 | 2-Methoxyphenyl |
| 64 | 2-Methylthiophenyl |
| 66 | 4-Fluoro-2-methoxyphenyl |
| 67 | 2-iso-Propoxyphenyl |
| 68 | 6-Fluoro-2-methoxyphenyl |
| 71 | 2-n-Propoxyphenyl |
| 72 | 2-n-Butoxyphenyl |
| 73 | 2-iso-Butoxyphenyl |

TABLE 5

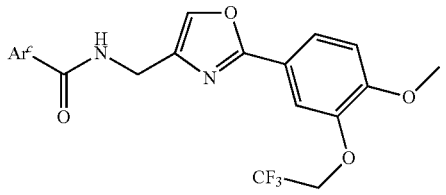

| Ex. No. | $Ar^c$ |
|---|---|
| 78 | 2-Methoxyphenyl |
| 79 | 2-Methylphenyl |
| 80 | 2-n-Propoxyphenyl |
| 81 | 2-iso-Propoxyphenyl |
| 82 | 4-Chloro-2-methoxyphenyl |

TABLE 6

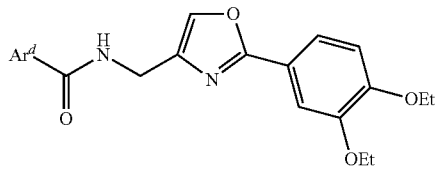

| Ex. No. | $Ar^d$ |
|---|---|
| 85 | 2-n-Propoxyphenyl |
| 86 | 2-Trifluoromethylphenyl |
| 88 | 2-Ethoxyphenyl |
| 89 | 4-Ethoxyphenyl |
| 90 | 5-Methoxy-2-trifluoromethoxyphenyl |
| 91 | 3-Ethoxyphenyl |

OEt: Ethoxy

TABLE 7

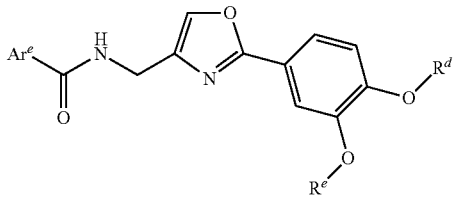

| Ex. No. | $Ar^e$ | $R^d$ | $R^e$ |
|---|---|---|---|
| 23 | 2-Trifluoromethylphenyl | Methyl | Benzyl |
| 24 | 2-Trifluoromethylphenyl | Methyl | H |
| 26 | 2-Trifluoromethylphenyl | Methyl | 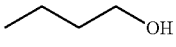 |
| 30 | 2-(2,2,2-Trifluoroethoxy)phenyl | Methyl | Benzyl |
| 31 | 2-(2,2,2-Trifluoroethoxy)phenyl | Methyl | H |
| 33 | 2-Methoxyphenyl | Methyl | Benzyl |
| 34 | 2-Methoxyphenyl | Methyl | H |
| 35 | 2-Methoxyphenyl | Methyl | cyclo-Pentyl |
| 83 | 2-Ethoxyphenyl | $—CH_2CF_3$ | 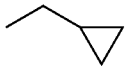 |
| 93 | 2-Ethoxyphenyl | Methyl | Methyl |

TABLE 8

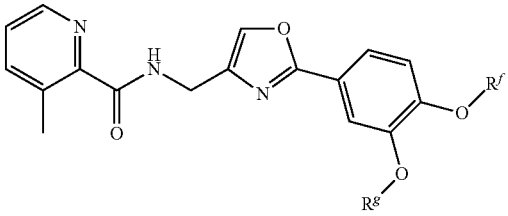

| Ex. No. | $R^f$ | $R^g$ |
|---|---|---|
| 16 | Methyl | Benzyl |
| 17 | Methyl | H |
| 18 | Methyl | Cyclopentyl |
| 19 | Methyl | $—CH_2CF_3$ |
| 20 | Methyl | Ethyl |
| 21 | Methyl | Allyl |

TABLE 8-continued

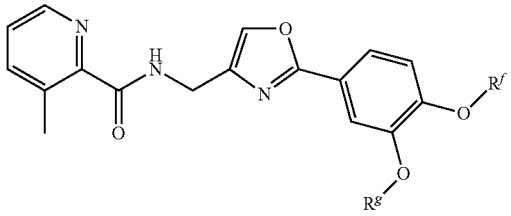

| Ex. No. | $R^f$ | $R^g$ |
|---|---|---|
| 22 | Methyl | 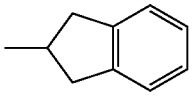 |
| 36 | Methyl | 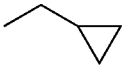 |
| 62 | Methyl | iso-Butyl |
| 84 | $—CH_2CF_3$ | 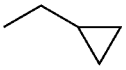 |
| 94 | Methyl | Methyl |
| 96 | $—CHF_2$ | Benzyl |
| 97 | $—CHF_2$ | H |
| 98 | $—CHF_2$ | 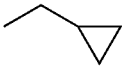 |
| 384 | Methyl | iso-Propyl |

TABLE 9

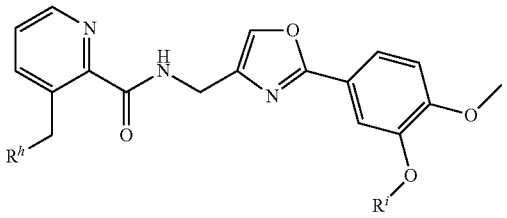

| Ex. No. | $R^h$ | $R^i$ |
|---|---|---|
| 27 | Ethyl | Benzyl |
| 28 | Ethyl | H |
| 29 | Ethyl | Cyclopentyl |
| 45 | H | 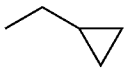 |
| 50 | Ethyl | 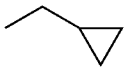 |
| 53 | iso-Propyl | 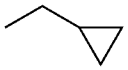 |
| 57 | Methyl | 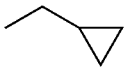 |

TABLE 9-continued

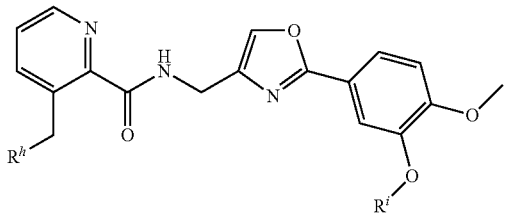

| Ex. No. | $R^h$ | $R^i$ |
|---|---|---|
| 58 | iso-Butyl | 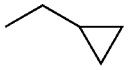 |
| 61 | n-Propyl | 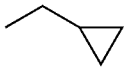 |
| 65 | Ethyl | iso-Butyl |
| 69 | Methyl | iso-Butyl |
| 70 | iso-Butyl | iso-Butyl |
| 74 | iso-Propyl | iso-Butyl |
| 76 | Methyl | $—CH_2CF_3$ |
| 77 | Ethyl | $—CH_2CF_3$ |
| 95 | Methyl | Methyl |

TABLE 10

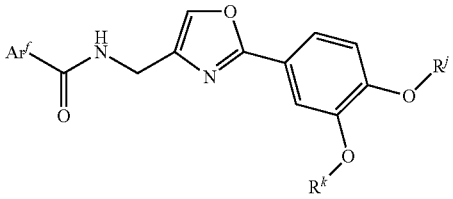

| Ex. No. | $Ar^f$ | $R^j$ | $R^k$ |
|---|---|---|---|
| 49 | 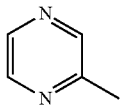 | Methyl | 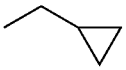 |
| 55 | 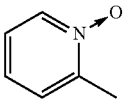 | Methyl | 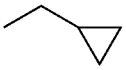 |
| 59 | 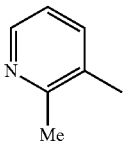 | Methyl | 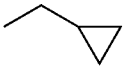 |
| 75 | 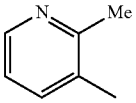 | Methyl | iso-Butyl |
| 87 | 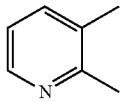 | Ethyl | Ethyl |

TABLE 10-continued

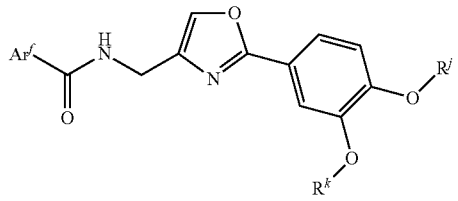

| Ex. No. | $Ar^f$ | $R^j$ | $R^k$ |
|---|---|---|---|
| 99 | 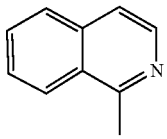 | Methyl | 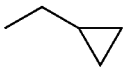 |

Me: Methyl

TABLE 11

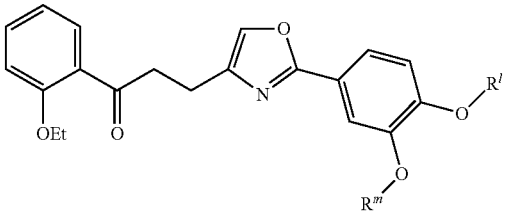

| Ex. No. | $R^l$ | $R^m$ |
|---|---|---|
| 101 | Methyl | H |
| 102 | Methyl | 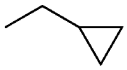 |
| 103 | Methyl | Ethyl |
| 104 | Methyl | Allyl |
| 105 | Methyl | Cyclopentyl |
| 106 | Methyl | iso-Butyl |
| 107 | Methyl | n-Propyl |
| 108 | Methyl | 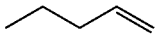 |
| 109 | Methyl | n-Butyl |
| 110 | Methyl | 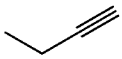 |
| 111 | Methyl | iso-Propyl |
| 112 | Methyl | $—CH_2CF_3$ |
| 113 | Methyl | 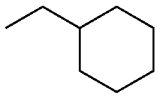 |
| 114 | Methyl | 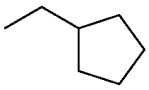 |
| 115 | Methyl | 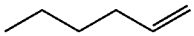 |
| 116 | Methyl | 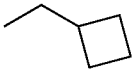 |

TABLE 11-continued

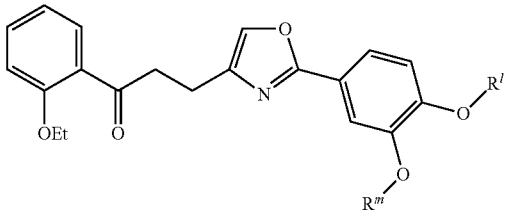

| Ex. No. | $R^l$ | $R^m$ |
|---|---|---|
| 117 | Methyl | 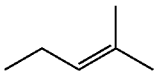 |
| 118 | Methyl | 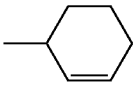 |
| 119 | Methyl | 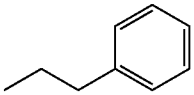 |
| 120 | Methyl | 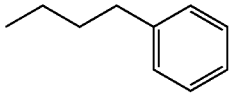 |
| 121 | Methyl | 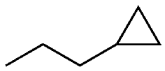 |
| 122 | Methyl | 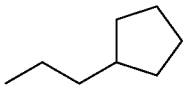 |
| 182 | Ethyl | Ethyl |
| 190 | Benzyl | Ethyl |
| 191 | H | Ethyl |
| 192 | iso-Propyl | Ethyl |
| 228 | $—CHF_2$ | Benzyl |
| 229 | $—CHF_2$ | H |
| 230 | $—CHF_2$ | iso-Propyl |

—OEt: Ethoxy

TABLE 12

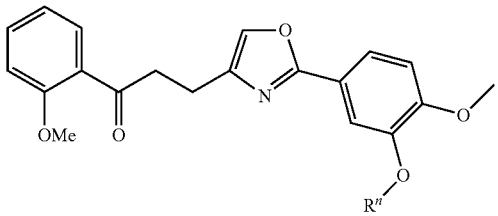

| Ex. No | $R^n$ |
|---|---|
| 169 | iso-Propyl |
| 170 | 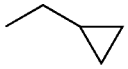 |
| 171 | Cyclopentyl |
| 172 | Ethyl |
| 173 | iso-Butyl |

TABLE 12-continued
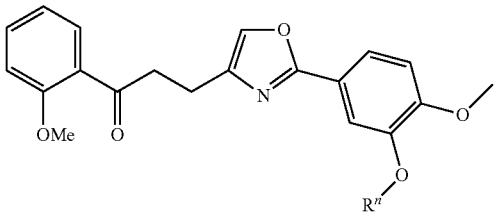
| Ex. No | $R^n$ |
|---|---|
| 174 | Allyl |
| 175 | —$CH_2CF_3$ |
—OMe: Methoxy
TABLE 13
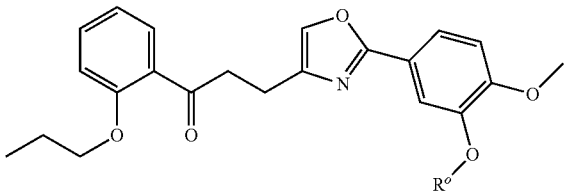
| Ex. No. | $R^o$ |
|---|---|
| 194 | H |
| 195 | Ethyl |
| 196 | Cyclopentyl |
| 197 | iso-Propyl |
| 198 | 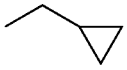 |
| 199 | 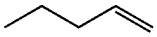 |
| 200 | Allyl |
| 201 | 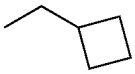 |
| 203 | —$CH_2CF_3$ |
TABLE 14
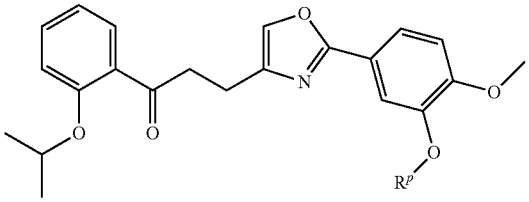
| Ex. No. | $R^p$ |
|---|---|
| 207 | H |
| 208 | 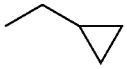 |
| 209 | Ethyl |
| 210 | iso-Propyl |
| 211 | Allyl |
TABLE 14-continued
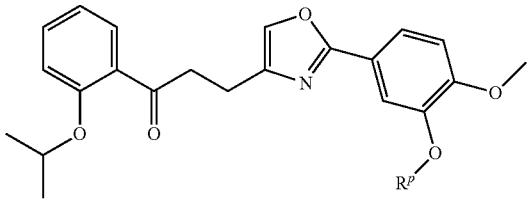
| Ex. No. | $R^p$ |
|---|---|
| 212 | 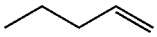 |
| 213 | —$CH_2CF_3$ |
| 214 | 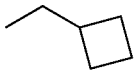 |
TABLE 15
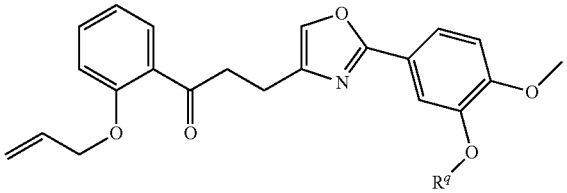
| Ex. No. | $R^q$ |
|---|---|
| 164 | Benzyl |
| 166 | Allyl |
| 177 | 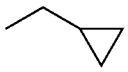 |
| 189 | Ethyl |
| 224 | iso-Propyl |
TABLE 16
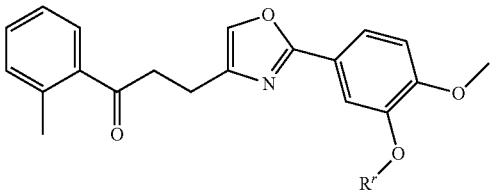
| Ex. No. | $R^r$ |
|---|---|
| 220 | H |
| 221 | 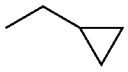 |
| 225 | Ethyl |
| 226 | Allyl |
| 227 | iso-Propyl |

TABLE 17
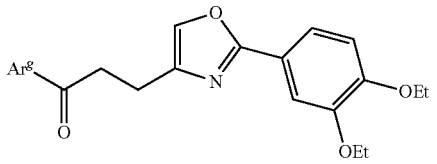
| Ex. No. | $Ar^g$ |
|---|---|
| 178 | 2-Allyloxyphenyl |
| 184 | 3-Ethoxyphenyl |
| 185 | 4-Ethoxyphenyl |
| 205 | 2-n-Propoxyphenyl |
| 216 | 2-iso-Propoxyphenyl |
| 218 | 2-Methylphenyl |
—OEt: Ethoxy
TABLE 18
| Ex. No. | Chemical Structure |
|---|---|
| 165 | 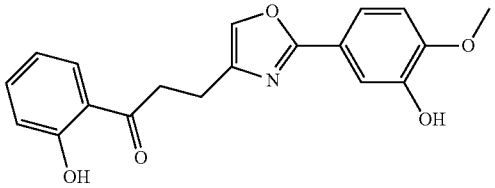 |
| 168 | 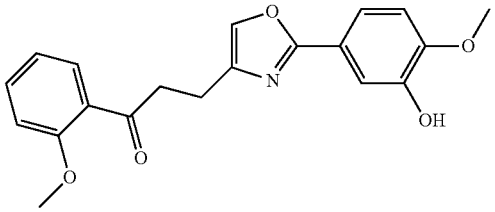 |
| 176 | 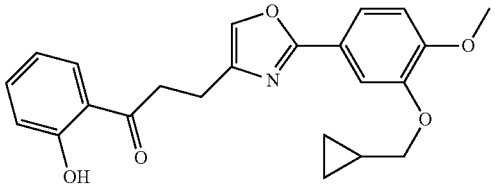 |
| 179 | 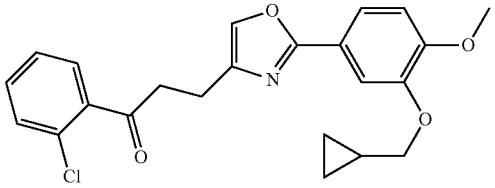 |
| 223 | 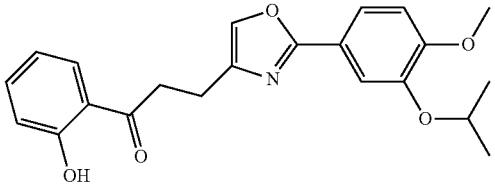 |
TABLE 18-continued
| Ex. No. | Chemical Structure |
|---|---|
| 231 | 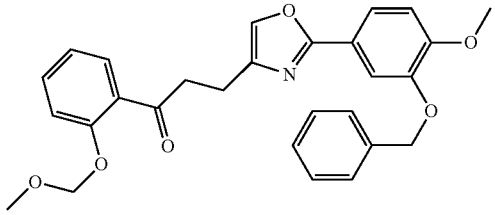 |
| 232 | 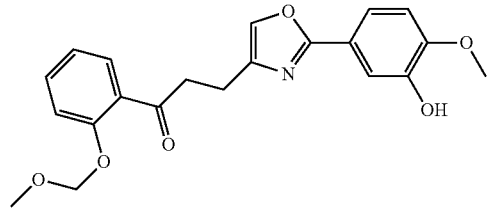 |
| 233 | 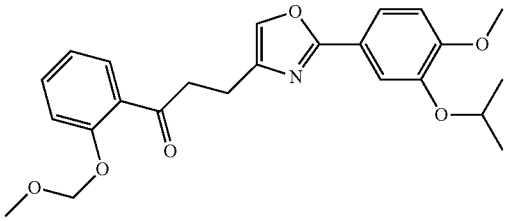 |
| 234 | 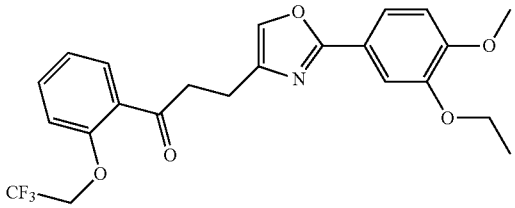 |
| 235 | 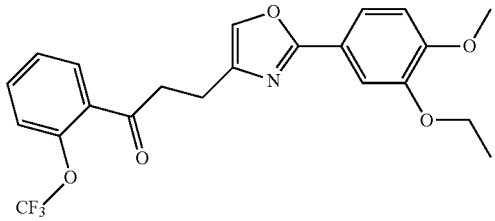 |
TABLE 19
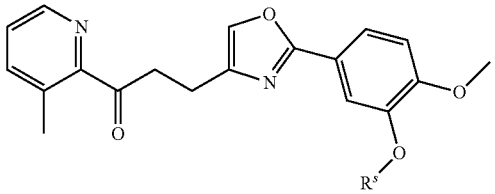
| Ex. No. | $R^5$ |
|---|---|
| 136 | H |
| 137 | 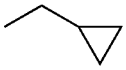 |

TABLE 19-continued
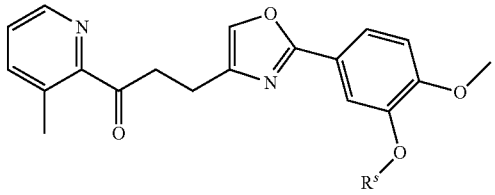
| Ex. No. | $R^s$ |
|---|---|
| 138 | Ethyl |
| 139 | iso-Propyl |
| 140 | Allyl |
| 141 | 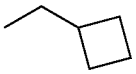 |
| 142 | iso-Butyl |
| 143 | n-Propyl |
| 144 | Cyclopentyl |
| 145 | 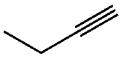 |
| 146 | 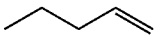 |
| 147 | n-Butyl |
| 148 | 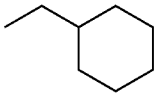 |
| 149 | 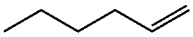 |
| 150 | $—CH_2CH_2Ph$ |
| 151 | $—CH_2CH_2CH_2Ph$ |
| 152 | 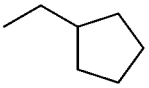 |
| 153 | 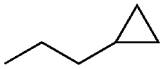 |
| 154 | 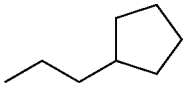 |
| 155 | $—CH_2CF_3$ |
| 156 | 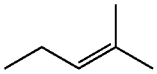 |
| 157 | 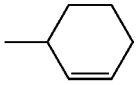 |
| 158 | Cyclohexyl |
| 159 | 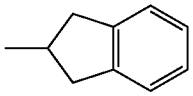 |
Ph: Phenyl
TABLE 20
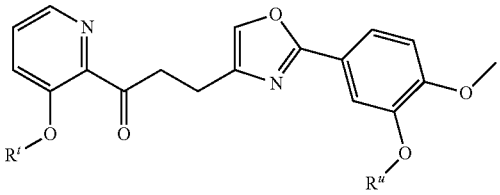
| Ex. No. | $R^t$ | $R^u$ |
|---|---|---|
| 125 | Methyl | H |
| 126 | Methyl | 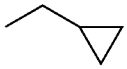 |
| 127 | Methyl | iso-Butyl |
| 128 | Methyl | Cyclopentyl |
| 129 | Methyl | $—CH_2CF_3$ |
| 131 | Ethyl | H |
| 132 | Ethyl | Cyclopentyl |
| 133 | Ethyl | 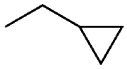 |
| 134 | Ethyl | iso-Butyl |
TABLE 21
| Ex. No. | Chemical Structure |
|---|---|
| 123 | 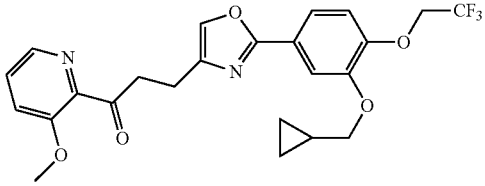 |
| 161 | 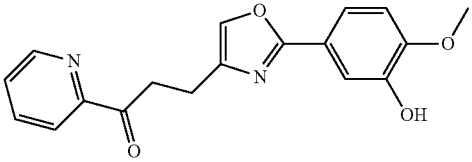 |
| 162 | 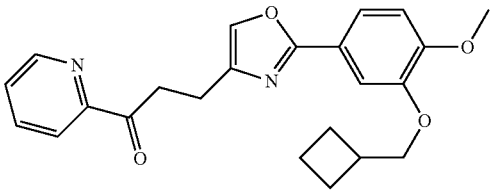 |
| 163 | 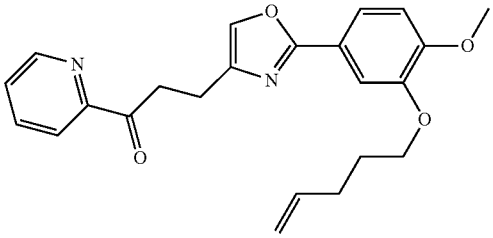 |

TABLE 21-continued

| Ex. No. | Chemical Structure |
|---|---|
| 181 | 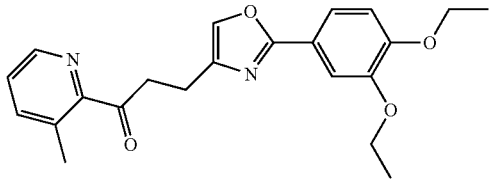 |
| 183 | 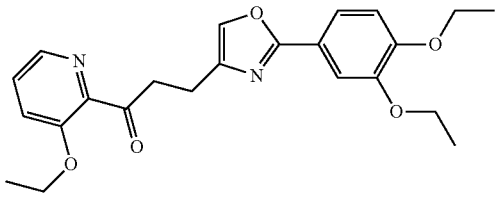 |
| 187 | 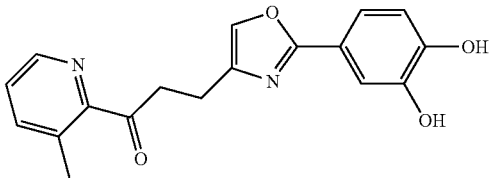 |
| 188 | 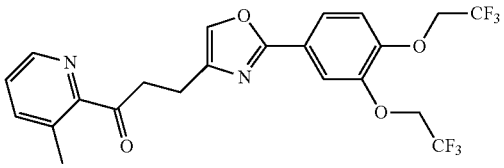 |

TABLE 22

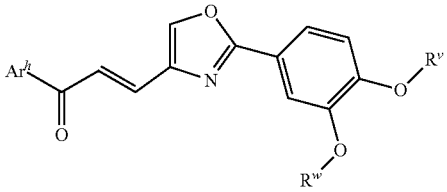

| Ex. No. | $Ar^h$ | $R^v$ | $R^w$ |
|---|---|---|---|
| 193 | 2-n-Propoxyphenyl | Methyl | Benzyl |
| 202 | 2-n-Propoxyphenyl | Methyl | $—CH_2CF_3$ |
| 204 | 2-n-Propoxyphenyl | Ethyl | Ethyl |
| 206 | 2-iso-Propoxyphenyl | Methyl | Benzyl |
| 215 | 2-iso-Propoxyphenyl | Ethyl | Ethyl |
| 217 | 2-Methylphenyl | Ethyl | Ethyl |
| 219 | 2-Methylphenyl | Methyl | Benzyl |
| 222 | 2-Benzyloxyphenyl | Methyl | iso-Propyl |

TABLE 23

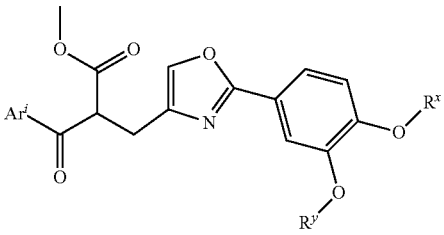

| Ex. No. | $Ar^i$ | $R^x$ | $R^y$ |
|---|---|---|---|
| 100 | 2-Ethoxyphenyl | Methyl | Benzyl |
| 124 | 3-Methoxypyridyl | Methyl | Benzyl |
| 130 | 3-Ethoxypyridyl | Methyl | Benzyl |
| 135 | 3-Methylpyridyl | Methyl | Benzyl |
| 160 | 2-Pyridyl | Methyl | Benzyl |
| 167 | 2-MethoxyPhenyl | Methyl | Benzyl |
| 180 | 3-MethylPyridyl | Ethyl | Ethyl |
| 186 | 3-MethylPyridyl | Benzyl | Benzyl |

TABLE 24

| Ex. No. | Chemical Structure |
|---|---|
| 236 | 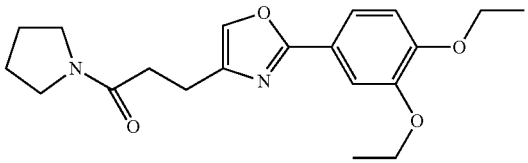 |
| 237 | 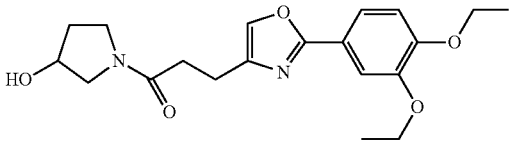 |
| 238 | 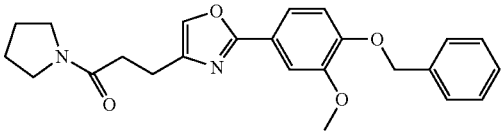 |
| 239 | 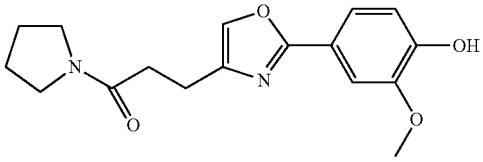 |
| 240 | 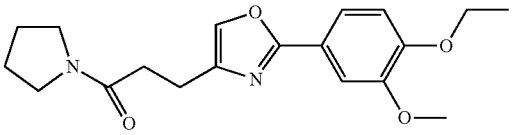 |

TABLE 25
| Ex. No. | Chemical Structure |
|---|---|
| 241 | 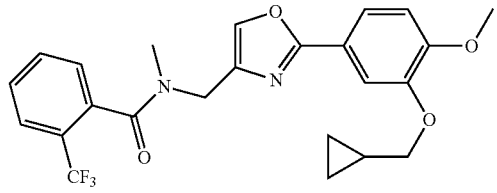 |
| 242 | 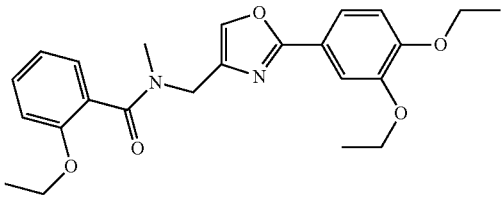 |
| 243 | 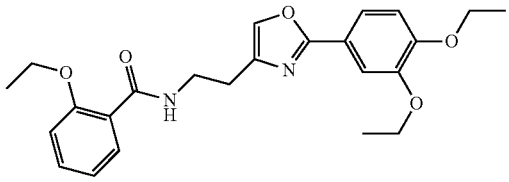 |
| 244 | 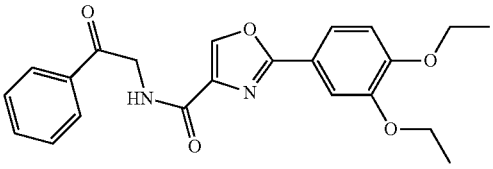 |
| 245 | 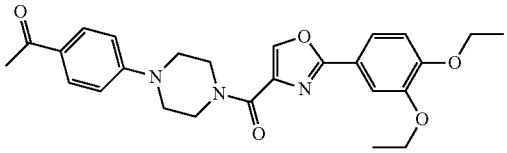 |
TABLE 26
| Ex. No. | Chemical Structure |
|---|---|
| 246 | 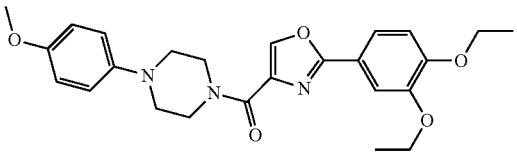 |
| 247 | 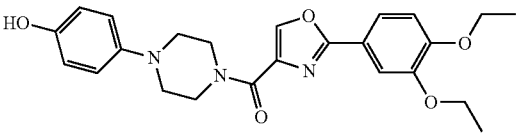 |
TABLE 26-continued
| Ex. No. | Chemical Structure |
|---|---|
| 248 | 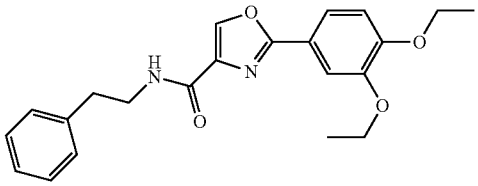 |
| 249 | 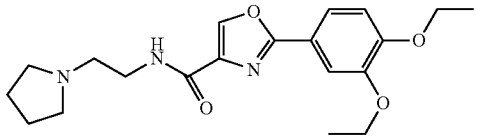 |
| 250 | 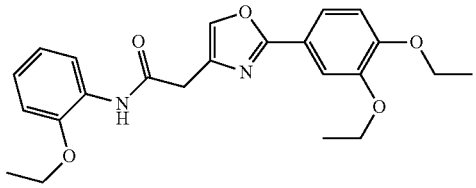 |
TABLE 27
| Ex. No. | Chemical Structure |
|---|---|
| 251 | 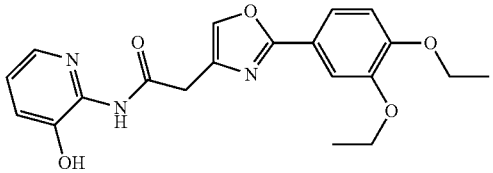 |
| 252 | 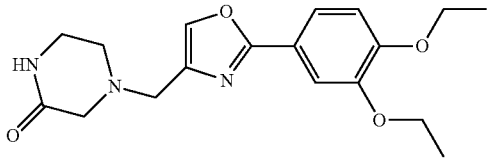 |
| 253 | 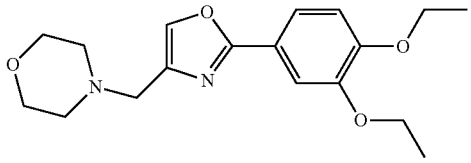 |
| 254 | 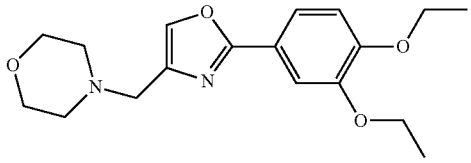 |

TABLE 27-continued
| Ex. No. | Chemical Structure |
|---|---|
| 255 | 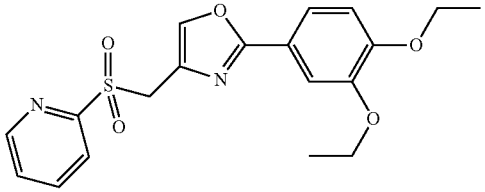 |
| 256 | 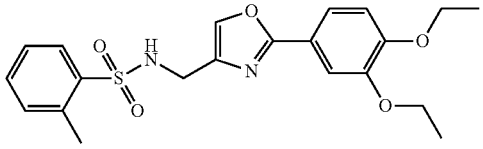 |
TABLE 28
| Ex. No. | Chemical Structure |
|---|---|
| 257 | 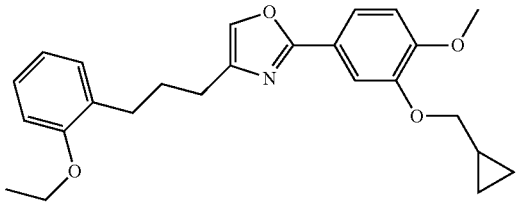 |
| 258 | 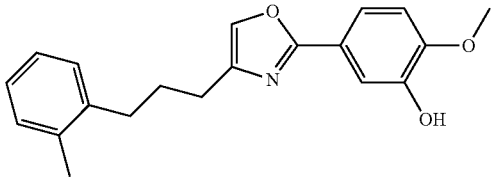 |
| 259 | 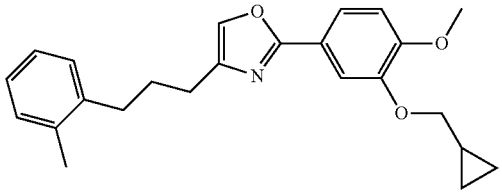 |
| 260 | 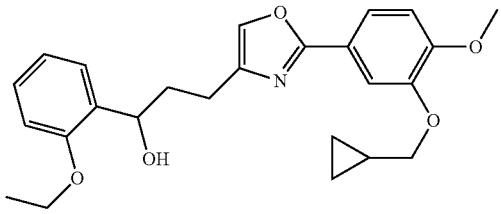 |
| 261 | 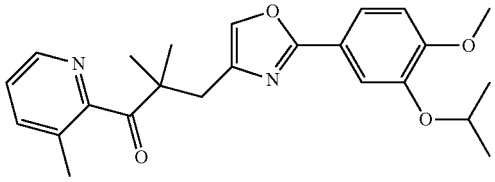 |
TABLE 29
| Ex. No. | Chemical Structure |
|---|---|
| 262 | 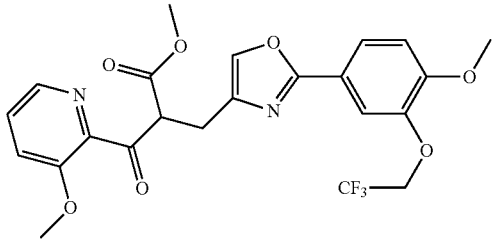 |
| 263 | 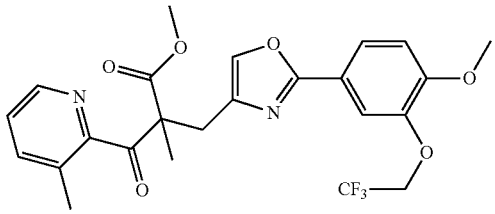 |
| 264 | 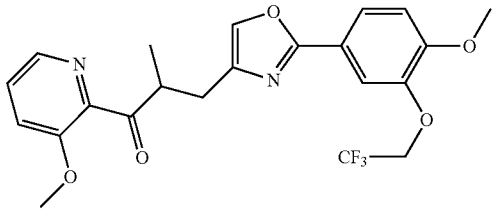 |
| 265 | 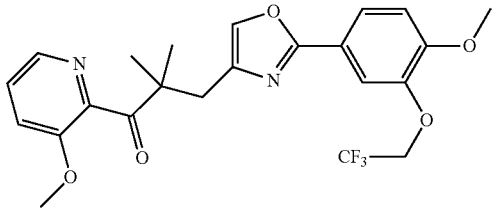 |
TABLE 30
| Ref. Ex. No. | Chemical Structure |
|---|---|
| 89 | 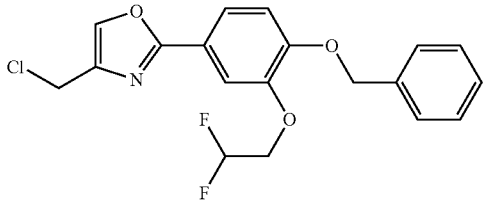 |
| 90 | 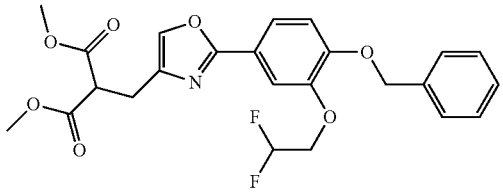 |

TABLE 30-continued

| Ref. Ex. No. | Chemical Structure |
|---|---|
| 91 | 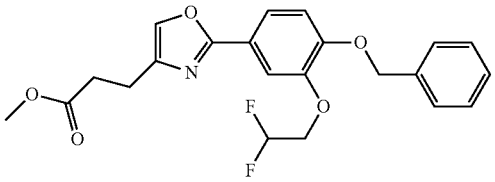 |
| 92 | 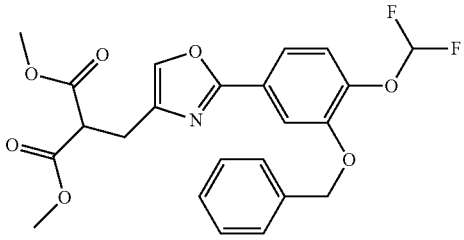 |
| 93 | 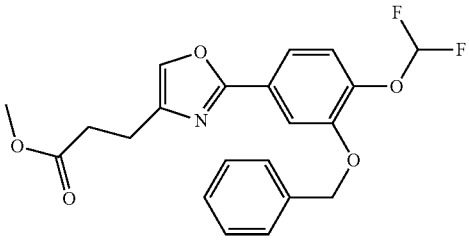 |
| 95 | 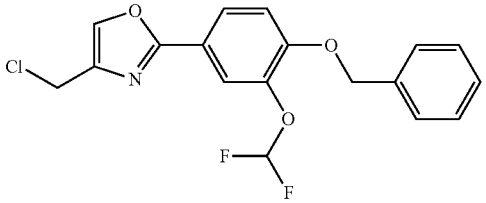 |

TABLE 31

| Ref. Ex. No. | Chemical Structure |
|---|---|
| 96 | 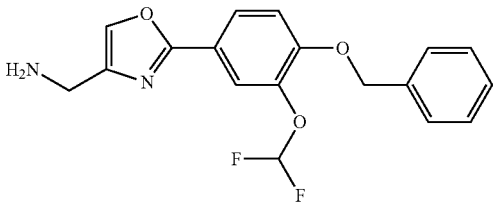 |
| 98 | 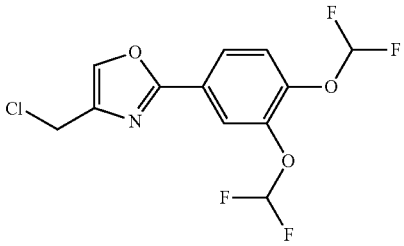 |

TABLE 31-continued

| Ref. Ex. No. | Chemical Structure |
|---|---|
| 99 | 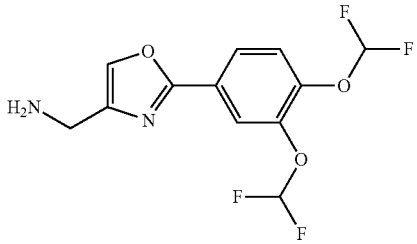 |

TABLE 32

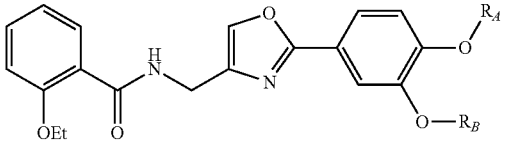

| Ex. No. | $R_A$ | $R_B$ |
|---|---|---|
| 325 | Methyl | 1-Ethylpropyl |
| 346 | Difluoromethyl | Benzyl |
| 347 | Difluoromethyl | H |
| 348 | Difluoromethyl | iso-Butyl |
| 349 | Difluoromethyl | Ethyl |
| 350 | Difluoromethyl | n-Propyl |
| 351 | Difluoromethyl | Allyl |
| 352 | Difluoromethyl | iso-Propyl |
| 353 | Difluoromethyl | Cyclopropylmethyl |
| 354 | Difluoromethyl | 3-Butenyl |
| 355 | Difluoromethyl | 1-Ethylpropyl |
| 373 | H | Difluoromethyl |
| 374 | iso-Propyl | Difluoromethyl |
| 375 | Cyclopropylmethyl | Difluoromethyl |
| 376 | n-Propyl | Difluorornethyl |
| 377 | Allyl | Difluoromethyl |
| 380 | Difluoromethyl | Difluoromethyl |
| 382 | Difluoromethyl | 2,2-Difluoroethyl |
| 383 | Difluoromethyl | 2,2,2-Trifluoroethyl |
| 385 | Difluoromethyl | Cyclobutylmethyl |

OEt: Ethoxy

TABLE 33

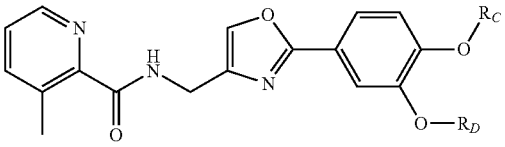

| Ex. No. | $R_C$ | $R_D$ |
|---|---|---|
| 324 | Methyl | 1-Ethylpropyl |
| 338 | Difluoromethyl | Ethyl |
| 339 | Difluoromethyl | Allyl |
| 340 | Difluoromethyl | n-Propyl |
| 341 | Difluoromethyl | iso-Propyl |
| 342 | Difluoromethyl | 1-Ethylpropyl |
| 343 | Difluoromethyl | 3-Butenyl |
| 344 | Difluoromethyl | iso-Butyl |
| 345 | Difluoromethyl | Cyclobutylmethyl |
| 367 | H | Difluoromethyl |
| 368 | Allyl | Difluoromethyl |
| 369 | Cyclobutylmethyl | Difluoromethyl |
| 370 | iso-Butyl | Difluoromethyl |
| 371 | 3-Butenyl | Difluoromethyl |

TABLE 33-continued

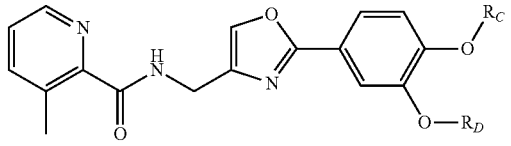

| Ex. No. | $R_C$ | $R_D$ |
|---|---|---|
| 379 | Difluoromethyl | Difluoromethyl |

TABLE 34

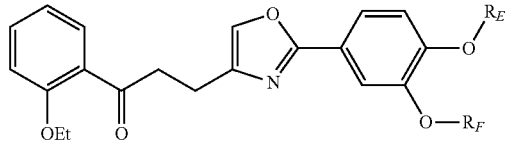

| Ex. No. | $R_E$ | $R_F$ |
|---|---|---|
| 313 | Methyl | Difluoromethyl |
| 314 | Methyl | 2,2-Difluoroethyl |
| 315 | Methyl | 2-Fluoro ethyl |
| 334 | Difluoromethyl | Ethyl |
| 335 | Difluoromethyl | Allyl |
| 336 | Difluoromethyl | Cyclopropylmethyl |
| 337 | Difluoromethyl | 3-Butenyl |
| 363 | H | Difluoromethyl |
| 364 | 3-Butenyl | Difluoromethyl |
| 365 | Allyl | Difluoromethyl |
| 366 | Ethyl | Difluoromethyl |
| 378 | Difluoromethyl | Difluoromethyl |

OEt: Ethoxy

TABLE 35

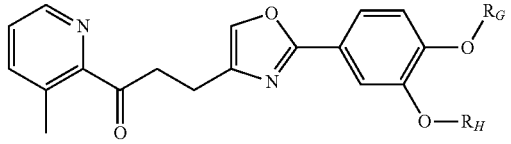

| Ex. No. | $R_G$ | $R_H$ |
|---|---|---|
| 308 | Methyl | Difluoromethyl |
| 309 | Methyl | 2,2-Difluoroethyl |
| 310 | Methyl | 2-Fluoroethyl |
| 311 | Methyl | sec-Butyl |
| 312 | Methyl | 1-Ethylpropyl |
| 317 | H | 2,2-Difluoroethyl |
| 318 | Ethyl | 2,2-Difluoroethyl |
| 319 | iso-Propyl | 2,2-Difluoroethyl |
| 327 | Difluoromethyl | H |
| 328 | Difluoromethyl | Cyclopropylmethyl |
| 329 | Difluoromethyl | n-Propyl |
| 330 | Difluoromethyl | Allyl |
| 331 | Difluoromethyl | 3-Butenyl |
| 332 | Difluoromethyl | iso-Propyl |
| 333 | Difluoromethyl | Ethyl |
| 356 | H | Difluoromethyl |
| 357 | iso-Propyl | Difluoromethyl |
| 358 | Allyl | Difluoromethyl |
| 359 | 3-Butenyl | Difluoromethyl |
| 360 | Cyclopropylmethyl | Difluoromethyl |
| 361 | n-Propyl | Difluoromethyl |
| 362 | Ethyl | Difluoromethyl |
| 381 | Difluoromethyl | Difluoromethyl |

TABLE 36

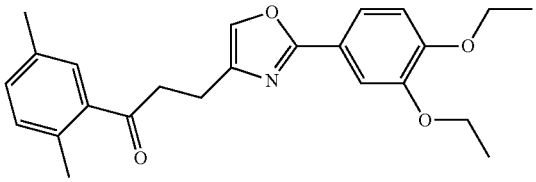

| Ex. No. | $R_I$ | $R_J$ | $R_K$ |
|---|---|---|---|
| 267 | Methyl | Benzyl | Difluoromethyl |
| 268 | Methyl | Benzyl | 2-Fluoroethyl |
| 269 | Methyl | Benzyl | 2,2-Difluoroethyl |
| 270 | Methyl | H | Difluoromethyl |
| 271 | Methyl | H | 2-Fluoroethyl |
| 272 | Methyl | H | 2,2-Difluoroethyl |
| 273 | Methyl | iso-Propyl | Difluoromethyl |
| 274 | Methyl | Ethyl | Difluoromethyl |
| 275 | Methyl | iso-Propyl | 2-Fluoroethyl |
| 276 | Methyl | 3-Butenyl | 2-Fluoroethyl |
| 277 | Methyl | iso-Butyl | 2-Fluoroethyl |
| 278 | Methyl | iso-Propyl | 2,2-Difluoroethyl |
| 279 | Methyl | n-Propyl | 2,2-Difluoroethyl |
| 280 | Methyl | Ethyl | 2,2-Difluoroethyl |
| 281 | Methyl | Allyl | 2,2-Difluoroethyl |
| 282 | Methyl | 3-Butenyl | 2,2-Difluoroethyl |
| 283 | Methyl | Cyclopropylmethyl | 2,2-Difluoroethyl |
| 284 | Methyl | 2,2-Difluoroethyl | 2,2-Difluoroethyl |
| 285 | Methyl | iso-Butyl | 2,2-Difluoroethyl |
| 288 | Ethyl | Ethyl | Difluoromethyl |
| 289 | Ethyl | Ethyl | 2-Fluoroethyl |
| 290 | Ethyl | Ethyl | 2,2-Difluoroethyl |
| 292 | Ethyl | Ethyl | Trifluoromethyl |
| 293 | Methyl | Cyclopropylmethyl | Trifluoromethyl |

TABLE 37

| Ex. No. | Chemical Structure |
|---|---|
| 266 | 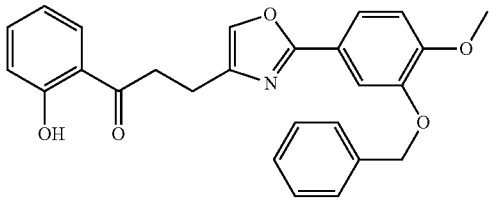 |
| 286 | 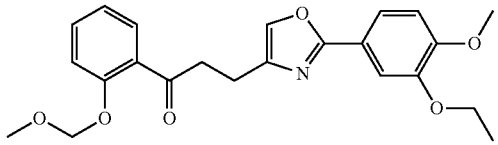 |
| 287 | 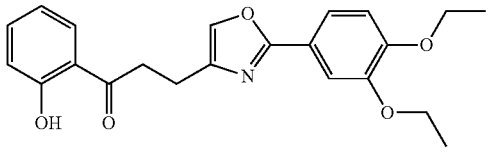 |

TABLE 37-continued
| Ex. No. | Chemical Structure |
|---|---|
| 291 | 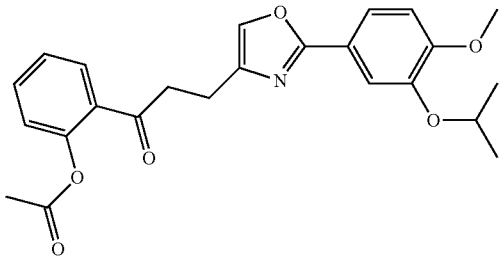 |
| 294 | 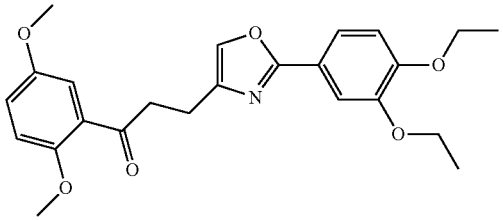 |
| 295 | 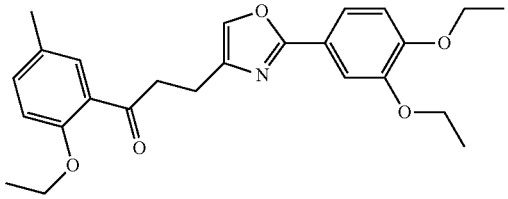 |
TABLE 38
| Ex. No. | Chemical Structure |
|---|---|
| 296 | 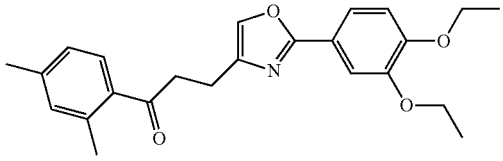 |
| 297 | 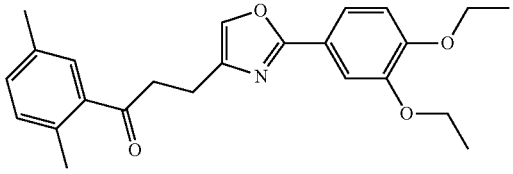 |
| 298 | 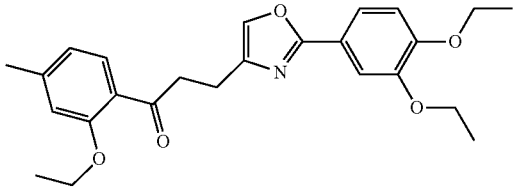 |
TABLE 38-continued
| Ex. No. | Chemical Structure |
|---|---|
| 299 | 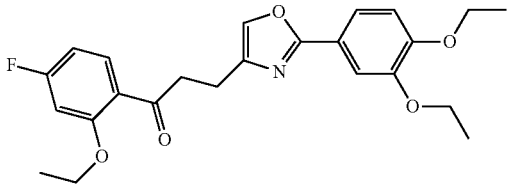 |
| 300 | 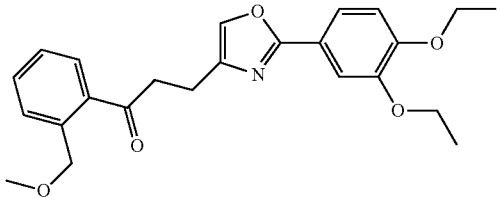 |
| 301 | 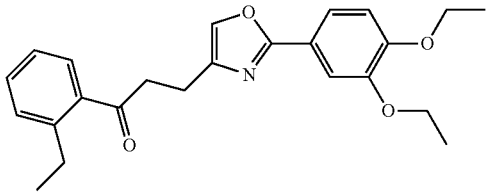 |
| 302 | 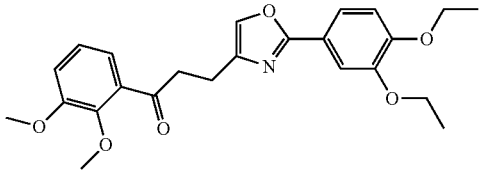 |
| 303 | 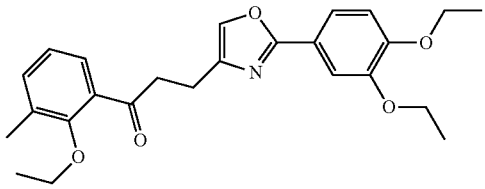 |
TABLE 39
| Ex. No. | Chemical Structure |
|---|---|
| 304 | 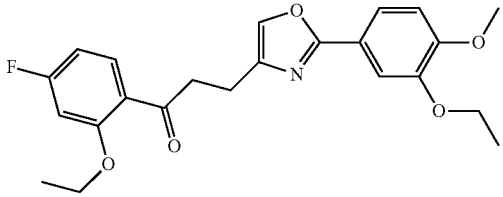 |
| 305 | 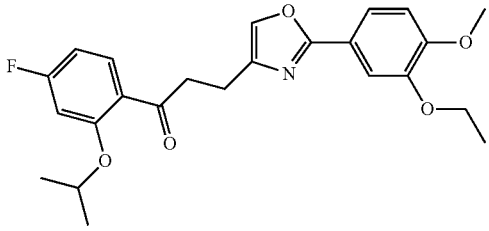 |

TABLE 39-continued

| Ex. No. | Chemical Structure |
|---|---|
| 306 | 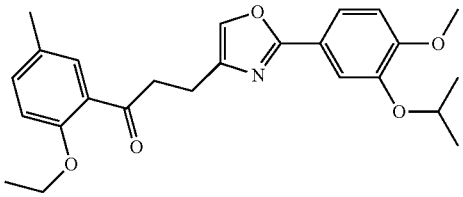 |
| 307 | 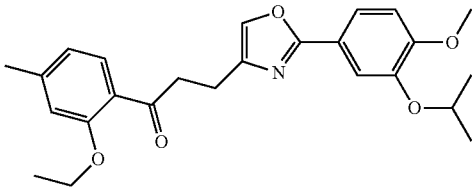 |
| 316 | 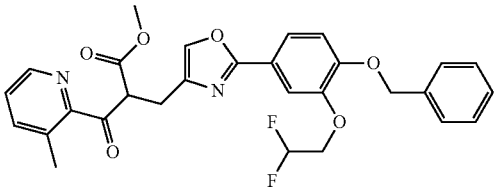 |
| 320 | 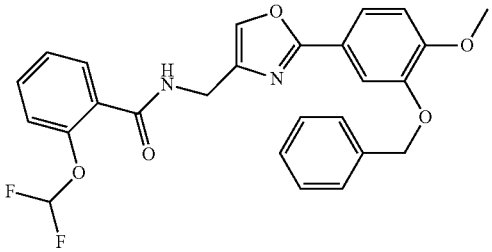 |
| 321 | 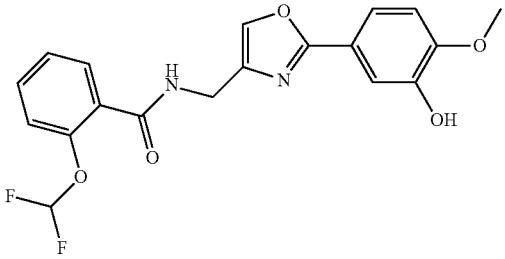 |

TABLE 40

| Ex. No. | Chemical Structure |
|---|---|
| 322 | 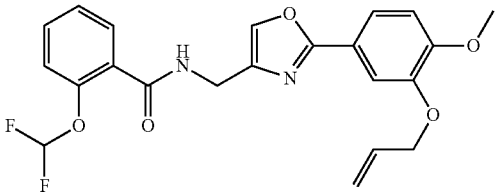 |

TABLE 40-continued

| Ex. No. | Chemical Structure |
|---|---|
| 323 | 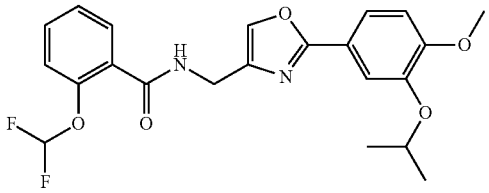 |
| 326 | 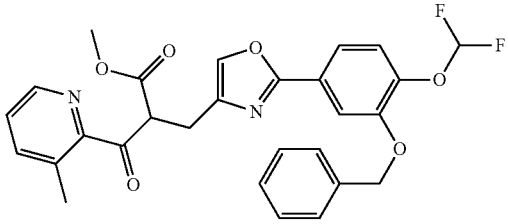 |

Test Example 1

Phosphodiesterase (PDE)4 Inhibitory Activity Evaluation Test (1) Large Scale Plasmid Preparation Plasmid containing genes (HPDE4D) coding for human PDE4D3 cDNA (stored in Otsuka America Pharmaceutical, Inc., Maryland Research Laboratories) was transformed in E. coli, cultured on a large scale, and purified using an EndoFree™ Plasmid Maxi Kit (Qiagen).

(2) Abundant Expression and Purification of PDE4D

COS-7 cells derived from African green monkey kidneys were passage cultured in D-MEM media containing 100 units/ml penicillin, 100 μg/ml streptomycin, and 10% FBS. The cells were transfected with the plasmid prepared in (1) above using Lipofectamine™ 2000 (hereinafter referred to as "LF2000", Invitrogen), following the manufacturer's protocol. The COS-7 cells were inoculated in a 10 cm culture dish on the previous day so as to be 90% confluent on the day of transfection. Culture dishes each containing a plasmid solution (solution A) in which 24 μg of plasmid was diluted in 1.5 ml Opti-MEM I Reduced Serum Medium (Invitrogen) and an LF2000 solution (solution B) in which 60 μl of LF2000 was diluted in 1.5 ml Opti-MEM I Reduced Serum Medium were separately allowed to stand for 5 minutes at room temperature. Solutions A and B were then mixed and the mixture was allowed to stand for 20 minutes at room temperature. The mixture was added to the cultured cells, and incubated at 37° C. (5% $CO_2$) overnight. On the following day, the medium was replaced, and the mixture was further incubated overnight to harvest the cells in the following manner. The cells were washed with PBS (Sigma) once, and 10 ml of a Trypsin-EDTA solution (Sigma) was added to each culture dish. After the solution was distributed to each of the culture dishes, the cells were detached, and the dishes were allowed to stand for about 5 minutes at 37° C. The detached cells from the dishes were suspended in media, collected into centrifuge tubes, and centrifuged at 1200 rpm for 5 minutes at 4° C., and supernatants were removed. The cells were further washed with PBS, and stored at −80° C. KHEM buffer (100 mM Hepes, 50 mM KCl, 10 mM EGTA, 1.92 mM $MgCl_2$, pH 7.4) containing 1 mM DTT, 1 μg/ml antipain, 1 μg/ml aprotinin, 1 μg/ml leupeptin, 1 μg/ml pepstatin A, 157 μg/ml benzamidine, and 120 μg/ml Pefabloc SC was added to the stored cells, and the contents were moved to a glass homogenizer to be homogenized on ice. The cell suspension was centrifuged at 1000 rpm for 5 minutes at 4° C., and the supernatant was further centrifuged at 14000 rpm for one hour. After centrifugation, the supernatant was dispensed into new tubes as PDE4D enzyme solutions, and stored in a deep freezer.

(3) Determination on Dilution Ratio of PDE4D Enzyme Solutions

The PDE4D enzyme solutions prepared in (2) above were dissolved in 20 mM Tris-HCl solution (pH 7.4) to give 10-, 25-, 50-, 100-, 200-, 400-, and 800-fold dilutions of the enzyme solutions. PDE4D activities were measured according to (4) below. The percentage of catalyzed cAMP to total cAMP was calculated, and such a dilution, in which the percentage was between 10% and 30%, was adopted in the inhibitory study below.

(4) Measurement of PDE4D Inhibitory Activity

Necessary amounts of test compounds were weighed, and 100% dimethylsulfoxide (DMSO) was added thereto to adjust the concentration to 10 mM. The solutions were stored in a freezer as stock solutions of each test compound. After being thawed when required, the solutions were diluted 20-fold with 100% DMSO to give a 500 μM concentration. Further, 10-fold serial dilutions were made with 100% DMSO to prepare test compounds of different concentrations. 2 μl of solutions containing one of each of the test compound were separately added into 1.2 ml tubes in which 23 μl of 20 mM Tris-HCl (pH 7.4) had been placed beforehand. 25 μl of a PDE4D enzyme solution diluted at an optimal ratio determined in (3) above were added on ice to each of the tubes, and 50 μl of a substrate solution containing 2 μM[$^3$H] cAMP prepared by dilution with a 20 mM Tris-HCl (pH 7.4) containing 10 mM $MgCl_2$ was added thereto. The final DMSO concentration in the reaction liquid was 2%. After mixing, the mixture was incubated for 10 minutes at 30° C. At the completion of the incubation, the tubes were placed in a bath containing boiling water for 3 minutes, and the reaction was stopped. After cooling the tubes in ice, 25 μl solution of 0.2 mg/ml snake venom was added thereto, and after mixing the mixture was incubated for 10 minutes at 30° C. At the completion of the incubation, 0.4 ml of a Dowex 1×8 resin solution prepared in an EtOH:$H_2O$ (1:1) solution was added thereto. After mixing, the tubes were allowed to stand at room temperature for at least an hour. 50 μl of the supernatant in one of each of the tubes was moved to one of the wells of a topcount plate, and the plate was dried overnight. $^3$H radioactivity (cpm) was measured using a TopCount™.

The $IC_{50}$ values (concentration which produced 50% inhibition of substrate hydrolysis) for the test compounds were determined with the Excel (Microsoft Excel 2000 SR-1) statistical package using regression analysis function.

The results are shown in Table 41. The table demonstrates that compounds represented by formula (1) have the outstanding PDE4 inhibitory activities.

In the structural formulae shown in the following table, -Me is a methyl group, -Et is an ethyl group, —OMe is a methoxy group, —OEt is an ethoxy group, and —SMe is a methylthio group.

TABLE 41

| Ex. No. | Chemical Structure | PDE 4 ($IC_{50}$: nM) |
|---|---|---|
| 3 | 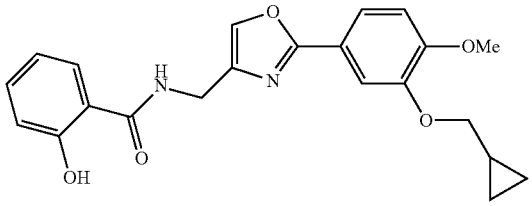 | <50 |
| 14 | 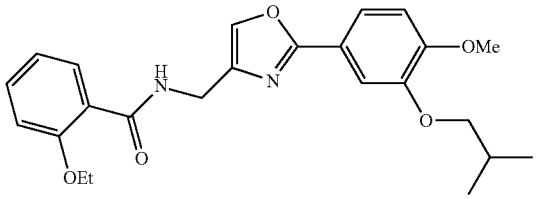 | <50 |
| 18 | 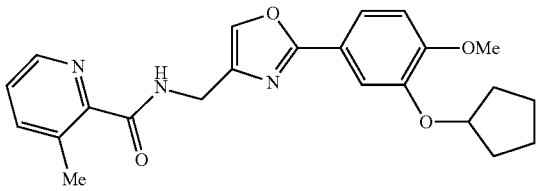 | <50 |

TABLE 41-continued
| Ex. No. | Chemical Structure | PDE 4 ($IC_{50}$: nM) |
|---|---|---|
| 19 | 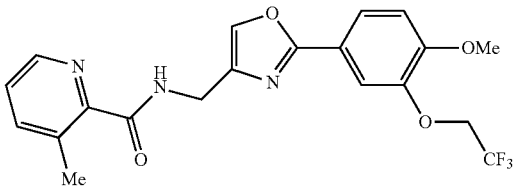 | <50 |
| 21 | 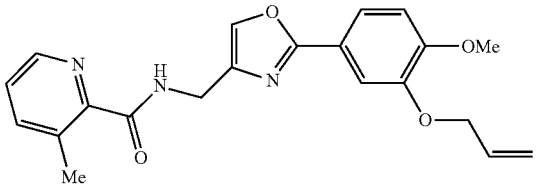 | <50 |
| 22 | 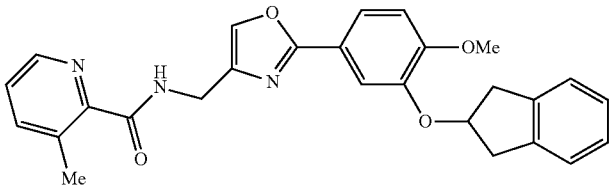 | <50 |
| 29 | 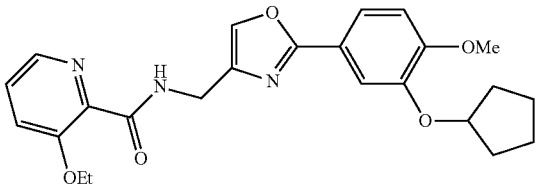 | <50 |
| 32 | 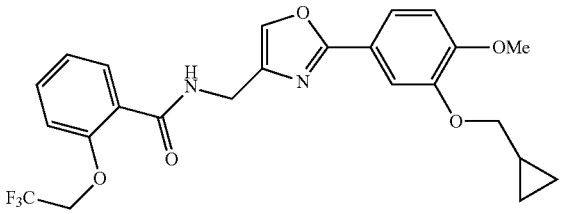 | <50 |
| 35 | 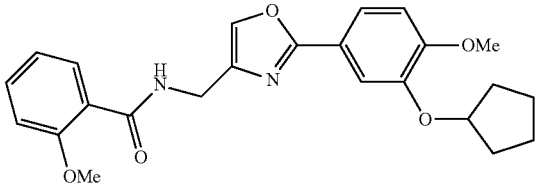 | <50 |
| 36 | 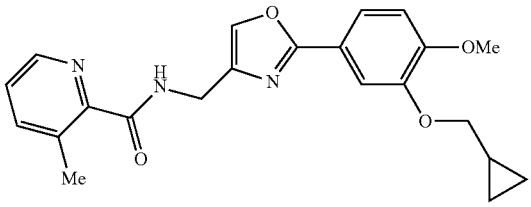 | <50 |

TABLE 41-continued
| Ex. No. | Chemical Structure | PDE 4 ($IC_{50}$: nM) |
|---|---|---|
| 42 | 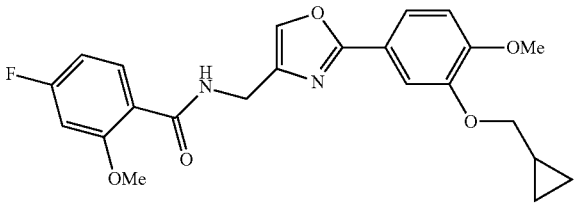 | <50 |
| 43 | 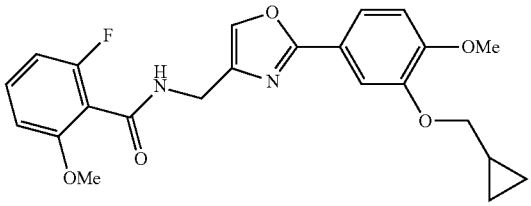 | <50 |
| 44 | 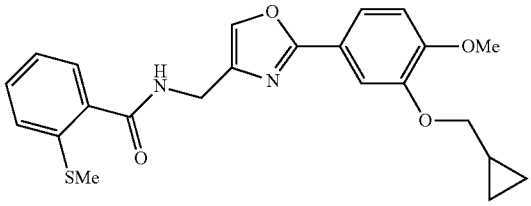 | <50 |
| 61 | 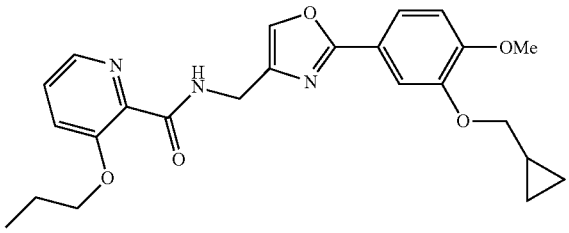 | <50 |
| 62 | 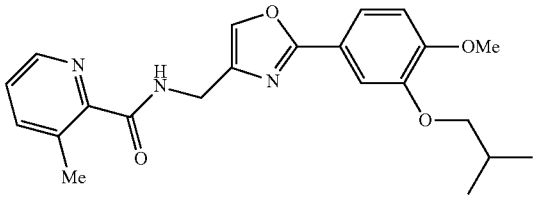 | <50 |
| 63 | 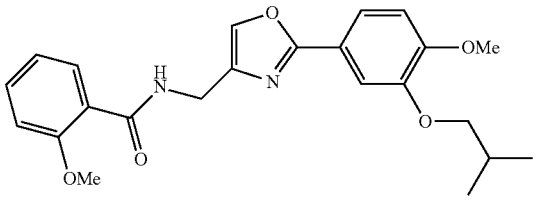 | <50 |
| 76 | 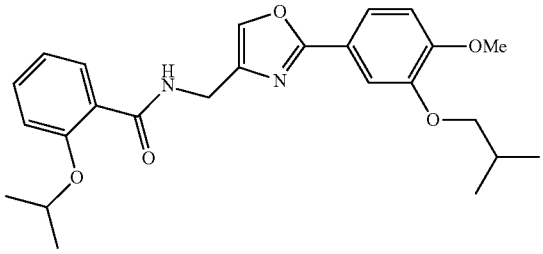 | <50 |

TABLE 41-continued
| Ex. No. | Chemical Structure | PDE 4 ($IC_{50}$: nM) |
|---|---|---|
| 98 | 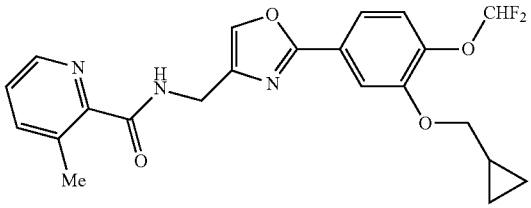 | <50 |
| 99 | 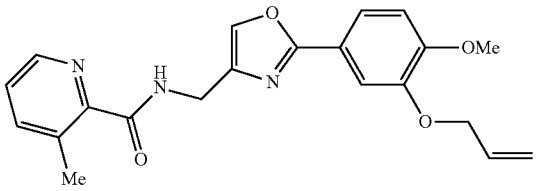 | <50 |
| 102 | 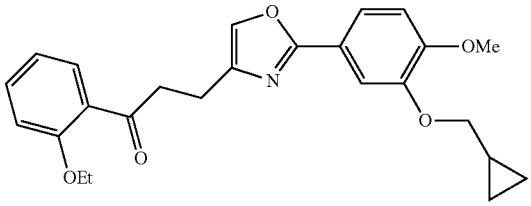 | <50 |
| 103 | 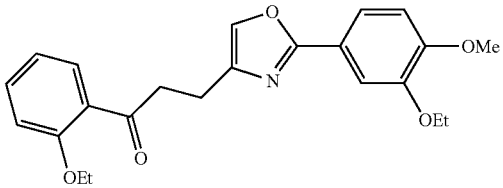 | <50 |
| 104 | 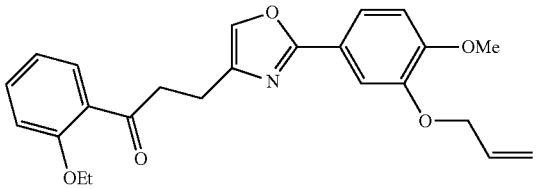 | <50 |
| 108 | 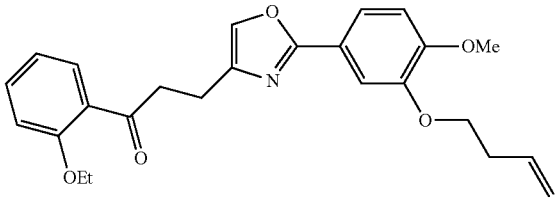 | <50 |
| 111 | 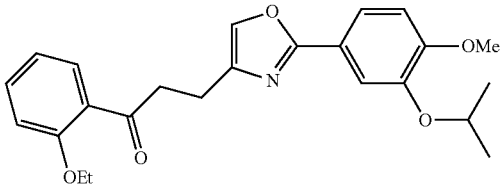 | <50 |

TABLE 41-continued
| Ex. No. | Chemical Structure | PDE 4 ($IC_{50}$: nM) |
|---|---|---|
| 112 | 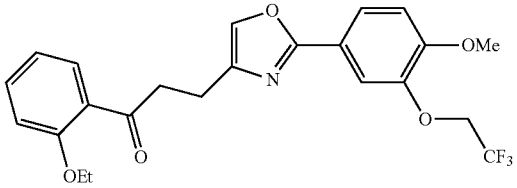 | <50 |
| 116 | 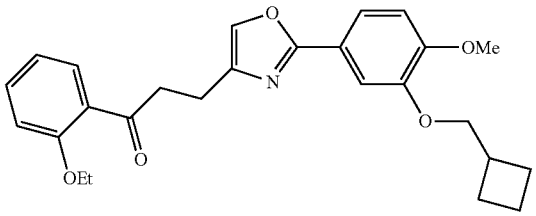 | <50 |
| 126 | 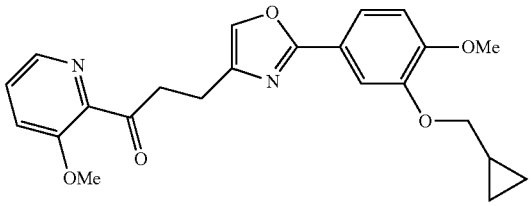 | <50 |
| 129 | 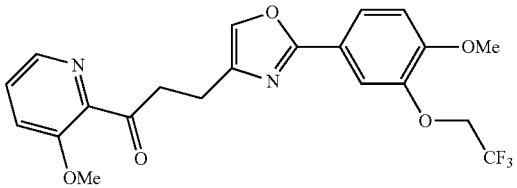 | <50 |
| 132 | 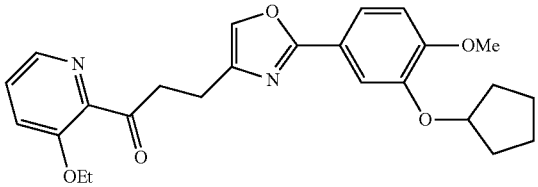 | <50 |
| 133 | 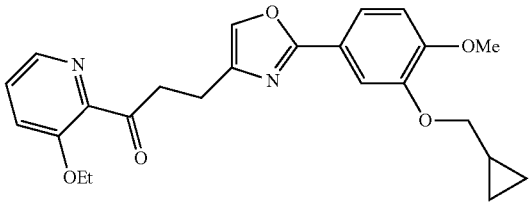 | <50 |
| 137 | 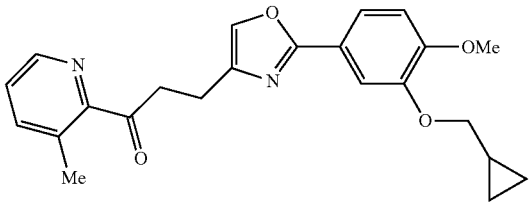 | <50 |

TABLE 41-continued
| Ex. No. | Chemical Structure | PDE 4 ($IC_{50}$: nM) |
|---|---|---|
| 138 | 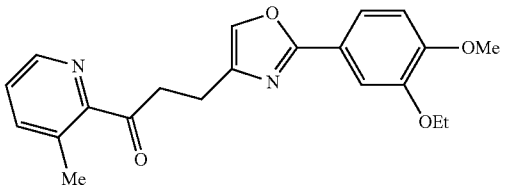 | <50 |
| 139 | 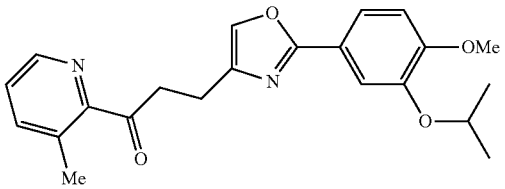 | <50 |
| 140 | 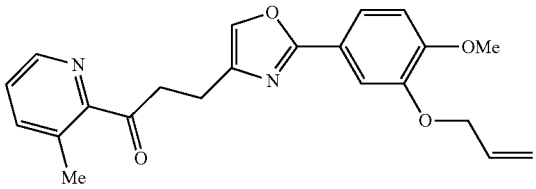 | <50 |
| 141 | 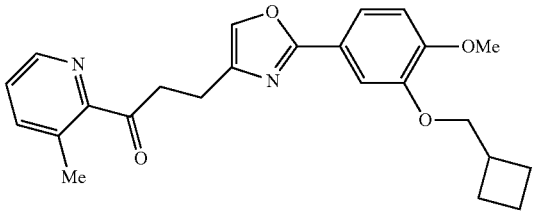 | <50 |
| 143 | 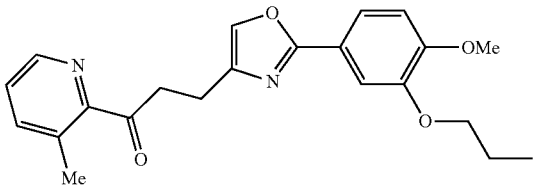 | <50 |
| 146 | 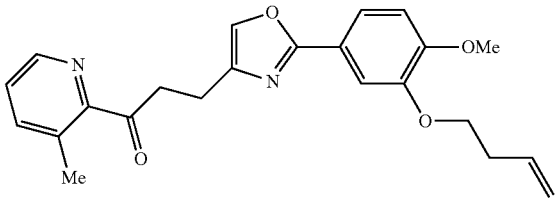 | <50 |
| 153 | 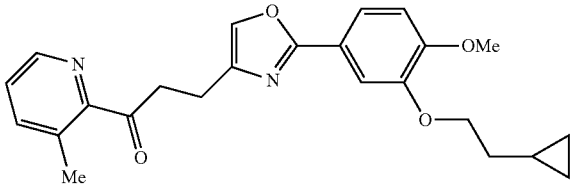 | <50 |

TABLE 41-continued
| Ex. No. | Chemical Structure | PDE 4 ($IC_{50}$: nM) |
|---|---|---|
| 155 | 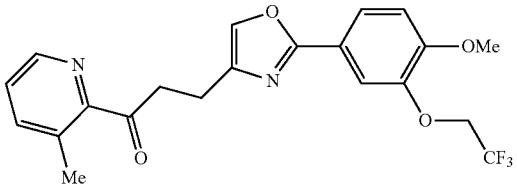 | <50 |
| 157 | 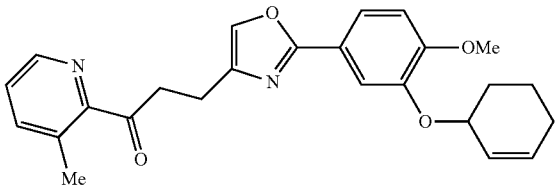 | <50 |
| 159 | 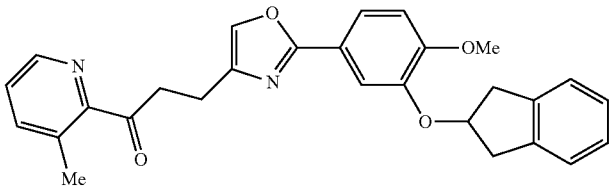 | <50 |
| 166 | 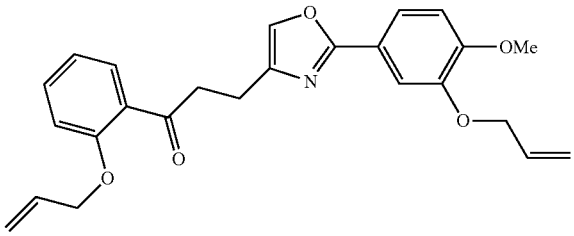 | <50 |
| 169 | 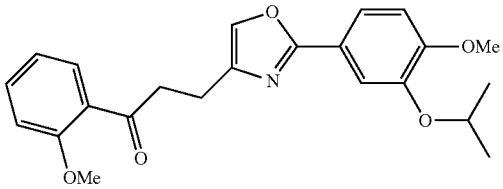 | <50 |
| 170 | 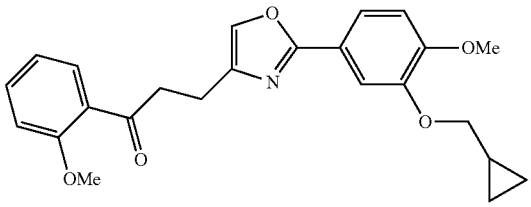 | <50 |
| 172 | 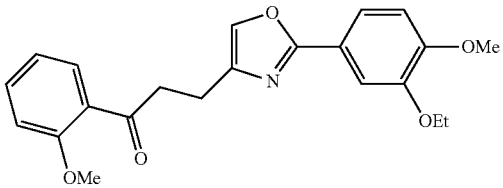 | <50 |

TABLE 41-continued
| Ex. No. | Chemical Structure | PDE 4 ($IC_{50}$: nM) |
|---|---|---|
| 174 | 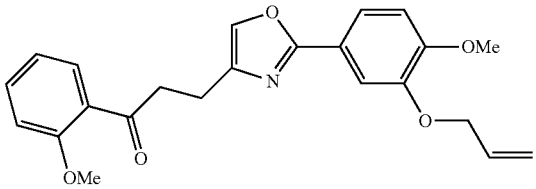 | <50 |
| 177 | 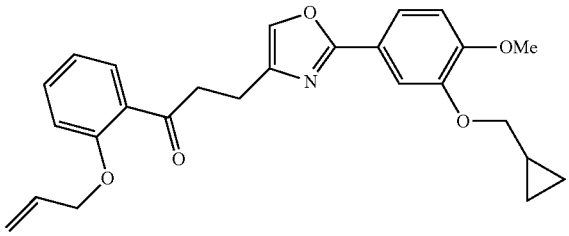 | <50 |
| 181 | 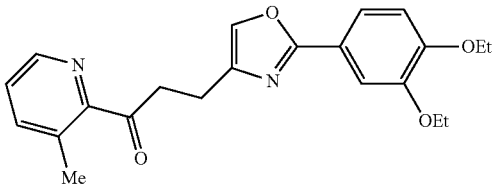 | <50 |
| 182 | 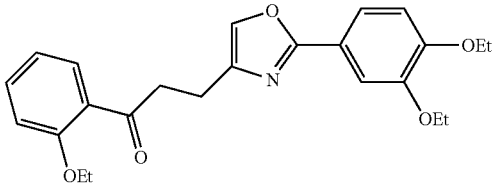 | <50 |
| 195 | 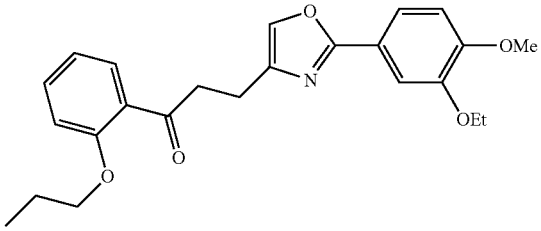 | <50 |
| 208 | 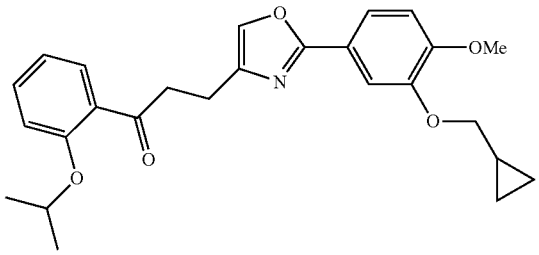 | <50 |
| 224 | 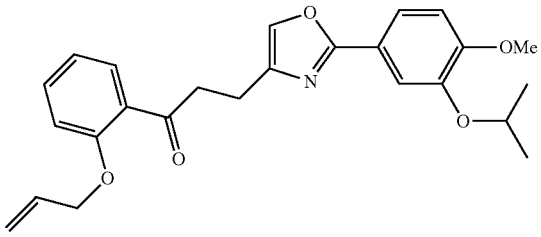 | <50 |

TABLE 41-continued
| Ex. No. | Chemical Structure | PDE 4 ($IC_{50}$: nM) |
|---|---|---|
| 232 | 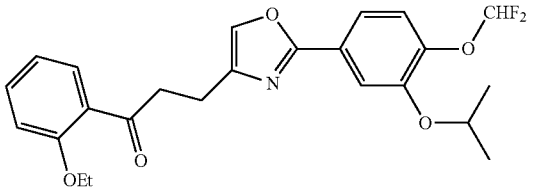 | <50 |
| 274 | 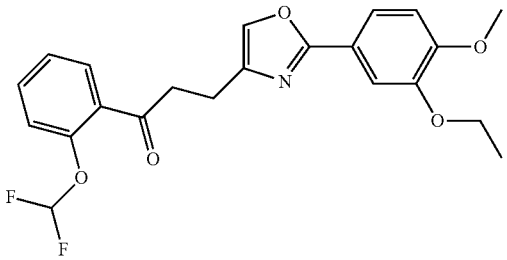 | <50 |
| 275 | 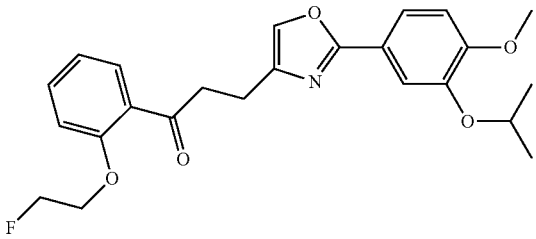 | <50 |
| 276 | 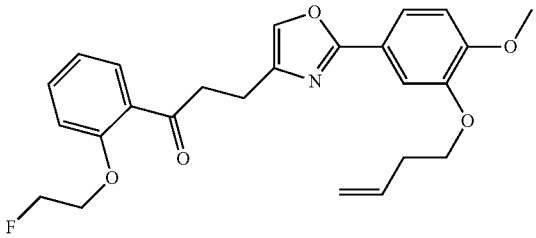 | <50 |
| 278 | 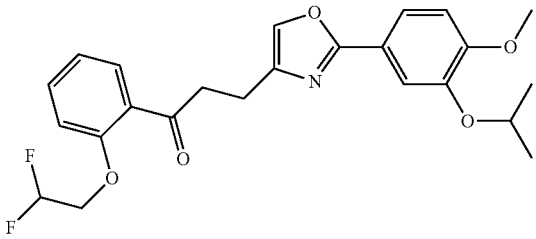 | <50 |
| 280 | 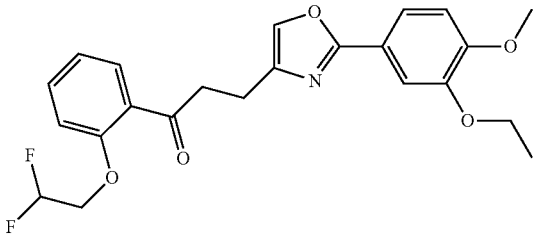 | <50 |

TABLE 41-continued
| Ex. No. | Chemical Structure | PDE 4 ($IC_{50}$: nM) |
|---|---|---|
| 281 | 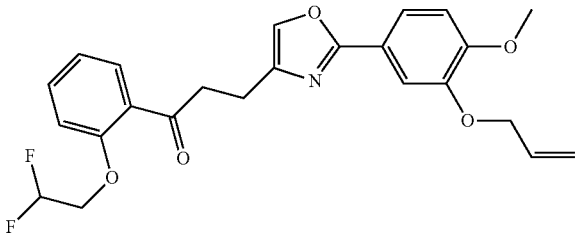 | <50 |
| 283 | 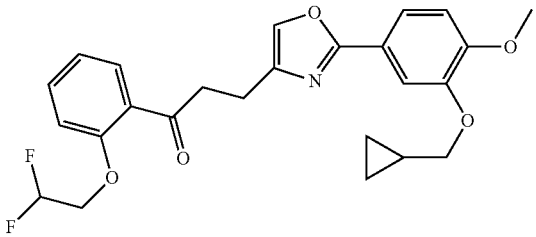 | <50 |
| 284 | 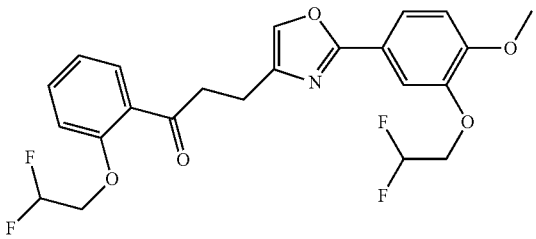 | <50 |
| 285 | 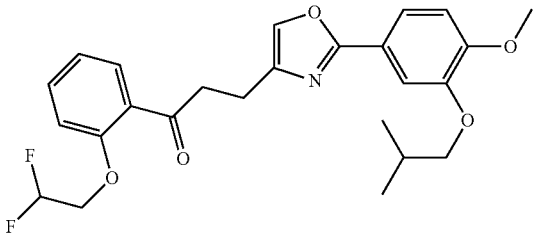 | <50 |
| 289 | 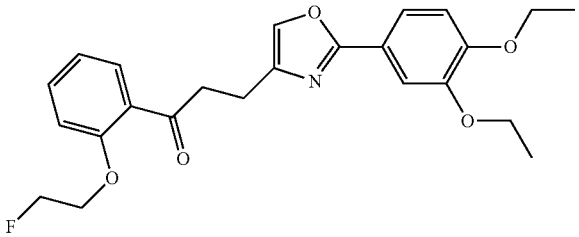 | <50 |
| 290 | 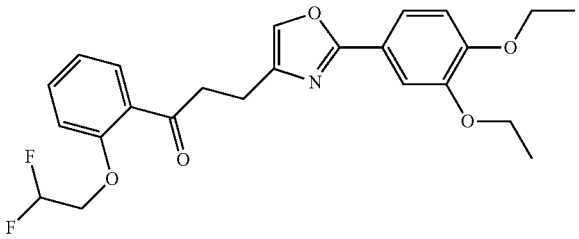 | <50 |

TABLE 41-continued
| Ex. No. | Chemical Structure | PDE 4 ($IC_{50}$: nM) |
|---|---|---|
| 299 | 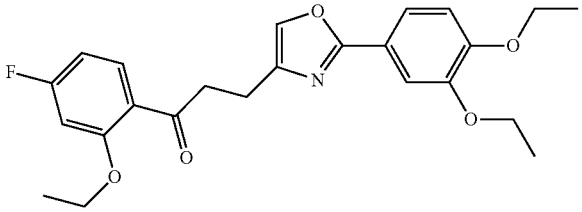 | <50 |
| 304 | 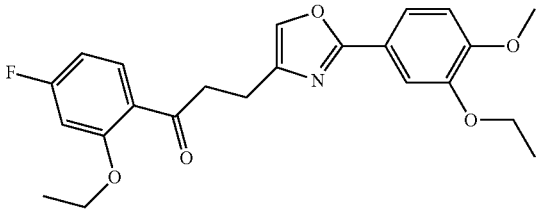 | <50 |
| 305 | 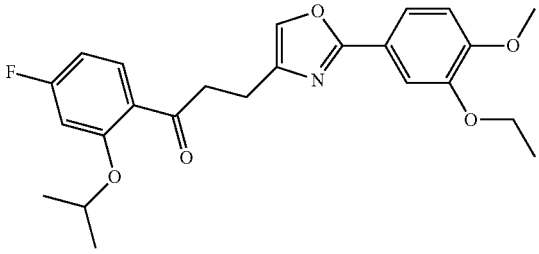 | <50 |
| 309 | 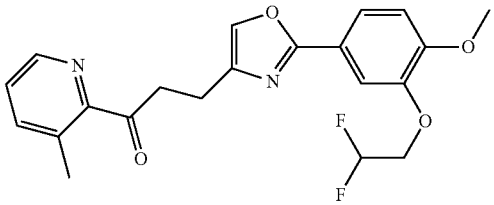 | <50 |
| 311 | 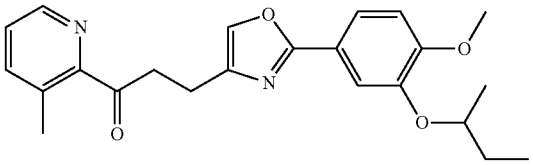 | <50 |
| 312 | 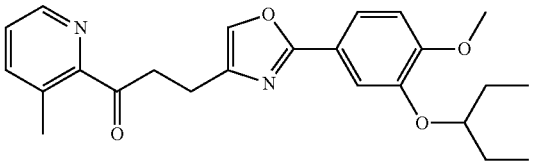 | <50 |
| 314 | 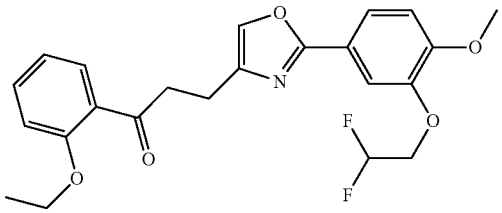 | <50 |

TABLE 41-continued
| Ex. No. | Chemical Structure | PDE 4 ($IC_{50}$: nM) |
|---|---|---|
| 315 | 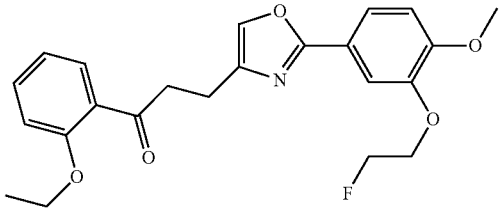 | <50 |
| 318 | 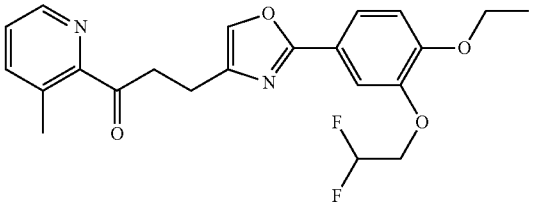 | <50 |
| 324 | 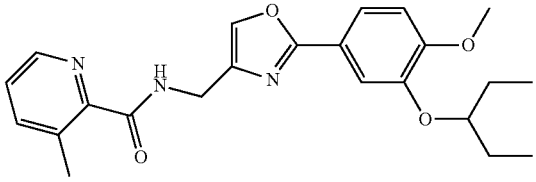 | <50 |
| 328 | 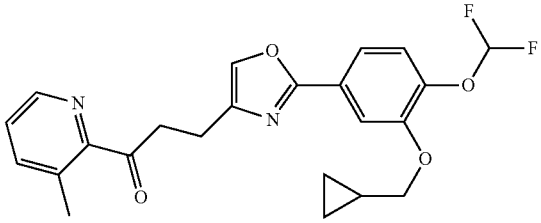 | <50 |
| 329 | 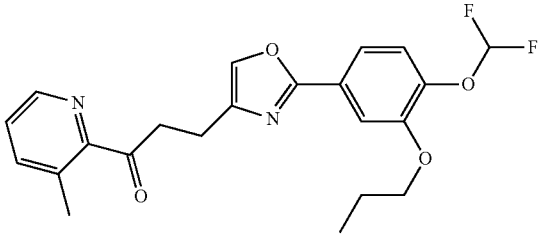 | <50 |
| 330 | 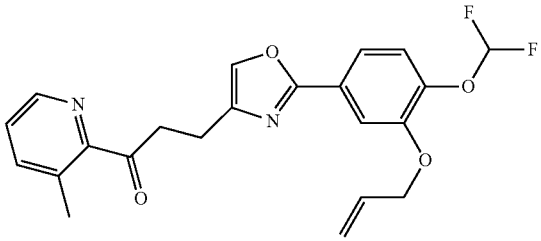 | <50 |

TABLE 41-continued
| Ex. No. | Chemical Structure | PDE 4 ($IC_{50}$: nM) |
|---|---|---|
| 331 | 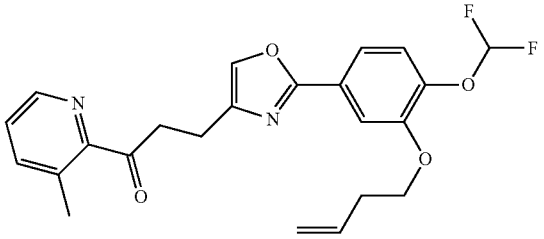 | <50 |
| 332 | 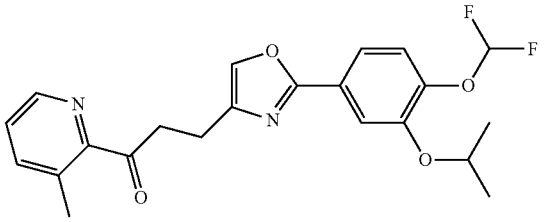 | <50 |
| 333 | 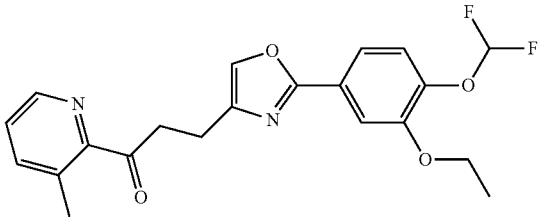 | <50 |
| 334 | 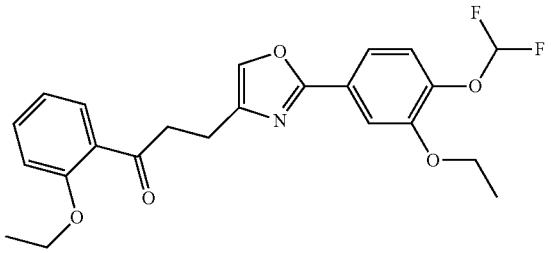 | <50 |
| 335 | 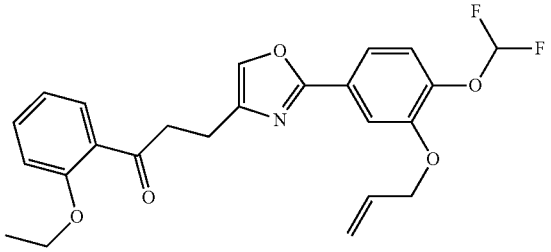 | <50 |
| 336 | 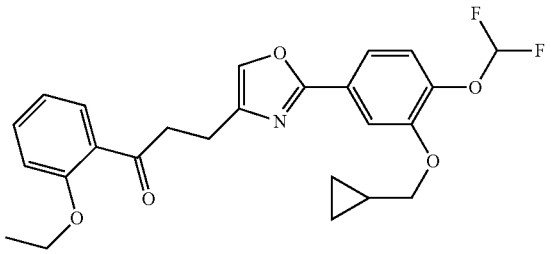 | <50 |

TABLE 41-continued
| Ex. No. | Chemical Structure | PDE 4 ($IC_{50}$: nM) |
|---|---|---|
| 337 | 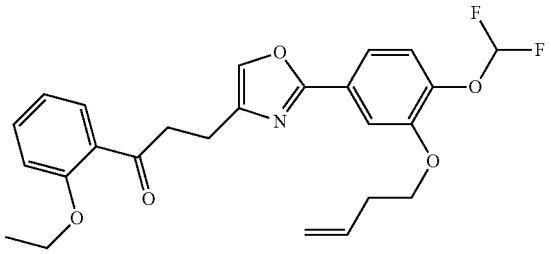 | <50 |
| 338 | 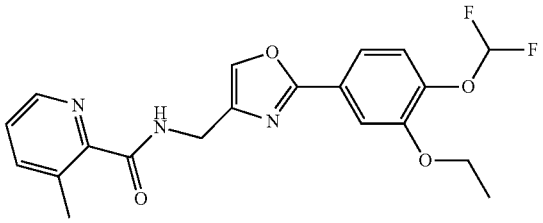 | <50 |
| 339 | 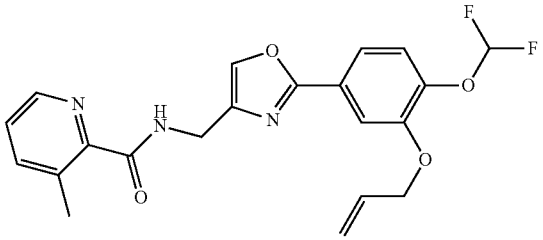 | <50 |
| 340 | 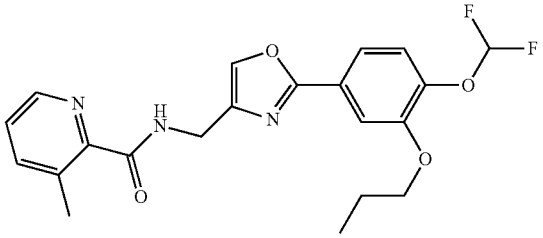 | <50 |
| 341 | 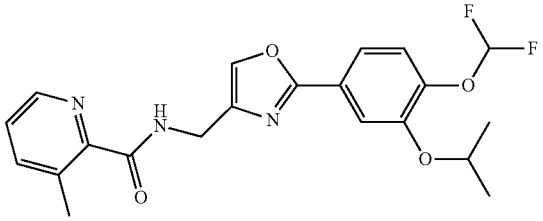 | <50 |
| 342 | 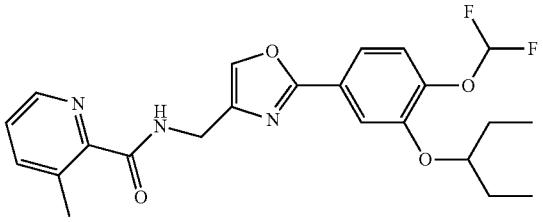 | <50 |

TABLE 41-continued
| Ex. No. | Chemical Structure | PDE 4 ($IC_{50}$: nM) |
|---|---|---|
| 343 | 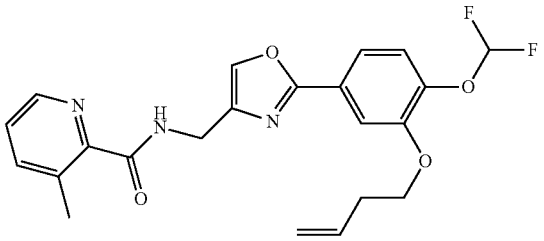 | <50 |
| 344 | 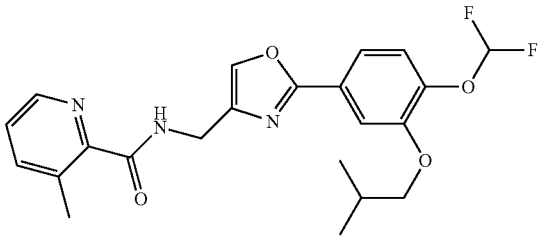 | <50 |
| 345 | 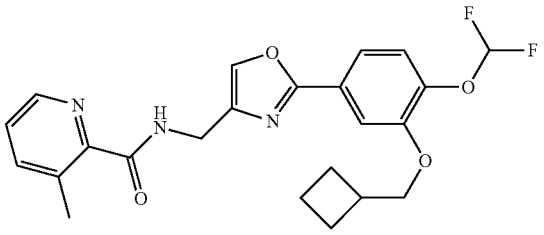 | <50 |
| 348 | 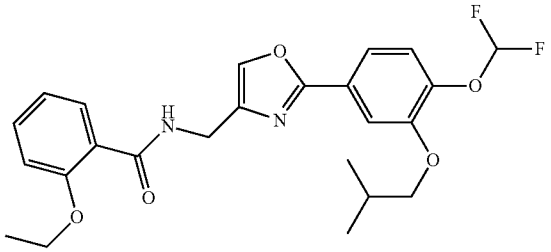 | <50 |
| 349 | 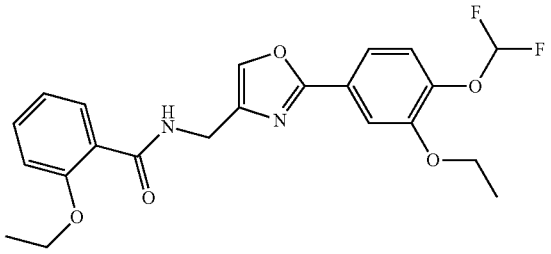 | <50 |
| 350 | 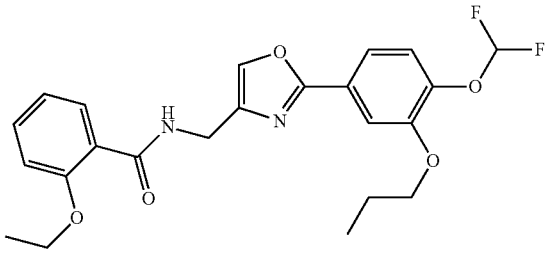 | <50 |

TABLE 41-continued
| Ex. No. | Chemical Structure | PDE 4 ($IC_{50}$: nM) |
|---|---|---|
| 351 | 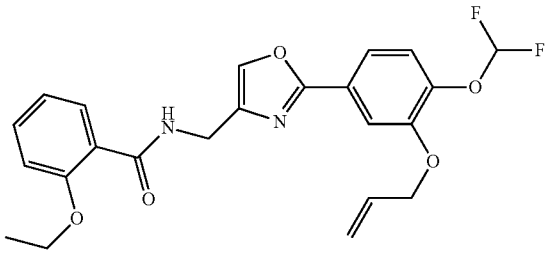 | <50 |
| 352 | 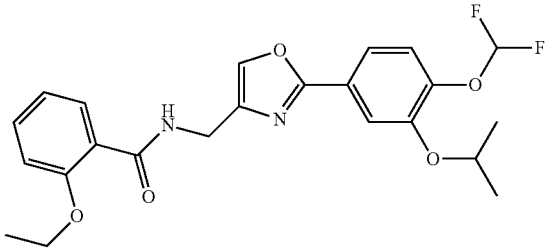 | <50 |
| 353 | 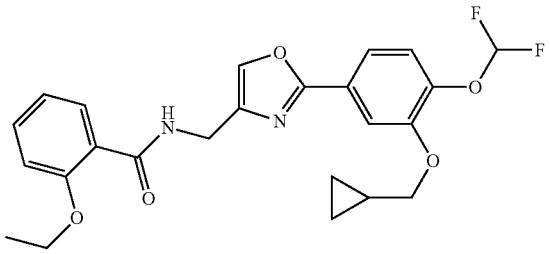 | <50 |
| 354 | 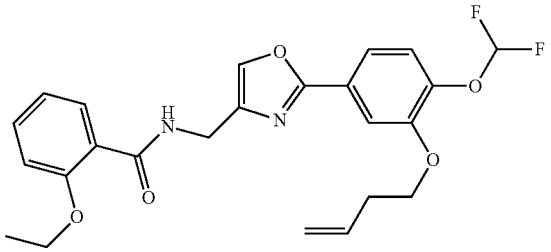 | <50 |
| 355 | 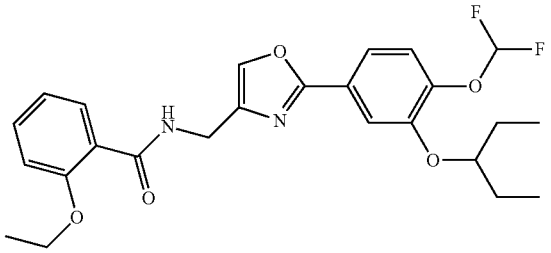 | <50 |
| 382 | 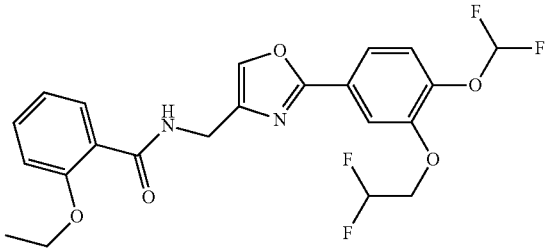 | <50 |

TABLE 41-continued

| Ex. No. | Chemical Structure | PDE 4 ($IC_{50}$: nM) |
|---|---|---|
| 383 | 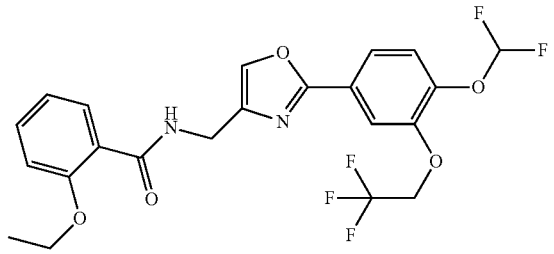 | <50 |
| 384 | 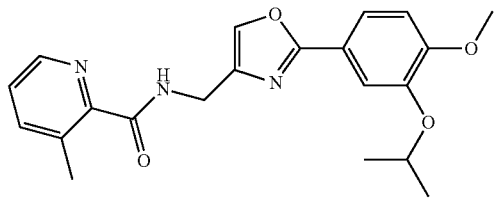 | <50 |

Test Example 2

Inhibitory Activity Measurement on TNF-α Production

TNF-α production inhibitory activity was evaluated according to the following tests.

(1) Isolation of Mononuclear Cells from Mouse Peripheral Blood

Mononuclear cells were isolated from heparinized blood obtained from male BALB/c mice (Charles River Laboratories, Japan) by density gradient centrifugation using Lympholyte-M (Cedarlane Laboratories). Viable cell numbers in the peripheral blood mononuclear cells were counted using trypan blue dye, and prepared in cell culture medium (RPMI 1640 medium containing 10% FCS) to $1.25\times10^6$ cells/ml.

(2) Induction of TNF-α Production

Test compounds were dissolved in DMSO, and test compound solutions were diluted for use in cell culture media. 20 μl test compound solutions of different concentrations and 160 μl peripheral blood mononuclear cell suspensions were placed in a 96-well plate, and cultured for 30 minutes. 20 μl (final concentration 1 μg/ml) lipopolysaccharide (LPS) derived from E. coli (serotype 055:B5) was added thereto to induce THF-α production. The mixtures were then cultured at 37° C. for 5 hours, and the culture supernatant was removed from each well.

(3) Measurement of TNF-α Concentration

TNF-α concentrations in the culture supernatants were measured by ELISA (OptEIA™ Set Mouse TNF-α, BD Pharmingen). The $IC_{50}$ values (concentration which produced 50% inhibition of TNF-α production) for the test compounds were determined with the Excel (Microsoft Excel 2000 SR-1) statistical package using regression analysis function.

The results obtained are shown in table 42.

TABLE 42

| Test compounds | TNF-α ($IC_{50}$: nM) |
|---|---|
| Compound of Ex. 18 | <50 |
| Compound of Ex. 43 | <50 |
| Compound of Ex. 126 | <50 |

TABLE 42-continued

| Test compounds | TNF-α ($IC_{50}$: nM) |
|---|---|
| Compound of Ex. 157 | <50 |
| Compound of Ex. 177 | <50 |

The invention claimed is:

1. An oxazole compound represented by Formula (1)

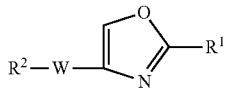

(1)

wherein $R^1$ is an aryl group which may have one or more substituents selected from the following (1-1) to (1-11):

(1-1) hydroxy groups, (1-2) unsubstituted or halogen-substituted lower alkoxy groups, (1-3) lower alkenyloxy groups, (1-4) lower alkynyloxy groups, (1-5) cyclo $C_{3-8}$ alkyl lower alkoxy groups, (1-6) cyclo $C_{3-8}$ alkyloxy groups, (1-7) cyclo $C_{3-8}$ alkenyloxy groups, (1-8) dihydroindenyloxy groups, (1-9) hydroxy lower alkoxy groups, (1-10) oxiranyl lower alkoxy groups, and (1-11) protected hydroxy groups;

$R^2$ is an aryl group or a nitrogen atom-containing heterocyclic group each of which may have one or more substituents selected from the following (2-1) to (2-10):

(2-1) hydroxy groups, (2-2) unsubstituted or halogen-substituted lower alkoxy groups, (2-3) unsubstituted lower alkyl groups, (2-4) lower alkenyloxy groups, (2-5) halogen atoms, (2-6) lower alkanoyl groups other than a formyl group, (2-7) lower alkylthio groups, (2-8) lower alkylsulfonyl groups, (2-9) oxo groups, and (2-10) lower alkoxy lower alkoxy groups; and the nitrogen atom-containing heterocyclic group in $R^2$ is selected from imidazolidinyl, hexahydropyrimidinyl, piperazinyl, octahydroisoindolyl, azocanyl, pyrrolyl, dihydropyrrolyl, imidazolyl, dihydroimidazolyl, triazolyl, dihydrotriazolyl, pyrazolyl, pyridyl and N-oxides thereof, dihydropyridyl, pyrimidinyl, dihydropyrimidinyl, pyrazinyl, dihydropyrazinyl, pyridazinyl, tetrazolyl, indolyl, isoindolyl, indolinyl, isoindolinyl, hexahydroisoindolinyl, benzoimidazolyl, quinolyl, isoquinolyl, indazolyl, quinazolinyl, dihydroquinazolinyl, benzotriazolyl, carbazolyl, oxazolyl, isooxazolyl, oxadiazolyl, oxazolidinyl, isooxazolidinyl, dihydrobenzoxazolyl, benzoxazinyl, dihydrobenzoxazinyl, benzoxazolyl, benzooxadiazolyl, thiazolyl, dihydrothiazolyl, isothiazolyl, thiadiazolyl, dihydrothiazinyl, thiazolyzinyl, benzothiazolyl, and benzothiadiazolyl; and W is a divalent group represented by Formula (i) or (ii):

$$—Y^1\text{-}A^1\text{-} \qquad \text{Formula (i)}$$

$$—Y^2—C(=O)— \qquad \text{Formula (ii)}$$

wherein $A^1$ is a lower alkenylene group, or a lower alkylene group which may have one or more substituents selected from the group consisting of hydroxy groups and lower alkoxycarbonyl groups, $Y^1$ is —C(=O)—, —C(=O)—N($R^3$)—, —S(O)$_m$—NH—, or —S(O)$_n$— wherein $R^3$ is a hydrogen atom or a lower alkyl group, and m and n are each independently an integer from 0 to 2, and $Y^2$ is a piperazinediyl group, or a divalent group represented by Formula (iii):

$$—C(=O)\text{-}A^2\text{-}N(R^5)— \qquad \text{Formula (iii)}$$

wherein $A^2$ is a lower alkylene group, and $R^5$ is a hydrogen atom or a lower alkyl group;

or a pharmaceutically acceptable salt thereof.

2. The compound according to claim 1, wherein $R^1$ is a phenyl group which has 1 to 3 substituents selected from the following (1-2), (1-3), (1-4) and (1-5):

(1-2) unsubstituted or halogen-substituted lower alkoxy groups, (1-3) lower alkenyloxy groups, (1-4) lower alkynyloxy groups, and (1-5) cyclo $C_{3-8}$ alkyl lower alkoxy groups;

$R^2$ is a phenyl group or a pyridyl group each of which may have 1 to 3 substituents selected from the group consisting of the following (2-2), (2-3), (2-4) and (2-5):

(2-2) unsubstituted or halogen-substituted lower alkoxy groups, (2-3) unsubstituted lower alkyl groups, (2-4) lower alkenyloxy groups, and (2-5) halogen atoms;

W is a divalent group represented by Formula (i):

$$—Y^1\text{-}A^1\text{-} \qquad \text{Formula (i)}$$

wherein $A^1$ is a lower alkylene group, and $Y^1$ is —C(=O)— or —*C(=O)—N($R^3$)*— wherein $R^3$ is a hydrogen atom.

3. The compound according to claim 2, wherein $R^1$ is a phenyl group having two substituents selected from the following (1-2), (1-3), (1-4) and (1-5):

(1-2) unsubstituted or halogen-substituted lower alkoxy groups, (1-3) lower alkenyloxy groups, (1-4) lower alkynyloxy groups, and (1-5) cyclo $C_{3-8}$ alkyl lower alkoxy groups;

$R^2$ is a phenyl group or a pyridyl group each of which may have 1 to 2 substituents selected from the following (2-2), (2-3), (2-4) and (2-5):

(2-2) unsubstituted or halogen-substituted lower alkoxy groups, (2-3) unsubstituted lower alkyl groups, (2-4) lower alkenyloxy groups, and (2-5) halogen atoms; and W is a divalent group represented by Formula (i):

$$—Y^1\text{-}A^1\text{-} \qquad \text{Formula (i)}$$

wherein $A^1$ is a lower alkylene group, and $Y^1$ is [—C(O)—] —*C(=O)*— or —C(=O)—N($R^3$)— wherein $R^3$ is a hydrogen atom.

4. The compound according to claim 3, wherein $R^1$ is a phenyl group substituted on the phenyl ring with two lower alkoxy groups, a phenyl group substituted on the phenyl ring with one lower alkoxy group and one cyclo [$C_{3-8}$,] *$C_{3-8}$* alkyl lower alkoxy group, a phenyl group substituted on the phenyl ring with one lower alkoxy group and one halogen-substituted lower alkoxy group, a phenyl group substituted on the phenyl group with one lower alkoxy group and one lower alkenyloxy group, a phenyl group substituted on the phenyl ring with one halogen-substituted lower alkoxy group and one cyclo $C_{3-8}$ alkyl lower alkoxy group, a phenyl group substituted on the phenyl ring with one halogen-substituted lower alkoxy group and one lower alkenyloxy group, or a phenyl group substituted on the phenyl ring with two halogen-substituted lower alkoxy groups;

$R^2$ is a lower alkoxyphenyl group, a lower alkenyloxyphenyl group, a halogen-substituted lower alkoxyphenyl group, a lower alkylpyridyl group, or a phenyl group substituted on the phenyl ring with one lower alkoxy group and one halogen atom; and W is a divalent group represented by Formula (i):

$$—Y^1\text{-}A^1\text{-} \qquad \text{Formula (i)}$$

wherein $A^1$ is a $C_{1-4}$ alkylene group, and $Y^1$ is —C(=O)— or —C(=O)—N($R^3$)— wherein $R^3$ is a hydrogen atom.

5. The compound according to claim 4, wherein $R^1$ is a phenyl group substituted on the phenyl ring with two lower alkoxy groups, a phenyl group substituted on the phenyl ring with one lower alkoxy group and one cyclo $C_{3-8}$ alkyl lower alkoxy group, a phenyl group substituted on the phenyl ring with one lower alkoxy group and one halogen-substituted lower alkoxy group, a phenyl group substituted on the phenyl group with one lower alkoxy group and one lower alkenyloxy group, a phenyl group substituted on the phenyl ring with one halogen-substituted lower alkoxy group and one cyclo $C_{3-8}$ alkyl lower alkoxy group, a phenyl group substituted on the phenyl ring with one halogen-substituted lower alkoxy group and one lower alkenyloxy group, or a phenyl group substituted on the phenyl ring with two halogen-substituted lower alkoxy groups;

$R^2$ is a lower alkoxyphenyl group, a lower alkenyloxy phenyl group, a halogen-substituted lower alkoxyphenyl group, a lower alkylpyridyl group, or a phenyl group substituted on the phenyl ring with one lower alkoxy group and one halogen atom; and W is a divalent group represented by Formula (i):

$$—Y^1\text{-}A^1\text{-} \qquad \text{Formula (i)}$$

wherein $A^1$ is a $C_{1-4}$ alkylene group, and $Y^1$ is —C(=O)—.

6. The compound according to claim 4, wherein $R^1$ is a phenyl group substituted on the phenyl ring with one lower alkoxy group and one halogen-substituted lower alkoxy group, a phenyl group substituted on the phenyl ring with one halogen-substituted lower alkoxy group and one cyclo $C_{3-8}$ alkyl lower alkoxy group, or a phenyl group substituted on the phenyl ring with one halogen-substituted lower alkoxy group and one lower alkenyloxy group;

$R^2$ is a lower alkoxyphenyl group or a lower alkylpyridyl group; and

W is a divalent group represented by Formula (i):

$$—Y^1\text{-}A^1\text{-} \qquad \text{Formula (i)}$$

wherein $A^1$ is a $C_{1-4}$ alkylene group, and $Y^1$ is —C(=O)—N($R^3$)— wherein $R^3$ is a hydrogen atom.

7. A pharmaceutical composition comprising the compound or a pharmaceutically acceptable salt according to any one of claims 1 to 6 as an active ingredient and a pharmaceutically acceptable carrier.

8. A method for treating dermatosis, the method comprising administering the compound or a pharmaceutically acceptable salt according to any one of claims 1 to 6 to a human or an animal in need thereof.

9. A process for producing an oxazole compound represented by Formula (1):

(1)

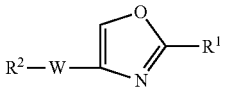

wherein $R^1$, $R^2$ and W are the same as defined in claim 1, or a salt thereof, the process comprising a reaction of a compound represented by Formula (2):

(2)

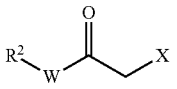

wherein $R^2$ and W are the same as defined above, and X is a halogen atom, or a pharmaceutically acceptable salt thereof, with a compound represented by Formula (3):

(3)

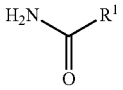

wherein $R^1$ is the same as defined above, or a salt thereof.

10. The compound or a pharmaceutically acceptable salt thereof according to claim 6, which is selected from the group consisting of the following compounds:

[N-[2-(4-difluoromethoxy-3-isobutoxyphenyl)oxazol-4-yl ethyl p-methylpicolinamide,]

*N-[2-(4-difluoromethoxy-3-isobutoxyphenyl)oxazol-4-ylmethyl]-3-methylpicolinamide,*

N-[2-(3-cyclobutylmethoxy-4-difluoromethoxyphenyl) oxazol-4-ylmethyl]-3-methylpicolinamide, N-[2-(4-difluoromethoxy-3-isobutoxyphenyl)oxazol-4-ylmethyl]-2-ethoxybenzamide, N-[2-(4-difluoromethoxy-3-ethoxyphenyl)oxazol-4-ylmethyl]-2-ethoxybenzamide, N-[2-(3-allyloxy-4-difluoromethoxyphenyl)oxazol-4-ylmethyl]-2-ethoxybenzamide,

[N-[2-(4-difluoromethoxy-3-isopropoxyphenyl)oxazol-4-ylmethyl]2-ethoxybenzamide, N-[2-(3-cyclopropylmethoxy-4-d fluoromethoxyphenyl) oxazol-4-ylmethyl]-2-ethoxybenzamide, and]

*N-[2-(4-difluoromethoxy-3-isopropoxyphenyl)oxazol-4-ylmethyl]-2-ethoxybenzamine,*

*N-[2-(3-cyclopropylmethoxy-4-difluoromethoxyphenyl) oxazol-4-ylmethyl]-2-ethoxybenzamide, and*

N-[2-(3-but-3-enyloxy-4-difluoromethoxyphenyl)oxazol-4-ylmethyl]-2-ethoxybenzamide.

*11. A compound which is N-[2-(4-difluoromethoxy-3-isopropoxyphenyl)oxazol-4-ylmethyl]-2-ethoxybenzamide, having the structure:*

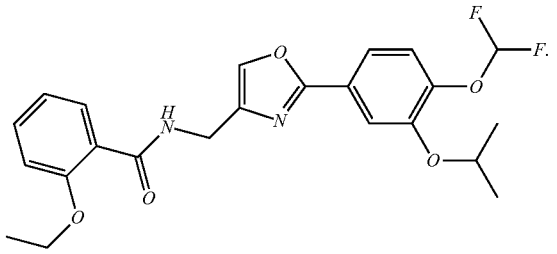

*12. A pharmaceutical composition comprising the compound according to claim 11 as an active ingredient and a pharmaceutically acceptable carrier.*

*13. A method for treating dermatosis, the method comprising administering the compound according to claim 11 to a human or an animal in need thereof.*

*14. A pharmaceutically acceptable salt of a compound, the compound being N-[2-(4-difluoromethoxy-3-isopropoxyphenyl)oxazol-4-ylmethyl]-2-ethoxybenzamide and having the structure:*

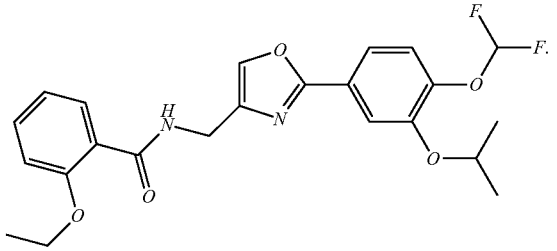

*15. A pharmaceutical composition comprising the pharmaceutically acceptable salt according to claim 14 as an active ingredient and a pharmaceutically acceptable carrier.*

*16. A method for treating dermatosis, the method comprising:*

*administering the pharmaceutically acceptable salt according to claim 14 to a human or an animal in need thereof.*

* * * * *